United States Patent
Pedersen et al.

(10) Patent No.: US 10,086,056 B2
(45) Date of Patent: Oct. 2, 2018

(54) VIRUS-LIKE PARTICLE WITH EFFICIENT EPITOPE DISPLAY

(71) Applicant: University of Copenhagen, Copenhagen K (DK)

(72) Inventors: Adam Frederik Sander Pedersen, Dragør (DK); Ali Salanti, Farum (DK); Thor Theander, Greve (DK); Susan Thrane, København N (DK); Christoph Mikkel Janitzek, København S (DK); Mette Ørskov Agerbaek, Valby (DK); Morten Agertoug Nielsen, Birkerød (DK); Jan Tobias Gustafsson, Lomma (SE)

(73) Assignee: University of Copenhagen, Copenhagen K (DK)

( * ) Notice: Subject to any disclaimer, the term of this patent is extended or adjusted under 35 U.S.C. 154(b) by 0 days.

(21) Appl. No.: 15/795,585

(22) Filed: Oct. 27, 2017

(65) Prior Publication Data
US 2018/0125954 A1    May 10, 2018

Related U.S. Application Data

(62) Division of application No. 15/542,623, filed as application No. PCT/DK2016/050011 on Jan. 15, 2016.

(30) Foreign Application Priority Data

Jan. 15, 2015 (DK) ................................ 2015 70019
Apr. 22, 2015 (DK) ................................ 2015 70237

(51) Int. Cl.
| | | |
|---|---|---|
| *A61K 39/00* | (2006.01) | |
| *A61K 39/385* | (2006.01) | |
| *A61P 35/00* | (2006.01) | |
| *C07K 14/005* | (2006.01) | |

(52) U.S. Cl.
CPC .......... *A61K 39/0011* (2013.01); *A61K 39/00* (2013.01); *A61K 39/385* (2013.01); *A61P 35/00* (2018.01); *C07K 14/005* (2013.01); *A61K 2039/5258* (2013.01); *A61K 2039/55516* (2013.01); *A61K 2039/6068* (2013.01); *A61K 2039/6075* (2013.01); *A61K 2039/627* (2013.01); *C07K 2319/735* (2013.01); *C12N 2795/00023* (2013.01); *C12N 2795/00034* (2013.01); *C12N 2795/00071* (2013.01)

(58) Field of Classification Search
None
See application file for complete search history.

(56) References Cited

U.S. PATENT DOCUMENTS

| | | |
|---|---|---|
| 7,094,409 B2 | 8/2006 | Bachmann et al. |
| 7,115,266 B2 | 10/2006 | Bachmann |
| 7,128,911 B2 | 10/2006 | Bachmann et al. |
| 7,666,408 B2 | 2/2010 | Bachmann |
| 2009/0155302 A1 | 6/2009 | Bachmann et al. |
| 2011/0081371 A1 | 4/2011 | Bachmann |

FOREIGN PATENT DOCUMENTS

| | | |
|---|---|---|
| EP | 2090319 A2 | 8/2009 |
| EP | 2534484 A1 | 12/2012 |
| GB | 2535753 A | 8/2016 |
| WO | WO-2003/024480 A2 | 3/2003 |
| WO | WO-2003/024481 A2 | 3/2003 |
| WO | WO-2003/039225 A2 | 5/2003 |
| WO | WO-2003/040164 A2 | 5/2003 |
| WO | WO-2003/059386 A2 | 7/2003 |
| WO | WO-2004/007538 A2 | 1/2004 |
| WO | WO-2004/009124 A2 | 1/2004 |
| WO | WO-2004/016282 A1 | 2/2004 |
| WO | WO-2004/084939 A2 | 10/2004 |
| WO | WO-2005/004907 A1 | 1/2005 |
| WO | WO-2005/068639 A2 | 7/2005 |
| WO | WO-2005/108425 A1 | 11/2005 |
| WO | WO-2005/117963 A1 | 12/2005 |
| WO | WO-2005/117983 A2 | 12/2005 |
| WO | WO-2006/027300 A2 | 3/2006 |
| WO | WO-2006/032674 A1 | 3/2006 |
| WO | WO-2006/037787 A2 | 4/2006 |
| WO | WO-2006/045796 A2 | 5/2006 |
| WO | WO-2006/045849 A1 | 5/2006 |
| WO | WO-2006/063974 A2 | 6/2006 |
| WO | WO-2006/097530 A2 | 9/2006 |

(Continued)

OTHER PUBLICATIONS

Andreasson et al. Murine pneumotropic virus chimeric Her2/neu virus-like particles as prophylactic and therapeutic vaccines against Her2/neu expressing tumors. Int. J. Cancer: 124, 150-156 (2009).*
GenBank: AAO18082.1, v-erb-b2 erythroblastic leukemia viral oncogene homolog 2, neuro/glioblastoma derived oncogene homolog (avian) [*Homo sapiens*]. Dated Jan. 12, 2003.*
NP_085472.1., coat protein [Acinetobacter phage AP205], dated Apr. 17, 2009.*
Bachmann, M. et al., Therapeutic vaccines for chronic diseases: successes and technical challenges, Vaccine, 49(3): 2815-2822. Oct. 12, 2011.
Bachmann, M. et al., The influence of antigen organization on B cell responsiveness, Science, 262(5138): 1448-1451, 1993.

(Continued)

*Primary Examiner* — Nianxiang Zou
(74) *Attorney, Agent, or Firm* — Dinsmore & Shohl LLP

(57) ABSTRACT

The invention relates to a virus-like particle (VLP) based vaccine. The virus-like particle constitutes a non-naturally occurring, ordered and repetitive antigen array display scaffold which can obtain a strong and long-lasting immune response in a subject. The VLP-based vaccine may be used for the prophylaxis and/or treatment of a disease including, but is not limited to, cancer, cardiovascular, infectious, chronic, neurological diseases/disorders, asthma, and/or immune-inflammatory diseases/disorders.

20 Claims, 26 Drawing Sheets

Specification includes a Sequence Listing.

(56) References Cited

FOREIGN PATENT DOCUMENTS

| WO | WO-2006/134125 A1 | 12/2006 |
|---|---|---|
| WO | WO-2007/039552 A1 | 4/2007 |
| WO | WO-2008/024427 A2 | 2/2008 |
| WO | WO-2008/074895 A1 | 6/2008 |
| WO | WO-2009/080823 A2 | 7/2009 |
| WO | WO-2009/109643 A2 | 9/2009 |
| WO | WO-2009/130261 A1 | 10/2009 |
| WO | WO-2010/012069 A1 | 2/2010 |
| WO | WO-2011/082381 A2 | 7/2011 |
| WO | WO-2011/098772 A1 | 8/2011 |
| WO | WO-2011/116226 A2 | 9/2011 |
| WO | WO-2012/048430 A1 | 4/2012 |
| WO | WO-2012/127060 A1 | 9/2012 |
| WO | WO-2012142113 A2 | 10/2012 |
| WO | WO-2013/003353 A2 | 1/2013 |
| WO | WO-2014/023947 A1 | 2/2014 |
| WO | WO-2014/088928 A1 | 6/2014 |
| WO | WO-2014/110006 A1 | 7/2014 |
| WO | WO-2014/116730 A2 | 7/2014 |
| WO | WO-2016/135291 A1 | 9/2016 |

OTHER PUBLICATIONS

Bachmann, M. et al., Neutralizing antiviral B cell responses, Annual Review of Immunology, 15: 235-270, 1997.

Bachmann, M. et al., Virus-like particles: combining innate and adaptive immunity for effective vaccination. In: Kaufmann, P.D.S. H.E. (Ed.),Novel Vaccination Strategies. Wiley-VCH Verlag GmbH & Co, pp. 415-432, 2004.

Bachmann, M. et al., Vaccine delivery: a matter of size, geometry, kinetics and molecular patterns, Nat Rev Immunol, 10(11): 787-796, 2010.

Bachmann, M. et al., Therapeutic vaccines for chronic diseases: successes and technical challenges, Philosophical Transactions of the Royal Society B: Biological Sciences, 366(1579):,2815-2822, 2011.

Baneyx et al, Recombinant protein folding and misfolding in *Escherichia coli*, Nature Biotech, 22: 1399, 2004.

Brune et al., Plug-and-Display: decoration of virus-like particles via isopeptide bonds for modular immunization, Scientific Reports, 6: 19234, Jan. 19, 2016.

Buck, C. et al., Production of Papillomavirus-Based Gene Transfer Vectors, Current Protocols in Cell Biology, 2001.

Chackerian, B. et al., Induction of autoantibodies to mouse CCR5 with recombinant papillomavirus particles, particles, Proceedings of the National Academy of Sciences of the United States of America, 96(5): 2373-2378, 1996.

Chackerian, B., Virus-like particles: flexible platforms for vaccine development, Expert Review of Vaccines, 6(3), 381-390. 2007.

Chackerian, B. et al., Virus-Like Display of a Neo-Self Antigen Reverses B Cell Anergy in a B Cell Receptor Transgenic Mouse Model, Journal of immunology (Baltimore, Md), 180(9): 5816-5825, 2008.

Fairhead, M. et al, SpyAvidin hubs enable precise and ultrastable orthogonal nanoassembly, JACS, 2014, 136, 12355.

Fierer, J. et al., Ligase peptide-peptide ligation polymerizes affibodies to enhance magnetic cancer cell capture, Proceedings of the National Academy of Sciences of the United States of America, 111(13): E1176-E1181, 2014.

Grgacic, E. et al., Virus-like particles: Passport to immune recognition, Particle-based Vaccines, Methods, 40(1): 60-65. 2006.

Jegerlehner et al, A molecular assembly system that renders antigens of choice highly repetitive for induction of protective B cell responses, Vaccine, pp. 3104-3112, 2002.

Cielens, I. et al., Mosaic RNA Phage VLPs Carrying Domain III of the West Nile Virus E Protein. Molecular Biotechnology, 2014.

Khan et al., Head-to-Head comparison of soluble vs. Qβ VLP circumsporozoite protein vaccines reveals selective enhancement of NANP repeat responses, PLOS ONE, 10(11), Nov. 16, 2015.

Kouskoff, V. et al. T Cell-Independent Rescue of B Lymphocytes from Peripheral Immune Tolerance, Science, 287(5462): 2501-2503, 2000.

Liu, Z. et al., A novel method for synthetic vaccine construction based on protein assembly, Scientific Reports, 4: 7266, 2014.

Meyer, D. et al., Reduced antibody response to streptavidin through site-directed mutagenesis, Protein Science, 10: 491-503, 2001.

Murray, K., Application of recombinant DNA techniques in the development of viral vaccines, Vaccine, 6:164-74, 1988.

Patel et al., Surface Functionalization of Virus-Like Particles by Direct Conjugation Using Azide-Alkyne Click Chemistry, Bioconjugate Chemistry, 22(3): 376-387, Mar. 1, 2011.

Peabody, D. et al., Immunogenic Display of Diverse Peptides on Virus-Like Particles of RNA Phage MS2, Journal of Molecular Biology, 380(1): 252-263, 2008.

Plotkin, S., Vaccines: past, present and future. Nat Med, May 4, 2005.

Pumpens, P. et al., HBV Core Particles as a Carrier for B Cell/T Cell Epitopes, Intervirology, 44(2-3): 98-114. 2001.

Pushko, P. et al., Analysis of RNA phage fr coat protein assembly by insertion, deletion and substitution mutagenesis, Protein Eng, 1993.

Raja, Krishnaswami S., et al., Icosahedral Virus Particles as Polyvalent Carbohydrate Display Platforms, ChemBioChem, 4(12): 1348-1351, 2003.

Smith, M. et al., Reengineering viruses and virus-like particles through chemical functionalization strategies, Current Opin Biotechnology, 24: 620-626, 2013.

Tissot, A. et al., Versatile Virus-Like Particle Carrier for Epitope Based Vaccines, Ho PL, ed. PLoS ONE, 2010.

Zakeri, B. et al., Spontaneous intermolecular amide bond formation between side chains for irreversible peptide targeting, J. Am. Chem. Soc., 132(13): 4526-4527, 2010.

Zakeri, B. et al., Peptide tag forming a rapid covalent bond to a protein, through engineering a bacterial adhesion, Proceedings of the National Academy of Sciences, 109(12): E690-E697, 2012.

Veggiani et al., Superglue from bacteria: unbreakable bridges for protein nanotechnology, Trends in Biotechnology, Elsevier Publications, Cambridge, GB, 32(10): 506-512, Aug. 26, 2014.

Amelung, S. et al., The FbaB-type fibronectin-binding protein of *Streptococcus pyogenes* promotes specific invasion into endothelial cells, Cellular Microbiology, 13(8): 1200-1211. 2011.

Bishop, B. et al., Crystal Structures of Four Types of Human Papillomavirus L1 Capsid Proteins, J Biol Chem, 282(43): 31803-31811, 2007.

Budzik, J. et al., Intramolecular amide bonds stabilize pili on the surface of bacilli, PNAS USA, 106(47): 19992-19997, 2009.

Chackerian, B. et al., Determinants of Autoantibody Induction by Conjugated Papillomavirus Virus-Like Particles, J. Immunol, 129: 6120-6126, 2002.

El Mortaji, L. et al., Stability and Assembly of Pilus Subunits of *Streptococcus* pneumoniae, J. Biol. Chem., 285(16): 12405-12415, 2010.

Forsgren, N. et al., Two intramolecular isopeptide bonds are identified in the crystal structure of the treptococcus gordonii SspB C-terminal domain, J Mol Biol, 397(3): 740-751, 2010.

Izoré, T. et al., Structural Basis of Host Cell Recognition by the Pilus Adhesin from *Streptococcus* neumoniae, Structure, 18: 106-115, 2010.

Kang, H. et al., Stabilizing Isopeptide Bonds Revealed in Gram-Positive Bacterial Pilus Structure, Science, 318: 1625, 2007.

Kang, H. et al., The Corynebacterium diphtheriae shaft pilin SpaA is built of tandem Ig-like modules with stabilizing isopeptide and disulfide bonds, PNAS USA, 106(40): 16967-16971, 2009.

Li, L. et al., Structural Analysis and Optimization of the Covalent Association between SpyCatcher and a Peptide Tag, J Mol Biol, 426(n. 2):399-317, 2014.

Nylander, Å. et al., Structure of the C-terminal domain of the surface antigen SpaP from the caries pathogen *Streptococcus* mutans, Acta Crystallogr Sect F Struct Biol Cryst Commum., F67: 23-26, 2011.

(56) References Cited

OTHER PUBLICATIONS

Oke, Muse et al., The Scottish Structural Proteomics Facility: targets, methods and outputs, J Struct Funct Geonomics, 11: 167-180, 2010.

Palladini, A. et al., Virus-like particle display of HER2 induces potent anti-cancer responses, OncoImmunology, 7(3): e1408749, 2018.

Pointon, J. et al., A Highly Unusual Thioester Bond in a Pilus Adhesin Is Required for Efficient Host Cell Interaction, J Bio Chem, 285(44): 33858-33866, 2010.

Schiller, J. et al., Why HIV Virions Have Low Numbers of Envelope Spikes: Implications for Vaccine Development, PLOS Pathogens, 10(8): e1004254, 2014.

Schwarz-Linek, U. et al., Yet more intramolecular cross-links in Gram-positive surface proteins, PNAS, 111(4): 1229-1230, 2014.

Shishovs, M. et al., Structure of AP205 Coat Protein Reveals Circular Permutation in ssRNA Bacteriophages, J Mol Biol, 428(21): 4267-4279, 2016.

Zakeri, B., Peptide targeting by spontaneous isopeptide bond formation, Thesis, Department of Biochemistry and St. Peters College, University of Oxford, 2011.

\* cited by examiner

VIRUS-LIKE PARTICLE WITH EFFICIENT EPITOPE DISPLAY

REFERENCE TO RELATED APPLICATIONS

This application is a divisional application U.S. patent application Ser. No. 15/542,623, filed Jul. 10, 2017, which is a U.S. national phase application of PCT/DK2016/050011, filed Jan. 15, 2016, which claims priority from Danish Patent Application No. PA 2015 70237, filed Apr. 22, 2015 and Danish Patent Application No. PA 2015 70019, filed Jan. 15, 2015. The entire content of each application is incorporated herein by reference.

FIELD OF THE INVENTION

The present invention relates to a technology and method for making a virus-like particle based vaccine with efficient epitope display and capable of inducing a strong and long-term protective immune response. The present invention solves the key challenge of obtaining a virus-like particle which presents a larger antigen on the particle surface at high density, with regular spacing, and with consistent orientation; three critical factors for obtaining optimal activation of the immune system.

BACKGROUND OF THE INVENTION

Vaccines have played, and still play, a major role in reducing the impact of infectious diseases on global health. The first generation of vaccines was based on attenuated or inactivated pathogens. These full-pathogen-based vaccines have proven extremely effective and, in some cases, have (e.g. small pox) led to the complete eradication of the target pathogen. There are however serious concerns associated with using full-pathogens for immunization as these have been seen to induce severe side effects at some frequency in populations, underscoring the need to develop safer vaccines (Plotkin S A et. al 2005). Along with the recent advances in recombinant DNA technology and genetic engineering, modern vaccine research has put effort into identifying critical antigenic targets of neutralizing antibodies with the aim of developing so called 'subunit vaccines' composed solely of well-defined, purified antigen components (Murray K. et al. 1988). The immunogenicity of subunit vaccines based on low valency soluble protein is, unfortunately, low compared to that of full pathogen-based vaccines. To induce a high-titer antibody response it is thus often necessary to use high antigen doses, booster administrations, and co-administration of adjuvants and even so these subunit vaccines are generally not capable of inducing long-term protective immunity. This is indeed exemplified by the many vaccine failures observed with low valency soluble proteins during the past several years and have led to the conjecture that the size, valency, and the spatial assembly of the vaccine antigen component are critical parameters for optimal activation of the immune system. Virus-like particles (VLPs), which are both highly immunogenic and safe, represent a major advancement in the development of subunit vaccines, combining many of the advantages of full pathogen-based vaccines and simple recombinant subunit vaccines. VLPs are composed of one or several recombinantly expressed viral proteins which spontaneously assemble into macromolecular particulate structures mimicking the morphology of the native virus coat—but lacking infectious genetic material. The particulate nature and size of VLPs (22-150 nm) appears to be optimal for efficient uptake by professional antigen presenting cells, particularly dendritic cells (DCs) as well as for entry into lymph vessels and hence VLPs efficiently stimulate both the humoral and cellular arms of the immune system (Bachmann, M F, Jennings, G T. 2010). Furthermore, surface structures presenting an antigen at high density, with regular spacing, and with consistent orientation are characteristic of microbial surface antigens for which the mammalian immune system has evolved to respond vigorously to. At the molecular level, the presentation of an epitope at high density, while being regularly spaced, and with consistent orientation enables efficient cross-linking of B-cell receptors (Bachmann, M F and Zinkernagel, R M. 1997) leading to strong B-cell responses, even in the absence of T-cell help (Bachmann, M F et al., 1993; Chackerian et al., 1999; Kouskoff, V. et al., 2000) and cumulative data from several studies indicate that B-cells, in fact, discriminate antigen patterns via the degree of surface Ig-cross-linking and use antigen repetitiveness as a self/nonself discriminator.

It has long been an attractive goal to exploit the VLPs as an immunogenicity-boosting platform for inducing immune responses against heterologous antigens by using them as molecular scaffolds for antigen presentation. Antibodies are believed to be the primary effectors of all current prophylactic microbial vaccines and hence the main focus for developing VLP-based vaccines is to induce strong humoral responses, which is especially true when targeting self-antigens. Traditionally this has been achieved either by incorporation of antigenic epitopes into VLPs by genetic fusion (chimeric VLPs) or by conjugating antigens to pre-assembled VLPs. The chimeric VLP approach is to date the most common method for displaying heterologous epitopes on VLPs (Pumpens, P and Grens, E. 2001; Bachmann, M F and Jennings, G T, 2004a; Chackerian, 2007; Grgacic, E V L. and Anderson, D A. 2006). However, this strategy is severely limited by both the size and nature of epitopes that can be inserted into VLPs, especially in their immunodominant regions, and it has in general not been possible to insert peptides longer than 20 amino acids without disrupting the fragile self-assembly process of the VLPs. In addition, this approach requires that critical epitopes have already been identified in the target antigen and that they can be presented in an immunodominant region on the VLP surface while maintaining their native conformation. Therefore, despite a still growing understanding of the VLP structure f assembly process, generating chimeric VLPs is still a trial-and-error process and it remains impossible to predict whether individual peptides will be compatible with VLP assembly or whether insertions will be immunogenic. Finally, due to the small size of inserted peptide sequences the induced antibody response will functionally be essentially monoclonal, which in some cases will set a limit to the potency of protection. On the other hand, chemical conjugation, e.g. through chemical biotinylation of exposed lysine residues, allows the attachment of diverse kinds of target antigens (incl. non-protein targets) to VLPs and this approach is, in principle, not restricted by the size of the antigen (Raja K S et al. 2003). However, so far only shorter peptides have successfully been coupled at high density and with consistent orientation to the surface of VLPs (Bachmann M F, Jennings G T. 2011) and in the case of larger antigens it remains highly challenging to control both the orientation and the total amount stoichiometry of the coupled antigen, affecting both the density and regularity of displayed epitopes, and thus potentially limiting the immune response. In addition to this, chemical coupling procedures are rarely compatible with large scale vaccine production. As a result the current technologies are not sufficient to ensure VLP display of antigens at high density, with regular spacing, and with consistent orientation, which are three critical factors for obtaining strong and long lasting activation of the immune system.

In brief:
Induction of a strong and long lasting immune response to pathogens as well as disease associated antigens is very difficult to obtain with simple subunit vaccines.
Virus-like particle (VLP) presentation of antigens has proven to be very efficient in inducing the highly functional long-term immune responses.
Coupling of an antigen onto the surface of a VLP, at high density, and with a consistent orientation for optimal epitope display, poses a major biotechnological challenge.

SUMMARY OF THE INVENTION

The present invention solves the challenges of obtaining a VLP which presents densely and regularly spaced surface antigens with consistent orientation. Such VLPs are capable of efficiently displaying epitopes and are thus able to induce long-term protective immunity in a subject. A general concept of the present invention is illustrated in FIG. 1. The inventors have identified bacteriophages (e.g. AP205) where a Spytag and/or a SpyCatcher can be fused to the capsid protein without compromising the self-assembly of the particle.

Surprisingly the inventors were able to fuse the entire 116 amino acid SpyCatcher to the N-terminal of the AP205 capsid protein. In addition, the inventors have managed to setup a system to produce antigens fused to a SpyCatcher and/or a SpyTag polypeptide, which ensures control of the orientation of the coupled antigen. The specific interaction between the SpyTag and SpyCatcher (Zakeri, B. et al. PNAS, 2012) ensures control of the overall amount/stoichiometry as well as display of antigens in a densely and repetitive ordered manner with consistent orientation which is important for yielding efficient epitope display and consequently a potent immune response. Surprisingly, the present inventors have found that the large SpyCatcher protein, which comprises more than 100 amino acids, may be fused to a capsid protein without disrupting the spontaneous VLP self-assembly process. The described antigen display scaffold is unique as it for the first time enables coupling of virtually any antigen at high density on a VLP surface, thereby presenting ordered arrays of the particular antigens which are all held in the same orientation, thereby solving three key issues of mounting an efficient immune response. The system can both be used to target self-antigens (i.e. break tolerance) as well as to efficiently target infectious organisms.

The SpyTag and SpyCatcher interact via a spontaneous isopeptide bond formation (Zakeri. B. et al. PNAS. 2012). This is a covalent interaction and ensures a high strength, one-to-one interaction between the SpyTag and SpyCatcher linked antigen. The flexibility of the isopeptide bond is limited by the conformation of the co-joined SpyTag-SpyCatcher polypeptide ensuring consistent orientation of the antigens thus displayed on the VLP.

The problems described above are solved by the aspects and embodiments of the present invention characterized in the claims. As illustrated in FIG. 1, a main aspect of the present invention concerns a vaccine for use in the prophylaxis and/or treatment of a disease wherein the vaccine comprises:

i. a virus capsid protein comprising a first peptide tag, and
ii. an antigen fused to a second peptide tag,
wherein the antigen and virus capsid protein are linked via an isopeptide bond between the first and second peptide tag, and wherein i-ii form a virus-like particle displaying said antigen.

In a preferred embodiment the virus capsid protein comprises an AP205 capsid protein and/or phage fr capsid protein fused to a SpyCatcher, wherein the capsid protein—SpyCatcher fusion protein is capable of forming a virus-like particle. In a further embodiment SpyCatcher is fused to the N-terminus of the AP205 capsid protein optionally via a linker.

Another main aspect of the present invention concerns vaccine for use in the prophylaxis and/or treatment of a disease wherein the vaccine comprises:

i. an AP205 capsid protein and/or a phage fr capsid protein comprising a SpyCatcher polypeptide insertion, and
ii. an antigen fused to SpyTag,
wherein the antigen and AP205 capsid protein and/or fr capsid protein are linked via the interaction between the Spytag and the SpyCatcher, and wherein i-ii form a virus-like particle displaying said antigen.

In one embodiment, the vaccine for use in the prophylaxis and/or treatment of a disease comprises:

iii. an AP205 capsid protein and/or a phage fr capsid protein comprising a SpyTag polypeptide insertion, and
iv. an antigen fused to SpyCatcher,
wherein the antigen and AP205 capsid protein and/or fr capsid protein are linked via the interaction between the Spytag and the SpyCatcher, and wherein i-ii form a virus-like particle displaying said antigen.

The problems described above are solved by the aspects and embodiments of the present invention characterized in the claims. As illustrated in FIG. 1, a main aspect of the present invention concerns a vaccine for use in the prophylaxis and/or treatment of a disease wherein the vaccine comprises:

i. an AP205 capsid protein and/or a phage fr capsid protein comprising a SpyCatcher polypeptide insertion such that the capsid protein can self-assemble into a VLP that displays the SpyCatcher in a context that it binds to SpyTag, and
ii. an antigen fused to SpyTag,
wherein the antigen and AP205 capsid protein and/or phage fr capsid protein are linked via the interaction between the Spytag and the SpyCatcher, and wherein i-ii form a virus-like particle displaying said antigen.

In one embodiment, the vaccine for use in the prophylaxis and/or treatment of a disease comprises:

i. an AP205 capsid protein and/or a phage fr capsid protein comprising a SpyTag polypeptide insertion such that the capsid protein can self-assemble into a VLP that displays the SpyTag in a context that it binds to SpyCatcher, and
ii. an antigen fused to SpyCatcher.
wherein the antigen and AP205 capsid protein and/or phage fr capsid protein are linked via the interaction between the Spytag and the SpyCatcher, and wherein i-ii form a virus-like particle displaying said antigen, In another aspect the present invention concerns a vector comprising at least one polynucleotide encoding i. an AP205 capsid protein and/or a phage fr capsid protein comprising a SpyCatcher polypeptide insertion, and
ii. an antigen fused to SpyTag, wherein the antigen and AP205 capsid protein and/or phage fr capsid protein are linked via the interaction between the Spytag and the SpyCatcher, and wherein i-ii form a virus-like particle displaying said antigen.

In one embodiment, the vector comprises at least one polynucleotide encoding
i. an AP205 capsid protein and/or a phage fr capsid protein comprising a SpyTag polypeptide insertion, and
ii. an antigen fused to SpyCatcher,
wherein the antigen and AP205 capsid protein and/or phage fr capsid protein are linked via the interaction between the Spytag and the SpyCatcher, and wherein i-ii form a virus-like particle displaying said antigen.

In another aspect the present invention concerns a host cell expressing at least one polypeptide encoded by said polynucleotide.

In another aspect the present invention concerns a composition comprising said vaccine.

A further aspect of the present invention concerns a method of manufacturing a pharmaceutical composition comprising said vaccine, wherein the method comprises the steps of
i. obtaining a first polypeptide; an AP205 capsid protein and/or a phage fr capsid protein comprising Spy-Catcher, and
ii. obtaining a second polypeptide; an antigen fused to SpyTag, and
iii. subjecting the first polypeptide to conditions which enable formation of virus-like particles, and
iv. obtaining a vaccine by linkage of the second polypeptide and said virus-like particles via the interaction between the SpyTag and SpyCatcher of said virus-like particles, and
v. generating a composition comprising said vaccine, thereby obtaining a pharmaceutical composition.

In one embodiment, the method of manufacturing a pharmaceutical composition comprising said vaccine comprises the steps of
i. obtaining a first polypeptide; an AP205 capsid protein and/or a phage fr capsid protein comprising SpyTag, and
ii. obtaining a second polypeptide; an antigen fused to SpyCatcher, and
iii. subjecting the first polypeptide to conditions which enable formation of virus-like particles, and
iv. obtaining a vaccine by linkage of the second polypeptide and said virus-like particles via the interaction between the SpyTag and SpyCatcher of said virus-like particles, and
v. generating a composition comprising said vaccine, thereby obtaining a pharmaceutical composition.

Yet an aspect of the present invention concerns a method of administering said vaccine to treat and/or prevent a clinical condition in a subject in need thereof comprising the steps of:
i. obtaining a composition comprising at least one vaccine, and/or
ii. administering said composition to a subject at least once for prophylaxis and/or treatment of a disease.

In another aspect the present invention concerns a kit of parts comprising
i. a composition comprising a vaccine, and
ii. a medical instrument or other means for administering the vaccine, and
iii. instructions on how to use the kit of parts.

In an aspect of the invention relates to a method for inducing an immune response in a subject, the method comprising the steps of
i. obtaining a composition comprising at least one vaccine, and
ii. administering said composition to a subject at least once for prophylaxis and/or treatment of a disease.

DETAILED DESCRIPTION OF THE INVENTION

The present invention solves the challenge of conjugating larger proteins (e.g. full length antigens) at high density and in a consistent orientation onto the surface of a VLP, thereby obtaining VLPs presenting densely and repetitive arrays of heterologous epitopes. The solution of the present invention represents a novel approach for making a versatile VLP-based vaccine delivery platform capable of efficiently displaying antigen epitopes and of inducing long-term protective immunity.

Figure 1:
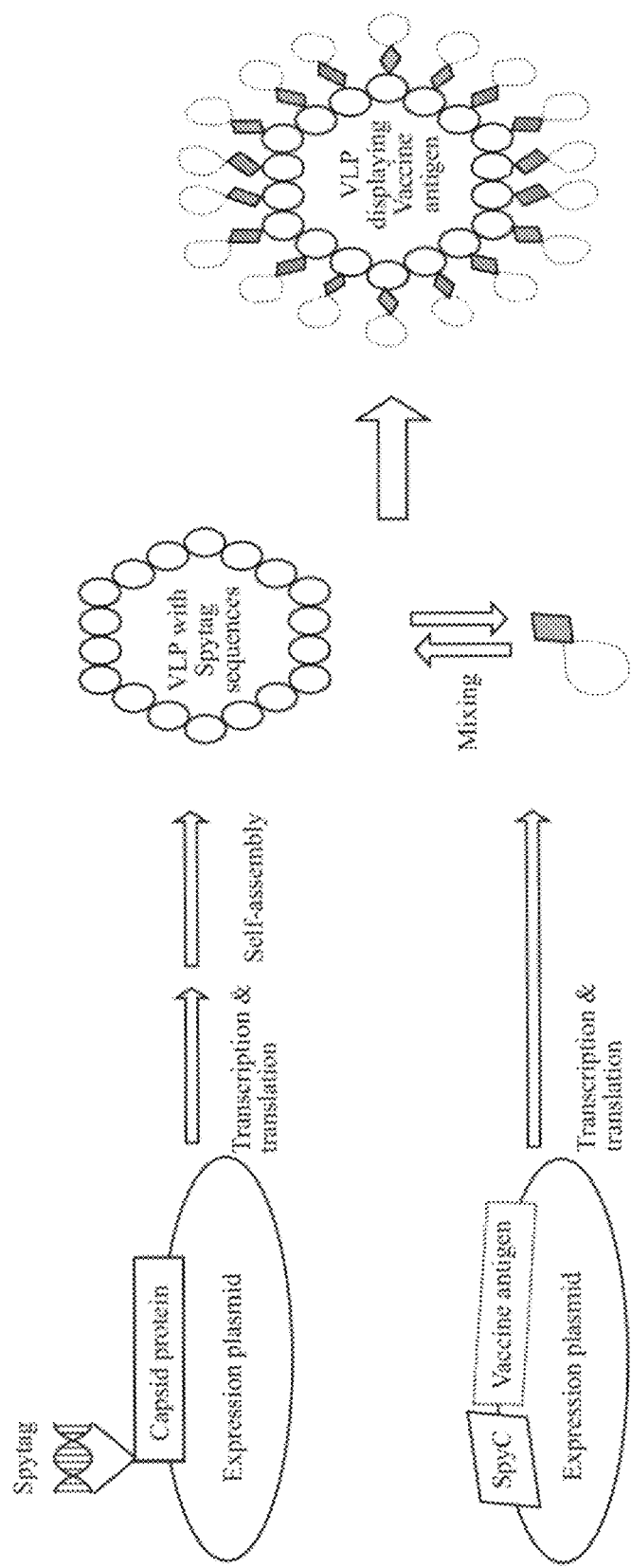
FIG. 1: A general aspect of the present invention. Production steps in making a fully biotinylated SpyTag-capsid protein coupled with a SpyCatcher-antigen. SpyC is an abbreviation of SpyCatcher.

A general aspect of the present invention is illustrated in FIG. 1.

Definitions

The term "virus-like particle" or "VLP" refers to one or several recombinantly expressed viral capsid proteins, which spontaneously assemble into macromolecular particulate structures mimicking the morphology of a virus coat, but lacking infectious genetic material.

The term "self-assembly" refers to a process in which a system of pre-existing components, under specific conditions, adopts a more organised structure through interactions between the components themselves. In the present context, self-assembly refers to the intrinsic capacity of an AP205 capsid protein and/or a phage fr capsid protein to self-assemble into virus-like particles in the absence of other viral proteins, when subjected to specific conditions. "Self-assembly" does not preclude the possibility that cellular proteins, e.g. chaperons, participate in the process of intracellular VLP assembly. The self-assembly process may be sensitive and fragile and may be influenced by factors such as, but not limited to, choice of expression host, choice of expression conditions, and conditions for maturing the virus-like particles. Virus capsid proteins may be able to form VLPs on their own, or in combination with several virus capsid proteins, these optionally all being identical. Examples of virus capsid proteins include but are not limited to: AP205 capsid protein and/or a phage fr capsid protein.

The term "consistent orientation", as used herein, refers to the orientation of the target antigen constructs of the present invention and their spatial orientation to an AP205 capsid protein and/or a phage fr capsid protein of the present invention. When linking an antigen fused to a SpyCatcher to an AP205 VLP and/or a phage fr VLP displaying a SpyTag, a molecule of the SpyCatcher tagged vaccine antigen can only be linked to a single AP205 capsid protein and/or a phage fr capsid protein at unique sites in both the vaccine antigen and the recombinant AP205 capsid protein and/or a recombinant phage fr capsid protein, thus creating a uniform and/or consistent presentation of said antigen with a consistent orientation. In contrast, for example, a streptavidin homo-tetramer may crosslink several AP205 capsid proteins and/or recombinant phage fr capsid proteins on the surface of a biotinylated VLP, thus creating an irregular and non-consistent orientation of said antigen (Chackerian, B. et al. 2008). Besides, it is highly challenging to use streptavidin as a bridging molecule e.g. for conjugating biotinylated antigens onto biotinylated VLPs, since the multiple biotin binding sites will allow cross-linking and aggregation of the biotinylated VLPs.

The term "regularly spaced" as used herein, refers to antigens of the present invention which forms a pattern on the surface of a VLP. Such pattern may be symmetric, circle-like, and/or bouquet like pattern of antigens.

The term "treatment" refers to the remediation of a health problem. Treatment may also be preventive and/or prophylactic or reduce the risk of the occurrence of a disease and/or infection. Treatment may also be curative or ameliorate a disease and/or infection.

The term "prophylaxis" refers to the reduction of risk of the occurrence of a disease and/or infection. Prophylaxis may also refer to the prevention of the occurrence of a disease and/or infection.

The term "loop" refers to a secondary structure of a polypeptide where the polypeptide chain reverses its overall direction and may also be referred to as a turn.

The term "vaccine cocktail" refers to a mixture of antigens administered together. A vaccine cocktail may be administered as a single dose or as several doses administered over a period of time. Time intervals may be, but not limited to administration within the same year, month, week, day, hour and/or minute. Co-vaccination and vaccine cocktail may be used interchangeably.

The term "self-antigens" refers to endogenous antigens that have been generated within previously normal cells as a result of normal cell metabolism The term "SpyTag" refers to a part of the CnaB2 domain from the FbaB protein from *Streptococcus pyogenes* optimized to bind SpyCatcher consisting of another part of the CnaB2 domain. The interaction occurs when the unprotonated amine of Lys31 nucleophilically attacks the carbonyl carbon of Asp117, catalyzed by the neighboring Glu77. The minimal peptide to mediate this binding is AHIVMVDA whereas a c-terminal extension giving the sequence: AHIVMVDAYKPTK provides the most optimal region, designated "SpyTag" (Zakeri, B. et al. PNAS. 2012).

The term "SpyCatcher" refers to a part of the CnaB2 domain from the FbaB protein from *Streptococcus pyogenes* optimized to bind SpyTag consisting of another part of the CnaB2 domain. SpyCatcher can be residue number 1-113 of CnaB2 and binding can be optimized by the following two mutations: I34E and M69Y (Zakeri, B. et al. PNAS, 2012). Truncated and homologous versions of SpyCatcher are also objects of the present invention and thus the term SpyCatcher herein denotes any variant of SpyCatcher that is still capable of interacting with SpyTag. Variants of SpyCatcher may include, but is not limited to truncated SpyCatcher variants. Truncated SpyCatcher variants may include, but is not limited to SEQ ID NO: 60 and SEQ ID NO: 61.

The term "sequence variant" refers to a polypeptide and/or polynucleotide sequence with at least 70%, such as 75%, such as 80%, such as 85%, such as 90%, such as 95%, such as 96%, such as, 97%, such as 98%, such as 99%, such as 99.5%, such as 100% sequence identity to said polypeptide and/or polynucleotide sequence.

The term "peptide tag" as used herein refers to a peptide sequence which is genetically grafted onto a recombinant protein. A first peptide tag may facilitate interactions with a second peptide tag e.g. by forming one or more covalent bonds such as isopeptide bonds. In an embodiment the first peptide tag described in the present invention comprises a SpyTag as described herein. In an embodiment the first peptide tag described in the present invention comprises a KTag as described herein. In an embodiment the second peptide tag described in the present invention comprises a KTag as described herein. In an embodiment the second peptide tag described in the present invention comprises a SpyCatcher as described herein. In an embodiment the second peptide tag described in the present invention comprises a SpyTag as described herein.

VLP Based Vaccine

The expression of viral structural proteins, such as Envelope or Capsid proteins, can result in the self-assembly of virus-like particles (VLPs). VLPs resemble viruses, but are non-infectious as they do not contain any viral genetic material. For the purpose of active immunization, VLPs have proven highly immunogenic and provide a potentially safer alternative to attenuated viruses since they lack genetic material. Besides, VLPs are a useful tool for the development of vaccines and can be used as molecular scaffolds for efficient antigen epitope display. This has been achieved by either genetic insertion or by chemical conjugation approaches. However, it has generally not been possible to incorporate peptides longer than 20 amino acids without disrupting the self-assembly process of the chimeric VLP. At the same time, the current technologies using chemical conjugation are not sufficient to enable VLP-presentation of larger proteins at high density and with a consistent orientation to ensure an orderly, high density, display of repetitive antigen epitopes, which are critical factors for obtaining strong and long-lasting immune responses.

The present inventors have solved these problems by a novel approach to linking antigens to a virus capsid protein such as an AP205 capsid protein and/or a phage fr capsid protein VLP using a SpyTag and SpyCatcher fusion without disrupting the self-assembly of the VLP. Thus in a main aspect, as illustrated in FIG. 1, the present invention concerns a vaccine for use in the prophylaxis and/or treatment of a disease wherein the vaccine comprises:
  i. a virus capsid protein comprising at least one first peptide tag, and
  ii. an antigen fused to a second peptide tag,
  wherein the antigen and virus capsid protein are linked via an isopeptide bond between the first and second peptide tag, and wherein i form a virus-like particle displaying said antigen.

In an embodiment the first peptide tag comprises at least one SpyCatcher, and the second peptide tag comprises a SpyTag,
wherein the antigen and the virus capsid protein are linked via the interaction between the SpyCatcher and the SpyTag interaction, and wherein i-ii form a virus-like particle displaying said antigen.

In an embodiment, the first peptide tag comprises two SpyCatchers. Thus in one embodiment, two SpyCatchers are fused to the AP205 capsid protein, one at each terminus.

In some embodiments the SpyCatcher is fused to the capsid protein via a spacer. In one embodiment the SpyCatcher is fused to the AP205 capsid protein via a spacer. Suitable spacers are known in the art and include spacers such as Gly-Gly-Ser-Gly-Ser (SEQ ID NO: 83).

In an embodiment the virus capsid protein is an AP205 capsid protein and the first peptide tag is a SpyCatcher, wherein the SpyCatcher is linked to the N-terminal of the AP205 capsid protein.

In an embodiment the first peptide tag comprises at least one Spytag, and the second peptide tag comprises a SpyCatcher,
wherein the antigen and virus capsid protein are linked via the interaction between the SpyCatcher and SpyTag interaction, and wherein i-ii form a virus-like particle displaying said antigen.

In an embodiment, the first peptide tag comprises two SpyTags. Thus in one embodiment, two SpyTags are fused to the AP205 capsid protein, one at each terminus.

In another embodiment the first peptide tag comprises a SpyTag, and the second peptide tag comprises a KTag, and wherein the vaccine optionally comprises a SpyLigase, and
wherein the antigen and virus capsid protein are linked via the interaction between the SpyTag and KTag, and wherein i-ii form a virus-like particle displaying said antigen. In a further embodiment the first peptide tag is a SpyTag and the second peptide tag is a KTag.

In another embodiment the first peptide tag comprises a KTag, and the second peptide tag comprises a SpyTag, and
wherein the vaccine optionally comprises a SpyLigase wherein the antigen and virus capsid protein are linked via the interaction between the KTag and SpyTag, and wherein i-ii form a virus-like particle displaying said antigen.

In another embodiment the virus capsid protein comprises or is an AP205 capsid protein and/or a phage fr capsid protein.

In an embodiment the first peptide tag as described herein is fused to the N- and/or C-terminus of AP205 capsid protein and/or fr protein capsid.

In an embodiment the at least one first peptide tag as described herein is fused to the N- and/or C-terminus of AP205 capsid protein and/or fr protein capsid via a spacer.

In an embodiment the first peptide tag as described herein is fused to the N-terminus of AP205 capsid protein.

In an embodiment the first peptide tag as described herein is fused to the C-terminus of AP205 capsid protein. In an embodiment the peptide tag fused to the C-terminus of AP205 is not a SpyCatcher.

In an embodiment the at least one first peptide tag as described herein is two first peptide tags, wherein the two peptide tags are identical, and wherein one of the two peptide tags is fused to the N-terminus of AP205 capsid protein and the other one is fused to the C-terminus of AP205 capsid protein. In one embodiment, the two first peptide tags are two SpyTags.

In an embodiment the first peptide tag as described herein is used to the N-terminus of fr capsid protein.

In an embodiment the first peptide tag as described herein is fused to the C-terminus of fr capsid protein.

In an embodiment the first peptide tag comprises a SpyTag, SpyCatcher and/or KTag as described herein. In a further embodiment the first peptide tag is a SpyTag, SpyCatcher and/or KTag as described herein.

In one embodiment where the first peptide tag is a SpyCatcher, the fusion to the capsid protein is to said capsid protein's N-terminus.

In another embodiment said interaction comprises an isopeptide bond based interaction. In another embodiment the SpyTag and KTag according to any one of the preceding claims are linked by means of a SpyLigase.

In a main aspect the present invention concerns a vaccine for use in the prophylaxis and/or treatment of a disease wherein the vaccine comprises.
  i. an AP205 capsid protein and/or a phage fr capsid protein comprising a SpyCatcher, and
  ii. an antigen fused to a SpyTag.
  wherein the antigen and AP205 and/or phage fr are irreversibly linked through a spontaneous isopeptide bond formation between Spytag and SpyCatcher, and wherein i-ii form a virus-like particle displaying said antigen. In a further aspect the SpyCatcher is fused to the N-terminus of the AP205 capsid protein.

In an embodiment the present invention concerns a vaccine for use in the prophylaxis and/or treatment of a disease wherein the vaccine comprises:
  i. an AP205 capsid protein and/or a phage fr capsid protein comprising a SpyCatcher having a polypeptide sequence at least 70%, such as 75%, such as 80%, such as 85%, such as 90%, such as 95%, such as 96%, such as, 97%, such as 98%, such as 99%, such as 99.5%, such as 100% identical to the polypeptide sequence of SEQ ID NO: 76, and
  ii. an antigen fused to a SpyTag,
  wherein the antigen and AP205 and/or phage fr are irreversibly linked through a spontaneous isopeptide bond formation between Spytag and SpyCatcher, and wherein i-ii form a virus-like particle displaying said antigen.

In another main aspect, as illustrated in FIG. 1, the present invention concerns a vaccine for use in the prophylaxis and/or treatment of a disease wherein the vaccine comprises:
  i. an AP205 capsid protein and/or a phage fr capsid protein comprising a SpyTag, and
  ii. an antigen fused to SpyCatcher,
  wherein the antigen and AP205 capsid protein and/or a phage fr capsid protein are irreversibly linked through a spontaneous isopeptide bond formation between Spytag and SpyCatcher, and wherein i-ii form a virus-like particle displaying said antigen.

In an embodiment, the AP205 capsid protein and/or a phage fr capsid protein comprising a SpyTag is able to form a virus-like particle.

The inventors of the present invention have demonstrated formation of AP205 VLP's by recombinant expression of the AP205 capsid protein, preferably in *Escherichia coli* cells, such as BL21 cells. Other conditions and expression hosts (such as *Saccharomyces cerevisiae* or *Pichia Pastoris*) may work as well.

In an embodiment, the antigen is capable of eliciting an immune reaction in an animal, such as a mammal, such as a cow, pig, horse, sheep, goat, llama, mouse, rat, monkey, most preferably such as a human being; or a bird such as a chicken, or fish such as a Salmon.

It has long been an attractive goal to exploit the VLPs as an immunogenicity-boosting platform for inducing immune responses against heterologous antigens by using them as molecular scaffolds for antigen display. Thus another aspect of the present invention relates to an antigen display scaffold, comprising an assembled virus-like particle comprising:
  i. an AP205 capsid protein and/or a phage fr capsid protein comprising a SpyCatcher, and
  ii. an antigen fused to SpyTag,
  wherein the antigen and the AP205 capsid protein and/or a phage fr capsid protein are linked through a spontaneous isopeptide bond formation between Spytag and SpyCatcher, and wherein i-ii form an antigen display scaffold. In a further aspect the SpyCatcher is fused to the N-terminus of the AP205 capsid protein.

Thus another aspect of the present invention relates to an antigen display scaffold, comprising an assembled virus-like particle comprising:
  i. an AP205 capsid protein and/or a phage fr capsid protein comprising a SpyTag, and
  ii. an antigen fused to SpyCatcher,
  wherein the antigen and the AP205 capsid protein and/or a phage fr capsid protein are linked through a spontaneous isopeptide bond formation between Spytag and SpyCatcher, and wherein i-ii form an antigen display scaffold.

Another aspect of the present invention relates to a method of producing a non-naturally occurring, ordered and repetitive antigen array comprising
  i. an AP205 capsid protein and/or a phage fr capsid protein comprising a SpyCatcher, and
  ii. an antigen fused to SpyTag,
  wherein the antigen and the AP205 capsid protein and/or a phage fr capsid protein are linked through a spontaneous isopeptide bond formation between Spytag and SpyCatcher, and wherein i-ii form a non-naturally occurring, ordered and repetitive antigen array. In a further aspect SpyCatcher is fused to the N-terminus of the capsid protein.

Another aspect of the present invention relates to a method of producing a non-naturally occurring, ordered and repetitive antigen array comprising
  i. an AP205 capsid protein and/or a phage fr capsid protein comprising at least one SpyTag, and
  ii. an antigen fused to SpyCatcher,
  wherein the antigen and the AP205 capsid protein and/or a phage fr capsid protein are linked through a spontaneous isopeptide bond formation between Spytag and SpyCatcher, and wherein i-ii form a non-naturally occurring, ordered and repetitive antigen array.

Diseases and Medical Indications

The present invention is a novel, generic, and easy-to-use-approach to conjugate various antigens to a VLP. Depending on the antigen, the VLP-based vaccines of the present invention can be used for prophylaxis and/or treatment of a wide range of diseases. The diseases which the present invention may be used for prophylaxis and/or treatment of include but are not limited to cancers, cardiovascular diseases, allergic diseases, chronic diseases, neurologic diseases, and/or infectious diseases.

In an embodiment an antigen which is associated with at least one cancer disease is linked to the virus capsid protein, such as the AP205 capsid protein and/or a phage fr capsid protein via the interaction between SpyCatcher and SpyTag. In a further embodiment the present VLP vaccine may be used for prophylaxis and/or treatment of the cancer and/or cancers which the antigen is associated with.

In an embodiment, an antigen which is associated with at least one cardiovascular disease is linked to the virus capsid protein, such as the AP205 capsid protein and/or a phage fr capsid protein via the interaction between SpyCatcher and SpyTag. In a further embodiment the present VLP vaccine can be used for prophylaxis and/or treatment of the cardiovascular disease and/or cardiovascular diseases which the antigen is associated with.

In an embodiment, an antigen which is associated with at least one allergic disease is linked to the virus capsid protein, such as the AP205 capsid protein and/or a phage fr capsid protein via the interaction between SpyCatcher and SpyTag. In a further embodiment the present VLP vaccine can be used for prophylaxis and/or treatment of the allergic disease and/or allergic diseases which the antigen is associated with.

In an embodiment, an antigen which is associated with at least one infectious disease is linked to the virus capsid protein, such as the AP205 capsid protein and/or a phage fr capsid protein via the interaction between SpyCatcher and SpyTag. In a further embodiment the present VLP vaccine can be used for prophylaxis and/or treatment of the infectious disease and/or infectious diseases which the antigen is associated with.

In an embodiment, an antigen which is associated with at least one chronic disease is linked to the virus capsid protein, such as the AP205 capsid protein and/or a phage fr capsid protein via the interaction between SpyCatcher and SpyTag. In a further embodiment the present VLP vaccine can be used for prophylaxis and/or treatment of the chronic disease and/or chronic diseases which the antigen is associated with.

In an embodiment, an antigen which is associated with at least one neurologic disease is linked to the virus capsid protein, such as the AP205 capsid protein and/or a phage fr capsid protein via the interaction between SpyCatcher and SpyTag. In a further embodiment the present VLP vaccine can be used for prophylaxis anchor treatment of the neurologic disease and/or neurologic diseases which the antigen is associated with.

A non-exhaustive list of antigens which may be used by the present invention is outlined in table 1 and table 2. In addition, table 1 show examples of specific diseases the antigens are associated with as well as examples of patient groups which may be in need of prophylaxis and/or treatment using the antigen-VLP vaccines of the present invention.

TABLE 1

Non-exhaustive list of antigens or parts hereof that could be used in treatment of specific diseases/medical indications in various patient groups.

| Examples of antigens (non-exhaustive) | Examples of a specific disease (non-exhaustive) | Examples of patient group (non-exhaustive) |
| --- | --- | --- |
| Her2/Neu (ERBB2) | Breast cancer | Females overexpressing Her2 |
| Her2/Neu (ERBB2) | Gastric cancer | Males and Females overexpressing Her2 |
| Her2/Neu (ERBB2) | Ovarian cancer | Females overexpressing Her2 |
| Her2/Neu (ERBB2) | Uterine serous carcinoma | Postmenopausal Females overexpressing Her2 |
| Survivin | Cancer types overexpressing Survivin | Males and non-pregnant Females overexpressing Survivin |
| PCSK9 | cardiovascular disease | Males and Females with dyslipidemia |
| PCSK9 | cardiovascular disease | Males and Females with atherosclerosis |
| PCSK9 | cardiovascular disease | Males and Females with hypercholesterolemia |
| Interleukin-5 | Asthma | Males and Females with eosinophilia |
| Interleukin-5 | nasal polyposis | Males and Females with eosinophilia |
| Interleukin-5 | atopic dermatitis | Males and Females with eosinophilia |
| Interleukin-5 | eosinophilic esophagitis | Males and Females with eosinophilia |
| Interleukin-5 | Hypereosinophilic syndrome | Males and Females with eosinophilia |
| Interleukin-5 | Churg-Strauss syndrome | Males and Females with eosinophilia |
| Ag85A | Tuberculosis | Males and Females with tuberculosis |
| PfRH5 | Malaria | Males and Females with malaria |
| VAR2CSA | Malaria | Females with malaria |
| PfEMP1, CIDR1a | Malaria | Males and Females with malaria |
| GLURP | Malaria | Males and Females with malaria |
| MSP3 | Malaria | Males and Females with malaria |
| Pfs25 | Malaria | Males and Females with malaria |
| CSP | Malaria | Males and Females with malaria |
| PfSEA-1 | Malaria | Males and Females with malaria |
| Hemagglutinin HA | Influenza | Males and Females with influenza |
| Interleukin-17 | Psoriasis | Males and Females with Psoriasis |
| Interleukin-17 | Multiple sclerosis | Males and Females with multiple sclerosis |
| Interleukin-17 | Rheumatoid arthritis | Males and Females with rheumatoid arthritis |
| Interleukin-17 | Inflammatory bowel diseases | Males and Females with inflammatory bowel diseases |
| Interleukin-17 | Asthma | Males and Females with Asthma |
| IL-33 | Asthma | Males and Females with Asthma |

TABLE 1-continued

Non-exhaustive list of antigens or parts hereof that could be used in treatment of specific diseases/medical indications in various patient groups.

| Examples of antigens (non-exhaustive) | Examples of a specific disease (non-exhaustive) | Examples of patient group (non-exhaustive) |
|---|---|---|
| IgE | Asthma | Males and Females with Asthma |
| Gp160 | HIV | Males and Females with HIV |
| Gp120 | HIV | Males and Females with HIV |
| Gp40 | HIV | Males and Females with HIV |
| GD2 | Cancer cell types expressing GD2 (e.g. melanomas, osteosarcoma and soft-tissue sarcomas) | Males and Females with GD2 expressing tumors. |
| EGF-R | Cancer cell types expressing EGF-R (e.g. metastatic colorectal and head and neck cancer) | Males and Females with EGF-R expressing tumors. |
| CEA | Cancer cell types expressing CEA (e.g. colon and rectal cancer or pancreatic, breast, ovary, or lung cancer. | Males and Females with CEA expressing tumors. |
| CD52 | Chronic lymphocytic leukemia (CLL),cutaneous T-cell lymphoma (CTCL) and T-cell lymphoma or multiple sclerosis | Males and Females with chronic lymphocytic leukemia (CLL),cutaneous T-cell lymphoma (CTCL) and T-cell lymphoma or multiple sclerosis. |
| CD21 | B-cell cancers | Males and Females with B-cell cancers |
| human melanoma protein gp100 | Cancer cell types expressing human melanoma protein gp 100 (e.g. Melanoma). | Males and Females with melanoma. |
| human melanoma protein melan-A/MART-1 | Cancer cell types expressing human melanoma protein melan-A/MART-1 (e.g. Melanoma) | Males and Females with melanoma. |
| tyrosinase | Melanoma | Males and Females with melanoma |
| NA17-A nt protein | Melanoma | Males and Females with melanoma |
| MAGE-3 protein | melanoma, non-small cell lung cancer, hematologic malignancies. | Males and Females with melanoma, non-small cell lung cancer or hematologic malignancies |
| p53 protein | Cancer cell types expressing p53 | Males and Females with tumors expressing p53 |
| HPV 16 E7 protein | Cancers of the cervix, vulva, vagina, penis, oropharynx and anus. | HPV infected males and females |
| HPV L2 | Cancers of the cervix, vulva, vagina, penis, oropharynx and anus. | HPV infected males and females |
| PD-L1 | Cancer types PD-L1 | Males and females with tumors expressing PD-L1 |
| PD-L1 | Cancer types PD1 | Males and females with tumors expressing PD1 |
| CTLA-4 | Cancer types CTLA-4 | Males and females with tumors expressing CTLA-4 |
| hCG | Cancer cell types expressing hCG | Males and Females with tumors expressing hCG |
| Fel d1 | Cat allergy | Males and females allergic to cats |
| (IHNV) G-protein | Infectious haematopoietic necrosis (IHN) | Salmon and trout infected with IHNV |

The disclosed antigens may as well be relevant for the use in other patient groups and/or against other specific or related diseases. In an embodiment at least two such as three, four, and/or five antigens may be combined In one embodiment, the AP205 capsid protein is fused at its N-terminus and/or at its C-terminus to a SpyCatcher and the antigen is fused to a SpyTag and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein.

In one embodiment, the AP205 capsid protein is fused to a SpyCatcher at its N-terminus and the antigen is fused to a SpyTag and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein. In another embodiment, the AP205 capsid protein is fused to a SpyCatcher at its C-terminus and the antigen is fused to a SpyTag and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein. In another embodiment, the AP205 capsid protein is fused to a SpyCatcher at its N-terminus and at its C-terminus and the antigen is fused to a SpyTag and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein.

In other embodiments, the AP205 capsid protein is fused at its N-terminus and/or at its C-terminus to a SpyTag and the antigen is fused to a SpyCatcher and is selected from the group consisting of interleukin-17, hemagglutinin, GD2, EGF-R, CEA, CD52, CD21, human melanoma protein gp100, human melanoma protein melan-A/MART1, tyrosinase. NA17-A nt, MAGE-3, HPV 16 E7, HPV L2, PD1, PD-L1, CTLA-4, p53, hCG, Fel d1 and (IHNV) G-protein.

In one embodiment, the AP205 capsid protein is fused to a SpyTag at its N-terminus and the antigen is fused to a SpyCatcher and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein. In another embodiment, the AP205 capsid protein is fused to a SpyTag at its C-terminus and the antigen is fused to a Spy SpyCatcher Tag and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD L1, CTLA-4, p53, hCG, Fel d1 and (IHNV) G-protein. AP205 capsid protein is fused to a SpyTag at its N-terminus and at its C-terminus and the antigen is fused to a SpyCatcher and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein.

TABLE 2

Non-exhaustive list of diseases/medical indications and target antigen/organisms of the present VLP vaccine.

| Disease: | Target antigen/Organism: |
|---|---|
| Cancer: | Her2/Neu (ERBB2)/*Homo Sapiens* |
| | Survivin (Baculoviral IAP repeat-containing protein 5)/*Homo Sapiens* |
| | GD2/*Homo Sapiens*. |
| | EGF-R/*Homo Sapiens*. |
| | CEA/*Homo Sapiens*. |
| | CD52/*Homo Sapiens*. |
| | human melanoma protein gp100/*Homo Sapiens*. |
| | human melanoma protein melan-A/MART-1/*Homo Sapiens*. |
| | tyrosinase/*Homo Sapiens*. |
| | NA17-A nt protein/*Homo Sapiens*. |
| | MAGE-3 protein/*Homo Sapiens*. |
| | p53 protein/*Homo Sapiens*. |
| | HPV 16 E7 protein/Human papillomavirus |
| | HPV L2 protein/Human papillomavirus |
| | PD1/*Homo Sapiens* |
| | PD-L1/*Homo Sapiens* |
| | CTLA-4/*Homo Sapiens* |
| | hCG/*Homo Sapiens*. |
| | (IHNV) G-protein/Infectious haematopoietic necrosis virus |
| Cardiovascular disease: | PCSK9 (Proprotein convertase subtilisin/kexin type 9)/*Homo Sapiens* |
| Asthma/Allergies: | IL-5 (Interleukin-5)/*Homo Sapiens* |
| | Fel d1 |
| Tuberculosis: | Ag85A (Diacylglycerol cyltransferase/mycolyltransferase)/*Mycobacterium tuberculosis* |
| Malaria: | Reticulocyte-binding protein homologue 5 (PfRH5)/*Plasmodium falciparum* |
| | VAR2CSA (domain, ID1-ID2a)/*Plasmodium falciparum* |
| | CIDR1a domain of PfEMP1, *Plasmodium falciparum* |
| | Glutamate rich protein (GLURP)/*Plasmodium falciparum* |
| | Merozoite surface protein 3 (MSP3)/*Plasmodium falciparum* |
| | 25 kDa ookinete surface antigen (Pfs25)/*Plasmodium falciparum* |
| | Circumsporozoite protein (CSP)/*Plasmodium falciparum* |
| | Schizont egress antigen-1 (PfSEA-1)/*Plasmodium falciparum* |
| Multiple sclerosis | CD52/*Homo sapiens* |
| Contraception | hCG |
| Influenza | HA |

The vaccine of the present invention may as well be used against other diseases and/or use other antigens.

In an embodiment of the present invention the medical indication is selected from the group consisting of a cardiovascular disease, an immune-inflammatory disease, a chronic disease, a neurologic disease and an infectious disease and cancer. In a particular embodiment the medical indication is an immune-inflammatory disease. In another particular embodiment the medical indication is a cardiovascular disease. In another embodiment the medical indication is a chronic disease. In another embodiment the medical indication is a neurologic disease. In another embodiment the medical indication is a cardiovascular disease or an immune-inflammatory disease.

In another embodiment the antigen is a polypeptide, peptide and/or an antigenic fragment of a polypeptide associated with an abnormal physiological response such as a cardiovascular disease and/or an allergic reaction/disease. In a particular embodiment the abnormal physiological response is a cancer.

In a further embodiment the antigen is a protein, peptide and/or an antigenic fragment associated with a medical indication disclosed in the present invention.

Cancer and Associated Antigens

In 2012 more than 14 million adults were diagnosed with cancer and there were more than 8 million deaths from cancer, globally. Consequently, there is a need for efficient cancer therapeutics.

One characteristic of cancer cells is abnormal expression levels of genes and proteins. One example of a cancer associated gene is HER2, which is overexpressed in 20% of all breast cancers and is associated with increased metastatic potential and poor patient survival. Although cancer cells express cancer associated antigens in a way that immunologically distinguishes them from normal cells, most cancer associated antigens are only weakly immunogenic because most cancer associated antigens are "self" proteins which are generally tolerated by the host. The present invention has solved this problem by an effective antigen-VLP based vaccine which is capable of activating the immune system to react against for example cancer associated antigens and overcome the immunological tolerance to such antigens. Different cancers are characterized by having different cancer associated antigens. Survivin is regarded to be overexpressed in most cancer cells and could also be used in the present invention. Therefore the present invention may be used in treatment/prophylaxis of most types of cancers that overexpress a tumor associated antigen.

The antigen is linked to the virus capsid protein of the present invention. By way of example the antigen is linked to the AP205 capsid protein and/or a phage fr capsid protein of the present invention via the interaction between SpyCatcher and SpyTag (see FIG. 1 for a general concept of the present invention). In one embodiment, the antigen is linked to AP205 capsid protein fused to one or more SpyTag via the interaction between SpyTag and SpyCatcher. In one embodiment, the antigen is linked to AP205 capsid protein fused to two SpyTags, one at each terminus.

In one embodiment the antigen is linked to AP205 capsid protein fused to one or more SpyCatcher via the interaction between SpyTag and SpyCatcher. In one embodiment, the antigen is linked to AP205 capsid protein fused to two SpyCatchers, one at each terminus.

Thereby the present invention provides effective antigen-VLP based vaccine which is capable of activating the immune system to react against for example cancer associated antigens and overcome immunological tolerance to such antigens. In an embodiment the VLP vaccine of the present invention can be used for prophylaxis and/or treatment of the cancer which the antigen is associated with.

An embodiment of the present invention comprises a cancer associated antigen linked to the AP205 capsid protein and/or a phage fr capsid protein via the interaction between SpyCatcher and SpyTag. In a further embodiment the present VLP vaccine can be used for prophylaxis and/or treatment of the cancer which the antigen is associated with.

In another embodiment the present invention is used in treatment/prophylaxis of any type of cancer which overexpresses an antigen. The type of cancer which the invention may be used against is determined by the choice of antigen.

It is known that oncoviruses can cause cancer. Therefore in an embodiment the vaccine of the present invention comprises an oncovirus associated antigen linked to the AP205 capsid protein and/or phage fr capsid protein via the interaction between the SpyCatcher, KTag and/or SpyTag.

In a further embodiment the present vaccine can be used for prophylaxis and/or treatment of the cancer which the antigen is associated with.

In an embodiment the antigen is a protein or peptide or an antigenic fragment of a polypeptide associated with a cancer selected from the group comprising of Adrenal Cancer, Anal Cancer, Bile Duct Cancer, Bladder Cancer, Bone Cancer, Brain/CNS Tumors in adults, Brain/CNS Tumors In Children, Breast. Cancer, Breast Cancer In Men, Cancer in Adolescents, Cancer in Children, Cancer in Young Adults, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor, Gestational Trophoblastic Disease, Hodgkin Disease, Kaposi Sarcoma, Kidney Cancer, Laryngeal and Hypopharyngeal Cancer, Leukemia, Acute Lymphocytic in Adults, Leukemia, Acute Myeloid Leukemia, Chronic Lymphocytic Leukemia, Chronic Myeloid Leukemia, Chronic Myelomonocytic Leukemia, Leukemia in Children, Liver Cancer, Lung Cancer, Non-Small Cell Lung Cancer, Small Cell Lung Cancer, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Adult Soft Tissue Cancer Sarcoma, Skin Cancer. Basal and Squamous Cell Skin Cancer, Melanoma Skin Cancer, Merkel Cell Skin cancer, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

In a preferred embodiment the cancer is selected from the group consisting of breast cancer, gastric cancer, ovarian cancer, and uterine serous carcinoma.

Linking the Her2/Neu (ERBB2) and/or Survivin or an antigenic fragment hereof to the VLP forms a VLP based vaccine which is capable of activating the immune system to react against for example cells with high Her2/Neu (ERBB2) and/or Survivin expression and overcome immunological tolerance. In an embodiment the Her2/Neu (ERBB2) and/or Survivin VLP vaccine of the present invention can be used for prophylaxis and/or treatment of the herein disclosed cancer disease and/or other cancer diseases.

Using a similar reasoning other cancer disease associated antigen-VLP based vaccines may be used against any cancer disease. Such antigens may be chosen from the group consisting of interleukin-17, hemagglutinin, GD2, EGF-R, CEA, C052, CD21, human melanoma protein gp100, human melanoma protein melan-A/MART1 tyrosinase, NA17-A nt, MAGE-3, HPV 16 E7, HPV L2, PD1, PD-L1, CTLA-4, p53, hCG, Fel d1 and (IHNV) G-protein.

In an embodiment the antigen of the present invention is Her2/Neu (ERBB2) and/or Survivin or an antigenic fragment hereof, wherein the antigen is associated with and directed against at least one of the herein disclosed types of cancers. In an embodiment the antigen of the present disclosure is interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, HPV L2, PD1, PD-L1, CTLA-4, p53, hCG, Fel d1 and (IHNV) G-protein or an antigenic fragment thereof, wherein the antigen is associated with and directed against at least one of the herein disclosed types of cancers.

In an embodiment the present invention concerns a vaccine for use in the prophylaxis and/or treatment of one of the herein disclosed cancers wherein the vaccine comprises:
  i. virus capsid protein, such as AP205 capsid protein and/or phage fr capsid protein comprising SpyCatcher, and
  ii. a cancer associated antigen such as Her2/Neu (ERBB2) and/or Survivin or an antigenic fragment of Her2/Neu (ERBB2) and/or Survivin fused to SpyTag,
wherein the antigen and the virus capsid protein, such as AP205 capsid protein and/or phage fr capsid protein are linked via the interaction between the Spytag and the SpyCatcher insert of the AP205 capsid protein and/or phage fr capsid protein, and wherein i-ii form a virus-like particle displaying said antigen.

In an embodiment the present invention concerns a vaccine for use in the prophylaxis and/or treatment of one of the herein disclosed cancers wherein the vaccine comprises:
  i. virus capsid protein, such as AP205 capsid protein and/or phage fr capsid protein comprising SpyTag and/or KTag, and
  ii. a cancer associated antigen such as Her2/Neu (ERBB2) and/or Survivin or an antigenic fragment of Her2/Neu (ERBB32) and/or Survivin fused to SpyCatcher,
wherein the antigen and the virus capsid protein, such as AP205 capsid protein and/or phage fr capsid protein are linked via the interaction between the SpyCatcher and the Spytag and/or KTag insert of the AP205 capsid protein and/or phage fr capsid protein, and wherein i-ii form a virus-like particle displaying said antigen.

In another embodiment the present invention concerns a vaccine for use in the prophylaxis and/or treatment of one of the herein disclosed cancers wherein the vaccine comprises:
  i. virus capsid protein, such as AP205 capsid protein and/or phage fr capsid protein comprising SpyTag and/or KTag, and
  ii. a cancer associated antigen consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein or an antigenic fragment hereof fused to SpyCatcher,
wherein the antigen and the virus capsid protein, such as AP205 capsid protein and/or phage fr capsid protein are linked via the interaction between the SpyCatcher and the Spytag and/or KTag insert of the AP205 capsid protein and/or phage fr capsid protein and wherein i-ii form a virus-like particle displaying said antigen.

In an embodiment the antigen fused to SpyCatcher at its N or C-termini and is selected from the group consisting of interleukin-17, hemagglutinin, GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53, hCG, Fel d1 and (IHNV) G-protein or an antigenic fragment hereof.

In an embodiment the present invention concerns a vaccine for use in the prophylaxis and/or treatment of one of the herein disclosed cancers wherein the vaccine comprises:
  i. virus capsid protein, such as AP205 capsid protein and/or phage fr capsid protein comprising a SpyCatcher, and
  ii. a cancer associated antigen such as GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53 and hCG or an antigenic fragment thereof fused to a SpyTag,
wherein the antigen and the virus capsid protein are linked via the interaction between the SpyCatcher and the Spytag, and wherein i-ii form a virus-like particle displaying said antigen. In a further embodiment SpyCatcher is fused to the N-terminus of the AP205 capsid protein. In a further embodiment, SpyCatcher is fused to the N-terminus of the AP205 capsid protein via a spacer. In a further embodiment SpyCatcher is fused to the C-terminus of the AP205 capsid protein. In a further embodiment, SpyCatcher is fused to the C-terminus of the AP205 capsid protein via a spacer. In a further embodiment SpyCatcher is fused to the C-terminus and to the N-terminus of the AP205 capsid protein. In a further embodiment, SpyCatcher is fused to the C-terminus and to the N-terminus of the AP205 capsid protein via a spacer.

In another embodiment the present invention concerns a vaccine for use in the prophylaxis and/or treatment of one of the herein disclosed cancers wherein the vaccine comprises:
  i. virus capsid protein, such as AP205 capsid protein and/or phage fr capsid protein comprising one or more SpyTags, and
  ii. a cancer associated antigen such as GD2, EGF-R, CEA, CD52, CD21, human melanoma protein gp100, human melanoma protein melan-A/MART1, tyrosinase, NA17-A nt, MAGE-3, HPV 16 E7, HPV L2, PD1, PD-L1, CTLA-4, p53 and hCG or an antigenic fragment thereof fused to a SpyCatcher,
wherein the antigen and the virus capsid protein are linked via the interaction between the SpyCatcher and the Spytag, and wherein i-ii form a virus-like particle displaying said antigen. In a further embodiment SpyTag is fused to the N-terminus of the AP205 capsid protein. In a further embodiment SpyTag is fused to the C-terminus of the AP205 protein. In another embodiment two SpyTags are fused to the AP205 capsid protein, one in each terminus, In an embodiment the antigen fused to SpyTag comprises a polypeptide sequence of SEQ ID NO: 79 and/or a sequence variant hereof.

Cardiovascular Diseases and Associated Antigens

An estimated 17.3 million people died from cardiovascular diseases in 2008, representing 30% of all global deaths. Addressing risk factors such as tobacco use, unhealthy diet and obesity, physical inactivity, high blood pressure, diabetes and raised lipids are important for prevention of cardiovascular diseases. However, the need for preventive pharmaceutical measures is increasingly important. The present invention may be used in treatment/prophylaxis of most types of cardiovascular diseases. The type of cardiovascular disease which the invention may be used against is decided by the choice of antigen.

In an embodiment of the invention the antigen is a protein or peptide or an antigenic fragment of a polypeptide associated with a disease selected from the group comprising a lipid disorder such as hyperlipidemia, type I, type II, type III, type IV, or type V hyperlipidemia, secondary hypertriglyceridemia, hypercholesterolemia, familial hypercholesterolemia, xanthomatosis, cholesterol acetyltransferase deficiency, an ateriosclerotic condition (e.g., atherosclerosis), a coronary artery disease, a cardiovascular disease, In an embodiment of the invention the antigen is a protein or peptide or an antigenic fragment of a polypeptide associated with a cardiovascular disease. In a further embodiment the cardiovascular disease is selected from the group consisting of dyslipidemia, atherosclerosis, and hypercholesterolemia.

One example of a polypeptide associated with a cardiovascular disease is PCSK9 which acts in cholesterol homeostasis. Blockage of PCSK9 has medical significance and can lower the plasma and/or serum low-density lipoprotein cholesterol (LDL-C) levels. Reducing LDL-C reduces the risk of for example heart attacks.

Linking the PCSK9 antigen to the VLP forms a PCSK9-VLP based vaccine which is capable of activating the immune system to produce antibodies that bind PCSK9 and either clear PCSK9 from the bloodstream or hinders binding of PCSK9 to the LDL receptor, thereby lowering the LDL-C levels and the risk of heart attacks. In an embodiment, the PCSK9-VLP vaccine of the present invention can be used for prophylaxis and/or treatment of the herein disclosed cardiovascular disease and/or other cardiovascular diseases. Using a similar reasoning other cardiovascular disease associated antigen-VLP based vaccines may be used against any cardiovascular disease.

In a preferred embodiment the antigen comprises PCSK9 or an antigenic fragment hereof, wherein the antigen is associated with and directed against at least one of the herein disclosed cardiovascular disease and/or other cardiovascular diseases.

In an embodiment the present invention concerns a vaccine for use in the prophylaxis and/or treatment of at least one of the herein disclosed cardiovascular diseases wherein the vaccine comprises:
  i. a virus capsid protein, such as AP205 capsid protein and/or phage fr capsid protein comprising a SpyTag and/or KTag, and
  ii a cardiovascular disease associated antigen such as PCSK9 or an antigenic fragment hereof fused to a SpyCatcher,
wherein the antigen and the virus capsid protein, such as the AP205 capsid protein and/or a phage fr capsid protein are linked via the interaction between the SpyCatcher and the Spytag and/or KTag of the virus capsid protein, such as the AP205 capsid protein and/or a phage fr capsid protein, and wherein i-ii form a virus-like particle displaying said antigen.

In an embodiment the antigen fused to SpyCatcher comprises SEQ ID NO: 20 and/or a sequence variant hereof. In an embodiment, the SpyTag is fused to the N-terminus of the AP205 capsid protein, optionally via a spacer.

In a most preferred embodiment the present invention concerns a vaccine for use in the prophylaxis and/or treatment of at least one of the herein disclosed cardiovascular diseases wherein the vaccine comprises:
  i. a virus capsid protein, such as AP205 capsid protein and/or phage fr capsid protein comprising a SpyCatcher, and
  ii. a cardiovascular disease associated antigen such as PCSK9 or an antigenic fragment hereof fused to a SpyTag,
wherein the antigen and the virus capsid protein, such as AP205 capsid protein and/or phage fr capsid protein are linked via the interaction between the SpyCatcher and the Spytag, and wherein ii form a virus-like particle displaying said antigen. In a further embodiment SpyCatcher is fused to the N-terminus of the AP205 capsid protein.

In an embodiment the antigen fused to SpyTag comprises SEQ ID NO: 81 and/or a sequence variant hereof. In an embodiment, the SpyCatcher is fused to the N-terminus of the AP205 capsid protein, optionally via a spacer. In another embodiment two SpyCatchers are fused to the AP205 capsid protein, one at each terminus.

In one embodiment the vaccine for use in the prophylaxis and/or treatment of at least one of the herein disclosed cardiovascular diseases comprises:
  i. a virus capsid protein, such as AP205 capsid protein and/or phage fr capsid protein comprising one or more SpyTag, and
  ii. a cardiovascular disease associated antigen such as PCSK9 or an antigenic fragment hereof fused to a SpyCatcher,
wherein the antigen and the virus capsid protein, such as AP205 capsid protein and/or phage fr capsid protein are linked via the interaction between the SpyCatcher and the Spytag, and wherein i-ii form a virus-like particle displaying said antigen. In a further embodiment SpyTag is fused to the N-terminus of the AP205 capsid protein, optionally via a spacer. In another embodiment two SpyTags are fused to the AP205 capsid protein, one at each terminus.

Immune-Inflammatory Diseases and Associated Antigens

The prevalence of immune-inflammatory diseases worldwide is rising dramatically in both developed and developing countries. According to World Health Organization statistics, hundreds of millions of subjects in the world suffer from allergic rhinitis and it is estimated that 300 million have asthma markedly affecting the quality of life of these individuals and negatively impacting the socio-economic welfare of society. Interleukin 5 (IL-5) has been shown to play an instrumental role in eosinophilic inflammation in various types of allergies, including severe eosinophilic asthma. Eosinophils are regulated in terms of their recruitment, activation, growth, differentiation and survival by IL-5 which, consequently, has identified this cytokine as a primary target for therapeutic interventions.

Linking an IL-5 antigen or a fragment hereof to the VLP of the present invention forms an IL-5-VLP based vaccine which is capable of activating the immune system to react against IL-5. Consequently an IL-5-VLP based vaccine described in the present invention may be used in the treatment/prophylaxis of eosinophilic asthma or other immune-inflammatory diseases. Other immune-inflammatory disease associated antigens (e.g. IgE or interleukin 17 or IL-17) may be used by the present invention using a similar reasoning. Consequently an IL-17-VLP based vaccine described in the present invention may be used in the treatment/prophylaxis of eosinophilic asthma or other immune-inflammatory diseases. The type of asthma or allergy or other immune-inflammatory disease which the invention may be used against is decided by the choice of antigen. In an embodiment the antigen is a protein or peptide or an antigenic fragment of a polypeptide associated with one or more asthma or immune-inflammatory diseases disclosed herein. In a preferred embodiment the asthma or immune-inflammatory disease is selected from the group consisting of eosinophilic asthma, allergy, nasal polyposis, atopic dermatitis, eosinophilic esophagitis, hypereosinophilic syndrome, and Churg-Strauss syndrome.

In a preferred embodiment the antigen comprises IL-5, IL-17 or an antigenic fragment hereof, wherein the antigen is associated with and directed against at least one of the herein disclosed asthma or allergy diseases and/or other immune-inflammatory diseases.

In an embodiment the present invention concerns a vaccine for use in the prophylaxis and/or treatment of one of the herein disclosed immune-inflammatory diseases wherein the vaccine comprises:
  i. a virus capsid protein, such as AP205 capsid protein and/or a phage fr capsid protein comprising a SpyTag and/or KTag, and
  ii. an antigen such as IL-5 or IL-17 or an antigenic fragment hereof fused to SpyCatcher,
wherein the antigen and the virus capsid protein, such as AP205 capsid protein and/or phage fr capsid protein are linked via the interaction between the SpyCatcher and the Spytag and/or KTag site of the virus capsid protein, and wherein i-ii form a virus-like particle displaying said antigen.

In an embodiment the antigen is IL-17.

In an embodiment the antigen fused to SpyCatcher is IL-5. In one embodiment the antigen comprises SEQ ID NO: 19 and/or a sequence variant hereof.

In one embodiment the AP205 capsid protein is fused to one or more SpyTags. In one embodiment, the AP205 capsid protein is fused to two SpyTags, one at each terminus of the capsid protein.

In a preferred embodiment the present invention concerns a vaccine for use in the prophylaxis and/or treatment of one of the herein disclosed immune-inflammatory diseases wherein the vaccine comprises:
  i. virus capsid protein, such as AP205 capsid protein and/or phage fr capsid protein comprising a SpyCatcher, and
  ii. an antigen such as IL-5 or IL-17 or an antigenic fragment hereof fused to SpyTag,
wherein the antigen and the virus capsid protein such as AP205 capsid protein and/or phage fr capsid protein are linked via the interaction between the SpyCatcher and the Spytag, and wherein i-ii form a virus-like particle displaying said antigen. In a further embodiment SpyCatcher is fused to the N-terminus of the AP205 capsid protein. In one embodiment SpyCatcher is fused to the AP205 capsid protein via a spacer.

In an embodiment the antigen is IL-17.

In an embodiment the antigen fused to SpyTag comprises SEQ ID NO. 80 and/or a sequence variant hereof.

Infectious Diseases and Associated Antigens

Tuberculosis and malaria are two major infectious diseases. In 2012, an estimated 207 million cases of malaria occurred which resulted in more than 500.000 deaths. Also in 2012, an estimated 8.6 million people developed tuberculosis and 1.3 million died from the disease. The current methods of treatment are insufficient and some have resulted in drug resistance. Consequently there is a need for new and efficient drugs for treatment/prophylaxis of tuberculosis and malaria. Linking a malaria or tuberculosis associated-antigen or a fragment hereof to the VLP of the present invention forms a VLP based vaccine which is capable of activating the immune system to react against for example malaria or tuberculosis. Using a similar line of reasoning the present invention may be used in treatment/prophylaxis of most infectious disease. The type of infectious disease which the invention may be used against is decided by the choice of antigen.

In an embodiment the antigen fused to the SpyTag or SpyCatcher of the present invention is a protein or peptide or an antigenic fragment of a polypeptide associated with an infectious disease such as tuberculosis and/or malaria.

In a further embodiment an antigen from *Plasmodium falciparum* is fused to the SpyCatcher of the present invention for use in treatment/prophylaxis of malaria, In a further embodiment an antigen from *Mycobacterium tuberculosis* is fused to the SpyCatcher of the present invention for use in treatment/prophylaxis of tuberculosis.

In a further embodiment the antigen is selected from the group consisting of Ag85A from *Mycobacterium tuberculosis*, PfRH5 from *Plasmodium falciparum*, VAR2CSA (domain, ID1-ID2a) from *Plasmodium falciparum*, CIDR1a domain, of PfEMP1 from *Plasmodium falciparum*, GLURP from *Plasmodium falciparum*, MSP3 from *Plasmodium falciparum*, Pfs25 from *Plasmodium falciparum*, CSP from *Plasmodium falciparum*, and PfSEA-1 from *Plasmodium falciparum* or an antigenic fragment of the disclosed antigens. In another embodiment the antigen comprises a fusion construct between MSP3 and GLURP (GMZ2) from *Plasmodium falciparum*.

In a further embodiment the antigen is a hemagglutinin (HA) antigen from the influenza virus or an antigenic fragment thereof.

In another embodiment the antigen of the present invention comprises a protein, or an antigenic fragment hereof, from the pathogenic organism which causes the infectious disease.

In one embodiment the present invention concerns a vaccine for use in the prophylaxis and/or treatment of one of the herein disclosed infectious diseases wherein the vaccine comprises:
  i. virus capsid protein, such as AP205 capsid protein and/or phage fr capsid protein comprising a SpyTag insert, and
  ii. an antigen associated with an infectious disease such as Ag85A from *Mycobacterium tuberculosis*, PfRH5 from *Plasmodium falciparum*, VAR2CSA (domain, ID1-ID2a) from *Plasmodium falciparum*, CIDR1a domain, of PfEMP1 from *Plasmodium falciparum*, GLURP from *Plasmodium falciparum*, MSP3 from *Plasmodium falciparum*, Pfs25 from *Plasmodium falciparum*, CSP from *Plasmodium falciparum*, PfSEA-1 from *Plasmodium falciparum* and/or HA from influenza virus or an antigenic fragment hereof fused to SpyCatcher,
wherein the antigen and the virus capsid protein, such as AP205 capsid protein and/or phage fr capsid protein are linked via the interaction between the SpyCatcher and the Spytag, and wherein i-ii form a virus-like particle displaying said antigen.

In an embodiment the antigen fused to SpyCatcher comprises SEQ ID NO: 21, SEQ ID NO: 22, SEQ. ID NO: 23, SEQ ID NO: 24, SEQ ID NO: 25, SEQ ID NO: 26, SEQ ID NO: 27, SEQ ID NO: 28 and/or SEQ ID NO: 82 and/or a sequence variant hereof. In one embodiment the antigen fused to SpyCatcher comprises SEQ ID NO: 21. In one embodiment the antigen fused to SpyCatcher comprises SEQ ID NO: 24. In one embodiment the antigen fused to SpyCatcher comprises SEQ ID NO: 28. In one embodiment, the antigen fused to SpyCatcher comprises SEQ ID NO: 82.

In one embodiment the present invention concerns a vaccine for use in the prophylaxis and/or treatment of one of the herein disclosed infectious diseases wherein the vaccine comprises:
  i. virus capsid protein, such as AP205 capsid protein and/or phage fr capsid protein comprising a SpyCatcher insert, and
  ii. an antigen associated with an infectious disease such as Ag85A from *Mycobacterium tuberculosis*, PfRH5 from *Plasmodium falciparum*, VAR2CSA (domain, ID1-ID2a) from *Plasmodium falciparum*, CIDR1a domain, of PfEMP1 from *Plasmodium falciparum*, GLURP from *Plasmodium falciparum*, MSP3 from *Plasmodium falciparum*, Pfs25 from *Plasmodium falciparum*, CSP from *Plasmodium falciparum*, PfSEA-1 from *Plasmodium falciparum* and/or HA from influenza virus or an antigenic fragment hereof fused to SpyTag, wherein the antigen and the virus capsid protein, such as AP205 capsid protein and/or phage fr capsid protein are linked via the interaction between the SpyCatcher and the Spytag, and wherein i-ii form a virus-like particle displaying said antigen. In a further embodiment SpyCatcher is fused to the N-terminus of the AP205 capsid protein.

In an embodiment the antigen fused to Spytag comprises SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28 and/or SEQ ID NO: 82 and/or a sequence variant hereof. In one embodiment the antigen fused to Spytag comprises SEQ ID NO: 21. In one embodiment the antigen fused to Spytag comprises SEQ ID NO: 24. In one embodiment the antigen fused to Spytag comprises SEQ ID NO: 28. In one embodiment, the antigen fused to Spytag comprises SEQ ID NO: 82.

Induction of an Immune Response in a Subject

Active vaccination (immunization), by delivering small doses of an antigen into a subject, is a way to activate a subject's immune system to develop adaptive immunity to the antigen. This allows a subjects body to react quickly and efficiently to future exposures.

An aspect of the invention relates to a method for inducing an immune response in a subject, the method comprising the steps of
  i. obtaining a composition comprising at least one vaccine of the present invention and/or
  ii. administering said composition to a subject at least once for prophylaxis and/or treatment of a disease, thereby inducing an immune response in the subject.

Another aspect of the present invention relates to a method of immunizing a subject in need thereof, said method comprises the steps of:
  i. obtaining a composition comprising at least one vaccine of the present invention, and/or
  ii. administering said composition to a subject at least once for prophylaxis and/or treatment of a disease. thereby immunizing the subject in need thereof.

Another aspect of the present invention relates to a method for obtaining a strong and long-lasting immune response in a subject in need thereof, said method comprising the steps of:
  i. obtaining composition comprising a vaccine of the present invention, and/or
  ii. administering the vaccine to treat and/or prevent a clinical condition in an subject in need thereof, wherein the vaccine obtain a strong and long-lasting immune response in the subject.

In an embodiment the method of inducing an immune response in a subject, immunizing a subject in need thereof, and/or obtaining a strong and long-lasting immune response further comprising at least one booster vaccine and/or a second active ingredient.

The AP205 VLP

An important element of the present VLP based vaccine is the AP205 capsid protein, which has the ability to spontaneously self-assemble into virus-like particles (VLPs). The use of AP205 VLP in the present invention is illustrated in FIG. 1. Surprisingly the present inventors have found that amino acid residues may be fused to the AP205 capsid protein at the AP205 capsid proteins N or C terminus without preventing VLP assembly while at the same time presenting the added amino acids on the outside of the assembled VLP where they are accessible for interactions. Specifically, SpyTag, SpyCatcher, and Ktag encoding residues may be fused to the N and/or C terminus of AP205. Thus it is an object of the present invention to fuse a protein tag to the N and/or C-terminus of the AP205 capsid protein. The AP205 capsid protein sequence is disclosed in SEQ ID NO. 58. Any variant of the AP205 protein that is capable of being expressed with a protein tag and that is still able to self-assemble into a VLP while presenting the protein tag on the outer surface of the VLP is an object of the present invention.

In an embodiment the AP205 capsid protein of the present invention comprises the amino acid sequence SEQ ID NO: 58, or a biologically active sequence variant that has at least 85%, or 90% or 95%, such as 96%, such as, 97%, such as 98%, such as 99%, such as 99.5%, such as 100% sequence identity to SEQ ID NO: 58. By "biological active" is meant the ability to form a virus-like particle.

Direct fusion of six different peptide sequences to the N or C-terminus of the AP205 capsid protein was shown in 2010 by Tissot A C. et al (Tissot A C. et al. PLoS ONE. 2010) to result in hybrid proteins capable of self-assembling into virus-like particles. However, the ability of fusing peptides to the N- or C-terminus of the AP205 coat protein without preventing VLP assembly is by no means certain and depends greatly on both the length and the precise amino acid composition of the fused peptide. Recently, Cielens I et al, (Cielens I. et al. Mol. Biotechnol. 2014) tried to fuse a 111 amino acid sequence of the virus-neutralising domain III (DIII) of the West Nile virus glycoprotein E to the C-terminus of the AP205 coat protein. In this study recombinant expression of the AP205-DIII fusion protein failed to assemble into VLPs. Moreover, it has also been investigated if the coat protein of the distantly related bacteriophage fr can tolerate the insertion of peptide sequences at different amino acid positions near the N- and C-terminus. This study show that several N-terminal insertion mutants of the fr coat protein failed to assemble into VLPs but instead formed dimers (P. Pushko. et al. Protein Eng, 1993). Also, in this study the C-terminus of the fr coat protein could only tolerate insertion of three amino acids whereas insertion of a longer peptide prevented VLP assembly. The mentioned peptide insertion was specifically at position 2/3, and 128/129 of the fr coat protein and hence only internal insertions of amino acids into the coat protein fr have been described to date. The present inventors also observed that fusion of a monovalent streptavidin domain (mSA) in the N-terminus of AP205 prevented formation of VLPs; mSA has a size comparable to the size of the SpyCatcher.

In a preferred embodiment the virus capsid protein comprises an AP205 capsid protein fused to a SpyCatcher, wherein the capsid protein—SpyCatcher fusion protein is capable of forming a virus-like particle. In a further embodiment SpyCatcher is fused to the N-terminus of the AP205 capsid protein optionally via a linker or spacer. In another embodiment SpyCatcher is fused to the C-terminus of the AP205 capsid protein optionally via a linker or spacer. In one embodiment, one SpyCatcher is fused to the C-terminus of the Ap205 capsid protein and one SpyCatcher is fused to the N-terminus of the AP205 capsid protein.

The inventors of the present invention have surprisingly shown that a SpyCatcher comprising more than 100 amino acids can be fused to a capsid protein such as an AP205 capsid protein and/or phage fr capsid protein, without disrupting the sensitive self-assembly process. In an embodiment the SpyCatcher is fused to the N-terminal of the AP205 capsid protein using a short flexible Gly-Gly-Ser-Gly-Ser linker (SEQ ID NO 83 or any other appropriate linker sequence). Attempts to fuse SpyCatcher to the C-terminal of AP205 capsid protein resulted in no assembly of VLPs. In another embodiment a SpyCatcher is fused to the N- and/or C-terminal of phage fr capsid protein using a short flexible Gly-Gly-Ser-Gly-Ser linker (SEQ ID NO: 83 or any other appropriate linker sequence).

In a most preferred embodiment the AP205-SpyCatcher fusion protein comprises the amino acid sequence of SEQ ID NO: 76 or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to the amino acid sequence of SEQ ID NO:76 and/or any of the herein disclosed AP205 capsid proteins comprising the SpyCatcher polypeptide in the N terminal. By "biologically active" is meant the ability to form a virus-like particle.

A preferred embodiment of the present invention relates to an AP205 capsid protein comprising an N-terminal SpyCatcher which is capable of forming/self-assembling into a virus-like particle. In an embodiment SpyCatcher is fused to the N-terminus of the AP205 capsid protein optionally via a linker. In an embodiment the SpyCatcher is fused to the first 100 amino acids in the N terminus of the AP205. In an embodiment the SpyCatcher is fused to the AP205 using a peptide linker, such as SEQ ID NO: 83. In an embodiment the AP205 capsid protein comprising a SpyCatcher has a polypeptide sequence at least 70%, such as 75%, such as 80%, such as 85%, such as 90%, such as 95%, such as 96%, such as, 97%, such as 98%, such as 99%, such as 99.5%, such as 100% identical to the polypeptide sequence of SEQ ID NO: 76. Another aspect of the present invention relates to an AP205 capsid protein comprising a N-terminal SpyCatcher which spontaneously can for a virus-like particle. In an embodiment SpyCatcher is fused to the N-terminus of the AP205 capsid protein optionally via a linker. In an embodiment the SpyCatcher is fused to the first 100 amino acids in the N terminal of the AP205. In an embodiment the SpyCatcher is fused to the AP205 N terminal using a peptide linker, such as SEQ ID NO: 83. In an embodiment the AP205 capsid protein comprising a SpyCatcher is having a polypeptide sequence at least 70%, such as 75%, such as 80%, such as 85%, such as 90%, such as 95%, such as 96%, such as, 97%, such as 98%, such as 99%, such as 99.5%, such as 100% identical to the polypeptide sequence of SEQ ID NO: 76.

In another embodiment the AP205 capsid protein is fused to SpyTag.

The Phage fr VLP

Phage fr, or more precisely the phage fr capsid protein, is also an important element of the present invention. The phage fr capsid protein has the ability to spontaneously self-assemble into virus-like particles. Furthermore the phage fr capsid protein is capable of self-assembly even when amino acid residues are be fused to the phage fr capsid protein at the fr capsid proteins N terminus. Importantly, the fused amino acids are presented on the outer surface of the assembled fr VLP. Specifically, SpyTag, SpyCatcher, and/or Ktag encoding residues may be fused to the N terminus and/or the C-terminus of phage fr capsid protein. Thus it is an object of the present invention to fuse a protein tag to the N-terminus of the phage fr capsid protein. The phage fr capsid protein sequence is disclosed in SEQ ID NO: 59 and/or 78. Any variant of the phage fr capsid protein that is still capable of being expressed with a protein tag and still self-assemble is an object of the present invention.

In an embodiment the Phage fr capsid protein of the present invention comprises the amino acid sequence SEQ ID NO: 59 and/or 78, or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to SEQ ID NO: 59 and/or 78. By "biological active" is meant the ability to form a virus-like particle.

A further aspect of the present invention relates to a phage fr capsid protein comprising a SpyCatcher which is capable of forming/self-assembling into a virus-like particle. In an embodiment the SpyCatcher is fused to any one of the first 50 amino acids in the N terminal end and/or any one of the last 50 in the C terminal end of the phage fr capsid protein. In an embodiment the SpyCatcher is fused to the phage fr capsid protein using a peptide linker, such as SEQ ID NO: 83. In an embodiment the phage fr capsid protein comprising a SpyCatcher is having a polypeptide sequence at least 70%, such as 75%, such as 80%, such as 85%, such as 90%, such as 95%, such as 96%, such as, 97%, such as 98%, such as 99%, such as 99.5%, such as 100% identical to the polypeptide sequence of SEQ ID NO: 78.

Another aspect of the present invention relates to a phage fr capsid protein comprising a SpyCatcher which spontaneously can form a virus-like particle. In an embodiment the SpyCatcher is fused to any one of the first 50 amino acids in the N terminal and/or any one of the last 50 in the C terminal of the phage fr capsid protein. In an embodiment the SpyCatcher is fused to the phage fr capsid protein using a peptide linker, such as SEQ ID NO: 83. In an embodiment the phage fr capsid protein comprising a SpyCatcher is having a polypeptide sequence at least 70%, such as 75%, such as 80%, such as 85%, such as 90%, such as 95%, such as 96%, such as, 97%, such as 98%, such as 99%, such as 99.5%, such as 100% identical to the polypeptide sequence of SEQ ID NO: 78.

SpyTag and/or KTag and its Position in AP205 and/or Phage fr

In an embodiment the present invention concerns a vaccine for use in the prophylaxis and/or treatment of a disease wherein the vaccine comprises:
  i. AP205 capsid protein comprising one or more SpyTag and/or KTag, and
  ii. an antigen fused to SpyCatcher,
  wherein the antigen and the AP205 capsid protein are linked via the interaction between the SpyCatcher and the Spytag and/or KTag, and wherein i-ii form a virus-like particle displaying said antigen.

In an embodiment the SpyTag and/or KTag polypeptide is fused to the N or C terminal of a virus capsid protein, such as an AP205 capsid protein and/or phage fr capsid protein.

In an embodiment, two tags, for example two SpyTags or two SpyCatcher tags, are fused to the capsid protein such as the AP205 capsid protein, one at each terminus. Without being bound by theory, increasing the number of accessible SpyTags or SpyCatchers on the surface of a VLP should maximize the antigen binding capacity and result in a higher density of displayed antigen. This is the case for fusion of two SpyTags to the AP205 capsid protein, as shown in the below examples and FIG. 13. Whether fusion of two tags instead of one improves antigen binding can easily be tested by the skilled person.

In an embodiment the AP205 capsid protein comprising the SpyTag and/or KTag polypeptide comprises the amino acid sequences selected from the group consisting of SEQ ID NO: (62, 64, 68, 69, 71, 74, and 76) or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to any of the herein disclosed AP205 capsid proteins comprising the SpyTag and/or KTag polypeptide. By "biological active" is meant the ability to form a virus-like particle.

In another embodiment the present invention concerns a vaccine for use in the prophylaxis and/or treatment of a disease wherein the vaccine comprises:
  i. a phage fr capsid protein comprising one or more SpyTag and/or KTag, and
  ii. an antigen fused to SpyCatcher,
wherein the antigen and phage fr capsid protein are linked via the interaction between the SpyCatcher and the Spytag insert site of the phage fr capsid protein, and wherein i-ii form a virus-like particle displaying said antigen.

In an embodiment the phage fr capsid protein comprising the SpyTag and/or KTag polypeptide comprises the amino acid sequences selected from the group consisting of SEQ ID NO: 66, SEQ ID NO: 70, and SEQ ID NO: 78 or a biologically active sequence variant that has at least 70%, such as 75%, such as 80%, such as 85%, such as 90%, 95%, such as 96%, such as, 97%, such as 98%, such as 99%, such as 99.5%, such as 100% sequence identity to any of the herein disclosed phage fr capsid proteins comprising the SpyTag and/or KTag polypeptide. By "biological active" is meant the ability to form a virus-like particle.

SpyCatcher and its Position in AP205 and/or Phage

In an embodiment the SpyCatcher polypeptide is fused to the N or C terminal and/or fused to the first 1-15 amino acids (N-terminal) or the last 1-15 amino acids (C-terminal) of a phage fr capsid protein, optionally using a linker as described herein. In an embodiment the SpyCatcher polypeptide is fused to the N terminal and/or fused to the first 1-15 amino acids (N-terminal) of a AP205 capsid protein, optionally using a linker as described herein. In an embodiment the SpyCatcher fused to the virus capsid protein comprises the amino acid sequence selected from the group comprising SEQ ID NO. 76, and SEQ 1D NO. 78, or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to the sequences of the group comprising SEQ ID NO. 76, and SEQ ID NO. 78. By "biologically active" is meant the ability to form a virus-like particle.

In an embodiment the present invention concerns a vaccine for use in the prophylaxis and/or treatment of a disease wherein the vaccine comprises:

i. the AP205 capsid protein and/or phage fr capsid protein comprising SpyCatcher, and
  ii. an antigen fused to SpyTag and/or KTag,
wherein the antigen and AP205 protein are linked via the interaction between the Spytag and/or KTag and the SpyCatcher, and wherein i-ii form a virus-like particle displaying said antigen. In an embodiment SpyCatcher is fused to the N-terminus of the AP205 capsid protein optionally via a linker. In one embodiment SpyCatcher is fused to the N-terminus of the AP205 capsid protein via a GGSGS linker (SEQ ID NO: 83).

In an embodiment the SpyCatcher polypeptide is fused to the N terminal of a virus capsid protein, such as the AP205 capsid protein or phage fr capsid protein. In one embodiment the SpyCatcher is fused to the N-terminal and to the C-terminal ends of a virus capsid protein such as the AP205 capsid protein.

In an embodiment the AP205 capsid protein comprising the SpyCatcher polypeptide comprises the amino acid sequences selected from the group consisting of SEQ ID NO: 76 and/or 78 or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to any of the amino acid sequence of SEQ ID NO:76 and/or any of the herein disclosed AP205 capsid proteins comprising the SpyCatcher polypeptide in the N terminal. By "biologically active" is meant the ability to form a virus-like particle.

In a preferred embodiment the virus capsid protein comprises an AP205 capsid protein fused to a SpyCatcher, wherein the capsid protein—SpyCatcher fusion protein is capable of forming a virus-like particle. In an embodiment SpyCatcher is fused to the N-terminus of the AP205 capsid protein optionally via a linker.

The inventors of the present invention have surprisingly shown that a SpyCatcher comprising more than 100 amino acids can be fused to a capsid protein such as an AP205 capsid protein and/or phage fr capsid protein, without disrupting the sensitive self-assembly process. In an embodiment the SpyCatcher is fused to the N-terminal of the AP205 capsid protein and/or phage fr capsid protein using a short flexible Gly-Gly-Ser-Gly-Ser linker such SEQ ID NO: 83 or a sequence variant that has at least 70%, such as 75%, such as 80%, such as 85%, such as 90%, such as 95%, such as 96%, such as, 97%, such as 98%, such as 99%, such as 99.5%, such as 100% sequence identity to SEQ ID NO: 83. Other peptide linkers may be used by the present invention.

In a most preferred embodiment the AP205-SpyCatcher fusion protein comprises the amino add sequence of SEQ ID NO: 76 or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to amino acid sequence of SEQ ID NO: 76 and/or any of the herein disclosed AP205 capsid proteins comprising the SpyCatcher polypeptide in the N-terminal. By "biologically active" is meant the ability to form a virus-like particle.

In another embodiment the present invention concerns a vaccine for use in the prophylaxis and/or treatment of a disease wherein the vaccine comprises:
  i. a phage fr capsid protein comprising SpyCatcher, and
  ii. an antigen fused to SpyTag and/or KTag,
wherein the antigen and phage fr capsid protein are linked via the interaction between the Spytag and/or KTag and the SpyCatcher insert site of the phage fr capsid protein, and wherein i-ii form a virus-like particle displaying said antigen.

In an embodiment the phage fr capsid protein comprising the SpyCatcher polypeptide comprises the amino acid sequences selected from the group consisting of SEQ ID NO: 78 or a biologically active sequence variant that has at least 70%, such as 75%, such as 80%, such as 85%, such as 90%, 95%, such as 96%, such as, 97%, such as 98%, such as 99%, such as 99.5%, such as 100% sequence identity to any of the herein disclosed phage fr capsid proteins comprising the SpyCatcher polypeptide. By "biological active" is meant the ability to form a virus-like particle.

Antigen Fused to SpyCatcher, SpyTag, and/or KTag.

SpyTag refers to a part of the CnaB2 domain from the FbaB protein from *Streptococcus pyogenes* optimized to bind SpyCatcher consisting of another part of the CnaB2 domain. The interaction occurs when the unprotonated amine of Lys31 nucleophilically attacks the carbonyl carbon of Asp117, catalyzed by the neighboring Glu77. The minimal peptide to mediate this binding is AHIVMVDA whereas a C-terminal extension giving the sequence: AHIVMV-DAYKPTK provides the most optimal region, designated "SpyTag" (Zakeri et al PNAS 2012).

SpyCatcher is a part of the CnaB2 domain from the FbaB protein from *Streptococcus pyogenes* and binds SpyTag consisting of another part of the CnaB2 domain. When these two polypeptides of the CnaB2 domain are mixed, they will spontaneously form an irreversible isopeptide bond thereby completing the formation of the CnaB2 domain.

Thus when fusing an antigen to SpyCatcher and mixing e.g. with a VLP comprising a genetically engineered SpyTag we obtain a uniform presentation of said antigens. The 1:1 interaction between the SpyTag and SpyCatcher enables display of an antigen at high density, while being regularly spaced, and with consistent orientation on the surface of a VLP, thus solving three major critical factors for obtaining prober activation of the immune system.

In an embodiment the antigen as described by the present invention is fused to SpyCatcher or truncated versions hereof, SpyTag, and/or KTag. Examples of antigens fused to Spytag is illustrated, but not limited to SEQ ID NO: 79, 80, 81 and/or 82. The SpyTag may be fused any of the herein disclosed antigens. In addition, KTag and/or SpyCatcher can be used instead of the SpyTag for example in, but not limited to SEQ ID NO: 79, 80, 81 and/or 82.

Surprisingly the inventors have found that the SpyCatcher-antigen fusion proteins of the present invention express very well under expression conditions described herein. Previous attempts of expressing antigen-monovalent streptavidin fusion proteins have almost exclusively resulted in poor expression levels and/or insoluble protein.

In an embodiment the SpyCatcher used by the present invention comprises the amino acid sequence of SEQ ID NO: 37.

Truncated and homologous versions of SpyCatcher are also objects of the present invention and thus the term SpyCatcher herein denotes any variant of SpyCatcher that is still capable of interacting with SpyTag and/or KTag. Variants of SpyCatcher may include, but is not limited to truncated SpyCatcher variants. Truncated SpyCatcher variants may include, but are not limited to SEQ NO 60 and SEQ ID NO: 61. SpyCatcher variants such as truncated SpyCatcher variants may exhibit lower immunogenicity than wildtype SpyCatcher does, without influencing the ability to bind to SpyTag and/or KTag.

In an embodiment the SpyCatcher used by the present invention comprises the amino acid sequence of SEQ ID NO: 60.

In an embodiment the SpyCatcher used by the present invention comprises the amino acid sequence of SEQ ID NO: 61, In another embodiment the ratio of AP205 capsid protein: SpyTag and/or KTag:SpyCatcher/antigen fusion is 1:1:1.

In another embodiment the ratio of Phage fr capsid protein:SpyTag and/or KTag:SpyCatcher/antigen fusion is 1:1:1.

In an embodiment the antigen as described by the present invention is fused to SpyCatcher or truncated versions hereof, SpyTag, and/or KTag.

Changing the position where the SpyCatcher is fused to the antigen (primarily at the N or C-termini) will allow changing the orientation of the antigen. This may be performed to enable the best possible display of the most immunogenic epitopes of the antigen. The best possible orientation may be different from antigen to antigen.

In another embodiment the antigen fused to SpyCatcher further comprises or includes an additional tag such as a purification tag. Such tags may be used for purification techniques known to the skilled person. The tag may be selected from the group comprising polyhistidine tag, Calmodulin-tag, polyglutamate tag, E-tag, FLAG-tag, HA-tag, Myc-tag, S-tag, SBP-tag, Softag 1, Softag 3, Strep-tag, Strep-tag II, TC tag, V5 tag, VSV-tag, and Xpress tag. Other peptide or non-peptide tags may be used instead or in combination with the above mentioned peptide tags. In a particular embodiment the tag is a polyhistidine tag, such as a 4× His, 5× His, 6× His, 7× His, 8× His, 9× His, or 10× His tag, In an embodiment SpyCatcher is fused to the antigen in any position. In another embodiment the SpyCatcher is fused to the antigen in the N-terminal, C-terminal, and/or is fused to the antigen into the coding sequence of the antigen. A person of skill will know how to fuse the antigen and SpyCatcher, without introducing stop-codons or causing frame shift or any other mutations.

In another embodiment SpyCatcher fused to the antigen comprises
  i. a polypeptide sequence selected from the group consisting of SEQ ID NO: 18, SEQ ID NO: 19, SEQ ID NO: 20, SEQ ID NO: 21, SEQ. ID NO: 22, SEQ ID NO: 23, SEQ ID NO: 24, SEQ ID NO: 25, SEQ ID NO: 26, SEQ ID NO: 27, and SEQ ID NO: 28, or
  ii a sequence variant of said polypeptide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to the sequences of the group comprising SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28.

In a preferred embodiment SpyCatcher fused to the antigen comprises
  i. a polypeptide sequence comprising SEQ ID NO: 19, and/or
  ii. a sequence variant of said polypeptide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to SEQ ID NO: 19.

In a most preferred embodiment SpyCatcher fused to the antigen comprises i. a polypeptide sequence comprising SEQ ID NO: 18, and/or
ii. a sequence variant of said polypeptide sequence, wherein the sequence variant has at least 70%, such as 75%, such as 80%, such as 85%, such as 90%, such as 95%, such as 96%, such as, 97%, such as 98%, such as 99% such as 99.5%, such as 100% sequence identity to SEQ ID NO: 18.

Peptide-Peptide Ligation by SpyLigase

Figure 2:
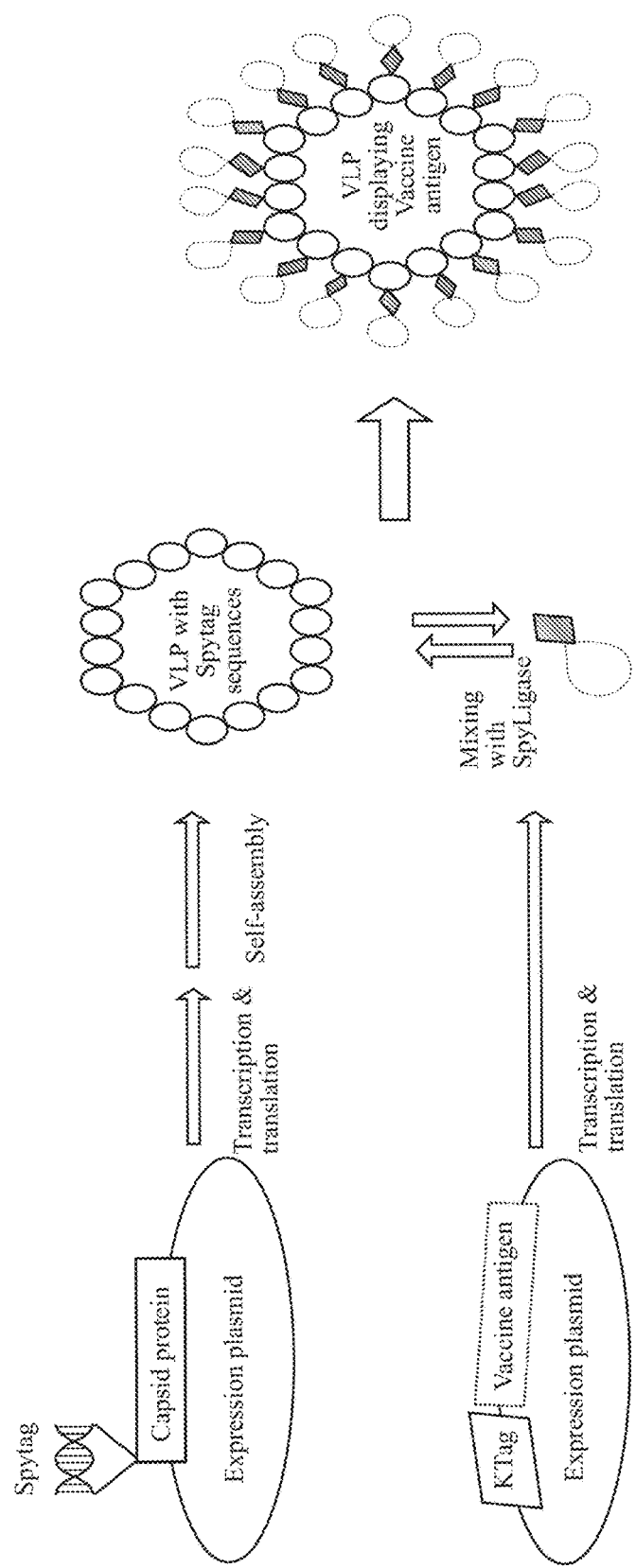
FIG. 2: A general aspect of the present invention. Production steps in making a SpyTag/KTag-capsid protein coupled with a SpyTag/KTag-antigen.

A KTag/SpyTag/SpyLigase system may also be used in the present invention. The CnaB2 domain from *Streptococcus pyogenes* can be used to generate a covalent peptide-peptide ligation system (Fierer J O. et al. 2014). This is done by splitting the CnaB2 into three parts a) the 13 amino acid SpyTag (SEQ ID NO: 36), b) the β-strand of CnaB2 (SEQ ID NO: 38)) named KTag, and c) the SpyLigase (SEQ ID 55) constructed from the remaining SpyCatcher polypeptide. By expressing the vaccine antigen with the small KTag fused at the C- or N-terminus and mixing that fusion protein with SpyTag-displaying VLPs together with the SpyLigase, the KTag-fusion antigen will be attached to the SpyTag-VLPs by covalent ligation of the SpyTag with the KTag facilitated by the SpyLigase. Conversely, the KTag may also be inserted genetically into the AP205 capsid protein and/or a phage fr capsid protein whereby the vaccine antigen should then be fused to the SpyTag at the C- or N-terminus. A general aspect of the KTag/SpyTag/SpyLigase system is illustrated in FIG. 2. The SpyTag may also be fused to the antigen and the KTag may be inserted into to the VLP (Fierer J O. et al. 2014).

Thus, an aspect of the present invention relates to a vaccine for use in the prophylaxis and/or treatment of a disease wherein the vaccine comprises:
i. a virus capsid protein, such as the AP205 capsid protein and/or a phage fr capsid protein comprising a SpyTag described herein, and
ii. an antigen fused to a KTag described herein, and
iii. optionally a SpyLigase
wherein the antigen and virus capsid protein, such as the AP205 capsid protein and/or a phage fr capsid protein are linked via the interaction between the SpyTag and KTag, and wherein i-ii form a virus-like particle displaying said antigen.

In another aspect the present invention relates to a vaccine for use in the prophylaxis and/or treatment of a disease wherein the vaccine comprises:
i. a virus capsid protein, such as the AP205 capsid protein and/or a phage fr capsid protein comprising a KTag described herein, and
ii. an antigen fused to a SpyTag described herein, and
iii. optionally a SpyLigase
wherein the antigen and virus capsid protein, such as the AP205 capsid protein and/or a phage fr capsid protein are linked via the interaction between the KTag and SpyTag, and wherein i-ii form a virus-like particle displaying said antigen.

In an embodiment the SpyTag and KTag described herein are linked by means of a SpyLigase as described herein.

In an aspect of the present invention relates to a vector comprising at least one polynucleotide encoding
i. a virus capsid protein, such as the AP205 capsid protein and/or a phage fr capsid protein comprising a SpyTag as described herein, and/or
ii. an antigen fused to a KTag as described herein, and/or
iii. optionally a SpyLigase.

Another aspect of the present invention relates to a vector comprising at least one polynucleotide encoding
i. a virus capsid protein, such as the AP205 capsid protein and/or a phage fr capsid protein comprising a KTag as described herein, and/or
ii. an antigen fused to a SpyTag as described herein, and
iii. optionally a SpyLigase Another aspect of the present invention relates to a host cell, wherein the host cell expresses:
i. a first polypeptide; a virus capsid protein, such as the AP205 capsid protein and/or phage fr capsid protein comprising a SpyTag as described herein, and
ii. a second polypeptide; an antigen fused to KTag as described herein, and
iii. optionally a SpyLigase
wherein the cell is selected from the group comprising bacteria, yeast, fungi, plant, mammalian and/or insect cells.

A further aspect of the present invention relates to a host cell, wherein the host cell expresses:
i. a first polypeptide; a virus capsid protein, such as the AP205 capsid protein and/or phage fr capsid protein comprising a KTag described herein, and
ii. a second polypeptide; an antigen fused to SpyTag described herein, and
iii optionally a SpyLigase wherein the cell is selected from the group co pr ng bacteria, yeast, fungi, plant, mammalian and/or insect cells.

In another aspect the present invention relates to a vaccine and/or a vector and/or a host cell and/or a method of manufacturing a pharmaceutical composition, as described in the present invention, wherein the SpyTag is replaced by a KTag and/or SpyTag, and/or wherein the SpyCatcher is replaced by SpyTag and/or KTag.

Isopeptid/C-Pilin System:

As part of a similar strategy for covalent coupling of vaccine-antigens at the surface of VLPs, another pair of split-protein binding partners may be used in the present invention. The major pilin protein, Spy0128, from *Streptococcus pyogenes* can be split into two fragments (split-Spy0128 (residues 18-299 of Spy0128) (SEQ ID NO: 57) and isopeptide (residues 293-308 of Spy0128 (TDKDMTIT-FTNKKDAE))) (SEQ ID NO: 56) which together are capable of forming an intermolecular covalent complex (Zakeri, B. et al. 2010). In line with the described SpyTag-SpyCatcher strategy, the Spy0128 isopeptide is genetically inserted into a surface exposed loop of the VLP and enables the stable attachment of vaccine antigens fused at the N or C-terminus with the split-Spy0128 binding partner.

Thus in a further aspect the present invention relates to a vaccine for use in the prophylaxis and/or treatment of a disease wherein the vaccine comprises:
i. a virus capsid protein, such as AP205 capsid protein and/or phage fr capsid protein comprising a Spy0128 isopeptide insertion described herein, and
ii. an antigen fused to a split-Spy0128 described herein, wherein the antigen and virus capsid protein, such as AP205 capsid protein and/or phage fr capsid protein are linked via the interaction between the Spy0128 isopeptide and split-Spy0128, and wherein i-ii form a virus-like particle displaying said antigen.

In one aspect the present invention concerns a vector comprising at least one polynucleotide encoding a) a virus capsid protein, such as AP205 capsid protein and/or phage fr capsid protein comprising a Spy0128 isopeptide insertion, and b) an antigen fused to split-Spy0128.

In another aspect the present invention relates to a vaccine and/or a vector and/or a host cell and/or a method of manufacturing a pharmaceutical composition, as described in the present invention, wherein the SpyTag, is replaced by a Spy0128 isopeptide, and wherein the SpyCatcher is replaced by split-Spy0128 as described herein.

Vector and Polynucleotide/Polypeptide Sequences

In molecular cloning, a vector is a DNA molecule used as a vehicle to artificially carry foreign genetic material into a cell, where it can be replicated and/or expressed. The four major types of vectors are plasmids, viral vectors, cosmids, and artificial chromosomes. The vector itself is generally a DNA sequence that consists of an insert (transgene) and a larger sequence that serves as the "backbone" of the vector. The purpose of a vector which transfers genetic information to another cell is typically to isolate, multiply, or express the insert in the target cell. Expression vectors (expression constructs) specifically are for the expression of transgenes in target cells, and generally have a promoter sequence that drives expression of the transgene.

The heterologous expression/production of the vaccine of the present invention comprises two peptide components 1) a virus capsid protein, such as AP205 capsid protein and/or phage fr capsid protein comprising one or two SpyTags or SpyCatchers and 2) an antigen fused to the other one of a SpyCatcher and a SpyTag. Thus in an embodiment of the present invention each of the peptide components are encoded by a polynucleotide sequence and each of the polynucleotide sequences may be expressed on one or two, different plasmids.

To enable heterologous expression/production of the vaccine one aspect of the present invention is a vector comprising at least one polynucleotide encoding
  i. a virus capsid protein, such as AP205 capsid protein and/or phage fr capsid protein comprising a SpyTag, and/or
  ii. an antigen fused to SpyCatcher.

In one embodiment the vaccine is a vector comprising at least one polynucleotide encoding
  i. a virus capsid protein, such as AP205 capsid protein and/or phage fr capsid protein comprising a SpyCatcher, and/or
  ii. an antigen fused to a SpyTag.

In another embodiment the vector comprises at least two polynucleotides of the following polypeptides:
  i. a virus capsid protein, such as AP205 capsid protein and/or phage fr capsid protein comprising one or more SpyTag, and/or
  ii. an antigen fused to a SpyCatcher.

In another embodiment the vector comprises at least two polynucleotides of the following polypeptides:
  i. a virus capsid protein, such as AP205 capsid protein and/or phage fr capsid protein comprising one or more SpyCatcher, and/or
  ii. an antigen fused to a SpyTag.

In one embodiment the vector comprises sequences encoding at least
  i. a virus capsid protein such as the AP205 capsid protein fused to two SpyTags, wherein one of the two SpyTags is fused to the C-terminal end of the capsid protein and the other of the two SpyTags is fused to the N-terminal end of the capsid protein,
  ii. an antigen fused to SpyCatcher.

In one embodiment the vector comprises sequences encoding at least
  i. a virus capsid protein such as the AP205 capsid protein fused to two SpyCatchers, wherein one of the two SpyCatchers is fused to the C-terminal end of the capsid protein and the other of the two SpyCatchers is fused to the N-terminal end of the capsid protein,
  ii. an antigen fused to a SpyTag.

In a further embodiment the antigen fused to the SpyCatcher has a polynucleotide sequence comprising:
  i. a polynucleotide sequence selected from the group consisting of SEQ ID 29, SEQ ID 30, SEQ ID 31, SEQ ID 32, SEQ ID 33, SEQ ID 34, SEQ ID 35, and/or
  ii. a sequence variant of said polynucleotide sequence, wherein the sequence variant has at least 70%, such as 75%, such as 80%, such as 85%, such as 90%, such as 95%, such as 96%, such as, 97%, such as 98%, such as 99%, such as 99.5%, such as 100% sequence identity to said SEQ ID 11, SEQ ID 12, SEQ ID 13, SEQ ID 14, SEQ ID 15, SEQ ID 16, SEQ ID 17, and/or
  iii. a sequence variant of said polynucleotide, wherein the codon usage is altered.

In an embodiment the SpyTag polypeptide, comprises the nucleotide sequence SEQ ID NO: 39.

In an embodiment the present invention relates a vector comprising at least one polynucleotide encoding
  i. an AP205 capsid protein comprising a SpyCatcher, and/or
  ii. an antigen fused to a SpyTag and/or KTag.

In a further embodiment SpyCatcher is fused to the N-terminus of the AP205 capsid protein optionally via a linker.

In an embodiment the AP205 capsid protein comprising a SpyCatcher comprises the polynucleotide sequence encoding the polypeptide sequence of Seq ID No: 76 or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to polypeptide sequence of Seq ID No: 76 and/or any of the herein disclosed AP205 capsid proteins comprising the SpyCatcher polypeptide in the N terminal. By "biological active" is meant the ability to form a virus-like particle.

In an embodiment the phage fr capsid protein comprising a SpyCatcher comprises the polynucleotide sequence encoding the polypeptide sequence of Seq ID No: 78 or a biologically active sequence variant that has at least 70%, such as 75%, such as 80%, such as 85% such as 90%, such as 95%, such as 96%, such as, 97%, such as 98%, such as 99%, such as 99.5%, such as 100% sequence identity to any of the herein disclosed phage fr capsid proteins comprising the SpyCatcher polypeptide. By "biologically active" is meant the ability to form a virus-like particle.

Host Cell

The invention further relates to a host cell comprising a polynucleotide and/or a vector. The polynucleotide may have a sequence that is codon-optimised. Codon optimisation methods are known in the art and allow optimised expression in a heterologous host organism or cell. In an embodiment the host cell may be selected from the group comprising bacteria, yeast, fungi, plant, mammalian and/or insect cells.

Methods for expressing a first polypeptide: a virus capsid protein, such as AP205 capsid protein and/or phage fr capsid protein comprising SpyTag, and/or a second polypeptide: an antigen fused to SpyCatcher in a host cell are known in the art. The first or second polypeptide may be heterologously expressed from corresponding polynucleotide sequences cloned into the genome of the host cell or they may be comprised within a vector. For example, a first and/or second polynucleotide coding for the first and/or second polypeptide is cloned into the genome, and a first and/or second polynucleotide coding for the first and/or second polypeptide is comprised within a vector transformed or transfected into the host cell. Alternatively, the first and/or second polynucleotide is comprised within a first vector and the first and/or second polynucleotide is comprised within a second vector and the first and/or second is comprised within a third vector.

Expression of the first and second, polypeptides in the host cell may occur in a transient manner. When the polynucleotide encoding one of the polypeptides is cloned into the genome, an inducible promoter may be cloned as well to control expression of the polypeptides. Such inducible promoters are known in the art. Alternatively, genes coding for suppressors of gene silencing may also be cloned into the genome or into a vector transfected within the host cell.

In a particular embodiment the host cell may be selected from the group comprising *Escherichia coli, Spodoptera frugiperda* (sf9), *Trichoplusia ni* (BTI-TN-5B1-4), *Pichia Pastoris, Saccharomyces cerevisiae, Hansenula polymorpha, Drosophila* Schneider 2 (S2), *Lactococcus lactis*, Chinese hamster ovary (CHO), Human Embryonic Kidney 293, *Nicotiana tabacum* cv. Samsun N N and *Solanum tuberosum* cv. Solara. Thus in an embodiment, the host cell is *Escherichia coli*. In another embodiment, the host cell is *Spodoptera frugiperda*. In another embodiment, the host cell is *Pichia Pastoris*. In another embodiment, the host cell is *Saccharomyces cerevisiae*. In another embodiment, the host cell is *Hansenula polymorpha*. In another embodiment, the host cell is Drosophila Schneider 2. In another embodiment, the host cell is *Lactococcus lactis*. In another embodiment, the host cell is Chinese hamster ovary (CHO). In another embodiment, the host cell is Human Embryonic Kidney 293. In another embodiment, the host cell is *Trichoplusia ni* (BTI-TN-5B1-4). In another embodiment, the host cell is *Nicotiana tabacum* cv. Samsun N N. In another embodiment, the host cell is *Solanum tuberosum* cv. Solara.

In another aspect the present invention relates to a host cell expressing at least one polypeptide encoded by any of the polynucleotides disclosed by the present invention.

In a preferred embodiment the expression of an AP205 capsid protein and/or phage fr capsid protein, comprising a SpyCatcher, wherein the capsid protein—SpyCatcher fusion protein is capable of forming a virus-like particle. In a further embodiment SpyCatcher is fused to the N-terminus of the AP205 capsid protein optionally via a linker.

The inventors of the present invention have surprisingly shown that a SpyCatcher comprising more than 100 amino acids can be fused to a capsid protein such as to the N terminal of an AP205 capsid protein and/or phage fr capsid protein, without disrupting the sensitive self-assembly process.

In an embodiment the host cell expresses:
  i. a first polypeptide; a virus capsid protein, such as AP205 capsid protein and/or phage fr capsid protein comprising a SpyCatcher, and/or
  ii. a second polypeptide; an antigen fused to a SpyTag, wherein the cell is selected from the group comprising bacteria, yeast, fungi, plant, mammalian and/or insect cells.

In a most preferred embodiment host cell expresses an AP205 capsid protein comprising a SpyCatcher comprising the amino acid sequence of SEQ ID NO: 76 or a biologically active sequence variant that has at least 70%, such as 75%, such as 80%, such as 85%, such as 90%, such as 95%, such as 96%, such as, 97%, such as 98%, such as 99%, such as 99.5%, such as 100% sequence identity to SEQ ID NO: 76 and/or any of the herein disclosed AP205 capsid proteins comprising the SpyCatcher polypeptide in the N terminal. By "biological active" is meant the ability to form a virus-like particle.

In an embodiment the host cell expresses:
  i. a first polypeptide; a virus capsid protein, such as AP205 capsid protein and/or phage fr capsid protein comprising a SpyTag, and/or
  ii. a second polypeptide; an antigen fused to a SpyCatcher, wherein the cell is selected from the group comprising bacteria, yeast, fungi, plant, mammalian and/or insect cells.

In a further embodiment the host cell, expresses
  i. a first polypeptide having a sequence at least 70%, such as 75%, such as 80% such as 85%, such as 90%©, such as 95%, such as 96%, such as, 97%, such as 98%, such as 99%, such as 99.5%, such as 100% identical to SEQ ID NO: 62 [Spy-AP205]; SEQ ID NO: 64 [AP205-Spy], SEQ ID NO: 66 [Spy-Phage fr], SEQ ID NO: 68 [tag-AP205], SEQ ID NO: 69 [AP205-Ktag], SEQ ID NO: 70 [Ktag-Phage fr], SEQ ID NO: 71 [Spy-AP205-Spy], SEQ ID NO: 76, SEQ ID NO: 78,
  ii. a second polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 82, SEQ ID NO: 79, SEQ ID NO: 80 and SEQ ID NO: 81, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28, wherein the cell is selected from the group comprising bacteria, yeast, fungi, plant, mammalian and/or insect cells.

In another embodiment the host cell expresses:
  i. a first polypeptide; an Phage fr capsid protein comprising a SpyTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 66, and/or
  ii. a second polypeptide; an antigen fused SpyCatcher such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO:18, wherein the cell is selected from the group comprising bacteria, yeast, fungi, plant, mammalian and/or insect cells.

In another embodiment the host cell expresses:
  i. a first polypeptide; an AP205 capsid protein comprising two SpyTags such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 71, and/or
  ii. a second polypeptide; an antigen fused SpyCatcher such as a polypeptide having a sequence at least 70%, such as 75%, such as 80%, such as 85%, such as 90%, such as 95%, such as 96%, such as, 97%, such as 98%, such as 99 such as 995%, such as 100% identical to SEQ ID NO 18, wherein the cell is selected from the group comprising bacteria, yeast, fungi, plant, mammalian and/or insect cells.

In another embodiment the host cell expresses:
  i. a first polypeptide; an AP205 capsid protein comprising a SpyTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 64, and/or
  ii. a second polypeptide; an antigen fused SpyCatcher such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO:18, wherein the cell is selected from the group comprising bacteria, yeast, fungi, plant, mammalian and/or insect cells.

In a further embodiment the host cell expresses:
i. a first polypeptide; an AP205 capsid protein comprising a SpyTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 62, and/or
ii. a second polypeptide; an antigen fused SpyCatcher such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO:18, wherein the cell is selected from the group comprising bacteria, yeast, fungi, plant, mammalian and/or insect cells.

In another embodiment the host cell expresses:
i. a first polypeptide; an AP205 capsid protein comprising a KTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 68, and/or
ii. a second polypeptide; an antigen fused SpyTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO:79, SEQ ID NO: 80, SEQ ID NO: 81, and/or SEQ ID NO: 82 wherein the cell is selected from the group comprising bacteria, yeast, fungi, plant, mammalian and/or insect cells.

In another embodiment the host cell expresses:
i. a first polypeptide; an AP205 capsid protein comprising a KTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO. 69, and/or
ii. a second polypeptide; an antigen fused SpyTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO:79, SEQ ID NO: 80, SEQ ID NO: 81, and/or SEQ ID NO: 82 wherein the cell is selected from the group comprising bacteria, yeast, fungi, plant, mammalian and/or insect cells.

In another embodiment the host cell expresses:
i. a first polypeptide; an Phage fr capsid protein containing a KTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO: 70, and/or
ii. a second polypeptide; an antigen fused SpyTag such as a polypeptide having a sequence at least 70%, such as 75%, such as 80%, such as 85%, such as 90%, such as 95%, such as 96%, such as, 97%, such as 98%, such as 99%, such as 99.5%, such as 100% identical to SEQ ID NO:79, SEQ ID NO: 80, SEQ ID NO: 81, and/or SEQ ID NO: 82 wherein the cell is selected from the group comprising bacteria, yeast, fungi, plant, mammalian and/or insect cells.

The inventors of the present invention have demonstrated formation of AP205 VLP's using *E. coli* cells, such as BL21 cells, incubated at 16° C. for 18 hours. Other conditions and expression hosts may yield VLP's.

In a particular embodiment *Trichoplusia* ni cells are used as host cell for expression of any of the disclosed polynucleotides and/or polypeptides. In another embodiment *Trichoplusia* ni cells are used to express a polypeptide having a sequence at least 70%, such as 75%, such as 80%, such as 85%, such as 90%, such as 95%, such as 96%, such as, 97%, such as 98%, such as 99%, such as 99.5%, such as 100% identical any of the polypeptides disclosed herein.

Composition Comprising the Vaccine

The vaccine of the present invention is to be used in the prophylaxis and/or treatment of a disease. Thus, one aspect of the present invention relates to a composition comprising the vaccine of the present invention. Such compositions may further comprise for example an adjuvant, a buffer, and/or salts or a combination hereof.

An adjuvant is a pharmacological and/or immunological agent that modifies the effect of other agents. Adjuvants may be added to a vaccine to modify the immune response by boosting it such as to give a higher amount of antibodies and/or a longer lasting protection, thus minimizing the amount of injected foreign material. Adjuvants may also be used to enhance the efficacy of a vaccine by helping to subvert the immune response to particular cell types of the immune system, for example by activating the T cells instead of antibody-secreting B cells dependent on the type of the vaccine. Thus in an embodiment the composition comprises at least one adjuvant. In an embodiment the adjuvant is aluminium based. Aluminum adjuvants may be aluminum phosphate, aluminum hydroxide, amorphous aluminum hydroxyphosphate sulfate and/or a combination hereof. Other adjuvants may be included as well.

In another embodiment the composition described above comprises at least one buffer. In an embodiment the buffer is PBS and/or histidine based. In another embodiment the buffer has a pH between pH 6-pH 7.5. In an embodiment the buffer, is isotonic such as has 0.6%-1.8% NaCl.

An emulsifier (also known as an "emulgent") is a substance that stabilizes an emulsion by increasing its kinetic stability. One class of emulsifiers is known as "surface active agents", or surfactants. Polysorbates are a class of emulsifiers used in some pharmaceuticals and food preparation. Common brand names for polysorbates include Alkest, Canarcel, and Tween. Some examples of polysorbates are Polysorbate 20, Polysorbate 40, Polysorbate 60, Polysorbate 80. In an embodiment the composition of the present invention comprises an emulsifier such as one of the above described polysorbates. In a particular embodiment the composition comprises 0.001-0.02% polysorbate 80. Other polysorbates or emulsifiers may be used in the present invention as well.

A Pharmaceutical Composition Comprising the Vaccine

The vaccine of the present invention is intended to be used in the prophylaxis and/or treatment of a disease. Accordingly, the present invention further provides a pharmaceutical formulation, which comprises the vaccine of the present invention and a pharmaceutically acceptable carrier therefor. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting, agents, tablet disintegrating agents, or an encapsulating material, Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. 3

The compounds of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils, and injectable organic esters, and may contain agents such as preserving, wetting, emulsifying or suspending, stabilizing and/or dispersing agents. Preferably, the formulation will comprise about 0.5% to 75% by weight of the active ingredient(s) with the remainder consisting of suitable pharmaceutical excipients as described herein.

The vaccine of the invention may be administered concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Thus, one aspect of the present invention relates to a pharmaceutical composition comprising a vaccine. Such pharmaceutical composition may comprise an adjuvant, a buffer, and/or salts or a combination hereof.

In an embodiment the pharmaceutical composition, further comprises a composition comprising a vaccine as described by the present invention.

A Method of Manufacture a Pharmaceutical Composition Comprising a Vaccine

The present invention further relates to a method of manufacturing a pharmaceutical composition comprising a vaccine. In one aspect the VLP based vaccine of the present invention, may at least be manufactured by the following steps:
  i. obtaining a first polypeptide comprising: a virus capsid protein, such as AP205 capsid protein and/or phage fr capsid protein comprising a SpyTag, and/or
  ii. obtaining a second polypeptide: an antigen fused to SpyCatcher, and
  iii. subjecting the first polypeptide to conditions which enable formation of virus-like particles, and/or
  iv. obtaining a vaccine by linkage of the second polypeptide and said virus-like particles via the interaction between the SpyCatcher and the SpyTag of said virus-like particles, and/or
  v. generating a composition comprising said vaccine.
  thereby obtaining a pharmaceutical composition.

In one aspect the VLP based vaccine of the present invention, may at least be manufactured by the following steps:
  i. obtaining a first polypeptide comprising: a virus capsid protein, such as AP205 capsid protein and/or phage fr capsid protein comprising a SpyCatcher, and/or
  ii. obtaining a second polypeptide: an antigen fused to SpyTag, and
  iii. subjecting the first polypeptide to conditions which enable formation of virus-like particles, and/or
  iv. obtaining a vaccine by linkage of the second polypeptide and said virus-like particles via the interaction between the SpyCatcher and the SpyTag of said virus-like particles, and/or
  v. generating a composition comprising said vaccine.
  thereby obtaining a pharmaceutical composition.

In the manufacture of the pharmaceutical composition other steps may be included for example a) isolation/purification of the VLP to yield a high purity/quality product. This will be accomplished using different techniques for protein purification. For this purpose several separation steps will be carried out using the differences in for instance protein size, physico-chemical properties, binding affinity or biological activity b) formulation by adding stabilizers to prolong the storage life or preservatives to allow multi-dose vials to be used safely as needed c) all components that constitute the final vaccine are combined and mixed uniformly e.g. In a single vial or syringe d) the vaccine is put in recipient vessel (e.g. a vial or a syringe) and sealed with sterile stoppers.

All the processes described above will have to comply with the standards defined for Good Manufacturing Practices (GMP) that will involve several quality controls and an adequate infrastructure and separation of activities to avoid cross-contamination. Finally, the vaccine may be labeled and distributed worldwide Method of Administrating a Vaccine Routes of Administration Systemic treatment. The main routes of administration are oral and parenteral in order to introduce the agent into the blood stream to ultimately target the sites of desired action. Appropriate dosage forms for such administration may be prepared by conventional techniques.

Oral administration. Oral administration is normally for enteral drug delivery, wherein the agent is delivered through the enteral mucosa.

Patenteral administration. Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration, subcutaneous administration. Furthermore, parenteral administration includes inhalations and topical administration.

Accordingly, the agent may be administered topically to cross any mucosal membrane of an animal to which the biologically active substance is to be given, e.g. In the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

The subcutaneous and intramuscular forms of parenteral administration are generally preferred.

Local treatment. The agent according to the invention may be used as a local treatment, ie. be introduced directly to the site(s) of action as will be described below.

Thus one agent may be applied to the skin or mucosa directly, or the agent may be injected into the diseased tissue or to an end artery leading directly to the diseased tissue.

Thus another aspect of the present invention relates to a method of administering a vaccine to treat and/or prevent a clinical condition in a subject in need thereof, comprising the steps of
 i. obtaining a composition comprising at least one vaccine according to the present invention, and/or
 ii. administering said composition to a subject at least once for prophylaxis and/or treatment of a disease.

In a preferred embodiment relates to a method of administering a vaccine to treat and/or prevent cancer, as disclosed herein, in a subject in need thereof, comprising the steps of
 i. obtaining a composition comprising at least one vaccine as disclosed herein, and/or
 ii. administering said composition to a subject intramuscular and/or intravenous at least once for prophylaxis and/or treatment of a cancer.

In a preferred embodiment relates to a method of administering a vaccine to treat and/or prevent a cardiovascular disease, as disclosed herein, in a subject in need thereof, comprising the steps of
 i. obtaining a composition comprising at least one vaccine as disclosed herein, and/or
 ii. administering said composition to a subject intramuscular and/or intravenous at least once for prophylaxis and/or treatment of a cardiovascular disease.

In another embodiment the vaccine of the present invention is administered by any type of injections or infusions selected from the group of bolus injection, continuous infusion, intravenous administration, intramuscular administration, subcutaneous administration, inhalation or topical administration or a combination hereof. In a particular embodiment the vaccine is administered by intramuscular administration and/or intravenous administration.

In medicine, a booster dose is an extra administration of a vaccine after an earlier dose. After initial immunization, a booster injection or booster dose is a re-exposure to the immunizing antigen cell. It is intended to increase immunity against that antigen back to protective levels after it has been shown to have decreased or after a specified period. In an embodiment the vaccine of the present invention is administered any number of times from one, two, three, four times or more.

In a further embodiment the vaccine is boosted by administration in a form and/or body part different from the previous administration. In another embodiment the vaccine is administered to the area most likely to be the receptacle of a given disease or infection which the vaccine is intended to prevent/reduce the risk of.

In another embodiment the recipient of the vaccine (the subject) of the present invention is an animal, for example a mammal, such as a Homo sapiens, cow, pig, horse, sheep, goat, llama, mouse, rat, monkey, and/or chicken. In a particular embodiment the subject is a *Homo sapiens*.

Administration of more than one vaccine is known in the art and refers to this concept as co-vaccination or to give a vaccine cocktail. Thus, in an embodiment of the vaccine, is co-administered with any other vaccine. In another embodiment the vaccine forms a part of a vaccine cocktail.

A Kit of Parts

In another aspect of the present invention relates to a kit of parts comprising
 i. a composition comprising a vaccine of the present invention, and/or
 ii. a medical instrument or other means for administering the vaccine, and/or
 iii. instructions on how to use the kit of parts.

In an embodiment the kit of parts comprises a second active ingredient or vaccine component for therapeutic use in the treatment or prevention of one or more of the diseased disclosed in the present invention.

In an embodiment the vaccine of the invention is administered separate, sequential, or simultaneously with at least one other pharmaceutical active ingredient and/or vaccine component.

Dosages and Dosing Regimes

The dosage requirements will vary with the particular drug composition employed, the route of administration and the particular subject being treated. It will also be recognized by one of skill in the art that the optimal quantity and spacing of individual dosages of a compound will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound given per day for a defined number of days, can be ascertained using conventional course of treatment determination tests.

The term "unit dosage form" refers to physically discrete units suitable as unitary dosages for human and animal subjects, each unit containing a predetermined quantity of a compound, alone or in combination with other agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "effective amount" or an amount necessary to achieve an "effective level" in the individual patient.

When the "effective level" is used as the preferred endpoint for dosing, the actual dose and schedule can vary, depending on inter-individual differences in pharmacokinetics, drug distribution, age, gender, size, health and metabolism. The "effective level" can be defined, for example, as the blood or tissue level desired in the patient that corresponds to a concentration of one or more compounds according to the invention.

EXAMPLES

Modification of VLPs without disrupting the delicate and sensitive self-assembly process is challenging. The inventors show several examples of successful introduction of SpyTag into various VLP loops without disrupting the self-assembly process. The examples below are non-limiting to the scope of the invention.

Gene Design of SpyTag-AP205

The synthetic Spytag-AP205 sequence was constructed by fusion of the SpyTag sequence (AHIVMVDAYKPTK) SEQ ID NO: 36 at either the N- and/or C-terminus of the AP205 (SEQ ID NO: 58) using a spacer sequence (GSG-TAGGGSGS; for N-terminal fusion or GGSG; for C-terminal fusion of SpyTag) in between the AP205 and SpyTag sequences. The gene sequence wasis further modified to contain an NcoI restriction site at the N-terminal and a C-terminal stop-codon followed by a NotI restriction site.

The gene sequence may be codon-optimized for expression in *Escherichia coli* cells or other expression systems and synthesized by Geneart, Life Technologies. Other AP205/Phage fr SpyTag constructs of the present invention is made using a similar approach.

Gene Design of SpyCatcher-AP205

The synthetic Spycatcher-AP205 sequence was constructed by fusion of the SpyCatcher sequence SEQ ID NO: 37 at the N- of the AP205 (SEQ ID NO: 58) using a spacer sequence (GGSGS) in between the AP205 and the SpyCatcher sequences. The gene sequence is further modified to contain an NcoI restriction site at the N-terminal. The gene sequence may be codon-optimized for expression in *Escherichia coli* cells or other expression systems and synthesized by Geneart, Life Technologies.

Gene Design of SpyCatcher-Phage fr

The synthetic Spycatcher-Phage fr sequence was constructed by fusion of the SpyCatcher sequence SEQ ID NO: 37 at the N-terminus of the Phage fr (SEQ ID NO: 59) using a spacer sequence (GGSGS) in between the Phage fr and the SpyCatcher sequences. The gene sequence is further modified to contain an NcoI restriction site at the N-terminal and a C-terminal stop-codon followed by a NotI restriction site. The gene sequence may be codon-optimized for expression in *Escherichia coli* cells or other expression systems and synthesized by Geneart, Life Technologies Expression and Purification of AP205 and/or Phage fr VLPs Plasmids were transformed into *E. coli* BL21 or JM109. A seed culture was prepared by inoculating a single colony into 2×YT medium containing 100 mg/l Ampicillin and the culture was grown overnight at 28° C. with shaking. For expression, the overnight culture was diluted in 2×YT medium containing 100 mg/l Ampicillin, and grown to and OD600 0.5-0.8 at 37° C. with shaking. The culture was then induced with IPTG (final concentration of 0.4 mM) and grown 4 hours 28° C. or 20 hours at 18-20° C. with vigorous aeration. Cells were resuspended in 20 mM Sodium phosphate buffer pH 7.2, 20 mM NaCl containing protease inhibitors and lysed by sonication at 80% Power with 5 pulsations for 2×5 min on ice (25 W effective). The lysates was clarified using centrifugation 40000 G 30 min. and purified using a Hitrap SP HP column using increasing concentration of NaCl at pH 7.2. Some VLPs were additionally purified by ultracentrifugation over an iodixanol (Optiprep) density gradient. Briefly, the lysate (containing VLPs) is first clarified by centrifugation at 5000×g and the supernatant is then layered onto an Optiprep density gradient (27/33/39%). VLPs are purified by density gradient ultracentrifugation in a SW60i rotor at 47,800 rpm for 3.5 hours (16° C.). Optiprep is subsequently removed by dialysis O/N against a PBS buffer pH 7.2, 0.02% PS80 using dialysis tubing with MWCO 300,000 kDa. Concentrations of the purified proteins are determined by the BCA assay.

Gene Design and Recombinant Expression of SpyTag-Binding Vaccine Antigens

Heterologous vaccine antigens were genetically fused with a GGS linker at either their C- or N-terminus to a previously described (WO 2011098772 A1) engineered SpyCatcher (SEQ ID NO: 37 (or 60 or 61)), thereby introducing SpyTag binding capability to the expressed antigen fusion proteins. SpyCatcher-antigen fusion genes expressed in *E. coli* are designed with a 6× Histidine tag and NcoI/BamHI restriction sites for subcloning into pET-15b vector. SpyCatcher-antigen fusion genes are expressed in either S2 cells, Human Embryonic Kidney 293 (HEK293) cells or in Baculovirus infected insect cells; designed with flanking EcoRI/BamHI (N-terminal) and NotI (C-terminal) sites and a 6×Histidine tag and subcloned into the pHP34s, pcDNA™4/HisMax or pAcGP67A (BD Biosciences) vector, respectively.

Engineered coat proteins were all expressed in *E. coli* and were purified by ultracentrifugation through an Optiprep™ step gradient (23%/29%/35%). Expression yield was determined by BCA assay. VLP assembly was confirmed by transmission electron microscopy and/or dynamic light-scattering analysis. For the estimation of the antigen coupling, capacity individual VLP coat proteins were first incubated at 4° C. for 24 hours with corresponding SpyTag- or SpyCatcher-fused antigen (mixed at a 1:1 molar ratio) and each sample was subsequently analyzed by SDS-PAGE/densiometric analysis to assess the amount of antigen which was bound via the SpyTag-SpyCatcher interaction to the VLP coat protein. Results are summarized in table 4:

TABLE 4

Comparison of different engineered AP205 and Phage fr coat proteins with regard to recombinant expression yield, ability to assemble into a virus-like particle (VLP) and their capacity for antigen display

| VLP name | SEQ ID NO. Protein (DNA) | Recombinant expression yield No/low/high | VLP assembly Yes/no | Antigen coupling capacity −, +, ++, +++ |
|---|---|---|---|---|
| SpyTag-AP205 | 62 (63) | High | Yes | ++ |
| AP205-SpyTag | 64 (65) | High | Yes | + |
| SpyTag-AP205-SpyTag | 71 (72) | High | Yes | +++ |
| AP205-ggsg-SpyCatcher | 74 (73) | Low | No | N/A |
| SpyCatcher-ggsgs-AP205 | 76 (75) | High | Yes | ++ |
| Spytag-Phage FR | 66 (67) | Low | Yes | + |
| SpyCatcher Phage FR | 78 (77) | Low | No | − |

Figure 12:
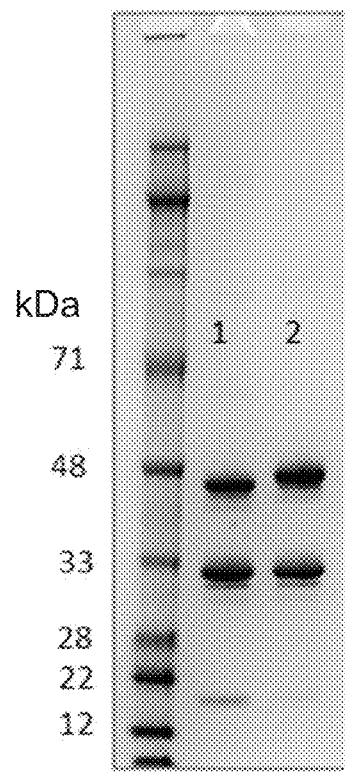
FIG. 12: Binding, capacity of AP205-SpyTag vs. SpyTag-AP205. SDS-PAGE of the AP205-SpyTag (SEQ ID NO: 64(65)) and SpyTag-AP205 (SEQ ID NO: 62(63)) coupled to SpyC-Antigen (SEQ ID NO: 19). Both VLPs are coupled in a molar ratio of 1:2 (VLP to Ag) and the SDS-PAGE gel shows that SpyTag-AP205 has a better binding capacity compared to AP205-SpyTag.

The influence of the position of the SpyTag on the AP205 capsid protein is shown in FIG. 12. As can be seen, fusion in the N-terminal end of AP205 results in a slightly better binding capacity compared to fusion in the C-terminal end.

Quality Assessment of SpyTag-VLPs and SpyCatcher-VLPs by Electron Microscopy

Figure 3:
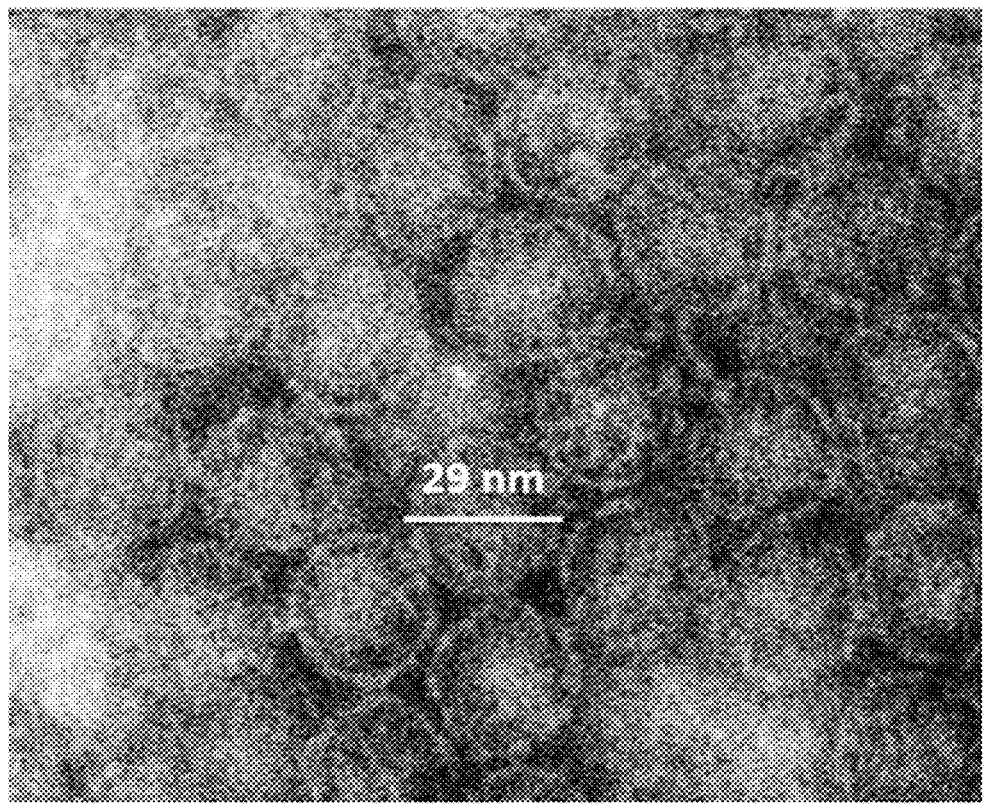
FIG. 3: Transmission electron microscopy of SpyTag-AP205 virus-like particles. The TEM picture shows non-aggregated VLPs of approx. 30 nm, assembled from Spy-AP205 (SEQ ID NO: 62).
Figure 6:
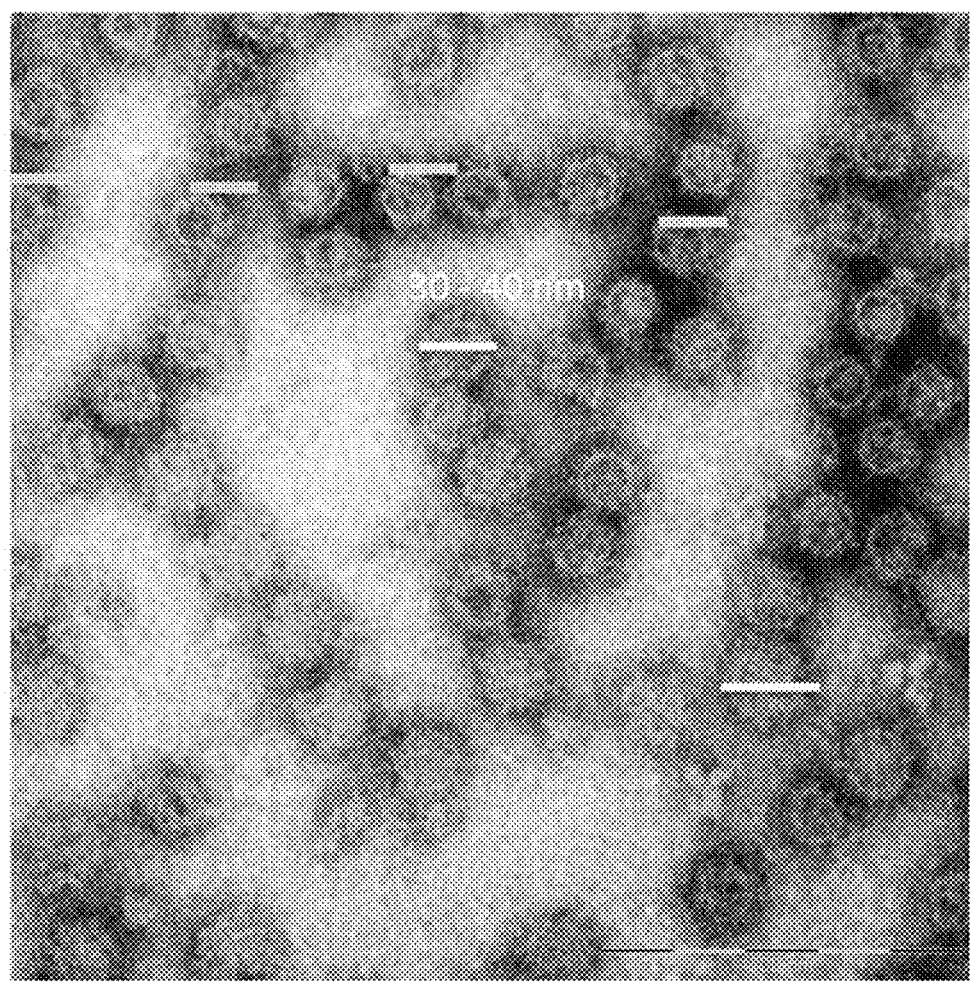
FIG. 6: Transmission electron microscopy of SpyCatcher-AP205 virus-like particles. The TEM picture shows non-aggregated VLPs of approx. 30 nm, assembled from Spy-Catcher-AP205 (SEQ ID NO: 76).

To verify the integrity of chimeric SpyTag-VLPs and SpyCatcher-VLPs, an aliquot of diluted particles was placed on 200-mesh mica carbon-coated grids, negatively stained with 2% phosphotungstic acid (pH=7.0) and examined by transmission electron microscopy (TEM) using a CM 100 BioTWIN (FIG. 3 and FIG. 6). As can be seen when comparing FIGS. 3 and 6 to FIG. 11, the AP205 VLPs obtained here have the same general structure as unmodified AP205 VLPs.

Figure 9:
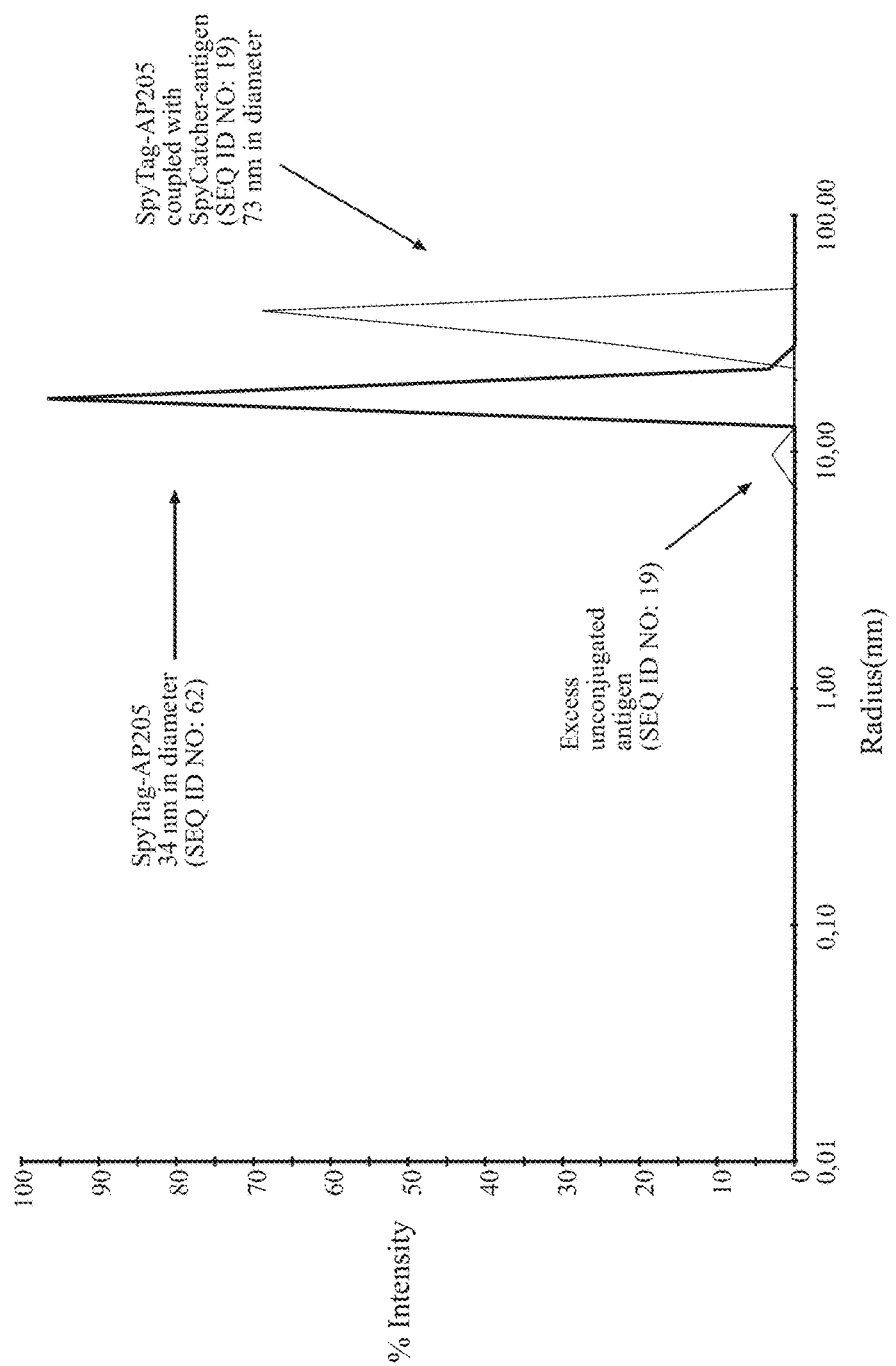
FIG. 9: Dynamic light scattering of SpyTag-AP205 virus-like particles alone or coupled with SpyCatcher-antigen. The graph shows VLPs assembled from SpyTag-AP205 (SEQ ID NO: 62). The SpyTag-AP205 particles are monodisperse and have a size of 34 nm. SpyTag-AP205 virus-like particles coupled with SpyCatcher-antigen (SEQ ID NO: 19) are also monodisperse and have a size of 73 nm, which is 39 nm larger compared to corresponding non-coupled SpyTag-AP205 VLPs.
Figure 10:
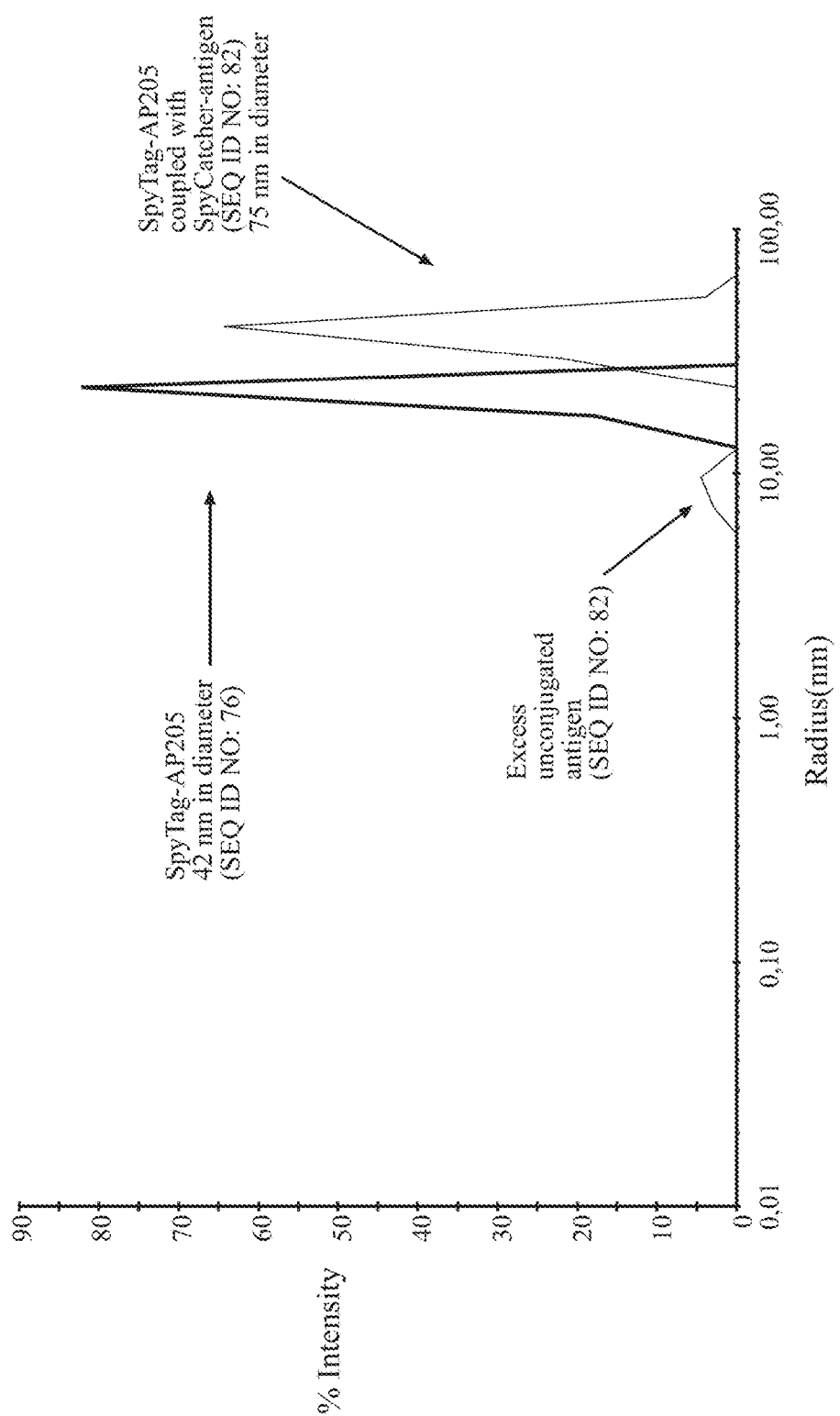
FIG. 10: Dynamic light scattering of SpyCatcher-AP205 virus-like particles alone or coupled with SpyTag-antigen. The graph shows VLPs assembled from SpyCatcher-AP205 (SEQ ID NO: 76). The SpyCatcher-AP205 particles are monodisperse and have a size of 42 nm. SpyCatcher-AP205 virus-like particles coupled with SpyTag-antigen (SEQ ID NO: 82) are also monodisperse and have a size of 75 nm, which is 33 nm larger compared to corresponding non-coupled SpyCatcher-AP205 VLPs.
Figure 11:
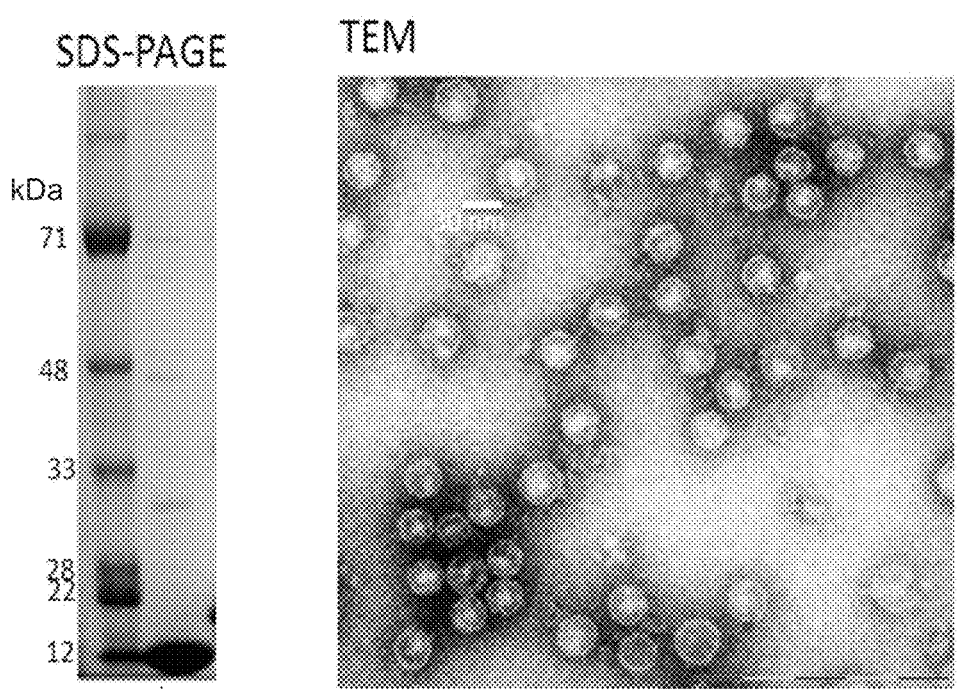
FIG. 11: Expression of AP205 VLP. Left panel: SDS-PAGE of AP205 VLPs (SEQ ID NO: 58). The SDS-PAGE shows that the coat proteins are between 12 and 22 kDa (the theoretical size is 14 kDa). Right panel: Transmission electron microscopy of AP205 virus-like particles. The TEM picture shows non-aggregated VLPs of approx. 30 nm, assembled from AP205 (SEQ ID NO: 58).

Quality Assessment of SpyTag-VLPs and SpyCatcher-VLPs by Dynamic Light Scattering To verify particle size and polydispersity of chimeric SpyTag VLPs and SpyCatcher-VLPs, an aliquot of particles was first clarified by centrifugation at 16000 G for 10 min. The supernatant was transferred to a disposable MicroGuyette and examined by dynamic light scattering (DLS) using a DynaPro NanoStar (FIG. 9 and FIG. 10).

Figure 4A:
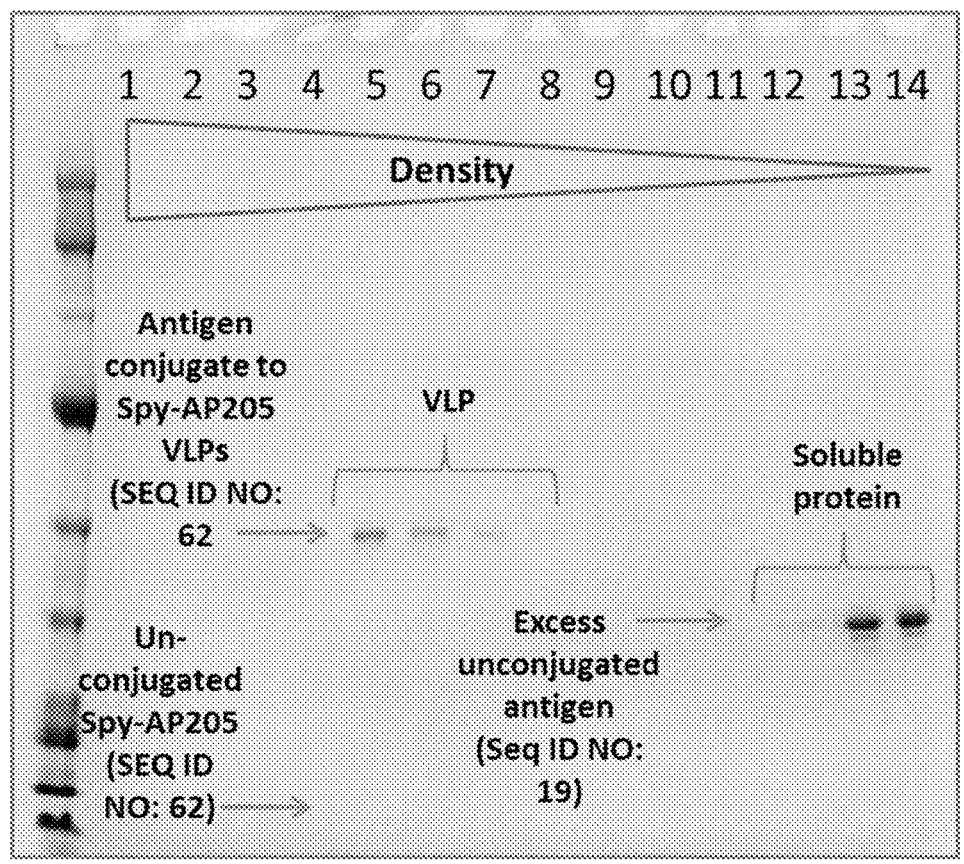
FIG. 4: SpyTag-VLP/SpyCatcher-antigen coupling efficiency. The figure (SDS-PAGE gels) shows collected fraction after density gradient ultracentrifugation of a mixture of SpyTag-AP205 VLPs (SEQ ID NO: 62) and two different spycatcher-antigen fusions (SEQ ID NO: 19 (FIG. 4A) and 21 (FIG. 4B), respectively). The molar relationship between conjugated spy-AP205 capsid protein and spycatcher-antigen as compared to the amount of unconjugated spy-AP205 capsid protein can be used to estimate the antigen-VLP coupling efficiency. From this experiment it is estimated that 80-100% of the spy-AP205 capsid protein is conjugated to a spyCatcher-antigen.
Figures 4, 4B:
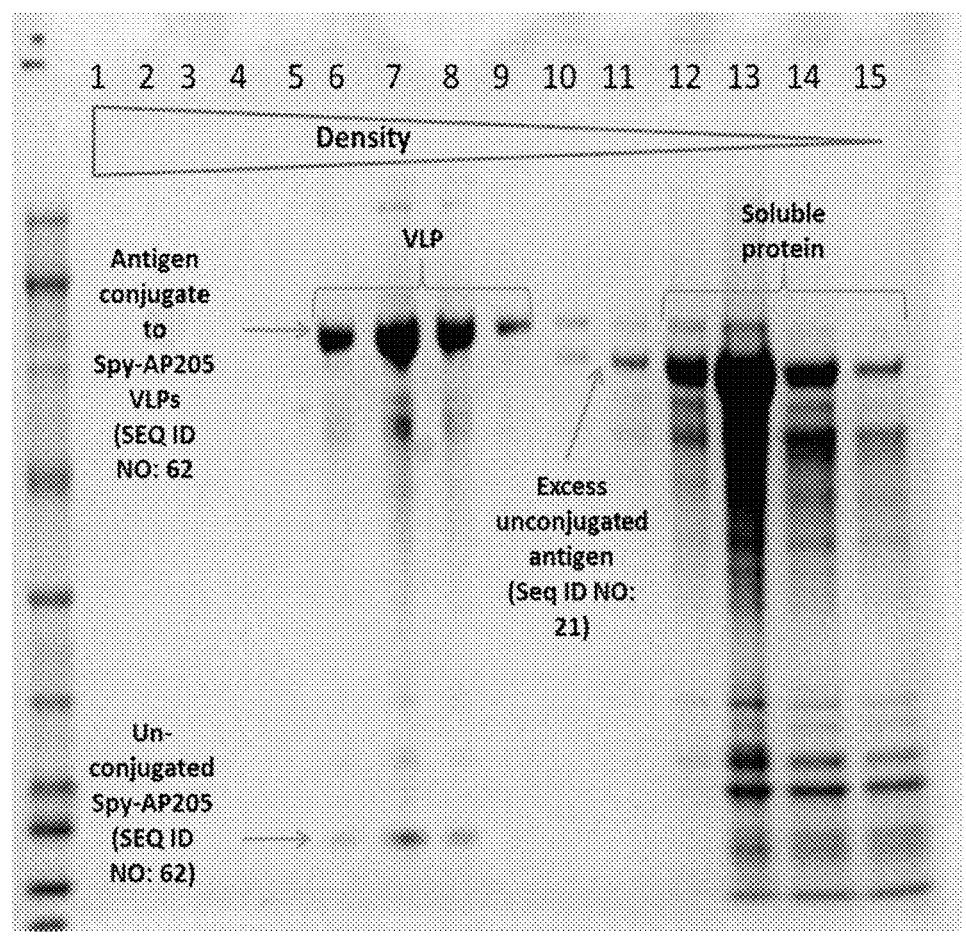

Verification of the SpyCatcher-Antigen Coupling onto Spytagged VLPs:

The overall amounts of antigen coupled onto the VLPs was estimated by density gradient ultracentrifugation of the VLP:spytag-Antigen:SpyCatcher mixture followed by SDS-PAGE of the VLP fraction (FIG. 4). The stoichiometry between the unconjugated SpyTag-AP205 capsid protein and the conjugated SpyCatcher-Antigen-AP205 capsid protein band shows the coupling efficacy. The stoichiometry can be modified by adding varying amounts of SpyCatcher fused antigen.

Figure 5:
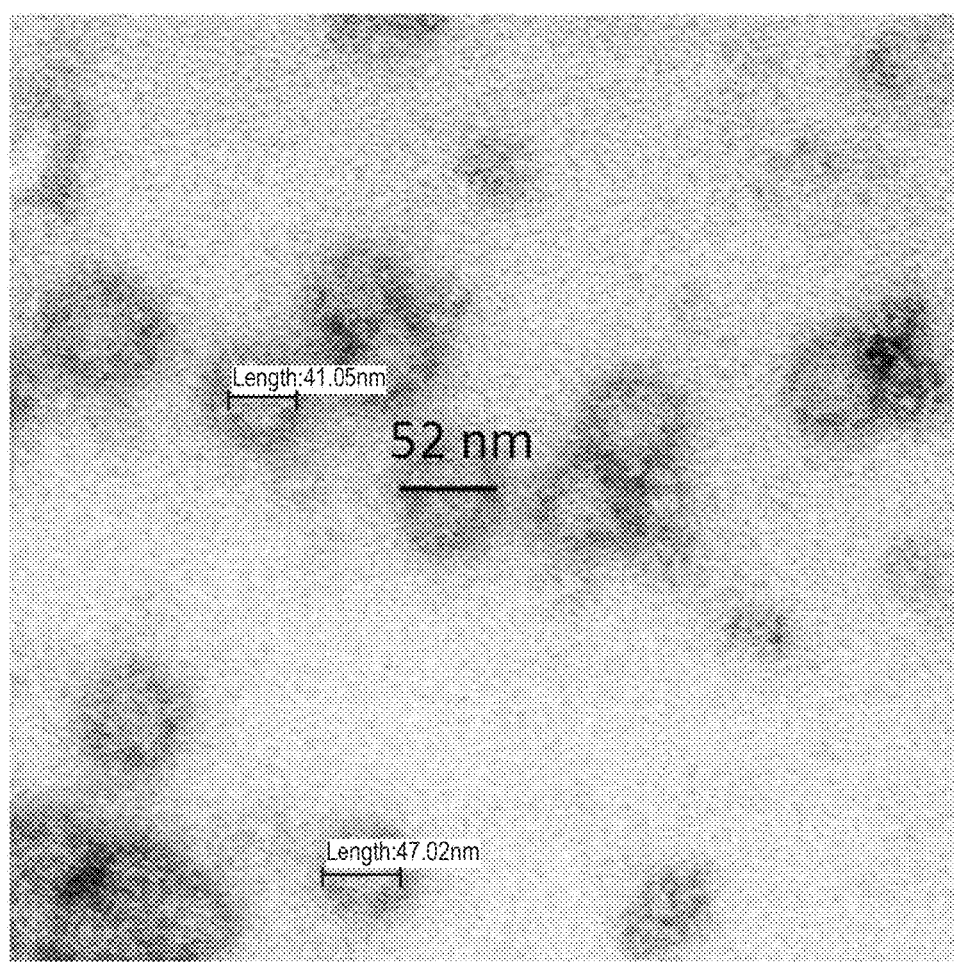
FIG. 5: Transmission electron microscopy of SpyTag-AP205 virus-like particles coupled with SpyCatcher-IL-5 (C63T/C105T) (SEQ ID NO: 19). The TEM picture shows non-aggregated VLPs assembled from spy-AP205 (SEQ ID NO: 62). The apparent average size of the antigen-coupled VLPs seem ~25-35 nm larger compared to corresponding non-coupled spy-AP205 VLPs.

The VLPs were also examined by transmission electron microscopy to assess their integrity after coupling of different SpyCatcher-antigens (FIG. 5). Specifically, an aliquot of diluted particles (post SpyCatcher-coupling) was placed on 200-mesh mica carbon-coated grids, negatively stained with 2% phosphotungstic acid (pH=7.0) and examined by transmission electron microscopy (TEM) using a CM 100 BioT-WIN. The size and polydispersity of the VLPs after coupling of different SpyCatcher-antigens was examined (FIG. 9). Specifically, an aliquot was clarified by ultracentrifugation and transferred to a cuvette and examined by dynamic light scattering (DLS) using a DynaPro NanoStar.

Figure 13:
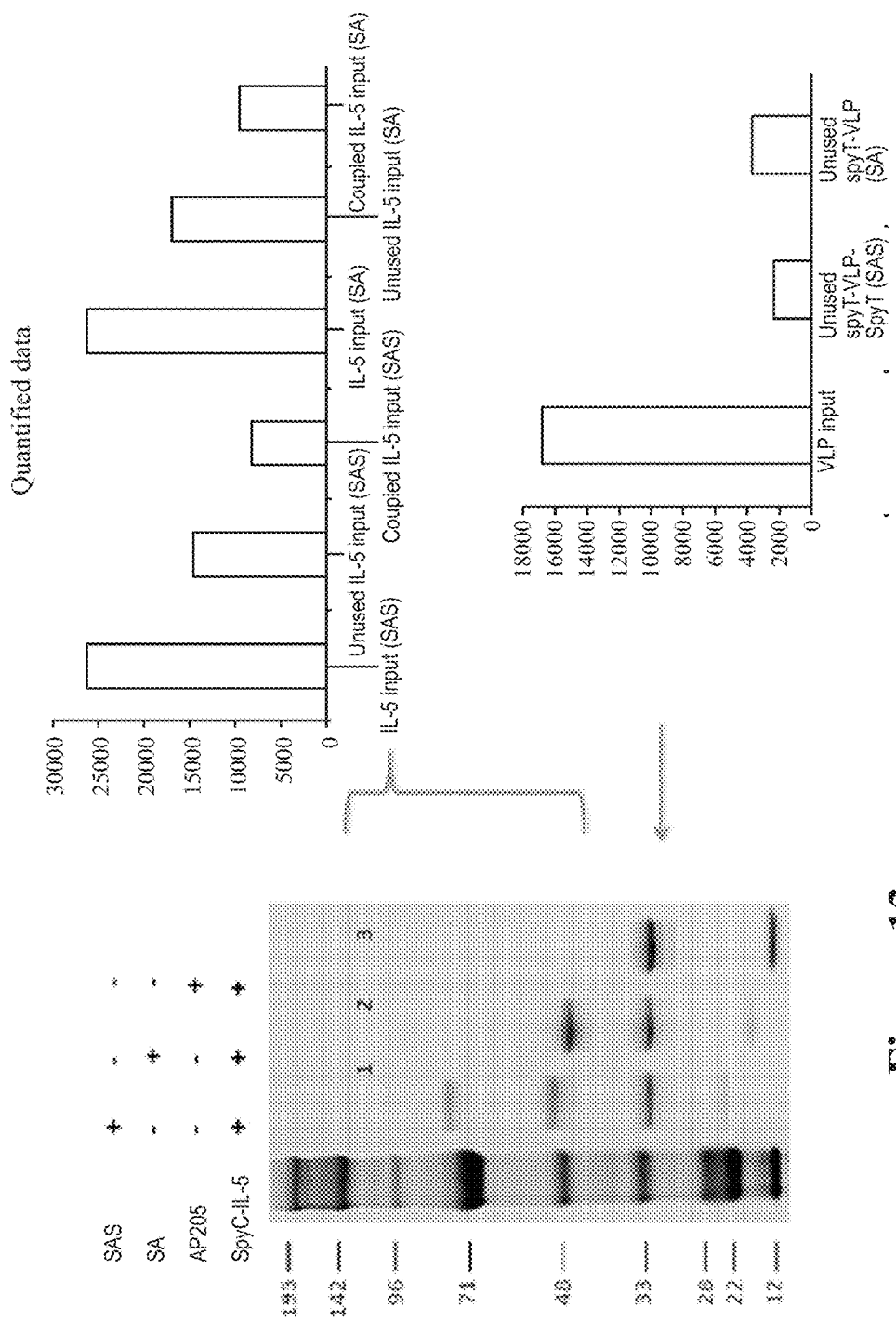
FIG. 13: Binding capacity of SpyTag-AP205-SpyTag (SAS) vs. SpyTag-AP205 (SA): (Left) SDS-PAGE of the SpyTag-AP205-SpyTag (SAS) VLPs (SEQ ID NO: 71(72)), lane 1, SpyTag-AP205 (SA) VLPs (SEQ ID NO: 62), lane 2 and AP205 VLPs, lane 3 (SEQ ID NO: 58) coupled in a molar ratio of 1:1 with SpyCatcher-Antigen (SEQ ID NO: 19).

FIG. 13 shows the binding capacity of AP205 VLPs to bind antigen when AP205 is fused to: no SpyTag, one SpyTag at the N-terminus, or two SpyTags at both the N- and C-terminus, respectively. The SDS-PAGE shows that SpyTag-AP205-SpyTag can bind either one or two SpyCatcher-Antigens per coat protein, SpyTag-AP205 can bind one SpyCatcher-Antigen per coat protein and AP205 cannot bind any SpyCatcher-Antigens. Comparing the intensities of individual protein bands shows that SpyTag-AP205-SpyTag (SAS) (SEQ ID NO: 71(72)) can bind more antigen compared to SpyTag-AP205 (SA) (SEQ ID NO: 62).

Figure 14:
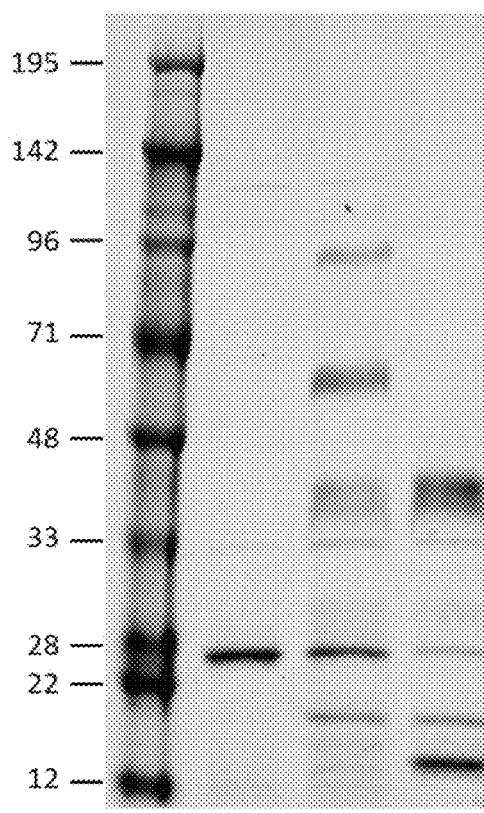
FIG. 14: Coupling of Pfs25 to SpyTag-AP205-SpyTag Virus-like particles. Reduced SDS-PAGE of SpyTag-AP205-SpyTag VLPs (SEQ ID NO: 71(72)), lane 1; SpyTag-AP205-SpyTag and Pfs25 (SEQ ID NO: 27) in a molar ratio of 1:1, lane 2, AP205 VLPs (SEQ ID NO: 58) and Pfs25 (SEQ ID NO: 27) in a molar ratio of 1:1, lane 3.

FIG. 14 shows the binding capacity of SpyTag-AP205-SpyTag VLPs to SpyCatcher-Pfs25. The SDS-PAGE shows that SpyTag-AP205-SpyTag can bind either one or two Pfs25 antigens per coat protein, whereas the AP205 VLPs do not bind to the Pfs25 antigen.

Figure 7:
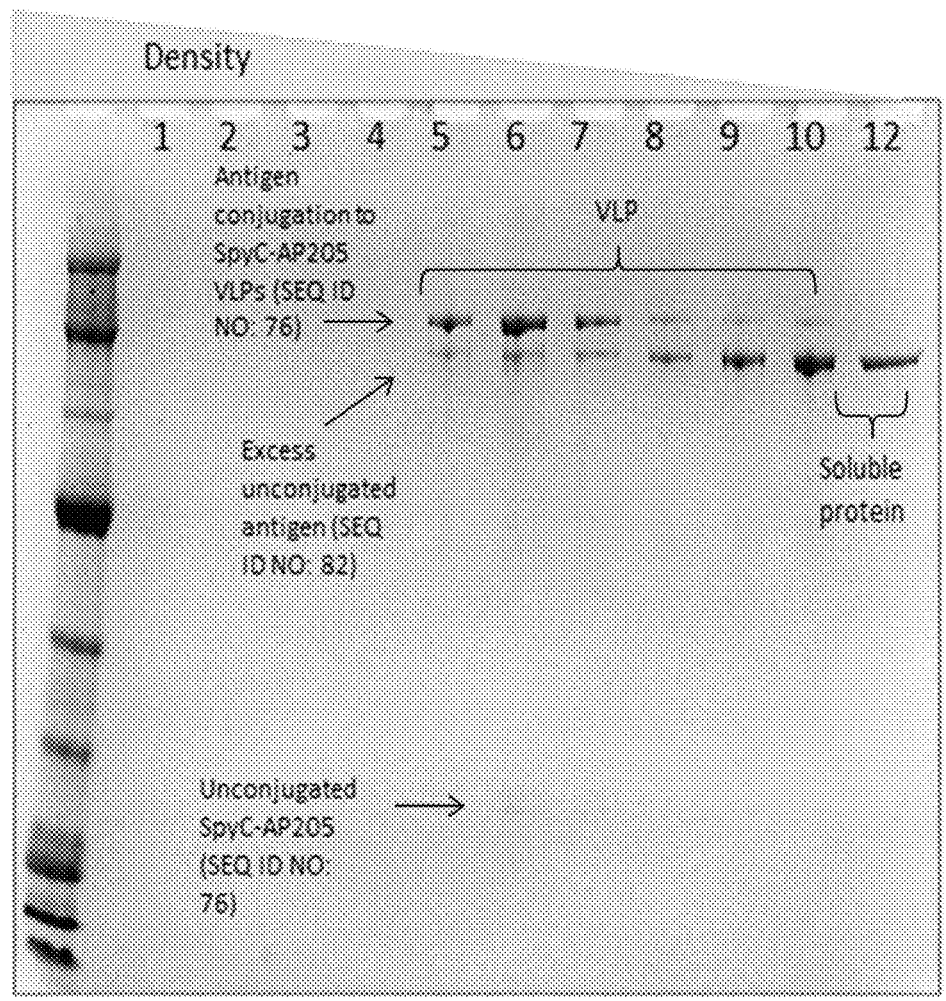
FIG. 7: SpyCatcher-VLP/SpyTag-antigen coupling efficiency. The figure (SDS-PAGE gels) shows collected fraction after density gradient ultracentrifugation of a mixture of SpyCatcher-AP205 VLPs (SEQ ID NO: 76) and a SpyTag-antigen fusion (SEQ ID NO: 82). The molar relationship between conjugated SpyCatcher-AP205 capsid protein and SpyTag-antigen as compared to the amount of unconjugated SpyCatcher-AP205 capsid protein can be used to estimate the antigen-VLP coupling efficiency. From this experiment it is estimated that 80-100% of the SpyCatcher-AP205 capsid protein is conjugated to a SpyTag-antigen.

Verification of the SpyTag-Antigen Coupling onto SpyCatcher-VLPs:

The overall amounts of antigen coupled onto the VLPs was estimated by density gradient ultracentrifugation of the VLP:SpyCatcher Antigen:SpyTag mixture followed by SDS-PAGE of the VLP fraction (FIG. 7). The stoichiometry between the unconjugated SpyCatcher-AP205 capsid protein and the conjugated SpyCatcher-AP205-SpyTag-antigen band shows the coupling efficacy. The stoichiometry can be modified by adding varying amounts of SpyTag fused antigen.

Figure 8:
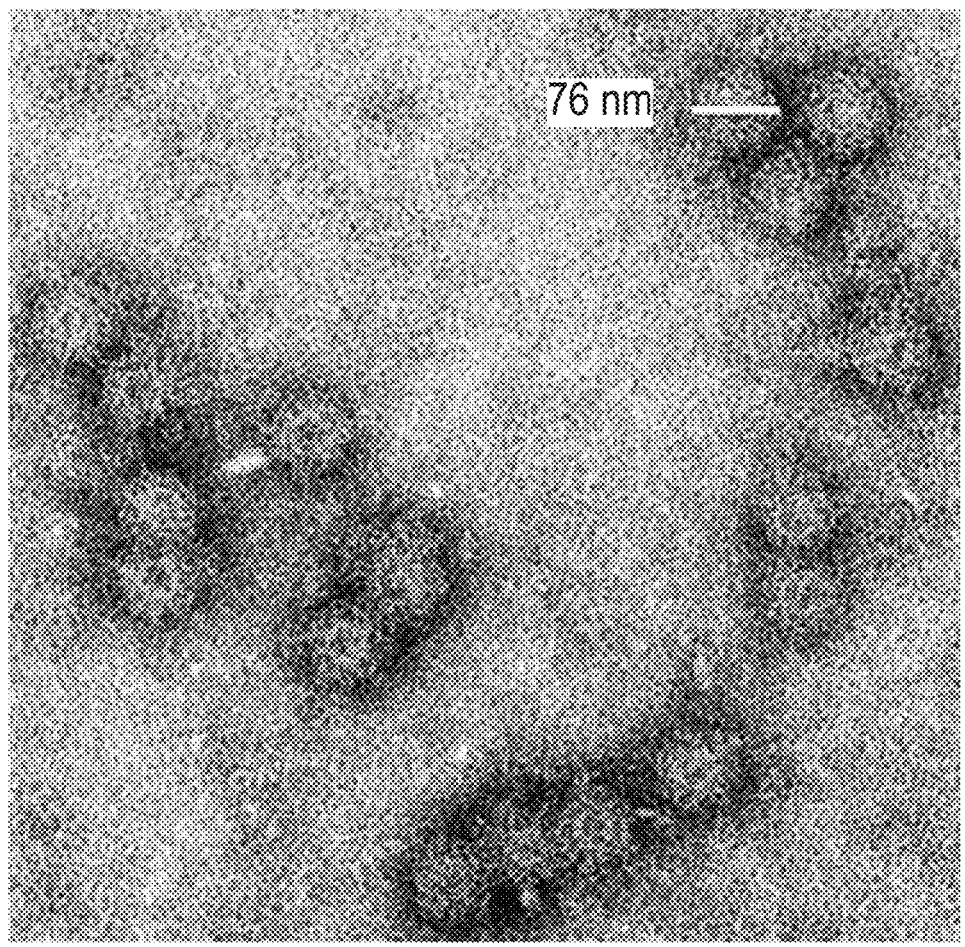
FIG. 8: Transmission electron microscopy of SpyCatcher-AP205 virus-like particles coupled with SpyTag-ID1ID2a (SEQ ID NO: 82). The TEM picture shows non-aggregated VLPs assembled from SpyCatcher-AP205 (SEQ ID NO: 76) The apparent average size of the antigen-coupled VLPs seem ~35 nm larger compared to corresponding non-coupled SpyCatcher-AP205 VLPs.

The VLPs were also examined by transmission electron microscopy to assess their integrity after coupling of different SpyTag-antigens (FIG. 8). Specifically, an aliquot of diluted particles (post SpyTag-antigen coupling) was placed on 200-mesh mica carbon-coated grids, negatively stained with 2% phosphotungstic acid (pH=7.0) and examined by transmission electron microscopy (TEM) using a CM 100 BioTWIN. The size and polydispersity of the VLPs after coupling of different SpyTag-antigens was examined (FIG. 10). Specifically, an aliquot was clarified by ultracentrifugation and transferred to a cuvette and examined by dynamic light scattering (DLS) using a DynaPro NanoStar.

Versatility of the VLP-Based Antigen Presentation Platform

The inventors have successfully engineered VLPs able to display a variety of antigens, as summarized in table 5.

TABLE 5

| SEQ ID NO: protein (DNA) | Antigen | Confirmed binding to SpyTag-AP205 (SEQ ID NO: 62) | Confirmed binding to SpyTag-AP205-SpyTag (SEQ ID NO: 71) | Confirmed binding to LongSpyTag-AP205-LongSpyTag (SEQ ID NO: 92) | Confirmed binding to SpyCatcher-AP205 (SEQ ID NO: 74) | Confirmed binding to SpyTag-fr (SEQ ID NO: 66) |
|---|---|---|---|---|---|---|
| 18 | SpyCatcher-Her2-ECD\|23-686 | YES | YES | | | |
| 19 | SpyCatcher-IL-5(C63T/C105T) | YES | YES | | | YES |
| 20 (29) | PCSK9\|31-692\|:SpyCatcher:HIS | YES | YES | | | |
| 21 (30) | SpyCatcher-ID1\|D2a-HIS | | | | YES | |
| 24 (33) | GMZ2:SpyC | YES | YES | YES | | |
| 27 | SpyCatcher-Pfs25-HIS | YES | YES | | | |
| 28 | HIS-PfCSP(aa92-397)-SpyCatcher | YES | YES | | | |
| 84 (85) | AG85A (SpyCatcher) | YES | YES | | | |
| 86 (87) | SpyC:Survivin (MP1804) | YES | YES | | | |
| 52 (53) | Spycatcher-ggs-CIDR1a-HIS | YES | YES | | | |

TABLE 5-continued

Summary

| SEQ ID NO: protein (DNA) | Antigen | Confirmed binding to SpyTag-AP205 (SEQ ID NO: 62) | Confirmed binding to SpyTag-AP205-SpyTag (SEQ ID NO: 71) | Confirmed binding to LongSpyTag-AP205-LongSpyTag (SEQ ID NO: 92) | Confirmed binding to SpyCatcher-AP205 (SEQ ID NO: 74) | Confirmed binding to SpyTag-fr (SEQ ID NO: 66) |
|---|---|---|---|---|---|---|
| 1 (2) | L2(aa11-88 x5)-ggs-spycatcher | YES | YES | | | |
| 3 (4) | SpyCatcher-R0.Pf6C | YES | YES | | | |
| 5 (6) | SpyCatcher Pf6C | YES | YES | | | |
| 7 (8) | SpyTag DBL1-ID2a | | | | YES | |
| 9 (10) | PDL1-SpyTag | | | | YES | |
| 11 (12) | CTLA-4-SpyTag | | | | YES | |
| 14 (15) | SpyTag-L-DER P2 | | | | YES | |
| 16 (17) | mini-HA-Stem-HIS-SpyT | | | | YES | |

Immunological Testing of the VLP-Based Antigen Presentation Platform:

To assess the immunological effect of the described VLP antigen-presentation platform, we immunized groups of mice (n=5) with either VLP-coupled or non-coupled soluble antigen (control group) formulated with or without extrinsic adjuvant. To take into account the possibility that AP205 VLPs themselves may have an adjuvant effect we further included a similar amount of unmodified AP205 VLPs (i.e. with no SpyTag or SpyCatcher fused) in the control group vaccine formulations. Each mouse was administered three intra muscular immunizations (50 microliter volume injected into each Tibialis anterior muscle) on day 1, 21 and 42, and sera were collected two weeks or three months after each immunization for subsequent analysis.

To study the kinetics of antibody responses, total antigen-specific immunoglobulins in mouse sera collected after $1^{st}$, $2^{nd}$ and $3^{rd}$ immunization, respectively, was measured in an ELISA assay using the naked vaccine antigen (i.e. with no spyTag or SpyCatcher) as the solid phase capturing antigen (plates were coated with 1 ug/ml antigen). The antibody titer of sera from mice immunized with the VLP-coupled-antigen was subsequently compared against that of the control group to evaluate the effect of the VLP antigen-display in terms of both antibody peak titers and kinetics i.e. how quickly the antibody response develops and to what magnitude, during the vaccination regime. Specifically, a three-fold dilution of the serum starting from 1:100 down to 1:5.904.900 was performed to compare antibody responses between the two groups of animals immunized with either antigen conjugated VLPs or non-coupled antigen. To compare the longevity of the induced humoral responses between VLP vaccinated mice and mice immunized with soluble SpyCatcher-antigen or SpyTag antigen (control group), sera are collected every third week after the last given immunization for a full year (or until a significant difference is observed between test and control groups) and are tested in the above described ELISA assay.

Figure 15:
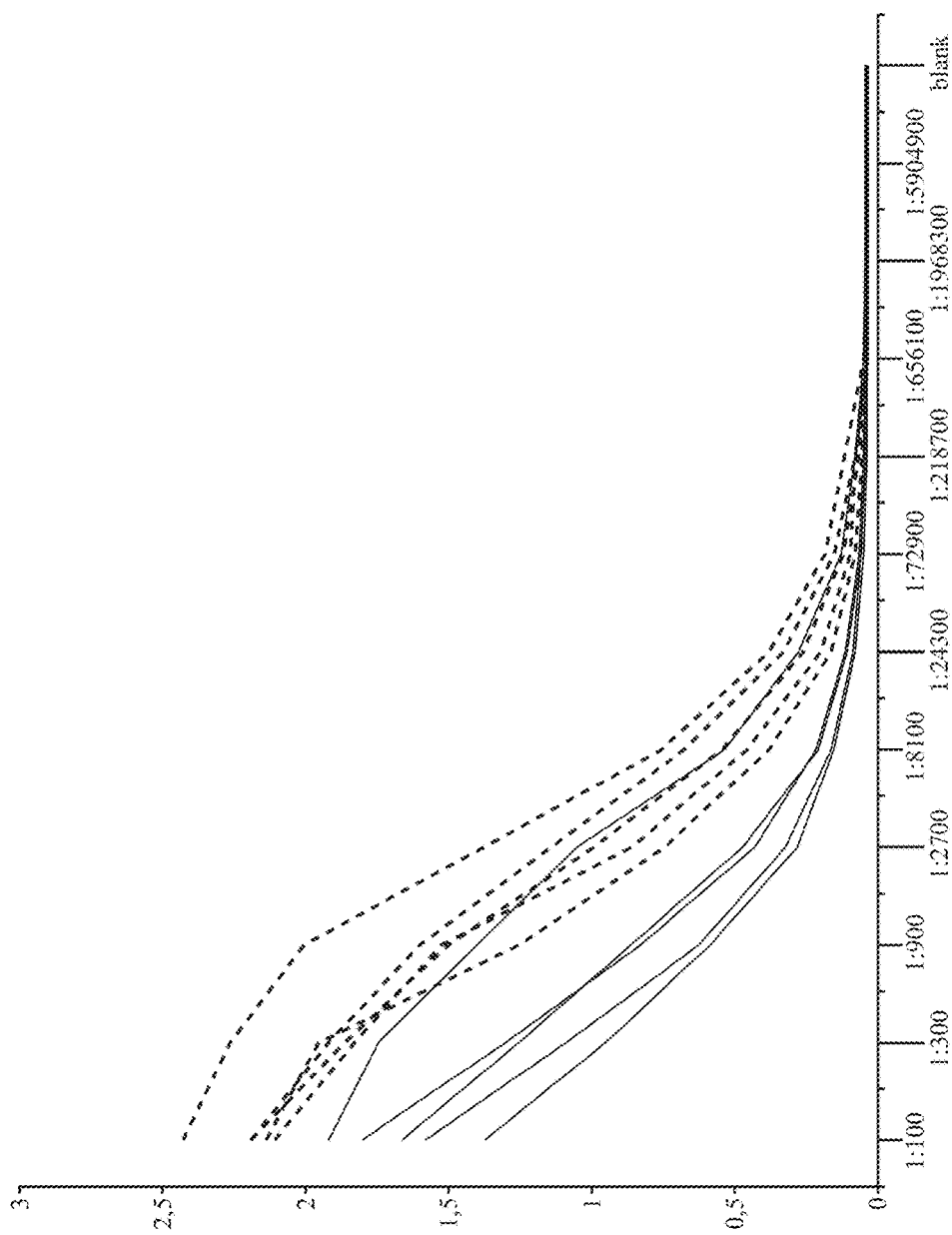
FIG. 15: Induction of higher titres of antibodies as a result of VLP display. The figure shows the Ig response against an antigen (SEQ ID NO: 7) two weeks after a prime-boost-boost immunization regimen. The dashed lines represent individual mice immunized with SpyCatcher-AP205 (SEQ ID NO: 76) coupled with SpyTag-antigen (SEQ ID NO: 7). The gray line represents individual mice immunized with soluble SpyTag-Antigen (SEQ ID NO: 7) and AP205 (SEQ ID NO: 58), which is unable to bind the antigen. Both vaccines were formulated without aluminum hydroxide gel. X-axis: serum dilution; Y-axis: OD490 nm.

FIG. 15 shows the Ig response against a SpyTag coupled antigen (SEQ ID NO: 7) two weeks after prime boost-boost immunization regimen (vaccines formulated without aluminum hydroxide gel). Soluble SpyTag-antigen and AP205 are unable to bind the antigen. Immunization of mice with VLP-displayed SpyTag-antigen (SEQ ID NO: 7) induces a higher Ig response compared to mice immunized with soluble SpyTag-Ag (SEQ ID NO: 7) and AP205 (SEQ ID NO: 58).

Figure 16:
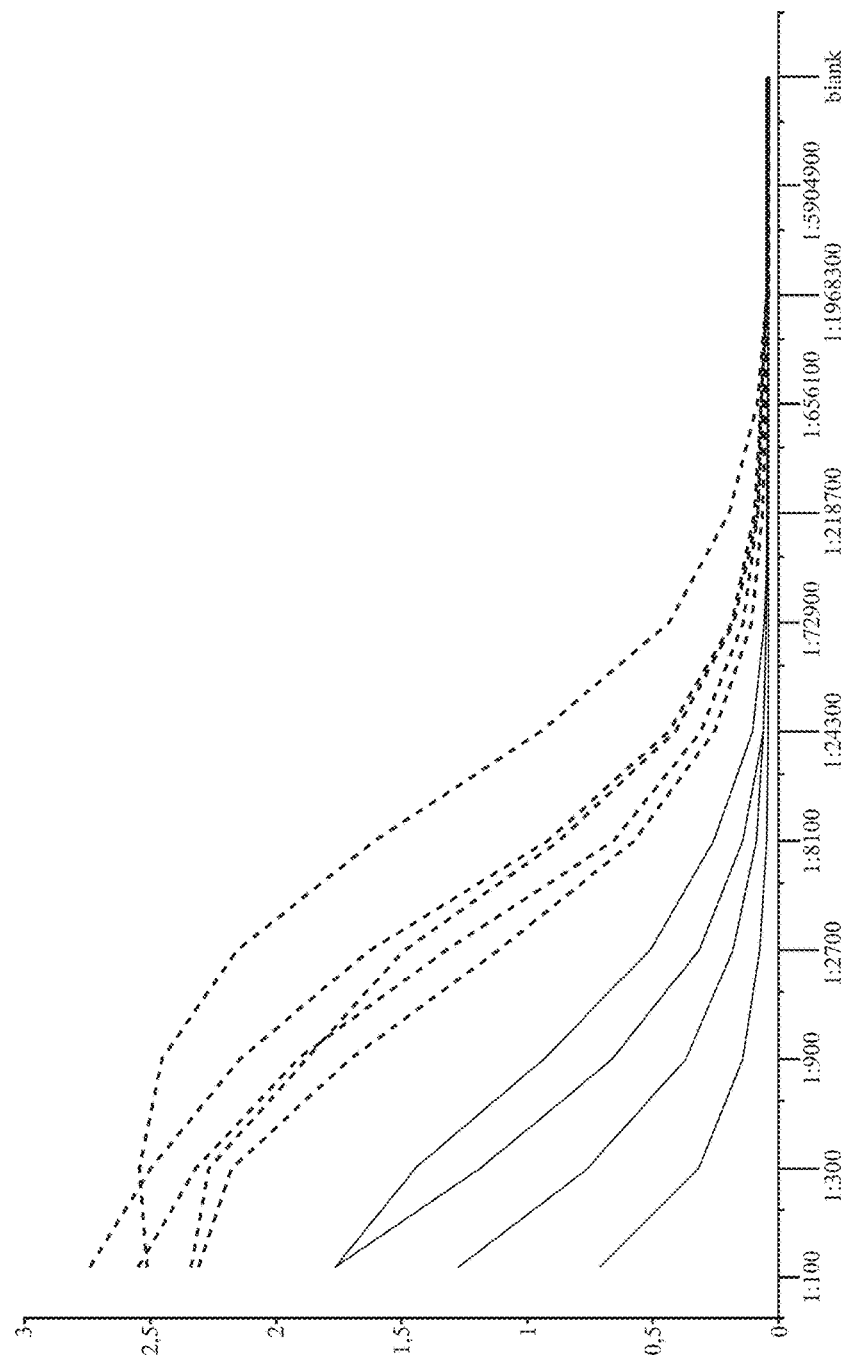
FIG. 16: The figure shows the Ig response against an antigen (SEQ ID NO: 27) three months after a prime-boost-boost immunization regimen. The dashed line represents individual mice immunized with SpyTag-AP205-SpyT (SEQ ID NO: 71) coupled with SpyCatcher-antigen (SEQ ID NO: 27). The gray line represents individual mice immunized with soluble SpyCatcher-antigen (SEQ ID NO: 27) and AP205 (SEQ ID NO: 58), which is unable to bind the antigen. Both vaccines were formulated with aluminum hydroxide gel. X-axis: serum dilution; Y-axis: OD490 nm.

FIG. 16 shows the Ig response against a SpyCatcher coupled antigen (SEQ ID NO: 27) three months after a prime-boost-boost immunization regimen. Immunization of mice with VLP-displayed SpyCatcher-antigen (SEQ ID NO: 27) induces a higher Ig response compared to mice immunized with soluble SpyCatcher-antigen (SEQ ID NO: 27) and AP205 (SEQ ID NO: 58).

FIGS. 15 and 16 show that the VLP vaccines disclosed herein can induce increased antibody titres.

Figure 17:
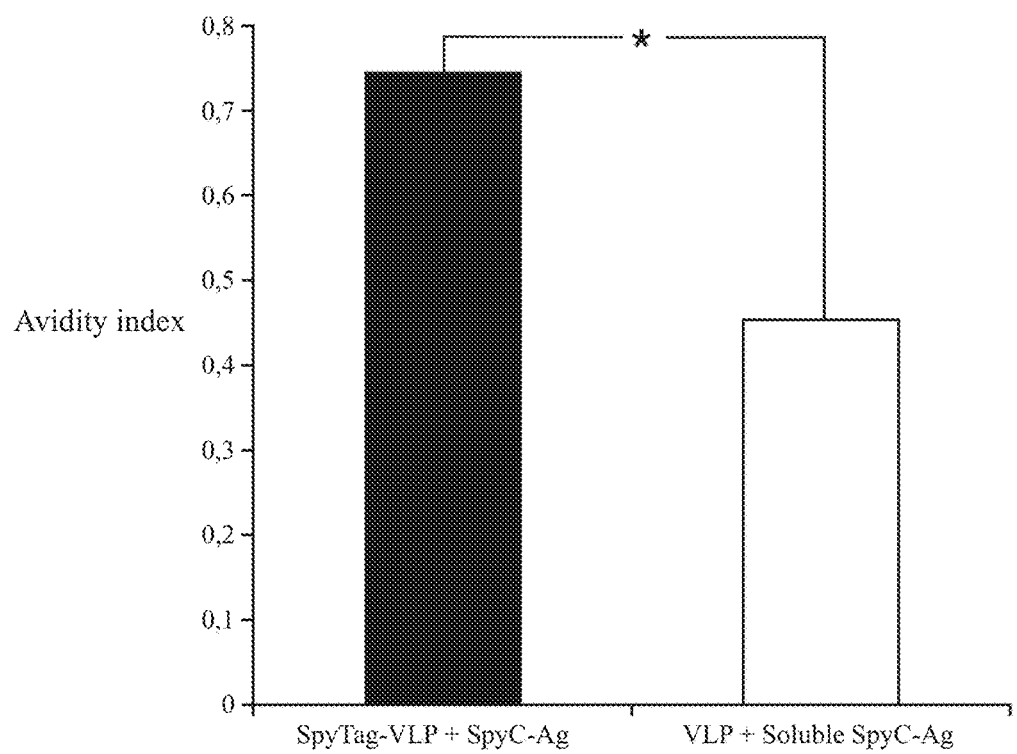
FIG. 17: The figure shows the avidity of antibodies induced in mice following a prime-boost-boost immunization regimen. Mouse anti-sera were obtained four month after last immunization. The black bar represents a pool of sera from mice immunized with SpyTag-AP205-SpyTag (SEQ ID NO: 71) coupled to the spyCatcher-antigen (SEQ ID NO: 27). The gray bar represents a pool of sera from mice immunized with soluble SpyCatcher-antigen (SEQ ID NO, 27) and AP205 (SEQ ID NO, 58), which is unable to bind the antigen. Both vaccines were formulated with aluminum hydroxide gel.
Figure 18:
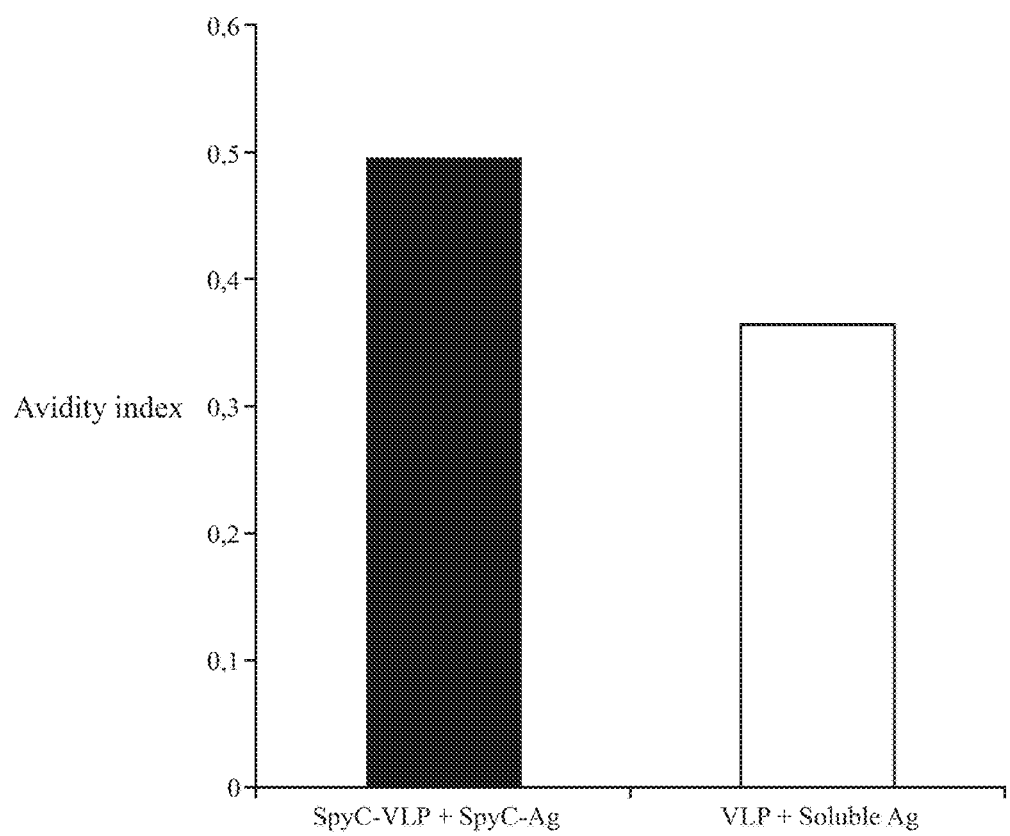
FIG. 18: The figure shows the avidity of antibodies induced in mice following a prime-boost-boost immunization regimen. Mouse anti-sera were obtained three month after last immunization. The black bar represents a pool of sera from mice immunized with SpyCatcher-AP205 (SEQ ID NO: 76) coupled to SpyTag-antigen (SEQ ID NO: 7). The gray bar represents a pool of sera from mice immunized with soluble SpyTag-Ag (SEQ ID NO: 7) and AP205 (SEQ ID NO: 58), which is unable to bind the antigen. Both vaccines were formulated without aluminum hydroxide gel.

The avidity of antibodies induced in mice following a prime-boost-boost immunization regimen was analysed (FIGS. 17 and 18). Mouse anti-sera were obtained four months after last immunization. Immunization of mice with VLP-displayed antigen (SEQ ID NO: 27) gives rise to antibodies with a significantly higher avidity compared to antibodies from mice immunized with soluble SpyCatcher-antigen (SEQ ID NO: 27) and AP205 (SEQ ID NO: 58) (FIG. 17). Both vaccines were formulated with aluminum hydroxide gel. This difference was statistically tested using non-parametric Two-sample Wilcoxon rank-sum (Mann-Whitney) test, which resulted in a probability score of $P>|z|=0.00002$.

FIG. 18 shows the avidity of antibodies obtained from a pool of sera from mice immunized with SpyCatcher-AP205 (SEQ ID NO: 76) coupled to SpyTag-antigen (SEQ ID NO: 7). The gray bar represents a pool of sera from mice immunized with soluble SpyTag-Ag (SEQ ID NO: 7) and AP205 (SEQ ID NO: 58), which is unable to bind the antigen. Both vaccines were formulated without aluminum hydroxide gel. Immunization of mice with SpyCatcher- AP205 (SEQ ID NO: 76) coupled to SpyTag-antigen (SEQ ID NO: 7) resulted in induction of antibodies with higher avidity compared to antibodies from mice immunized with soluble SpyTag-Ag (SEQ ID NO: 7) and AP205 (SEQ ID NO: 58).

Taken together, the results of FIG. 17 and FIG. 18 show that the present VLP vaccines can be used to induce antibodies with increased avidity compared to corresponding soluble protein vaccines.

Figure 19:
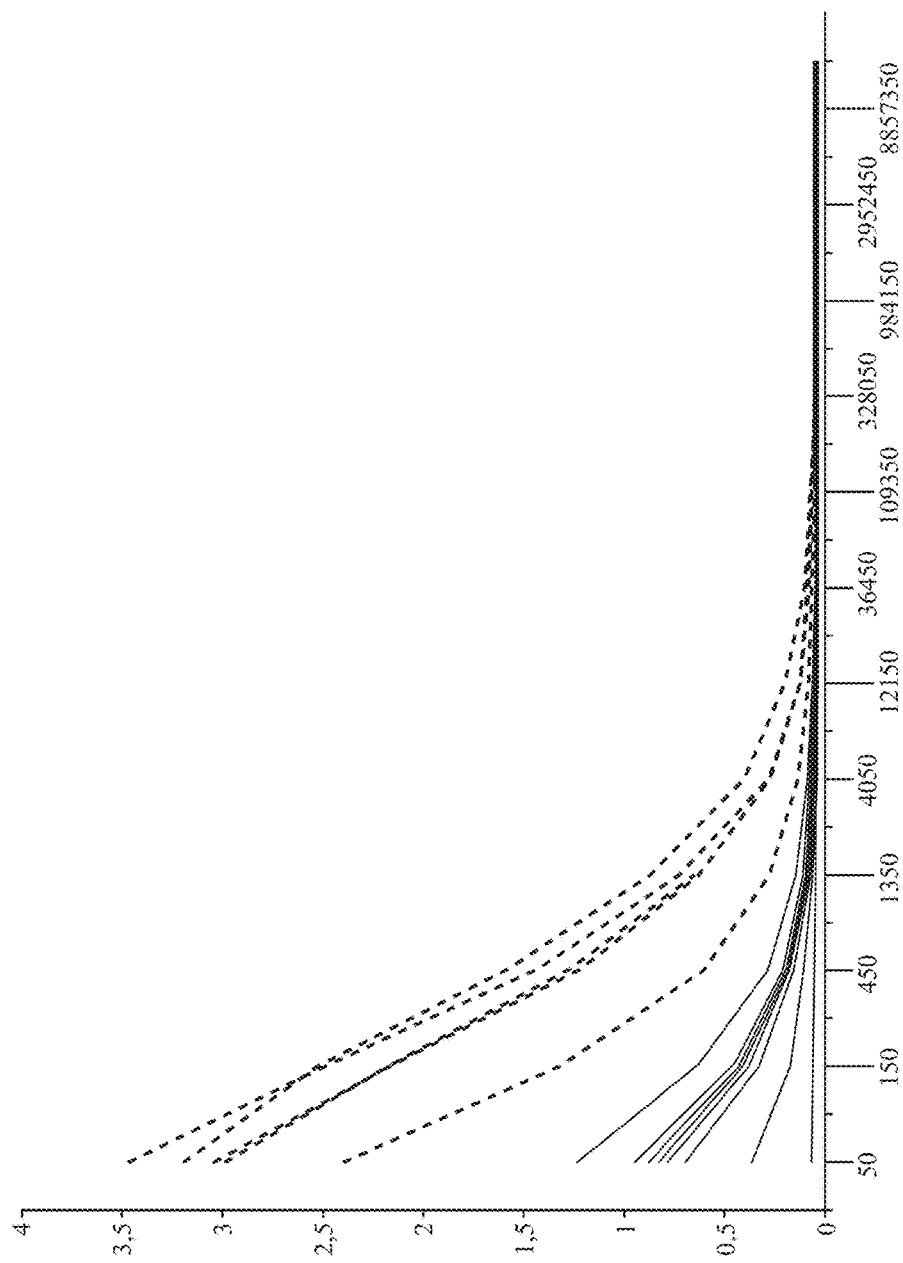
FIG. 19: Ig response against an antigen (SEQ ID NO: 52) following a single immunization. The dashed lines represent individual mice immunized with SpyTag-AP205 (SEQ ID NO: 62) coupled to SpyCatcher-antigen (SEQ ID NO: 52). The gray lines represent individual mice immunized with soluble SpyCatcher-antigen (SEQ ID NO: 52) and AP205 (SEQ ID NO: 58), which is unable to bind the antigen. Both vaccines were formulated with aluminum hydroxide gel. X-axis: serum dilution; Y-axis: OD490 nm.

We also analysed how fast antibodies were induced upon vaccination with VLP-displayed antigens (FIG. 19). The Ig response against an antigen (SEQ ID NO: 52) following a single immunization was analysed (FIG. 18) in individual mice immunized with SpyTag-AP205 (SEQ ID NO: 62) coupled to SpyCatcher-antigen (SEQ ID NO: 52) or with soluble SpyCatcher-antigen (SEQ ID NO: 52) and AP205 (SEQ ID NO: 58), which is unable to bind the antigen. Both vaccines were formulated with aluminum hydroxide gel. A single immunization of mice with SpyTag-AP205 (SEQ ID NO: 62) coupled to spyCatcher-antigen (SEQ ID NO: 52) induced a faster Ig response compared to mice immunized with soluble SpyCatcher-antigen (SEQ ID NO: 52) and AP205 (SEQ ID NO: 58).

Figure 20:
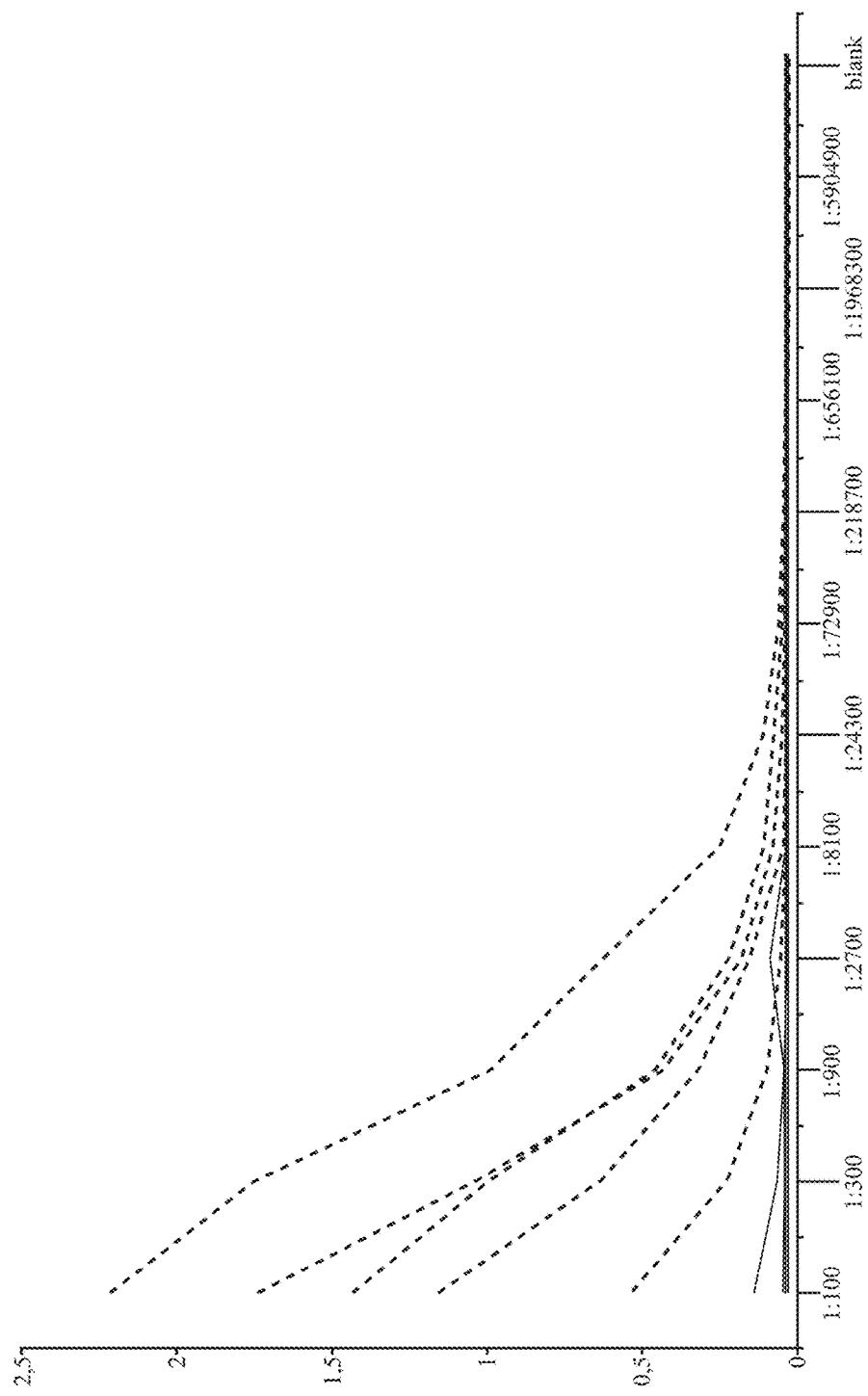
FIG. 20: The figure shows the Ig response against an antigen (SEQ ID NO: 27) following a single immunization. The dashed lines represent individual mice immunized with SpyTag-AP205-SpyTag (SEQ ID NO: 71) coupled to SpyCatcher-antigen (SEQ ID NO: 27). The gray lines represent individual mice immunized with soluble SpyCatcher-antigen (SEQ ID NO: 27) and AP205 (SEQ ID NO: 58), which is unable to bind the antigen. Both vaccines were formulated with aluminum hydroxide gel. X-axis: serum dilution; Y-axis: OD490 nm.

The same experiment was performed in mice immunized with SpyTag-AP205-SpyTag (SEQ ID NO: 71) coupled to SpyCatcher-antigen (SEQ ID NO: 27) or with soluble SpyCatcher-antigen (SEQ ID NO: 27) and AP205 (SEQ ID NO: 58), which is unable to bind the antigen (FIG. 20). Both vaccines were formulated with aluminum hydroxide gel. A single immunization of mice with SpyTag-AP205-SpyTag (SEQ ID NO: 71) coupled to SpyCatcher-antigen (SEQ ID NO: 27) induced a faster Ig response compared to mice immunized with soluble SpyCatcher-antigen (SEQ ID NO: 27) and AP205 (SEQ ID NO: 58).

The data presented in FIGS. 19 and 20 show that a single immunization with VLP-presented antigens results in a faster induction of antibodies.

Human memory B cells have been proposed to play a role in maintaining serum antibody levels over time and thus to evaluate the potential of the VLP-based antigen presentation platform to induce long-term immunological memory we also compare the ability of the VLP-based vaccine to generate memory B-cells against that of the soluble antigen vaccine (control). The memory B cell ELISPOT is the accepted standard for measuring the relative frequency of memory B cells and relies on the detection of memory B cells that have differentiated into plasma cells after stimulation with three polyclonal (CpG, *Staphylococcus aureus* Cowan (SAC, Sigma), and Pokeweed Mitogen (PWM, Sigma)). Following the stimulation, the number of antigen-specific memory B cells and total memory B cells are enumerated and the ratio between the number of antigen-specific spots and the total number of memory B cell spots is estimated and reported as a percentage.

Antigen-Specific Qualitative Testing of Induced Immune Responses:

Testing of the VLP:SpyTag and SpyCatcher:VLP Platform, Respectively to Induce VAR2CSA Specific Antibodies To qualitatively assess the induced antibody responses, we performed an optimized parasite binding-inhibition assay that test the capacity of the collected sera to inhibit binding between the human receptor, Chondroitin Sulfate A (CSA), and parasitized erythrocytes expressing the VAR2CSA ligand. This was done by coating 96 well plates with the purified CSA receptor and adding radio-labeled malaria parasites expressing VAR2CSA in the presence or absence of VAR2CSA specific antibodies in sera from animals immunizing animals with VAR2CSA (SpyCatcher-ID1ID2a/SpyTag-ID1ID2a) conjugated VLPs or soluble VAR2CSA antigen alone (SpyCatcher-ID1ID2a/SpyTag-ID1ID2a). Another qualitative measure of the functional IgG response is to estimate the total amount of opsonizing IgG in a serum sample. This is done by incubating VAR2CSA expressing malaria parasites with serum in a 5 fold dilution series starting from 1:100 followed by washing of the infected erythrocytes and detection of bound VAR2CSA specific IgG using an Alexa488 conjugated secondary antibody specific to mice/rat or rabbit IgG followed by flow cytometry analysis.

Figure 25:
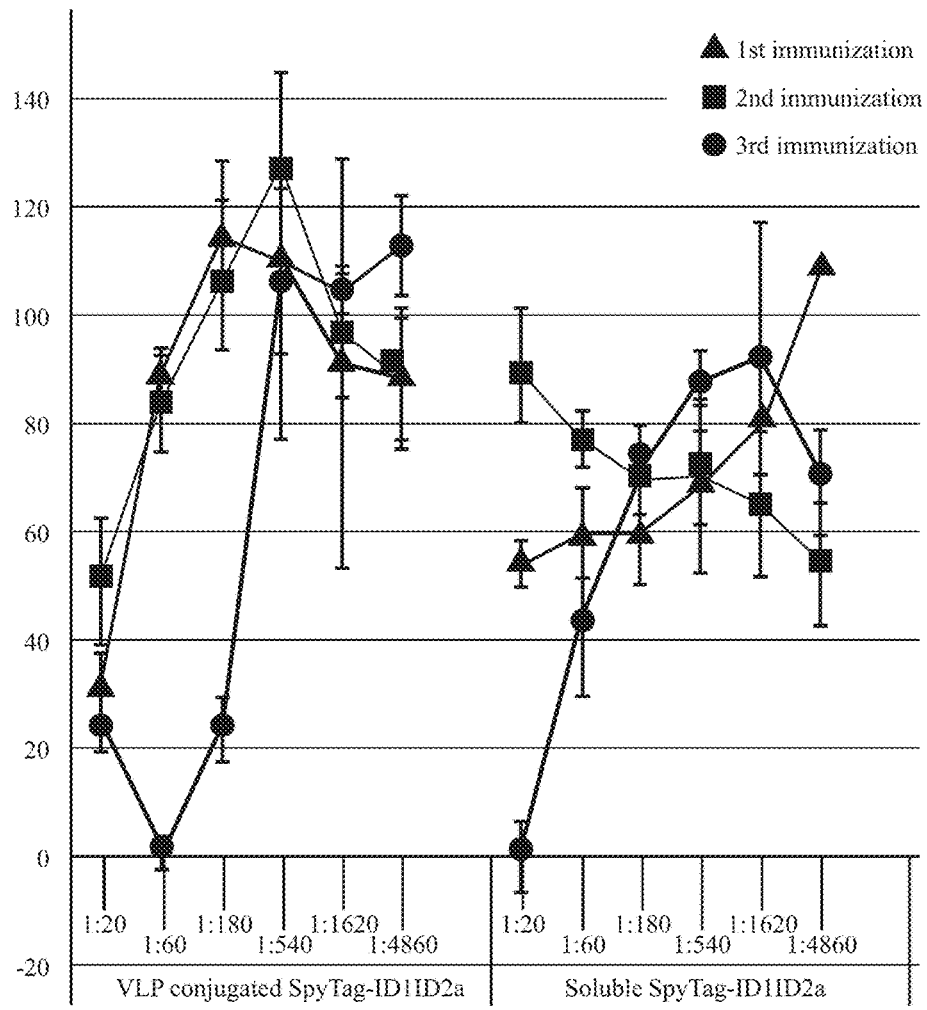
FIG. 25: Antigen-specific qualitative testing of induced immune responses: Testing of the SpyCatcher-VLP platform to induce VAR2CSA specific antibodies The parasite binding-inhibition assay show normalized parasite binding after incubation with pooled anti-sera (3-fold dilutions starting from 1:20) from mice (n=5) vaccinated with SpyTag-ID1ID2a (SEQ ID NO: 82) conjugated to SpyCatcher-VLPs (SEQ ID NO: 76) or soluble SpyTag-ID1ID2a (SEQ ID NO: 82) mixed with unmodified AP205 VLPs (SEQ ID NO: 58). Parasite binding results are shown after first (▲), second (■) and third (●) immunization. The assay show that anti-sera from mice immunized with VLP-conjugated SpyTag-ID1ID2a (SEQ ID NO: 82) has a greater binding-inhibition capacity compared to anti-sera from mice immunized with soluble SpyTag-ID1ID2a (SEQ ID NO: 82).

Specifically, the functional antibody response was assessed by measuring the capacity of mouse anti-sera to inhibit binding between native VAR2CSA expressed on parasitized erythrocytes and CSA in a static binding-assay. *P. falciparum* (FCR3 genotype)-infected red blood cells, expressing the native VAR2CSA, were first incubated with mouse anti-serum (3 fold dilution series, starting from 1:20) and then allowed to incubate on decorin coated plates for 90 min. Unbound IE were washed away and the remaining IEs were quantified. Normalized parasite binding after incubation with pooled anti-sera from mice (n=5) vaccinated with SpyTag-ID1ID2a (SEQ ID NO: 82) conjugated to SpyCatcher-VLPs (SEQ ID NO: 76) or soluble SpyTag-ID1ID2a (SEQ ID NO: 82) mixed with unmodified AP205 VLPs (SEQ ID NO: 58) are shown after first (▲), second (■) and third (●) immunization (FIG. 25). The assay show that anti-sera from mice immunized with VLP-conjugated SpyTag-ID1ID2a (SEQ ID NO: 82) has a greater binding-inhibition capacity compared to anti-sera from mice immunized with soluble SpyTag-ID1ID2a (SEQ ID NO: 82).

Testing of the VLP:SpyTag and SpyCatcher:VLP Platform, Respectively, to Induce Humoral Immunity Against Self-Antigens.

To demonstrate the capacity of the VLP:SpyTag and the SpyCatcher:VLP platform, respectively, to break immune tolerance to self-antigens, associated with both cardiovascular disease (PCSK9), immune-inflammatory disease (IL-5) and cancer (Her2/Survivin), we genetically fuse the self-antigens to a SpyCatcher or SpyTag and couple them onto SpyTag or Spycatcher VLPs, respectively, as previously described. In some cases (IL-5, Survivin, CTLA-4 and PD-L1) we at first use the mouse gene homologues for the immunization of mice. Specifically, our working procedure is to firstly couple HER2 (SpyCatcher:Her2-ECD|23-686|), Survivin, IL-5(SpyCatcher:IL-5 (C63T/C105T)) and PCSK9(PCSK9|31-692|SpyCatcher-HIS) to the SpyTaggedVLPs or, similarly, couple the (SpyTag:Her2-ECD|23-686|), Survivin, IL-5(SpyTag:IL-5 (C63T/C105T) to the SpyCatcher:VLPs. Then we use the antigen coupled VLPs to immunize mice, and measure seroconversion of the animals in group a) mice immunized with conjugated VLPs and b) mice immunized with the non-coupled soluble antigen and unmodified (i.e. with no SpyTag/SpyCatcher) VLPs. The antigen-specific immunoglobulin titer will be estimated in a 3 fold dilution series of the sera. A positive seroconversion is defined as ELISA OD measurements above 2× standard deviation of a mock immunized animal. Serum conversion and induction of specific antibodies to HER2 and Survivin is further confirmed by western blotting using the sera and cell lysates from different cancerous cell lines (e.g. melanoma, prostate, breast and lung cancer).

This experiment was performed with IL-5, CTLA-4 and PD-L1.

Figure 21:
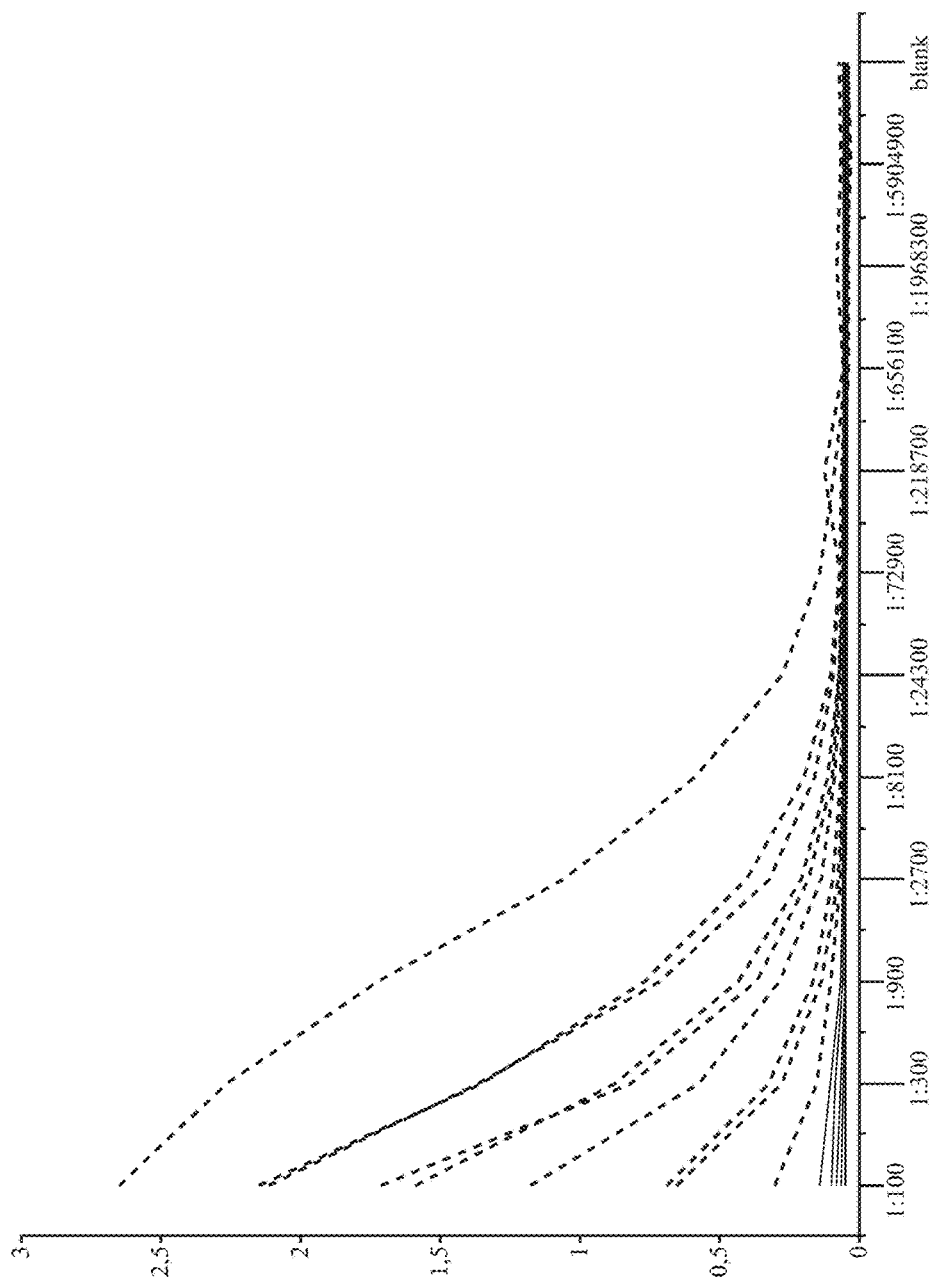
FIG. 21: Breakage of self-tolerance as a result of VLP display. The figure shows the Ig response against the self-antigen IL-5 (SEQ ID NO: 19) five months after a prime-boost-boost immunization regimen. The dashed line represents individual mice immunized with SpyTag-AP205-SpyTag (SEQ ID NO: 71) coupled to the IL-5 SpyCatcher-(self)-antigen (SEQ ID NO: 19). The gray line represents individual mice immunized with soluble SpyCatcher-antigen (SEQ ID NO: 19) and AP205 (SEQ ID NO: 58), which is unable to bind the spycatcher-antigen. Both vaccines were formulated in aluminum hydroxide gel. X-axis: serum dilution; Y-axis: OD490 nm.

The Ig response against the self-antigen IL-5 (SEQ ID NO: 19) was analysed five months after a prime-boost-boost immunization regimen. Individual mice were immunized with SpyTag-AP205-SpyTag (SEQ ID NO: 71) coupled to the IL-5 SpyCatcher-(self)-antigen (SEQ ID NO: 19) or with soluble SpyCatcher-antigen (SEQ ID NO: 19) and AP205 (SEQ ID NO: 58), which is unable to bind the SpyCatcher-antigen. Both vaccines were formulated in aluminum hydroxide gel. Immunization of mice with VLP-displayed self-antigen (SEQ ID NO: 19) resulted in breakage of immune tolerance and induction of antigen specific antibodies, whereas immunization with the (non-displayed) soluble self-antigen (SEQ ID NO: 19) did not induce antigen specific antibodies (FIG. 21).

Figure 22:
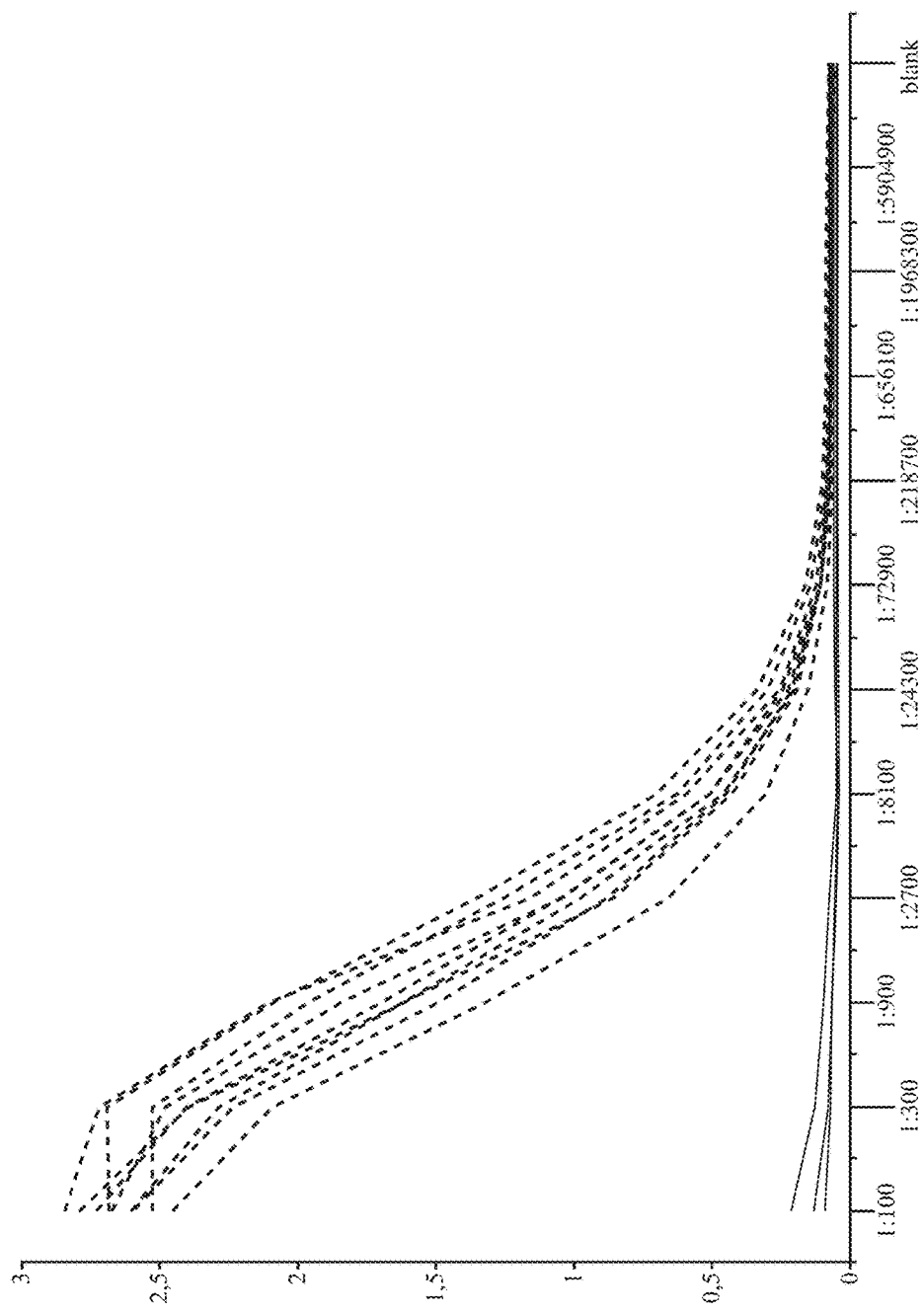
FIG. 22: The figure shows the Ig response against the self-antigen CTLA-4 (SEQ ID NO: 11) two weeks after a prime-boost immunization regimen. The dashed line represents individual mice immunized with SpyTag-AP205-SpyTag (SEQ ID NO: 71) coupled to the CTLA-4 self-antigen (SEQ ID NO: 11). The gray line represents individual mice immunized with soluble SpyCatcher-antigen (SEQ ID NO: 11) and AP205 (SEQ ID NO: 58), which is unable to bind the spycatcher-antigne. Both vaccines were formulated in aluminum hydroxide gel, X-axis: serum dilution; Y-axis: OD490 nm.

The Ig response against the self-antigen CTLA-4 (SEQ ID NO: 11) two weeks after a prime-boost immunization regimen was analysed in individual mice immunized with SpyTag-AP205-SpyTag (SEQ ID NO: 71) coupled to the CTLA-4 self-antigen (SEQ ID NO: 11) or with soluble SpyCatcher-antigen (SEQ ID NO: 11) and AP205 (SEQ ID NO: 58), which is unable to bind the SpyCatcher-antigen. Both vaccines were formulated in aluminum hydroxide get Immunization of mice with VLP-displayed self-antigen (SEQ ID NO: 11) resulted in breakage of immune tolerance and induction of antigen specific antibodies, whereas immunization with the (non-displayed) soluble self-antigen (SEQ ID NO: 11) does not induce antigen specific antibodies (FIG. 22).

Figure 23:
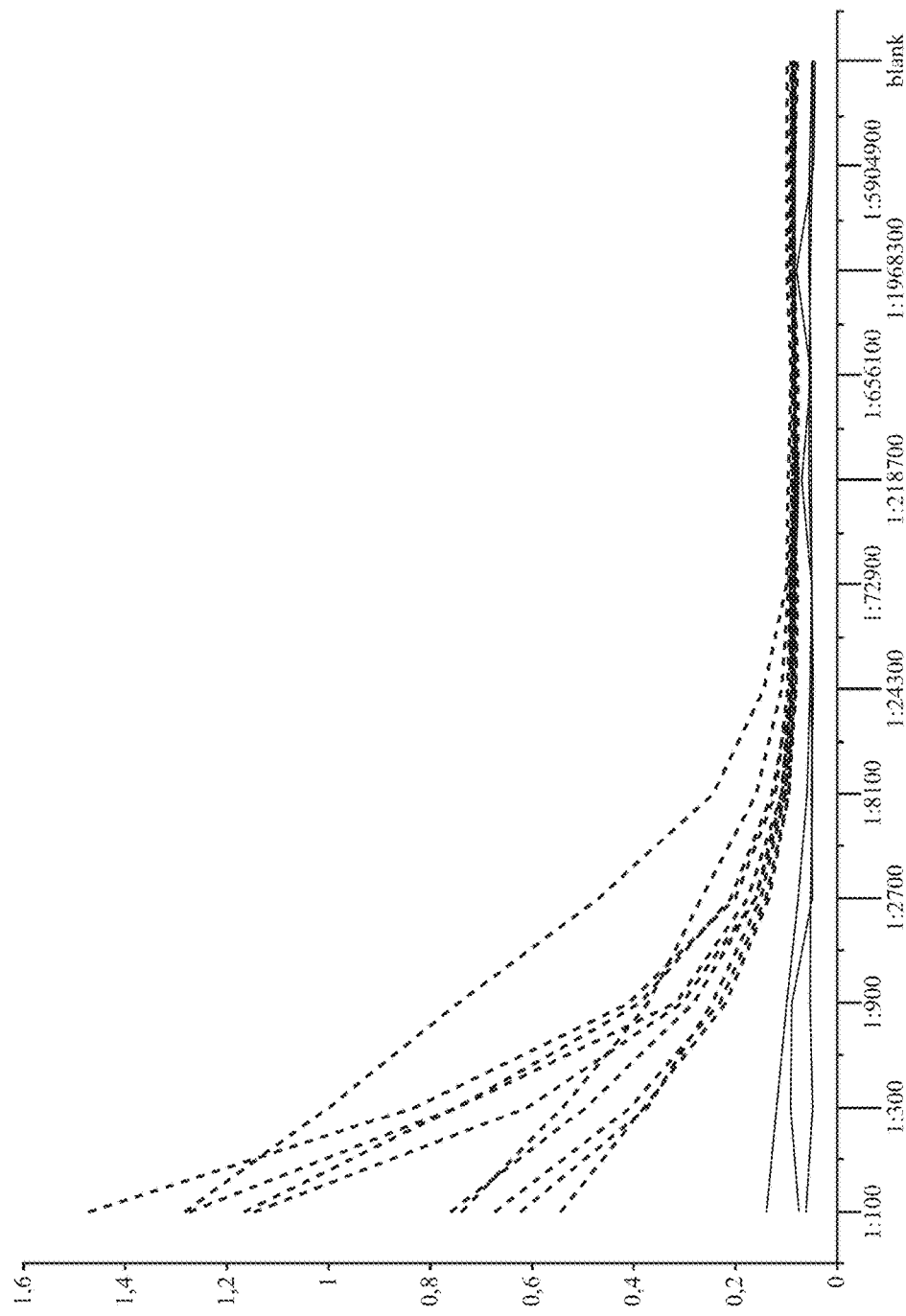
FIG. 23: Breakage of self-tolerance as a result of VLP display. The figure shows the Ig response against the self-antigen PD-L1 (SEQ ID NO: 9) two weeks after a prime-boost immunization regimen. The dashed line represents individual mice immunized with SpyTag-AP205-SpyTag (SEQ ID NO: 71) coupled to the PD-L1 self-antigen (SEQ ID NO: 9). The gray line represents individual mice immunized with soluble self-antigen (SEQ ID NO: 9) and AP205 (SEQ ID NO: 58), which is unable to bind the SpyCatcher-antigen. Both vaccines were formulated in aluminum hydroxide gel. X-axis: serum dilution; Y-axis: OD490 nm.

The Ig response against the self-antigen PD-L1 (SEQ ID NO: 9) two weeks after a prime-boost immunization regimen in individual mice immunized with SpyTag-AP205-SpyTag (SEQ ID NO. 71) coupled to the PD-L1 self-antigen (SEQ ID NO: 9) or with soluble self-antigen (SEQ ID NO: 9) and AP205 (SEQ ID NO: 58), which is unable to bind the SpyCatcher-antigen. Both vaccines were formulated in aluminum hydroxide gel. Immunization of mice with VLP-displayed self-antigen (SEQ ID NO: 9) resulted in breakage of immune tolerance and induction of antigen specific antibodies, whereas immunization with the (non-displayed) soluble self-antigen (SEQ ID NO: 9) does not induce antigen specific antibodies (FIG. 23).

Testing of the Functionality of the VLP-Presented Antigen Vaccine

Figure 24:
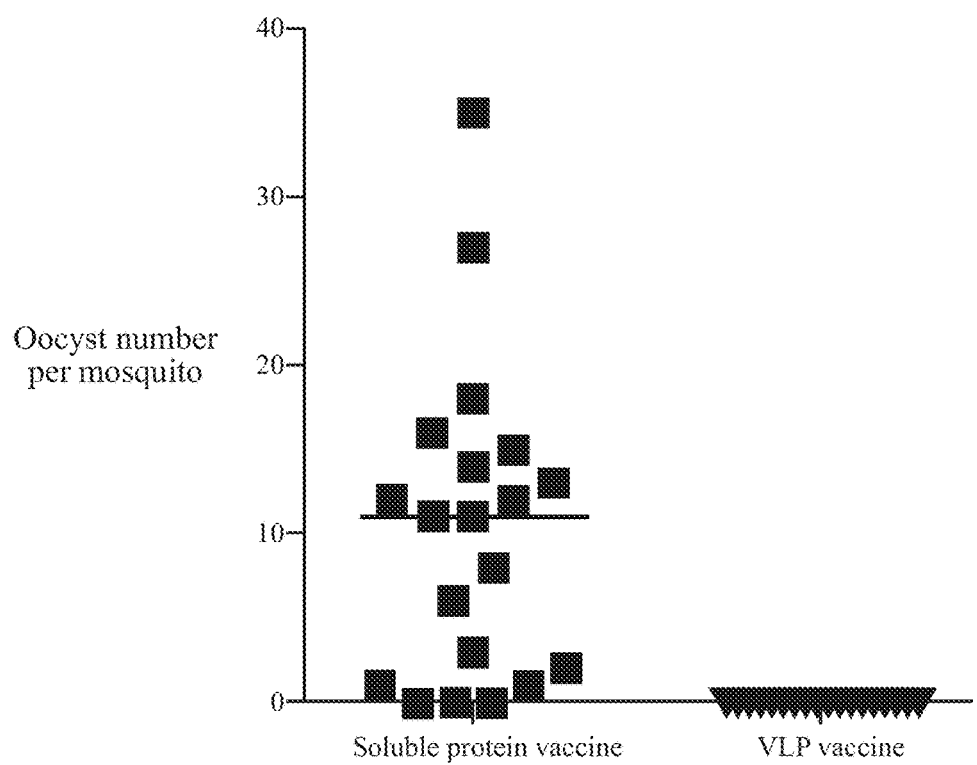
FIG. 24: Immunization with a Pfs25 VLP vaccine resulted in induction of functional antibodies which were able to block the transmission of *Plasmodium falciparum* parasites in vitro. Mice were immunized two times with 2.5 ug of either A) spycatcher-Pfs25 antigen (SEQ ID NO: 27) displayed on the SpyTag-AP205-SpyT (SEQ ID NO: 71) VLP or B) soluble spycatcher-Pfs25 antigen (SEQ ID NO: 27) mixed with the AP205 VLP (SEQ ID NO: 58), which is unable to bind/display the antigen. Both vaccines were formulated with aluminum hydroxide gel. Transmission-blocking efficacy of antibodies was evaluated by standard mosquito membrane feeding assay (SMFA) using purified IgG from immune sera.

Immunization with a Pfs25 VLP vaccine resulted in induction of functional antibodies which were able to block the transmission of *Plasmodium falciparum* parasites in vitro. Mice were immunized two times with 2.5 ug of either A) spycatcher-Pfs25 antigen (SEQ ID NO: 27) displayed on the SpyTag-AP205-SpyT (SEQ ID NO: 71) VLP or B) soluble spycatcher-Pfs25 antigen (SEQ ID NO: 27) mixed with the AP205 VLP (SEQ ID NO: 58), which is unable to bind/display the antigen. Both vaccines were formulated with aluminum hydroxide gel Transmission-blocking efficacy of antibodies was evaluated by standard mosquito membrane feeding assay (SMFA) using purified IgG from immune sera. Results show that antibodies induced in mice immunized with VLP-displayed Pfs25 (VLP vaccine) had ~100% percent transmission-blocking activity when tested in the SMFA in vitro assay (FIG. 24).

Testing of the VLP:SpyTag and the SpyCatcher:VLP Platform to Induce Cancer Inhibitory Antibodies.

Standard animal models are established to study the effect of immunizing animals with tumor antigens on the growth of an established subcutaneous tumor, 100,000 tumor cells expressing HER2 and/or Survivin are injected into the left flank. This is done in both vaccinated animals and mock immunized animals, to study the prophylactic effect of the vaccine. Tumor growth is monitored by measuring the size of the growing tumor as well as by scanning of the animal when using luciferase transfected tumor cell lines. Alternatively, the therapeutic effect of the vaccine is determined by immunizing animals with established tumors and monitoring tumor regression/progression by size measurements and/or by fluorescent scannings.

Testing of the VLP:SpyTag and the SpyCatcher:VLP Platform to Induce Anti-PCSK9 Antibodies Capable of Lowering Plasma/Serum Cholesterol Levels.

The goal of making a VLP-based vaccine based on the PCSK9 antigen is to induce a humoral response capable of lowering blood cholesterol. Therefore, to test the VLP:SpyTag platform or the SpyCatcher:VLP platform, we measure cholesterol levels in plasma and serum samples obtained from VLP-PCSK9 immunized mice and compare against the levels measured in mice immunized with the non-coupled PCSK9 antigen, as previously described in the present invention. Cholesterol levels in plasma and serum samples are measured using a WAKO Cholesterol E Assay kit (Cat# 439-17501) following the manufacturers' instructions. Dilutions of cholesterol standard or test plasma/serum samples (4 μl volume) are added to wells of a 96-well plate and 196 μl of prepared cholesterol reagent added. The plate is incubated for 5 minutes at 37° C. and the absorbance of the developed color read at 600 nm within 30 minutes.

Sequences

TABLE 6

Overview of the sequences disclosed in the present invention

| SEQ ID NO: protein (DNA) | | |
|---|---|---|
| | | Antigens: |
| 18 | A1 | >SpyCatcher-Her2-ECD\|23-686 (*Homo Sapiens*) |
| 19 | A2 | >SpyCateher-IL-5(C63T/C105T) (*Mus musculus*)) |
| 20 (29) | A3 | >PCSK9\|31-692\|:SpyCatcher:HIS (*Homo Sapiens*) |
| 21 (30) | A4 | >SpyCatcher-ID1ID2a-HIS (*Plasmodium falciparum*) |
| 22 (31) | A5 | >SpyCatcher-RO-HIS (*Plasmodium falciparum*) |
| 23 (32) | A6 | >HIS-RO-SpyCatcher (*Plasmodium falciparum*) |
| 24 (33) | A7 | >HIS-GMZ2ggsSpyCatcher (*Plasmodium falciparum*) |
| 25 (34) | A8 | >HIS-GMZ2T:ggsSpyCatcher (*Plasmodium falciparum*) |
| 26 (35) | A9 | >SpyCatcher-PfRH5-HIS (*Plasmodium falciparum*) |
| 27 | A10 | >SpyCatcher-Pfs25-HIS (*Plasmodium falciparum*) |
| 28 | A11 | >HIS-PfCSP(aa92-397)-SpyCatcher (*Plasmodium falciparum*) |
| 40 | A12 | >Survivin:SpyCatcher (*Homo Sapiens*) |
| 41 | A13 | >-SpyCatcher:Survivin (*Homo Sapiens*) |
| 42 | A14 | >Survivin(F101A/L102A): SpyCatcher (*Homo Sapiens*) |
| 43 | A15 | > SpyCatcher:Survivin(F101A/L102A) (*Homo Sapiens*) |
| 44 (48) | A16 | > SpyCatcher:Survivin(F101A/L102A) (*Mus musculus*)) |
| 45 (49) | A17 | >Survivin (F101A/L102A): SpyCatcher (*Mus musculus*)) |

TABLE 6-continued

Overview of the sequences disclosed in the present invention

| SEQ ID NO: protein (DNA) | | |
|---|---|---|
| 46 (50) | A18 | >SpyCatcher:Survivin (*Mus Musculus*) |
| 47 (51) | A19 | >Survivin:SpyCatcher (*Mus Musculus*) |
| 52 (53) | A20 | >SpyCatcher:CIDR1a-HIS |
| 84 (85) | A21 | SpyCatcher-Ag85A (*Mycobacterium tuberculosis*) |
| 86 (87) | A22 | SpyCatcher-ggs-survivin (*Homo Sapiens*) |
| 1 (2) | | L2(aa11-88 x5)-ggs-spycatcher (Human papillomavirus) |
| 3 (4) | | SpyCatcher-R0.Pf6C (*Plasmodium falciparum*) |
| 5 (6) | | SpyCatcher Pf6C (*Plasmodium falciparum*) |
| 7 (8) | | SpyTag-DBL1-ID2a (*Plasmodium falciparum*) |
| 9 (10) | | PDL1-SpyTag (*musculus*) |
| 11 (12) | | CTLA-4-SpyTag (*Mus musculus*)) |
| 14 (15) | | SpyTag-L-DER P2 (*Dermatophagoides pteronyssinus*) |
| 13 | | AMA1-SpyTag |
| 88 (89) | | Mini-HA-stem-Spytag |
| 90 | | Infectious hematopoietic necrosis virus (IHNV) G-protein-Spytag |
| 91 | | SpyTag-IHNV G-protein Misc. |
| 36 (39) | | SpyTag amino acid sequence |
| 37 (54) | | SpyCatcher |
| 38 | | The β-strand of CnaB2 (KTag) |
| 55 | | SpyLigase |
| 56 | | isopeptide Spy0128 |
| 57 | | Split-Spy0128 |
| 58 | | AP205 |
| 59 | | PhageFr |
| 60 | | SpyCatcherΔN |
| 61 | | SpyCatcherΔNC |
| 62 (63) | | Spy-AP205 |
| 64 (65) | | AP205-spy |
| 66 (67) | | Spy-Phage fr |
| 68 | | Ktag-AP205 |
| 69 | | AP205-Ktag |
| 70 | | Ktag-Phage fr |
| 71 (72) | | Spy-AP205-Spy |
| 74 (73) | | AP205-ggsg-Spycatcher |
| 76 (75) | | SpyCatcher-ggsgs-AP205 |
| 78 (77) | | SpyCatcher-ggsgs-Phage fr |
| 79 | | SpyTag-Her2-ECD|23-686 |
| 80 | | SpyTag-IL-5(C63T/C105T) |
| 81 | | PCSK9|31-692|:Spytag |
| 82 | | SpyTag-ID1ID2a-HIS |
| 83 | | Short flexible linker |
| 92 (93) | | SpyTag-IHNV G-protein |
| 94 (95) | | mSA-AP205 DNA |

>SEQ ID NO: 1 L2(aa11-88 x5)-ggs-spycatcher
MKRASATQLYKTCKQAGTCPPDIIPKVEGKTIADQILQYGSMGVFFGG
LGIGTGSGTGGRTGYIPLGTRPPTATDTLAKRASVIDLYKTCKQSGTC
PPDVVPKVEGTTLADKILQWSSLGIFLGGLGIGTGSGTGGRTGYIPLG
GRSNTVVDVGPKRASATQLYQTCKLIGTCPPDVIPKVEHNTIADQILK
WGSLGVFFGGLGIGTGSGTGGRTGYVPLGTSAKPSITSGPKRAAPKDI
YPSCKISNTCPPDIQNKIEHTTIADKILQYGSLGVFLGGLGIGTARGS
GGRIGYTPLGEGGGVRVATRPKRDSVTHIYQTCKQAGTCPPDVINKVE

QTTVADNILKYGSAGVFFGGLGISTGRGTGGATGYVPLGEGPGVRVGG

TPGGSGAMVDTLSGLSSEQGQSGDMTIEEDSATHIKFSKRDEDGKELA

GATMELRDSSGKTISTWISDGQVKDFYLYPGKYTFVETAAPDGYEVAT

AITFTVNEQGQVTVNGKATKGDAHI

>SEQ ID NO: 2 L2(aa11-88 x5)-ggs-spycatcher DNA
ATGAAACGTGCAAGCGCAACCCAGCTGTATAAAACCTGTAAACAGGCA

GGCACCTGTCCGCCTGATATCATTCCGAAAGTTGAAGGTAAAACCATT

GCCGATCAGATTCTGCAGTATGGTAGCATGGGCGTGTTTTTTGGTGGT

CTGGGTATTGGCACCGGTAGCGGCACAGGTGGACGTACCGGTTACATT

CCGCTGGGCACCCGTCCGCCTACCGCAACCGATACCCTGGCAAAACGT

GCCAGCGTTACCGATCTGTACAAAACATGCAAACAGAGCGGAACATGT

CCTCCGGATGTTGTTCCTAAAGTGGAAGGCACCACCCTGGCAGATAAA

ATCCTGCAGTGGTCAAGCCTGGGTATTTTCCTGGGTGGCTTAGGCATA

GGTACAGGTAGTGGTACAGGCGGTCGCACAGGCTATATCCCGCTGGGT

GGTCGTAGCAATACCGTTGTTGATGTTGGTCCGAAACGTGCATCAGCC

ACACAGCTGTATCAGACCTGCAAACTGACCGGTACGTGCCCACCTGAT

GTTATCCCGAAAGTGGAACATAATACAATTGCAGACCAGATTCTGAAA

TGGGGTTCACTGGGCGTATTCTTCGGAGGCCTGGGCATCGGAACCGGT

TCAGGTACGGGTGGCCGTACCGGCTATGTGCCTCTGGGTACAAGCGCA

AAACCGAGCATTACCAGCGGTCCTAAACGCGCAGCACCGAAAGATATT

TATCCGAGCTGTAAAATTAGCAATACCTGCCCTCCGGATATCCAGAAC

AAAATTGAACATACCACCATTGCCGACAAAATCTTACAGTACGGTTCT

CTGGGTGTGTTTCTGGGAGGTTTAGGTATCGGTACGGCACGTGGTAGC

GGTGGTCGCATTGGTTATACACCGCTGGGTGAAGGTGGTGGTGTTCGT

GTTGCAACCCGTCCTAAACGTGATAGCGTTACCCATATTTATCAGACG

TGTAAACAAGCAGGTACTTGTCCACCAGATGTGATTAACAAAGTGGAA

CAGACAACCGTTGCGGATAACATTCTGAAATATGGTAGTGCCGGTGTG

TTTTTTGGCGGACTGGGCATTTCAACCGGTCGTGGTACGGGTGGTGCA

ACCGGTTACGTGCCTCTGGGCGAAGGTCCGGGTGTGCGTGTGGGTGGT

ACACCGGGTGGTAGCGGTGCAATGGTTGATACCCTGAGCGGTCTGAGC

AGCGAACAGGGTCAGAGCGGTGATATGACCATTGAAGAAGATAGCGCA

ACCCACATCAAATTCAGCAAACGTGATGAAGATGGTAAAGAACTGGCA

GGCGCAACAATGGAACTGCGTGATAGCAGCGGTAAAACCATTAGCACC

TGGATTAGTGATGGTCAGGTGAAAGATTTTTATCTGTACCCTGGCAAA

TACACCTTTGTTGAAACCGCAGCACCGGATGGTTATGAAGTTGCAACC

GCAATTACCTTTACCGTTAATGAACAGGGCCAGGTTACCGTGAATGGT

AAAGCAACCAAAGGTGATGCACATATTtaa

>SEQ ID NO: 3 Spycatcher-R0.Pf6C
GAMVDTLSGLSSEQGQSGDMTIEEDSATHIKFSKRDEDGKELAGATME

LIRDSSGKTISTWISDGQVKDFYLYPGKYTFVETAAPDGYEVATAITF

TVNEQGQVTVNGKATKGDAHIGGSRSTSENRNKRIGGPKLRGNVTSNI

KFPSDNKGKIIRGSNIDKLNKNSEDVLEQSEKSLVSENVPSGLDIDDI

PKESIFIQEMEGQTHSELNPETSEFISKOLNNNGSKNESSDIISENNK

SNKVQNHFESLSDLELLENSSQDNLDKDTISTEPFPNQKHKDLQQDLN

DEPLEPFPTQIHKDYKEKNLINEEDSEPFPRCKFIKKVDNIANEEKNW

HENGSANGNQGSLKLKSFDEHLKDEKIENERNHENLSIPNDPIEQUAC

PEQETNIQEQLYNEKQNVEEKQNSQIPSLDLKEPTNEDILPNHNPLEN

IKQSESEINHVQDHALPKENIIDKLDNCKEHIDQSQHNINVLQENNIN

NHQLEPQEKPNIESFEPKNIDSEIILPENVETEEIIDDVPSPKHSNHE

TFEEETSESEHEEAVSEKNAHETVEHEETVSQESNPEKADNDGNVSQN

SNNELNENEFVESEKSEHEARSEKKVIHGCNFSSNVSSKHTFTDSLDI

SLVDDSAHISCNVHLSEPKYNHLVGLNCPGDIIPDCFFQVYQPESEEL

EPSNIVYLDSQINIGDIEYYEDAEGDDKIKLFGIVGSIPKTTSFTCIC

KKDKKSAYMTVTIDSA

>SEQ ID NO: 4 Spycatcher-RO.Pf6C DNA
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATTGGTGGTAGCAGATCCACAAGTGAGAATAGAAATAAA

CGAATCGGGGGTCCTAAATTAAGGGGTAATGTTACAAGTAATATAAAG

TTCCCATCAGATAACAAAGGTAAAATTATAAGAGGTTCGAATGATAAA

CTTAATAAAAACTCTGAAGATGTTTTAGAACAAAGCGAAAAATCGCTT

GTTTCAGAAAATGTTCCTAGTGGATTAGATATAGATGATATCCCTAAA

GAATCTATTTTTATTCAAGAAGATCAAGAAGGTCAAACTCATTCTGAA

TTAAATCCTGAAACATCAGAACATAGTAAAGATTTAAATAATAATGGT

TCAAAAAATGAATCTAGTGATATTATTTCAGAAAATAATAAATCAAAT

AAAGTACAAAATCATTTTGAATCATTATCAGATTTAGAATTACTTGAA

AATTCCTCACAAGATAATTTAGACAAAGATACAATTTCAACAGAACCT

TTTCCTAATCAAAAACATAAAGACTTACAACAAGATTTAAATGATGAA

CCTTTAGAACCCTTTCCTACACAAATACATAAAGATTATAAAGAAAAA

AATTTAATAAATGAAGAAGATTCAGAACCATTTCCCAGACAAAAGCAT

AAAAAGGTAGACAATCATAATGAAGAAAAAAACGTATTTCATGAAAAT

GGTTCTGCAAATGGTAATCAAGGAAGTTTGAAACTTAAATCATTCGAT

GAACATTTAAAAGATGAAAAAATAGAAAATGAACCACTTGTTCATGAA

AATTTATCCATACCAAATGATCCAATAGAACAAATATTTAATCAACCT

GAACAAGAAACAAATATCCAGGAACAATTGTATAATGAAAAACAAAAT

GTTGAAGAAAAACAAAATTCTCAAATACCTTCGTTAGATTTAAAAGAA

CCAACAAATGAAGATATTTTACCAAATCATAATCCATTAGAAAATATA

AAACAAAGTGAATCAGAAATAAATCATGTACAAGATCATGCGCTACCA

AAAGAGAATATAATAGACAAACTTGATAATCAAAAAGAACACATCGAT

CAATCACAACATAATATAAATGTATTACAAGAAAATAACATAAACAAT

CACCAATTAGAACCTCAAGAGAAACCTAATATTGAATCGTTTGAACCT

AAAAAATATAGATTCAGAAATTATTCTTCCTGAAAATGTTGAAACAGAA

GAAATAATAGATGATGTGCCTTCCCCTAAACATTCTAACCATGAAACA

TTTGAAGAAGAAACAAGTGAATCTGAACATGAAGAAGCCGTATCTGAA

AAAAATGCCCACGAAACTGTCGAACATGAAGAAACTGTGTCTCAAGAA

AGCAATCCTGAAAAAGCTGATAATGATGGAAATGTATCTCAAAACAGC

AACAACGAATTAAATGAAAATGAATTCGTTGAATCGGAAAAAAGCGAG

CATGAAGCAAGATCCGAAAAAAAAGTCATACACGGATGTAACTTCTCT

TCAAATGTTAGTTCTAAACATACTTTTACAGATAGTTTAGATATTTCT

TTAGTTGATGATAGTGCACATATTTCATGTAACGTACATTTGTCTGAA

CCAAAATATAATCATTTGGTAGGTTTAAATTGTCCTGGTGATATTATA

CCAGATTGCTTTTTTCAAGTATATCAACCTGAATCAGAAGAACTTGAA

CCATCCAACATTGTTTATTTAGATTCACAAATAAATATAGGAGATATT

GAATATTATGAAGATGCTGAAGGAGATGATAAAATTAAATTATTTGGT

ATAGTTGGAAGTATACCAAAAACGACATCTTTTACTTGTATATGTAAG

AAGGATAAAAAAAGTGCTTATATGACAGTTACTATAGATTCAGCA

>SEQ ID NO: 5 SpyCatcher-Pf6C
GAMVDTLSGLSSEQGQSGDMTIEEDSATHIKFSKRDEDGKELAGATME

LRDSSGKTISTWISDGQVKDFYLYPGKYTFVETAAPDGYEVATAITFT

VNEQGQVTVNGKATKGDAHIGGSRSEKKVIHGCNFSSNVSSKHTFTDS

LDISLVDDSAHISCNVHLSEPKYNHLVGLNCPGDIIPDCFFQVYQPES

EELEPSNIVYLDSQINIGDIEYYEDAEGDDKIKLFGIVGSIPKTTSFT

CICMDKKSAYMTVTIDSARS

>SEQ ID NO: 6 SpyCatcher-Pf6C DNA
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATTGGTGGTAGCAGATCCGAAAAAAAAGTCATACACGGA

TGTAACTTCTCTTCAAATGTTAGTTCTAAACATACTTTTACAGATAGT

TTAGATATTTCTTTAGTTGATGATAGTGCACATATTTCATGTAACGTA

CATTTGTCTGAACCAAAATATAATCATTTGGTAGGTTTAAATTGTCCT

GGTGATATTATACCAGATTGCTTTTTTCAAGTATATCAACCTGAATCA

GAAGAACTTGAACCATCCAACATTGTTTATTTAGATTCACAAATAAAT

ATAGGAGATATTGAATATTATGAAGATGCTGAAGGAGATGATAAAATT

AAATTATTTGGTATAGTTGGAAGTATACCAAAAACGACATCTTTTACT

```
TGTATATGTAAGAAGGATAAAAAAAGTGCTTATATGACAGTTACTATA

GATTCAGCAAGATCTtaa

>SEQ ID NO: 7 SpyTag-DBL1-ID2a
MAHIVMVDAYKPTKNKIEEYLGAKSDDSKIDELLKADPSEVEYYRSGG

DGDYLKNNICKITVNHSDSGKYDPCEKKLPPYDDNDQWKCQQNSSDGS

GKPENICVPPRRERLCTYNLENLKFDKIRDNNAFLADVLLTARNEGEK

IVQNHPDINSSNVCNALERSFADLADIIRGTDQWKGTNSNLEKNLKQM

FAKIRENDKVLQDKYPKDQKYTKLREAWWNANRQKVWEVITCGARSND

LLIKRGWRTSGKSDRKKNFELCRKCGHYEKEVPTKLDWPQFLRWLTEW

IEDFYREKQNLIDDMERHREECTREDHKSKEGTSYCSTCKDKCKKYCE

CVKKWKTEWENQENKYKDLYEQNKNKTSQKNTSRYDDYVKDFFEKLEA

NYSSLENYIKGDPYFAEYATKLSFILNPSDANNPSGETANHNDEACNC

NESGISSVGQAQTSGPSSNKTCITHSSIKTNKKKECKDVKLGVRENDK

DLKICVIEDTSLSGVDNCCCQDLLGIWENCSDNKRGSSSNDSCDNKNQ

DECQKKLEKVFASLTNGYKCDKCKSGTSRSKKKWIWKKSSGNEEGLQE

EYANTIGLPPRTQSLYLGNLPKLENVCEDVKIDINFDTKEKFLAGCLI

VSFHEGKNLKKRYPQNKNSGNKENLCKALEYSFADYGDLIKGTSIWDN

EYTKDLELNLQNNFGKLFGKYIKKNNTAECIDTSYSSIDELRESWWNT

NKKYIWTANIKHGAEMNITTCNADGSVTGSGSSCDDIPTIDLIPQYLR

FLQEWVENFCEQRQAKVKDVITNCKSCKESGNKCKTECKTKCKDECEK

YKKHEACGTAGGGIGTAGSPWSKRWDQIYKRYSKHIEDAKRNRKAGTK

NCGTSSTTNAAASTDENKCVQSDIDSFFMALIDIGLTTPSSYLSNVLD

DNICGADKAPWTTYTTYTTTEKCNKERDKSKSQSSDTLVVVNVPSPLG

NTPYRYKYACQCKIPTNEETCDDRKEYMNQWSCGSARTMKRGYKNDNY

ELCKYNGVDVKPTIVRSNSSKLD

>SEQ ID NO: 8 SpyTag-DBL1-ID2a DNA
atgGCTCACATCGTGATGGTGGACGCTTACAAGCCCACCAAGAACAAG

ATCGAGGAATATCTGGGAGCTAAGTCCGATGACAGCAAGATCGACGAA

CTGCTGAAGGCCGATCCTAGCGAAGTGGAGTACTACAGAAGCGGAGGC

GACGGCGACTACCTGAAGAACAACATCTGCAAGATCACCGTGAACCAC

AGCGATAGCGGCAAGTATGACCCCTGCGAGAAGAAGCTGCCCCCCTAC

GACGACAACGACCAGTGGAAGTGCCAGCAGAACAGCAGCGACGGCAGC

GGCAAGCCCGAGAACATCTGCGTGCCCCCCAGACGGGAGCGGCTGTGC

ACCTACAACCTGGAAAACCTGAAGTTCGACAAGATCCGGGACAACAAC

GCCTTCCTGGCCGACGTGCTGCTGACCGCCCGGAACGAGGGCGAGAAG

ATCGTGCAGAACCACCCCGACACCAACAGCAGCAACGTGTGCAACGCC

CTGGAACGGTCCTTCGCTGACCTGGCTGACATCATCCGGGGCACCGAT

CAGTGGAAGGGCACCAACTCCAATCTGGAAAAGAACCTGAAGCAGATG

TTCGCCAAGATCAGAGAAAACGACAAGGTGCTGCAGGACAAGTACCCC

AAGGACCAGAAGTACACCAAGCTGCGGGAGGCCTGGTGGAACGCCAAC

CGGCAGAAAGTGTGGGAAGTGATCACCTGTGGCGCCAGAAGCAACGAT

CTGCTGATCAAGCGGGGCTGGCGGACCAGCGGCAAGAGCGACCGGAAG

AAAAACTTCGAGCTGTGCCGGAAGTGCGGCCACTACGAGAAAGAGGTG

CCCACCAAGCTGGACTACGTGCCCCAGTTCCTGCGGTGGCTGACCGAG

TGGATCGAGGACTTCTACCGGGAGAAGCAGAACCTGATCGACGACATG

GAACGGCACCGGGAGGAATGCACCAGAGAGGACCACAAGAGCAAAGAG

GGCACCAGCTACTGCAGCACATGCAAGGACAAGTGCAAGAAATACTGC

GAGTGCGTGAAGAAATGGAAAACCGAGTGGGAGAACCAGGAAAACAAG

TACAAGGACCTGTACGAGCAGAACAAGAACAAGACCAGCCAGAAGAAC

ACCAGCAGATACGACGACTACGTGAAGGACTTCTTCGAGAAGCTGGAA

GCCAACTACAGCAGCCTGGAAAACTACATCAAGGGCGACCCCTATTTC

GCTGAGTACGCTACAAAACTGAGCTTCATCCTGAACCCCAGCGACGCC

AACAACCCCAGCGGCGAGCAGCCAACCACAACGACGAGGCCTGCAAC

TGCAACGAGAGCGGCATCAGCAGCGTGGGCCAGGCTCAGACATCCGGC

CCTAGCAGCAACAAGACCTGTATCACCCACAGCTCCATCAAGACCAAC

AAGAAAAAAGAATGCAAGGACGTGAAGCTGGGCGTGCGGGAGAACGAC

AAGGATCTGAAGATCTGCGTGATCGAGGACACCAGCCTGAGCGGCGTG

GACAACTGCTGCTGCCAGGATCTGCTGGGCATCCTGCAGGAAAACTGC

AGCGACAACAAGCGGGGCAGCAGCTCCAACGACAGCTGCGACAATAAG

AACCAGGACGAGTGCCAGAAAAAGCTGGAAAAGGTGTTCGCCAGCCTG

ACCAACGGCTACAAGTGCGATAAGTGCAAGAGCGGCACCTCCCGGTCC

AAGAAGAAGTGGATCTGGAAGAAGTCCAGCGGCAACGAGGAAGGCCTG

CAGGAAGAGTACGCCAACACCATCGGCCTGCCCCCCAGGACCCAGAGC

CTGTACCTGGGCAATCTGCCCAAACTGGAAAACGTGTGCGAGGATGTG

AAGGACATCAACTTCGACACCAAAGAGAAGTTTCTGGCCGGCTGCCTG

ATCGTGTCCTTCCACGAGGGCAAGAATCTGAAGAAGCGCTACCCCCAG

AATAAGAACAGCGGCAACAAAGAAAACCTGTGCAAGGCTCTGGAATAC

AGCTTCGCCGACTACGGCGACCTGATCAAGGGCACCTCCATCTGGGAC

AACGAGTACACAAAGGACCTGGAACTGAATCTGCAGAACAACTTCGGC

AAGCTGTTCGGCAAGTACATCAAGAAGAACAATACCGCCGAGCAGGAC

ACCTCCTACAGCTCCCTGGACGAGCTGCGCGAGTCTTGGTGGAATACC

AATAAGAAGTACATCTGGACCGCCATGAAGCACGGCGCCGAGATGAAC

ATCACCACCTGTAACGCCGACGGCTCCGTGACCGGCAGCGGCTCCAGC

TGCGACGACATCCCCACCATCGACCTGATCCCCCAGTACCTGAGATTT

CTGCAGGAATGGGTCGAGAACTTCTGCGAGCAGCGGCAGGCAAAGTG

AAGGACGTGATCACCAACTGCAAGAGCTGCAAAGAATCCGGCAACAAA

TGCAAGACCGAGTGCAAAACCAAGTGCAAGGATGAGTGCGAGAAGTAC

AAGAAGTTCATCGAGGCCTGCGGCACAGCCGGCGGAGGCATCGGAACA

GCCGGCAGCCCCTGGTCCAAGAGATGGGACCAGATCTACAAGCGGTAC

AGCAAGCACATCGAGGACGCCAAGCGGAACCGGAAGGCCGGCACCAAG

AACTGCGGCACCAGCTCCACCACCAACGCCGCTGCCAGCACCGACGAG

AATAAGTGCGTGCAGAGCGACATCGACAGCTTTTTCAAGCACCTGATC
```

```
GATATCGGCCTGACCACCCCCAGCAGCTACCTGAGCAACGTGCTGGAC

GACAACATCTGTGGCGCCGACAAGGCCCCCTGGACAACCTATACAACA

TACACTACAACCGAGAAGTGCAACAAAGAGCGGGACAAGAGCAAGAGC

CAGAGCAGCGACACCCTGGTGGTGGTGAACGTGCCCAGCCCCCTGGGC

AACACACCCTACCGGTACAAGTACGCCTGCCAGTGCAAGATCCCCACC

AACGAGGAAACATGCGACGACCGGAAGAATACATGAACCAGTGGTCC

TGCGGGAGCGCTCGGACCATGAAGAGAGGGTATAAGAACGATAACTAC

GAACTGTGCAAGTACAACGGCGTGGATGTGAAGCCCACCACCGTGCGG

AGCAACTCCAGCAAGCTGGAC

>SEQ ID NO: 9 PD-L1-SpyTag
FTITAPKDLYVVEYGSNVTMECRFPVERELDLLALVVYWEKEDEQVIQ

FVAGEEDLKPQHSNFRGRASLPKDQLLKGNAALQITGVKLQDAGVYCC

IISYGGADYKRITLKVNAPYRKINQRISVDPATSEHELICQAEGYPEA

EVIWINSDHQPVSGKRSVTTSRTEGMLLNVTSSLRVNATANDVFYCTF

WRSQPGQNHTAELIIPELPATHPPQNRTHGGSAHIVMVDAYKPTK

>SEQ ID NO: 10 PD-L1-SpyTag DNA
TTCACCATCACCGCTCCCAAGGACCTGTACGTGGTCGAGTACGGTTCC

AACGTGACAATGGAATGCCGTTTCCCCGTCGAGCGCGAGCTGGACCTG

TTGGCTTTGGTGGTGTACTGGGAGAAGGAAGATGAGCAAGTCATCCAG

TTCGTGGCTGGCGAAGAGGACCTGAAGCCCCAGCACTCCAACTTCCGT

GGTCGTGCTTCCCTGCCTAAGGACCAGCTGCTGAAGGGCAACGCTGCT

CTGCAGATCACCGACGTGAAGCTGCAGGACGCTGGTGTCTACTGCTGC

ATCATCTCCTACGGTGGTGCTGACTACAAGCGTATCACCCTCAAAGTG

AACGCTCCCTACCGCAAGATCAACCAGCGCATCTCCGTGGACCCCGCT

ACCTCTGAGCACGAGCTGATCTGCCAGGCTGAGGGTTACCCCGAGGCT

GAAGTGATCTGGACCAACTCCGACCACCAGCCCGTGTCCGGAAAGCGT

TCCGTGACCACCTCTCGTACCGAGGGCATGCTGCTGAACGTGACCTCC

TCCCTGCGTGTGAACGCTACCGCTAACGACGTGTTCTACTGCACCTTC

TGGCGTTCCCAGCCCGGCCAGAACCACACCGCTGAGCTGATCATCCCC

GAGCTGCCTGCTACCCACCCCCCTCAAAACCGTACCCACGGTGGTTCC

GCTCACATCGTGATGGTGGACGCTTACAAGCCCACTAAATAA

>SEQ ID NO: 11 CTLA-4-spyTag
EAIQVTQPSVVLASSHGVASFPCEYSPSHNTDEVRVTVLRQTNDQMTE

VCATTFTEKNTVGFLDYPFCSGTFNESRVNLTIQGLRAVDTGLYLCKV

ELMYPPPYFVGMGNGTQIYVIDPEPSPDSDGGSAHIVMVDAYKPTK

>SEQ ID NO: 12 CTLA-4-spyTag DNA
GAGGCTATCCAAGTGACCCAGCCCTCCGTGGTGCTGGCTTCCTCTCAC

GGTGTTGCCAGCTTCCCTTGCGAGTACTCCCCCTCCCACAACACCGAC

GAAGTGCGTGTGACCGTGCTGCGTCAGACCAACGACCAGATGACCGAA

GTGTGCGCTACCACCTTCACCGAGAAGAACACCGTCGGTTTCTTGGAC

TACCCCTTCTGCTCCGGCACCTTCAACGAGTCCCGTGTGAACCTGACC

ATCCAGGGCCTGCGTGCTGTGGACACCGGACTGTACCTGTGCAAGGTC

GAGCTGATGTACCCTCCCCCCTACTTCGTGGGCATGGGCAACGGCACC

CAGATCTACGTGATCGACCCCGAGCCTTCCCCCGACTCTGACGGTGGT

TCTGCTCACATCGTGATGGTGGACGCTTACAAGCCCACTAAATAA

>SEQ ID NO: 13 AMA1-SpyTag
QNYWEHPYQNSDVYRPINEHREHPKEYEYPLHQEHTYQQEDSGEDENT

LQHAYPIDHEGAEPAPQEQNLFSSIEIVERSNYMGNPWTEYMAKYDIE

EVHGSGIRVDLGEDAEVAGTQYRLPSGKCPVFGKGIIIENSNTTFLTP

VATGNQYLKDGGFAFPPTEPLMSPMTLDEMRHFYKDNKYVKNLDELTL

CSRHAGNMIPDNQKNSNYKYPAVYDDKDKKCHILYIAAQENNGPRYCN

KDESKRNSMFCFRPAKDISFQNYTYLSKNWDNWEKVCPRKNWNAKFGL

WVDGNCEDIPHVNEFPAIDLFECNKLVFELSASDQPKQYEQHLTDYEK

IKEGFKNKNASMIKSAFLPTGAFKADRYKSHGKGYNWGNYNTETQKCE

IFNVKPTCLINNSSYIATTALSHPIEVENNFPCSLYKDEIMKEIERES

KRIKLNDNDDEGNKKIIAPRIFISDDKDSLKCPCDPEMVSNSTCRFFV

CKCVERRAEVTSNNEVVVKEEYKDEYADIPEHKPTYDKMKGGSGAHIV

MVDAYKPTK

>SEQ ID NO: 14 SpyTag-L-Der p2
AHIVMVDAYKPTKGGSDQVDVKDCANHEIKKVLVPGCHGSEPCIIHRG

KPFQLEAVFEANQNSKTAKIEIKASIDGLEVDVPGIDPNACHYMKCPL

VKGQQYDIKYTWNVPKIAPKSENVVVTVKVMGDDGVLACAIATHAKIR

DAS

>SEQ ID NO: 15 SpyTag-L-Der p2 DNA
GCTCACATCGTGATGGTGGACGCTTACAAGCCACCAAGGGTggatccG

ATCAAGTCGATGTCAAAGATTGTGCCAATCATGAAATCAAAAAGTTT

TGGTACCAGGATGCCATGGTTCAGAACCATGTATCATTCATCGTGGTA

AACCATTCCAATTGGAAGCCGTTTTCGAAGCCAACCAAAACTCAAAAA

CCGCTAAAATTGAAATCAAAGCTTCAATCGATGGTTTAGAAGTTGATG

TTCCCGGTATCGATCCAAATGCATGCCATTATATGAAATGTCCATTGG

TTAAAGGACAACAATATGATATTAAATATACATGGAATGTTCCGAAAA

TTGCACCAAAATCTGAAAATGTTGTCGTCACTGTCAAAGTTATGGGTG

ATGATGGTGTTTTGGCCTGTGCTATTGCTACTCATGCTAAAATCCGCG

ATgctagc

>SEQ ID NO: 16 miniHAstem-HIS-SpyTag
MKVKLLVLLCTFTATYADTICIGYHANNSTDTVDTVLEKNVTVHSVN

LLENGGGGKYVCSAKLRMVTGLRNKPSKQSQGLFGAIAGFTEGGWTGR

AVDGWYGYFIHHQNEQGSGYAADQKSTQNAINGITNKVNSVIEKMNTQ

YTAIGCEYNKSERCMKQEDKIEEIESKIWTYNAELLVLLENERTLDFH

DSNVKNLYEKVKSQLKNNAKEIGNGCFEFYHKCNDECMESVKNGTYDY

PKYSEESKLNREKIDGVKLESMGVYQIEGHHHHHHGGAHIVMVDAYK

PTK

>SEQ ID NO: 17 miniHAstem-HIS-SpyTag DNA
ATGAAAGTGAAGCTGCTGGTGCTGCTGTGCACCTTCACCGCCACCTAC

GCCGACACCATCTGCATCGGCTACCACGCCAACAACAGCACCGACACC

GTGGATACCGTGCTGGAAAAGAACGTGACCGTGACCCACAGCGTGAAC
```

-continued
```
CTGCTGGAAAATGGCGGCGGAGGCAAATACGTGTGCAGCGCCAAGCTG

CGGATGGTCACCGGCCTGAGAAACAAGCCCAGCAAGCAGAGCCAGGGC

CTGTTCGGAGCCATTGCCGGCTTTACAGAGGGCGGCTGGACCGGCATG

GTGGATGGTGGTACGGCTATCACCACCAGAACGAGCAGGGCAGCGGC

TACGCCGCCGATCAGAAGTCTACCCAGAACGCCATCAACGGCATCACC

AACAAAGTGAACAGCGTGATCGAGAAGATGAACACCCAGTACACCGCC

ATCGGCTGCGAGTACAACAAGAGCGAGCGGTGCATGAAGCAGATCGAG

GACAAGATCGAAGAGATCGAGTCTAAGATCTGGACCTACAACGCCGAA

CTGCTGGTGCTGCTGGAAAACGAGCGGACCCTGGACTTCCACGACAGC

AACGTGAAGAACCTGTACGAGAAAGTGAAAAGCCAGCTGAAGAACAAC

GCCAAAGAGATCGGCAACGGCTGCTTCGAGTTCTACCACAAGTGCAAC

GACGAGTGCATGGAAAGCGTGAAGAATGGCACCTACGACTACCCCAAG

TACAGCGAGGAAAGCAAGCTGAACCGCGAGAAGATCGACGGCGTGAAG

CTGGAATCTATGGGCGTGTACCAGATTGAGGGCCACCACCATCACCAT

CATCACGGCGGAGCCCACATCGTGATGGTGGACGCCTACAAGCCCACC

AAATAA
```
>SEQ ID NO: 18 A1 >SpyCatcher-Her2-ECD|23-686
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHIGGSTQVCTGTDMKLRLPASPETHLDMLR
HLYQGCQVVQGNLELTYLPTNASLSFLQDIQEVQGYVLIAHNQVRQVP
LQRLRIVRGTQLFEDNYALAVLDNGDPLNNTTPVTGASPGGLRELQLR
SLTEILKGGVLIQRNPQLCYQDTILWKDIFHKNNQLALTLIDINRSRA
CHPCSPMCKGSRCWGESSEDCQSLTRTVCAGGCARCKGPLPTDCCHEQ
CAAGCTGPKHSDCLACLHFNHSGICELHCPALVTYNTDTFESMPNPEG
RYTFGASCVTACPYNYLSTDVGSCTLVCPLHNQEVTAEDGTQRCEKCS
KPCARVCYGLGMEHLREVRAVTSANIQEFAGCKKIFGSLAFLPESFDG
DPASNTAPLQPEQLQVFETLEEITGYLYISAWPDSLPDLSVFQNLQVI
RGRILHNGAYSLTLQGLGISWLGLRSLRELGSGLALIHHNTHLCFVHT
VPWDQLFRNPHQALLHTANRPEDECVGEGLACHQLCARGHCWGPGPTQ
CVNCSQFLRGQECVEECRVLQGLPREYVNARHCLPCHPECQPQNGSVT
CFGPEADQCVACAHYKDPPFCVARCPSGVKPDLSYMPIWKFPDEEGAC
QPCPINCTHSCVDLDDKGCPAEQRASPLTSIISAVVGILLVVVLGVVF
GILIKRROQKIRKYTHHHHHH >SEQ ID NO: 19 A2 >SpyCatcher-IL-5(C63T/C105T)
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHIGGSIPTEIPTSALVKETLALLSTHRTLL
IANETLRIPVPVHKNHQLTTEEIFQGIGTLESQTVQGGTVERLFKNLS
LIKKYIDGQKKKTGEERRRVNQFLDYLQEFLGVMNTEWIIES*SGRK >SEQ ID NO: 20 A3 >PCSK9|31-692|:SpyCatcher:HIS
QEDEDGDYEELVLALRSEEDGLAEAPEHGTTATFHRCAKDPWRLPGTY
VVVLKEETHLSQSERTARRLQAQAARRGYLTKILHVFHGLLPGFLVKM
SGDLLELALKLPHVDYIEEDSSVFAQSIPWNLERITPPRYRADEYQPP
DGGSLVEVYLLDTSIQSDHREIEGRVMVTDFENVPEEDGTRFFIRQAS
KCDSHGTHLAGVVSGRDAGVAKGASWIRSLRVINCQGKGTVSGTLIGL
EFIRKSQLVQPVGPLVVLLPLAGGYSRVLNAACQRLARAGVNILVTAA
GNFRDDACLYSPASAPEVITVGATNAQDQPVTLGTLGTNFGRCVDLFA
PGEDIIGASSDCSTCFVSQSGTSQAAAHVAGIAAMMLSAEPELTLAEL
RQRLIHFSAKDVINEAWFPEDQRVLTPNLVAALPPSTHGAGWQLFCRT
VWSAHSGPTRMATAVARCAPDEELLSCSSFSRSGKRRGERMEAQGGKL
VCRAHNAFGGEGVYAIARCCLLPQANCSVHTAPPAEASMGTRVHCHQQ
GHVLTGCSSHWEVEDLGTHKPPVLRPRGQPNQCVGHREASHASCCHAP
GLECKVKEHGIPAPQEQVTVACEEGWTLTGCSALPGTSHVLGAYAVQN
TCVVRSRDVSTTGSTEGAVTAVAICCRSRHLAQASQELQGGSGAMVD
TLSGLSSEQGQSGQMTIEEDSATHIKFSKRDEDGKELAGATMELRDSS
GKTISTWISDGQVKDFYLYPGKYTFVETAAPDGYEVATAITFTVNEQG
QVTVNGKATKGDAHIHHHHHH >SEQ ID NO: 21 A4 >SpyCatcher-ID1ID2a-HIS
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHIGGSNYIKGDPYFAEYATKLSFILNPSDA
NNPSGETANHNDEACNCNESGISSVGQAQTSGPSSNKTCITHSSIKTN
KKKECKDVKLGVRENDKDLKICVIEDTSLSGVDNCCCQDLLGILQENC
SDNKRGSSSNDSCDNKNQDECQKKLEKVFASLTNGYKCDKCKSGTSRS
KKKWIWKKSSGNEEGLQEEYANTIGLPPRTQSLYLGNLPKLENVCEDV
KDINFDTKEKFLAGCLIVSFHEGKNLKKRYPQNKNSGNKENLCKALEY
SFADYGDLIKGTSIWDNEYTKDLELNLQNNFGKLFGKYIKKNNTAERD
TSYSSLDELRESWWNTNKKYIWTAMKHGAEMNITTCNADGSVTGSGSS
CQDIPTIDLIPQYLRFLQEWVENFCEQRQAKVKDVITNCKSCKESGNK
CKTECKTKCKDECEKYKKFIEACGTAGGGIGTAGSPWSKRWDQIYKRY
SKHIEDAKRNRKAGTKNCGTSSTTNAAASTDENKCVQSDIDSFFKHLI
DIGLTTPSSYLSNVLDDNICGADKAPWTTYTTYTTTEKCNKERDKSKS
QSSDTLVVVNVPSPLGNTPYRYKYACQCKIPTNEETCDDRKEYIVINQ
WSCGSARTIVIKRGYKNDNYELCKYNGVDVKPTTVRSNSSKLDHHHHH
H >SEQ ID NO: 22 A5 >SpyCatcher-RO-HIS
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHIGGSTSENRNKRIGGPKLRGNVTSNIKFP
SDNKGKIIRGSNDKLNKNSEDVLEQSEKSINSENVPSGLDIDDDIPKES
IFIQEDQEGQTHSELNPETSEHSKDLNNNGSKNESSDIISENNKSNKV -continued
QNHFESLSDLELLENSSQDNLDKDTISTEPFPNQKHKDLQQDLNDEPL
EPEPTQIHKDYKEKNLINEEDSEPPFPRQKFIKKVDNHNEEKNWHENGS
ANGNQGSLKLKSFDEHLKDEKIENEPINHENLSIPNDPIEQILNQPEQ
ETNIQEQLYNEKQNVEEKQNSQIPSLDLKEPTNEDILPNHNPLENIKQ
SESEINHVQDHALPKENIIDKLDNQKEHIDQSQHNINVLQENNINNHQ
LEPQEKPNIESFEPKNIDSEIILPENVETEEIIDDVPSPKHSNHEFFE
EETSESEHEEAVSEKNAHETVEHEETVSQESNPEKADNDGNVSQNSNN
ELNENEFVESEKSEHEARSKAKEASSYDYILGWEFGGGVPEHKKEENM
LSHLYVSSKDKENISKENDDVLDEKEEEREETEEEELEEKNEEETESE
ISEDEEEEEEEEEKEEEENDKKKEQEKEQSNENNDQKKDMEAQNLISKN
QNNNEKNVKEAAESIMKTLAGLIKGNNQIDSTLKDLVEELSKYFKNHR
SHHHHHH >SEQ ID NO: 23 A6 >HIS-R0-SpyCatcher
GSTSENRNKRIGGPKLRGNVISNIKFPSDNKGKIIRGSNDKLNKNSED
VLEQSEKSINSENVPSGLDIDDIPKESIFIQEDQEGQTHSELNPETSE
HSKDLNNNGSKNESSDIISENNKSNKVQNHFESLSDLELLENSSQDNL
DKDTISTEPFPNQKHKDLQQDLNDEPLEPFPTQIHKDYKEKNLINEED
SEPFPRQKHKKVDNHNEEKNVFHENGSANGNQGSLKLKSFDEHLKDEK
IENEPLVHENLSIPNDIDIECKNQPEQETNIQEQLYNEKQNVEEKCIN
SQIPSLDLKEPTNEDILPNHNPLENIKQSESEINHVQDHALPKENIID
KLDNQKEHIDQSQHNINVLQENNINNHQLEPQEKPNIESFEPKNIDSE
IILPENVETEEIIDDVPSPKHSNHETFEEETSESEHEEAVSEKNAHET
VEHEETVSQESNPEKADNDGNVSQNSNNELNENEFVESEKSEHEAGGS
GANIVDTLSGLSSEQGQSGDMTIEEDSATHIKFSKRDEDGKELAGATM
ELRDSSGKTISTWISDGQVKDFYLYPGKYTFVETAAPDGYEVATAITF
TVNEQGQVTVNGKATKGDAHI >SEQ ID NO: 24 A7 >HIS-GMZ2ggsSpyCatcher
GSTSENRNKRIGGPKLRGNVTSNIKFPSDNKGKIIRGSNDKLNKNSED
VLEQSEKSINSENVPSGLDIDDIPKESIFIQEDQEGQTHSELNPETSE
HSKDLNNNGSKNESSDIISENNKSNKVQNHFESLSDLELLENSSQDNL
DKDTISTEPFPNQKHKDLQQDLNDEPLEPFPTQIHKDYKEKNLINEED
SEPFPRQKHKKVDNHNEEKNVFHENGSANGNQGSLKLKSFDEHLKDEK
IENEPLVHENLSIPNDPIEQILNQPEQETNIQEQLYNEKQNVEEKQNS
QIPSLDLKEPTNEDILPNHNPLENIKQSESEINHVQDHALPKENIIDK
LDNQKEHIDQSQHNINVLQENNINNHQLERCEKPNIESFEPKNIDSEI
ILPENVETEEIIDDVPSPKIISNHETFEEETSESEHEEAVSEKNAHET
VEHEETVSQESNPEKADNDGNVSQNSNNELNENEFVESEKSEHEARSK
AKEASSYDYILGWEFGGGVPEHKKEENMLSHLYVSSKDKENISKENDD
VLDEKEEEAEETEEEELEEKNEEETESEISEDEEEEEEEEEKEEEENDK
KKEQEKEQSNENNDQKKIDMEAQNLISKNQNNNEKNVKEAAESIMKTL -continued
AGLIKGNNQIDSTLKDLVEELSKYFKNHGGSGAMVDTLSGLSSEQGQS
GDMTIEEDSATHIKFSKRDEDGKELAGATMELRDSSGKTISTWISDGC
NKDFYLYPGKYTFVETAAPQGYEVATAITFIVNEQGQVTVNGKATKGD
AHI >SEQ ID NO: 25 A8 >HIS-GMZ2T:ggsSpyCatcher
GSTSENRNKRIGGPKLRGNVTSNIKFPSDNKGKIIRGSNDKLNKNSED
VLEQSEKSLVSENVPSGLDIDDIPKESIFIQEDQEGQTHSELNPETSE
HSKDLNNNGSKNESSDIISENNKSNKVQNHFESLSDLELLENSSQDNL
DKDTISTEPFPNQKHKDLQQDLNDEPLEPFPTQIHKDYKEKNLINEED
SEPFPRQKHKKVDNHNEEKNVFHENGSANGNQGSLKLKSFDEHLKDEK
IENEPLVHENLSIPNDPIECHLNQPEQETNIQEQLYNEKQNVEEKQNS
QIPSLDLKEPTNEDILPNHNPLENIKQSESEINHVQDHALPKENIIDK
LDNQKEHIDQSQHNINVLQENNINNHQLEPQEKPNIESFEPKNIDSQI
LPENVETEEIIDDVPSPKHSNHETFEEETSESEHEEAVSEKNAHETVE
HEETVSCIESNPEKADNDGNVSQNSNNELNENEFVESEKSEHEARSKT
KEYAEKAKNAYEKAKNAYQKANQAVLKAKEASSYDYILGWEFGGGVPE
HKKEENMLSHLYVSSKDKENISKENDDVLDEKEEEAEETEEEELEGGS
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHI >SEQ ID NO: 26 A9 >SpyCatcher-PfRH5-HIS
GAMVDTLSGLSSEQGQSGDMTIEEDSATHIKESKRDEDGKELAGATME
LRDSSGKTISTWISDGQVKDFYLYPGKYTFVETAAPDGYEVATAITFT
VNEQGQVTVNGKATKGDAHIGGSLSFENAIKKTKNCENNLTLLPIKST
EEEKDDIKNGKDIKKEIDNDKENIKTNNAKDHSTYIKSYLNTNVNDGL
KYLFIPSHNSFIKKYSVFNQINDGMLLNEKNDVKNNEDYKNVDYKNVN
FLQYHFKELSNYNIANSIDILQEKEGHLDFVIIPHYTFLDYYKHLSYN
SIYHKYSTYGKYIAVDAFIKKINETYDKVKSKCNDIKNDLIATIKKLE
HPYDINNKNDDSYRYDISEEIDDKSEETDDETEEVEDSIQDTDSNHTP
SNKKKNDLMNRTFKKMMDEYNTKKKKLIKCIKNHENDFNKICMDMKNY
GTNLFEQLSCYNNNFCNTNGIRFHYDEYIHKLILSVKSKNLNKDLSDM
TNILQQSELLLTNLNKKMGSYIYIDTIKFIHKEMKHIFNRIEYHTKII
NDKTKIIQDKIKLNIWRTFQKDELLKRILDMSNEYSLFITSDHLRQML
YNTFYSKEKHLNNIFHHLIYVLQMKFNDVPIKMEYFQTYKKNKPLTQH
HHHHH >SEQ ID NO: 27 A10 >SpyCatcher-Pfs25-HIS
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHIGGSNKLYSLFLFLFIQLSIKYNNAKVTV
DTVCKRGFLIQMSGHLECKCENDLVLVNEETCEEKVLKCDEKTVNKPC

GDFSKCIKIDGNPVSYACKCNLGYDMVNNVCIPNECKNVTCGNGKCIL

DTSNPVKTGVCSCNIGKVPNVQDQNKCSKDGETKCSLKCLKENETCKA

VDGIYKCDCKDGFIIDNESSICTAFSAYNILNLSIMFILFSVCFFIM

>SEQ ID NO: 28 A11 >HIS-PfCSP(aa92-397)-
SpyCatcher
KLKQPADGNPDPNANPNVDPNANPNVDPNANPNVDPNANPNANPNANP

NANPNANPNANPNANPNANPNANPNANPNANPNANPNANPNANPNANP

NANPNANPNVDPNANPNANPNANPNANPNANPNANPNANPNANPNANP

NANPNANPNANPNANPNANPNANPNANPNANPNANPNKNNQGNGQGHN

MPNDPNRNVDENANANSAVKNNNNEEPSDKHIKEYLNKIQNSLSTEWS

PCSVTCGNGIQVRIKPGSANKPKDELDYANDIEKKICKMEKCSSVFNV

VNSSIGLIMVLSFLFLNGGSGAMVDTLSGLSSEQGQSGDMTIEEDSAT

HIKFSKRDEDGKELAGATMELRDSSGKTISTWISDGQVKDFYLYPGKY

TFVETAAPDGYEVATAITFTVNEQGQVTVNGKATKGDAHI

>SEQ ID NO: 29 A3 >PCSK9|31-692|:SpyCatcher:
HIS DNA
TTTCATATGCCAAGTACGCCCCCTATTGACGTCAATGACGGTAAATGG

CCCGCCTGGCATTATGCCCAGTACATGACCTTATGGGACTTTCCTACT

TGGCAGTACATCTACGTATTAGTCATCGCTATTACCATGGTGATGCGG

TTTTGGCAGTACATCAATGGGCGTGGATAGCGGTTTGACTCACGGGGA

TTTCCAAGTCTCCACCCCATTGACGTCAATGGGAGTTTGTTTTGGCAC

CAAAATCAACGGGACTTTCCAAAATGTCGTAACAACTCCGCCCCATTG

ACGCAAATGGGCGGTAGGCGTGTACGGTGGGAGGTCTATATAAGCAGA

GCTCTCTGGCTAACTAGAGAACCCACTGCTTACTGGCTTATCGAAATT

AATACGACTCACTATAGGGAGACCCAAGCTGGCTAGCGTTTAAACTTA

AGCTTAGCGCAGAGGCTTGGGGCAGCCGAGCGGCAGCCAGGCCCCGGC

CCGGGCCTCGGTTCCAGAAGGGAGAGGAGCCCGCCAAGGCGCGCAAGA

GAGCGGGCTGCCTCGCAGTCCGAGCCGGAGAGGGAGCGCGAGCCGCGC

CGGCCCCGGACGGCCTCCGAAACCATGCAGGAAGATGAGGACGGCGAC

TACGAGGAACTGGTGCTGGCCCTGCGGAGCGAAGAGGATGGACTGGCC

GAGGCCCCTGAGCACGGCACCACCGCCACCTTCCACAGATGCGCCAAG

GACCCTTGGCGGCTGCCCGGCACATACGTGGTGGTGCTGAAAGAGGAA

ACCCACCTGAGCCAGAGCGAGCGGACCGCCAGAAGGCTGCAGGCCCAG

GCCGCCAGAAGAGGCTACCTGACCAAGATCCTGCACGTGTTCCACGGC

CTGCTGCCCGGCTTCCTGGTGAAAATGAGCGGCGACCTGCTGGAACTG

GCCCTGAAGCTGCCCCACGTGGACTACATCGAAGAGGACAGCAGCGTG

TTCGCCCAGAGCATCCCCTGGAACCTGGAACGGATCACCCCCCCCAGA

TACCGGGCCGACGAGTACCAGCCTCCTGACGCGGCAGCCTGGTGGAA

GTGTACCTGCTGGACACCAGCATCCAGAGCGACCACCGCGAGATCGAG

GGCAGAGTGATGGTGACAGACTTCGAGAACGTGCCCGAAGAGGACGGC

ACCCGGTTCCACAGACAGGCCAGCAAGTGCGACAGCCACGGCACACAT

CTGGCCGGCGTGGTGTCTGGCAGAGATGCCGGCGTGGCCAAGGGCGCC

AGCATGAGAAGCCTGCGGGTGCTGAACTGCCAGGGCAAGGGCACCGTG

TCCGGCACCCTGATCGGCCTGGAATTCATCCGGAAGTCCCAGCTGGTG

CAGCCCGTGGGCCCTCTGGTGGTGCTGCTGCCTCTGGCTGGCGGCTAC

AGCAGAGTGCTGAACGCCGCCTGCCAGAGACTGGCCAGAGCTGGCGTG

GTGCTGGTGACAGCCGCCGGAAACTTCCGGGACGACGCCTGCCTGTAC

AGCCCCGCCTCTGCCCCCGAAGTGATCACCGTGGGCGCCACCAACGCC

CAGGACCAGCCTGTGACACTGGGCACCCTGGGCACAAACTTCGGCAGA

TGCGTGGACCTGTTCGCCCCTGGCGAGGACATCATCGGCGCCAGCAGC

GACTGCAGCACCTGTTTCGTGTCCCAGAGCGGCACCAGCCAGGCCGCT

GCCCATGTGGCCGGAATCGCCGCCATGATGCTGAGCGCCGAGCCTGAG

CTGACCCTGGCCGAGCTGCGGCAGCGGCTGATCCACTTCTCCGCCAAG

GACGTGATCAACGAGGCCTGGTTCCCCGAGGACCAGAGAGTGCTGACC

CCCAACCTGGTGGCCGCCCTGCCTCCTTCTACACACGGCGCTGGCTGG

CAGCTGTTCTGCAGGACAGTGTGGTCCGCCCACAGCGGCCCCACCAGA

ATGGCCACAGCCGTGGCCAGATGCGCCCCTGATGAGGAACTGCTGAGC

TGCAGCAGCTTCTCCAGAAGGGGCAAGGGGAGAGGCGAGCGGATGGAA

GCCCAGGGCGGCAAGCTCGTGTGCAGAGCCCACAATGCCTTCGGCGGC

GAGGGCGTGTACGCCATTGCCAGATGCTGCCTGCTGCCTCAGGCCAAC

TGCAGCGTGCACACAGCCCCTCCAGCCGAGGCCAGCATGGGCACCAGA

GTGCACTGCCACCAGCAGGGCCACGTGCTGACCGGCTGTAGCAGCCAC

TGGGAGGTGGAAGATCTGGGCACCCACAAGCCCCCCGTGCTGAGGCCC

AGAGGCCAGCCTAATCAGTGCGTGGGCCACAGAGAGGCCTCCATCCAC

GCCAGCTGTTGCCACGCCCCTGGCCTGGAATGCAAAGTGAAAGAGCAC

GGCATCCCTGCCCCCCAGGAACAGGTCACAGTGGCCTGCGAGGAAGGC

TGGACCCTGACAGGCTGTTCCGCCCTGCCAGGCACCTCTCACGTGCTG

GGCGCCTACGCCGTGGACAATACCTGCGTCGTGCGCAGCCGGGACGTG

TCCACAACCGGCTCTACAAGCGAGGGCGCCGTGACCGCCGTGGCCATC

TGCTGCAGAAGCAGACACCTGGCCCAGGCCTCCAGGAACTGCAGGGC

GGATCTGGTGCAATGGTTGATACCCTGAGCGGTCTGAGCAGCGAACAG

GGTCAGAGCGGTGATATGACCATTGAAGAAGATAGCGCAACCCACATC

AAATTCAGCAAACGTGATGAAGATGGTAAAGAACTGGCAGGCGCAACA

ATGGAACTGCGTGATAGCAGCGGTAAAACCATTAGCACCTGGATTAGT

GATGGTCAGGTGAAAGATTTTTATCTGTACCCTGGCAAATACACCTTT

GTTGAAACCGCAGCACCGGATGGTTATGAAGTTGCAACCGCAATTACC

TTTACCGTTAATGAACAGGGCCAGGTTACCGTGAATGGTAAAGCAACC

AAAGGTGATGCACATATTCACCACCACCATCACCACTAAGCGGCCGCT

TTT

>SEQ ID NO: 30 A4 >SpyCatcher-ggs-ID1ID2a-
HIS DNA
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT
CAGGTGAAAGATTTTTATCTGTACCCTGGCAAATACACCTTTGTTGAA
ACCGCAGCACCGGATGGTTATGAAGTTGCAACCGCAATTACCTTTACC
GTTAATGAACAGGGCCAGGTTACCGTGAATGGTAAAGCAACCAAAGGT
GATGCACATATTGGTGGTAGCGGTCCGGCAACCGAACAGGGTCAGGAT
ACCTTTACCAAAGTTAAAGGTGGCAGCAACTATATCAAAGGCGATCCG
TATTTTGCAGAGTATGCAACCAAACTGAGCTTTATTCTGAATCCGAGT
GATGCAAATAATCCGAGCGGTGAAACCGCAAATCACAATGATGAAGCC
TGTAATTGTAACGAAAGCGGTATTAGCAGCGTTGGTCAGGCACAGACC
AGCGGTCCGAGCAGCAATAAAACCTGTATTACCCATAGCAGCATTAAA
ACCAATAAAAAGAAAGAATGCAAAGATGTGAAACTGGGCGTGCGCGAA
AATGATAAAGATCTGAAATTTGCGTGATCGAGGATACCAGCCTGAGC
GGTGTTGATAATTGTTGTTGTCAGGATCTGCTGGGTATTCTGCAAGAA
AATTGCAGCGATAATAAACGTGGTAGCAGCAGCAATGATAGCTGCGAT
AACAAAAATCAGGATGAATGCCAGAAAAAACTGGAAAAGTTTTTGCC
AGCCTGACGAATGGTTACAAATGCGATAAATGTAAAAGCGGCACCAGC
CGCAGCAAAAGAAATGGATTTGGAAAAAAAGCAGCGGCAATGAAGAA
GGTCTGCAAGAGGAATATGCAAATACCATTGGTCTGCCTCCGCGTACC
CAGAGCCTGTATCTGGGTAATCTGCCGAAACTGGAAAATGTGTGTGAA
GATGTGAAAGATATCAATTTTGATACCAAAGAAAAATTTCTGGCAGGC
TGCCTGATTGTGAGCTTTCATGAAGGTAAAAACCTGAAAAAACGCTAT
CCGCAGAATAAAAACAGCGGTAACAAAGAAATCTGTGCAAAGCACTG
GAATACAGCTTTGCAGATTATGGCGATCTGATTAAAGGCACCAGCATT
TGGGATAACGAGTATACCAAAGATCTGGAACTGAATCTGCAGAACAAT
TTCGGTAAACTGTTCGGCAAATATATCAAAAAAAACAATACCGCAGAG
CAGGATACCAGCTATAGCAGCCTGGATGAACTGCGTGAAAGTTGGTGG
AATACCAACAAAAAATACATTTGGACCGCCATGAAACATGGTGCCGAA
ATGAATATTACCACCTGTAATGCAGATGGTAGCGTTACCGGTAGCGGT
AGCAGCTGTGATGATATTCCGACCATTGATCTGATTCCGCAGTATCTG
CGTTTTCTGCAAGAATGGGTTGAAAACTTTTGTGAACAGCGTCAGGCG
AAAGTGAAAGATGTTATTACCAATTGCAAAAGCTGCAAAGAAAGCGGC
AATAAATGCAAAACCGAGTGCAAAACCAAATGCAAAGACGAGTGCGAG
AAATACAAAAAATTCATTGAAGCATGTGGTACAGCCGGTGGTGGTATT
GGCACCGCAGGTAGCCCGTGGTCAAAACGTTGGGATCAGATCTATAAA
CGCTACAGCAAACACATCGAAGATGCCAAACGTAATCGTAAAGCAGGC
ACCAAAAATTGTGGCACCAGCAGCACCACCAATGCAGCAGCAAGCACC
GATGAAAACAAATGTGTTCAGAGCGATATCGATAGCTTCTTCAAACAT
CTGATTGATATTGGTCTGACCACCCCGAGCAGCTATCTGAGCAATGTT
CTGGATGATAACATTTGCGGTGCAGATAAAGCACCGTGGACCACCTAT
ACCACATATACCACCACAGAAAATGCAACAAAGAGCGCGATAAAGC
AAAGCCAGAGCAGCGATACCCTGGTTGTTGTTAATGTTCCGAGTCCG

CTGGGTAATACCCCGTATCGTTATAAGTATGCCTGCCAGTGTAAAATC
CCGACCAATGAAGAAACCTGTGATGATCGCAAAGAATACATGAATCAG
TGGTCATGTGGTAGCGCACGTACCATGAAACGTGGCTATAAAAACGAT
AATTATGAACTGTGCAAATATAACGGCGTGGATGTTAAACCGACCACC
GTTCGTAGCAATAGCAGCAAACTGGATCATCATCATCACCATCATTAA
GGATCC

>SEQ ID NO: 31 A5 >SpyCatcher-ggs-R0-HIS DNA
GGTGCAATGGTTGATACCCTGAGCGGTCTGAGCAGCGAACAGGGTCAG
AGCGGTGATATGACCATTGAAGAAGATAGCGCAACCCACATCAAATTC
AGCAAACGTGATGAAGATGGTAAAGAACTGGCAGGCGCAACAATGGAA
CTGCGTGATAGCAGCGGTAAAACCATTAGCACCTGGATTAGTGATGGT
CAGGTGAAAGATTTTTATCTGTACCCTGGCAAATACACCAAGTTGAAA
CCGCAGCACCGGATGGTTATGAAGTTGCAACCGCAATTACCTTTACCG
TTAATGAACAGGGCCAGGTTACCGTGAATGGTAAAGCAACCAAAGGTG
ATGCACATATTGGTGGTAGCACAAGTGAGAATAGAAATAAACGAATCG
GGGGTCCTAAATTAAGGGGTAATGTTACAAGTAATATAAAGTTCCCAT
CAGATAACAAAGGTAAAATTATAAGAGGTTCGAATGATAAACTTAATA
AAAACTCTGAAGATGTTTTAGAACAAAGCGAAAAATCGCTTGTTTCAG
AAAAATGTTCCTAGTGGATTAGATATAGATGATATCCCTAAAGAATCTA
TTTTTATTCAAGAAGATCAAGAAGGTCAAACTCATTCTGAATTAAATC
CTGAAACATCAGAACATAGTAAAGATTTAAATAATAATGGTTCAAAAA
ATGAATCTAGTGATATTATTTCAGAAAATAATAAATCAAATAAAGTAC
AAAATCATTTTGAATCATTATCAGATTTAGAATTACTTGAAAATTCCT
CACAAGATAATTTAGACAAAGATACAATTTCAACAGAACCTTTTCCTA
ATCAAAAACATAAAGACTTACAACAAGATTTAAATGATGAACCTTTAG
AACCCTTTCCTACACAAATACATAAAGATTATAAAGAAAAAATTTAA
TAAATGAAGAAGATTCAGAACCATTTCCCAGACAAAAGCATAAAAAGG
TAGACAATCATAATGAAGAAAAAACGTATTTCATGAAAATGGTTCTG
CAAATGGTAATCAAGGAAGTTTGAAACTTAAATCATTCGATGAACATT
TAAAAGATGAAAAAATAGAAATGAACCACTTGTTCATGAAATTTAT
CCATACCAAATGATCCAATAGAACAAATATTTAAATCAACCTGAACAAG
AAACAAATATCCAGGAACAATTGTATAATGAAAAACAAAATGTTGAAG
AAAAACAAAATTCTCAAATACCTTCGTTAGATTTAAAGAACCAACAA
ATGAAGATATTTTACCAAATCATAATCCATTAGAAAATATAAAACAAA
GTGAATCAGAAATAAATCATGTACAAGATCATGCGCTACCAAAAGAGA
ATATAATAGACAAACTTGATAATCAAAAAGAACACATCGATCAATCAC
AACATAATATAAATGTATTACAAGAAATAACATAAACAATCACCAAT
TAGAACCTCAAGAGAAACCTAATATTGAATCGTTTGAACCTAAAAATA
TAGATTCAGAAATTATTCTTCCTGAAAATGTTGAAACAGAAGAAATAA
TAGATGATGTGCCTTCCCCTAAACATTCTAACCATGAAACATTTGAAG
AAGAAACAAGTGAATCTGAACATGAAGAAGCCGTATCTGAAAAAAATG

CCCACGAAACTGTCGAACATGAAGAAACTGTGTCTCAAGAAAGCAATC

CTGAAAAAGCTGATAATGATGGAAATGTATCTCAAAACAGCAACAACG

AATTAAATGAAAATGAATTCGTTGAATCGGAAAAAAGCGAGCATGAAG

CAAGATCCAAAGCAAAAGAAGCTTCTAGTTATGATTATATTTTAGGTT

GGGAATTTGGAGGAGGCGTTCCAGAACACAAAAAAGAAGAAAATATGT

TATCACATTTATATGTTTCTTCAAAGGATAAGGAAAATATATCTAAGG

AAAATGATGATGTATTAGATGAGAAGGAAGAAGAGGCAGAAGAAACAG

AAGAAGAAGAACTTGAAGAAAAAAATGAAGAAGAAACAGAATCAGAAA

TAAGTGAAGATGAAGAAGAAGAAGAAGAAGAAGAAGAAAAGGAAGAAG

AAAATGACAAAAAAAAGAACAAGAAAAAGAACAAAGTAATGAAAATA

ATGATCAAAAAAAGATATGGAAGCACAGAATTTAATTTCTAAAAACC

AGAATAATAATGAGAAAAACGTAAAAGAAGCTGCTGAAAGCATCATGA

AAACTTTAGCTGGTTTAATCAAGGGAAATAATCAAATAGATTCTACCT

TAAAAGATTTAGTAGAAGAATTATCCAAATATTTTAAAAATCATAGAT

CTCATCACCATCATCACCATTAGggatcctttt

>SEQ ID NO: 32 A6 >HIS-R0-ggs-Spycatcher DNA
GGATCCACAAGTGAGAATAGAAATAAACGAATCGGGGGTCCTAAATTA

AGGGGTAATGTTACAAGTAATATAAAGTTCCCATCAGATAACAAAGGT

AAAATTATAAGAGGTTCGAATGATAAACTTAATAAAAACTCTGAAGAT

GTAAAGAACAAAGCGAAAAATCGCTTGTTTCAGAAAATGTTCCTAGTG

GATTAGATATAGATGATATCCCTAAAGAATCTATTTTTATTCAAGAAG

ATCAAGAAGGTCAAACTCATTCTGAATTAAATCCTGAAACATCAGAAC

ATAGTAAAGATTTAAATAATAATGGTTCAAAAAATGAATCTAGTGATA

TTATTTCAGAAAATAATAAATCAAATAAAGTACAAAATCATTTTGAAT

CATTATCAGATTTAGAATTACTTGAAAATTCCTCACAAGATAATTTAG

ACAAAGATACAATTTCAACAGAACCTTTTCCTAATCAAAAACATAAAG

ACTTACAACAAGATTTAAATGATGAACCTTTAGAACCCTTTCCTACAC

AAATACATAAAGATTATAAAGAAAAAAATTTAATAAATGAAGAAGATT

CAGAACCATTTCCCAGACAAAAGCATAAAAAGGTAGACAATCATAATG

AAGAAAAAACGTATTTCATGAAAATGGTTCTGCAAATGGTAATCAAG

GAAGTTTGAAACTTAAATCATTCGATGAACATTTAAAAGATGAAAAAT

AGAAAATGAACCACTTGTTCATGAAAATTTATCCATACCAAATGATC

CAATAGAACAAATATTAAATCAACCTGAACAAGAAACAAATATCCAGG

AACAATTGTATAATGAAAACAAAATGTTGAAGAAAAACAAAATTCTC

AAATACCTTCGTTAGATTTAAAAGAACCAACAAATGAAGATATTTTAC

CAAATCATAATCCATTAGAAAATATAAAACAAAGTGAATCAGAAATAA

ATCATGTACAAGATCATGCGCTACCAAAAGAGAATATAATAGACAAAC

TTGATAATCAAAAGAACACATCGATCAATCACAACATAATATAAATG

TATTACAAGAAAATAACATAAACAATCACCAATTAGAACCTCAAGAGA

AACCTAATATTGAATCGTTTGAACCTAAAAATATAGATTCAGAAATTA

TTCTTCCTGAAAATGTTGAAACAGAAGAAATAATAGATGATGTGCCTT

CCCCTAAACATTCTAACCATGAAACATTTGAAGAAGAAACAAGTGAAT

CTGAACATGAAGAAGCCGTATCTGAAAAAAATGCCCACGAAACTGTCG

AACATGAAGAAACTGTGTCTCAAGAAAGCAATCCTGAAAAAGCTGATA

ATGATGGAAATGTATCTCAAAACAGCAACAACGAATTAAATGAAAATG

AATTCGTTGAATCGGAAAAAAGCGAGCATGAAGCAGGTGGTAGCGGTG

CAATGGTTGATACCCTGAGCGGTCTGAGCAGCGAACAGGGTCAGAGCG

GTGATATGACCATTGAAGAAGATAGCGCAACCCACATCAAATTCAGCA

AACGTGATGAAGATGGTAAAGAACTGGCAGGCGCAACAATGGAACTGC

GTGATAGCAGCGGTAAAACCATTAGCACCTGGATTAGTGATGGTCAGG

TGAAAGATTTTTATCTGTACCCTGGCAAATACACCTTTGTTGAAACCG

CAGCACCGGATGGTTATGAAGTTGCAACCGCAATTACCTTTACCGTTA

ATGAACAGGGCCAGGTTACCGTGAATGGTAAAGCAACCAAAGGTGATG

CACATATT

>SEQ ID NO: 33 A7 >HIS-GMZ2ggs-Spycatcher
GGATCCACAAGTGAGAATAGAAATAAACGAATCGGGGGTCCTAAATTA

AGGGGTAATGTTACAAGTAATATAAAGTTCCCATCAGATAACAAAGGT

AAAATTATAAGAGGTTCGAATGATAAACTTAATAAAAACTCTGAAGAT

GTTTTAGAACAAAGCGAAAAATCGCTTGTTTCAGAAAATGTTCCTAGT

GGATTAGATATAGATGATATCCCTAAAGAATCTATTTTTATTCAAGAA

GATCAAGAAGGTCAAACTCATTCTGAATTAAATCCTGAAACATCAGAA

CATAGTAAAGATTTAAATAATAATGGTTCAAAAAATGAATCTAGTGAT

ATTATTTCAGAAAATAATAAATCAAATAAAGTACAAAATCATTTTGAA

TCATTATCAGATTTAGAATTACTTGAAAATTCCTCACAAGATAATTTA

GACAAAGATACAATTTCAACAGAACCTTTTCCTAATCAAAAACATAAA

GACTTACAACAAGATTTAAATGATGAACCTTTAGAACCCTTTCCTACA

CAAATACATAAAGATTATAAAGAAAAAAATTTAATAAATGAAGAAGAT

TCAGAACCATTTCCCAGACAAAAGCATAAAAAGGTAGACAATCATAAT

GAAGAAAAAACGTATTTCATGAAAATGGTTCTGCAAATGGTAATCAA

GGAAGTTTGAAACTTAAATCATTCGATGAACATTTAAAAGATGAAAAA

ATAGAAAATGAACCACTTGTTCATGAAAATTTATCCATACCAAATGAT

CCAATAGAACAAATATTAAATCAACCTGAACAAGAAACAAATATCCAG

GAACAATTGTATAATGAAAACAAAATGTTGAAGAAAAACAAAATTCT

CAAATACCTTCGTTAGATTTAAAAGAACCAACAAATGAAGATATTTTA

CCAAATCATAATCCATTAGAAAATATAAAACAAAGTGAATCAGAAATA

AATCATGTACAAGATCATGCGCTACCAAAAGAGAATATAATAGACAAA

CTTGATAATCAAAAGAACACATCGATCAATCACAACATAATATAAAT

GTATTACAAGAAAATAACATAAACAATCACCAATTAGAACCTCAAGAG

AAACCTAATATTGAATCGTTTGAACCTAAAAATATAGATTCAGAAATT

ATTCTTCCTGAAAATGTTGAAACAGAAGAAATAATAGATGATGTGCCT

TCCCCTAAACATTCTAACCATGAAACATTTGAAGAAGAAACAAGTGAA

TCTGAACATGAAGAAGCCGTATCTGAAAAAAATGCCCACGAAACTGTC

GAACATGAAGAAACTGTGTCTCAAGAAAGCAATCCTGAAAAAGCTGAT

AATGATGGAAATGTATCTCAAAACAGCAACAACGAATTAAATGAAAAT

GAATTCGTTGAATCGGAAAAAAGCGAGCATGAAGCAAGATCCAAAGCA

AAAGAAGCTTCTAGTTATGATTATATTTTAGGTTGGGAATTTGGAGGA

GGCGTTCCAGAACACAAAAAAGAAGAAAATATGTTATCACATTTATAT

GTTTCTTCAAAGGATAAGGAAAATATATCTAAGGAAAATGATGATGTA

TTAGATGAGAAGGAAGAAGAGGCAGAAGAAACAGAAGAAGAAGAACTT

GAAGAAAAAATGAAGAAGAAACAGAATCAGAAATAAGTGAAGATGAA

GAAGAAGAAGAAGAAGAAGAAAAGGAAGAAGAAAATGACAAAAAA

AAAGAACAAGAAAAAGAACAAAGTAATGAAAATAATGATCAAAAAAA

GATATGGAAGCACAGAATTTAATTTCTAAAAACCAGAATAATAATGAG

AAAAACGTAAAAGAAGCTGCTGAAAGCATCATGAAAACTTTAGCTGGT

TTAATCAAGGGAAATAATCAAATAGATTCTACCTTAAAAGATTTAGTA

GAAGAATTATCCAAATATTTTAAAAATCATGGTGGTAGCGGTGCAATG

GTTGATACCCTGAGCGGTCTGAGCAGCGAACAGGGTCAGAGCGGTGAT

ATGACCATTGAAGAAGATAGCGCAACCCCACATCAAATTCAGCAAACGT

GATGAAGATGGTAAAGAACTGGCAGGCGCAACAATGGAACTGCGTGAT

AGCAGCGGTAAAACCATTAGCACCTGGATTAGTGATGGTCAGGTGAAA

GATTTTTATCTGTACCCTGGCAAATACACCTTTGTTGAAACCGCAGCA

CCGGATGGTTATGAAGTTGCAACCGCAATTACCTTTACCGTTAATGAA

CAGGGCCAGGTTACCGTGAATGGTAAAGCAACCAAAGGTGATGCACAT

ATT

>SEQ ID NO: 34 A8 >HIS-GMZ2T:ggs-Spycatcher DNA
GGATCCACAAGTGAGAATAGAAATAAACGAATCGGGGGTCCTAAATTA

AGGGGTAATGTTACAAGTAATATAAAGTTCCCATCAGATAACAAAGGT

AAAATTATAAGAGGTTCGAATGATAAACTTAATAAAAACTCTGAAGAT

GTTTTAGAACAAAGCGAAAAATCGCTTGTTTCAGAAAATGTTCCTAGT

GGATTAGATATAGATGATATCCCTAAAGAATCTATTTTTATTCAAGAA

GATCAAGAAGGTCAAACTCATTCTGAATTAAATCCTGAAACATCAGAA

CATAGTAAAGATTTAAATAATAATGGTTCAAAAAATGAATCTAGTGAT

ATTATTTCAGAAAATAATAAATCAAATAAAGTACAAAATCATTTTGAA

TCATTATCAGATTTAGAATTACTTGAAAATTCCTCACAAGATAATTTA

GACAAAGATACAATTTCAACAGAACCTTTTCCTAATCAAAAACATAAA

GACTTACAACAAGATTTAAATGATGAACCTTTAGAACCCTTTCCTACA

CAAATACATAAAGATTATAAAGAAAAAATTTAATAAATGAAGAAGAT

TCAGAACCATTTCCCAGACAAAAGCATAAAAAGGTAGACAATCATAAT

GAAGAAAAAACGTATTTCATGAAAATGGTTCTGCAAATGGTAATCAA

GGAAGTTTGAAACTTAAATCATTCGATGAACATTTAAAAGATGAAAAA

ATAGAAAATGAACCACTTGTTCATGAAAATTTATCCATACCAAATGAT

CCAATAGAACAAATATTTAAATCAACCTGAACAAGAAACAAATATCCAG

GAACAATTGTATAATGAAAACAAAATGTTGAAGAAAAACAAAATTCT

CAAATACCTTCGTTAGATTTAAAAGAACCAACAAATGAAGATATTTTA

CCAAATCATAATCCATTAGAAAATATAAAACAAAGTGAATCAGAAATA

AATCATGTACAAGATCATGCGCTACCAAAAGAGAATATAATAGACAAA

CTTGATAATCAAAAGAACACATCGATCAATCACAACATAATATAAAT

GTATTACAAGAAAATAACATAAACAATCACCAATTAGAACCTCAAGAG

AAACCTAATATTGAATCGTTTGAACCTAAAAATATAGATTCAGAAATT

ATTCTTCCTGAAAATGTTGAAACAGAAGAAATAATAGATGATGTGCCT

TCCCCTAAACATTCTAACCATGAAACATTTGAAGAAGAAACAAGTGAA

TCTGAACATGAAGAAGCCGTATCTGAAAAAAATGCCCACGAAACTGTC

GAACATGAAGAAACTGTGTCTCAAGAAAGCAATCCTGAAAAAGCTGAT

AATGATGGAAATGTATCTCAAAACAGCAACAACGAATTAAATGAAAAT

GAATTCGTTGAATCGGAAAAAAGCGAGCATGAAGCAAGATCCAAAACA

AAAGAATATGCTGAAAAAGCAAAAATGCTTATGAAAAGGCAAAAAAT

GCTTATCAAAAAGCAAACCAAGCTGTTTTAAAAGCAAAAGAAGCTTCT

AGTTATGATTATATTTTAGGTTGGGAATTTGGAGGAGGCGTTCCAGAA

CACAAAAAAGAAGAAAATATGTTATCACATTTATATGTGTTCTTCAAAG

GATAAGGAAAATATATCTAAGGAAAATGATGATGTATTAGATGAGAAG

GAAGAAGAGGCAGAAGAAACAGAAGAAGAAGAACTTGAAGGTGGTAGC

GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATT

>SEQ ID NO: 35 A9 >Spycatcher-ggs-PfRH5-HIS DNA
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATTGGTGGTAGCCTGTCCTTCGAGAACGCCATCAAGAAG

ACCAAGAACCAGGAAAACAACCTGACCCTGCTGCCCATCAAGTCCACC

GAGGAAGAAGGACGACATCAAGAACGGCAAGGATATCAAGAAGGAA

ATCGACAACGACAAGGAAAACATCAAGACCAACAACGCCAAGGACCAC

TCCACCTACATCAAGTCTTACCTGAACACCAACGTGAACGACGGCCTG

AAGTACCTGTTCATCCCATCCCACAACAGCTTCATCAAGAAGTACTCC

GTTTTCAACCAGATCAACGACGGCATGCTGCTGAACGAGAAGAACGAC

```
GTGAAGAACAACGAGGACTACAAGAACGTCGACTACAAGAACGTGAAC

TTCCTGCAGTACCACTTCAAGGAACTGTCCAACTACAACATCGCCAAC

TCCATCGACATCCTGCAAGAAAAGGAAGGCCACCTGGACTTCGTGATC

ATCCCCCACTACACTTTCTTGGACTACTACAAGCACCTGTCCTACAAC

AGCATCTACCACAAGTACAGCACCTACGGCAAGTACATCGCTGTGGAC

GCTTTCATCAAGAAGATCAACGAGACTTACGACAAAGTGAAGTCCAAG

TGTAACGATATCAAGAACGACCTGATCGCCACCATCAAGAAGCTCGAG

CACCCCTACGACATCAACAACAAGAACGACGACAGCTACCGCTACGAC

ATCTCCGAAGAGATCGACGACAAGTCCGAGGAAACCGACGACGAGACT

GAGGAAGTCGAGGACTCCATCCAGGACACCGACTCCAACCACACCCCC

TCCAACAAGAAGAAGAACGATCTGATGAACCGCACCTTCAAGAAGATG

ATGGACGAGTACAACACTAAGAAGAAGAAGCTGATCAAGTGCATCAAG

AACCACGAGAACGACTTCAACAAGATCTGCATGGACATGAAGAACTAC

GGCACCAACCTGTTCGAGCAGCTGTCCTGCTACAACAACAACTTCTGC

AACACTAACGGCATCCGCTTCCACTACGATGAGTACATCCACAAGCTG

ATCCTGTCCGTCAAGAGCAAGAACCTGAACAAGGACCTGAGCGACATG

ACCAACATCCTCCAGCAGTCCGAGCTGCTGCTGACCAACTTGAACAAG

AAGATGGGCTCCTACATCTACATCGACACTATCAAGTTCATCCACAAG

GAAATGAAGCACATCTTCAACCGCATCGAGTACCACACCAAGATCATC

AACGATAAGACTAAGATCATCCAAGACAAGATCAAGCTGAACATCTGG

CGCACAACCAAAAGGACGAACTGCTGAAGCGTATCCTGGACATGTCTA

ACGAGTACTCCCTCTTCATCACCTCCGACCACCTGAGGCAGATGCTGT

ACAACACCTTCTACTCCAAGGAAAAGCACCTCAACAACATCTTCCACC

ACCTGATCTACGTGCTGCAGATGAAGTTCAACGACGTCCCCATCAAGA

TGGAATACTTCCAGACCTACAAGAAGAACAAGCCCCTGACCCAGCATC

ATCACCACCACCAC

>SEQ ID NO: 36 (SpyTag sequence)
AHIVMVDAYKPTK

>SEQ ID NO: 37 SpyCatcher
GAMVDTLSGLSSEQGQSGDMTIEEDSATHIKFSKRDEDGKELAGATME

LRDSSGKTISTWISDGQVKDFYLYPGKYTFVETAAPDGYEVATAITFT

VNEQGQVTVNGKATKGDAHI

>SEQ ID NO: 38 The β-strand of CnaB2 (KTag)
ATHIKFSKRD

>SEQ ID NO: 39 DNA sequence of the SpyTag
GCTCACATCGTGATGGTGGACGCTTACAAGCCCACCAAG >SEQ ID NO: 40 >Survivin:ggs-Spycatcher
(Homo Sapiens)
MGAPTLPPAWQPFLKDHRISTFKNWPFLEGCACTPERMAEAGFIHCPT

ENEPDLAQCFFCFKELEGWEPDDDPIEEHKKHSSGCAFLSVKKQFEEL

TLGEFLKLDRERAKNKIAKETNNKKKEFEETAKKVRRAIEQLAAMDgg sGAMVDTLSGLSSEQGQSGDMTIEEDSATHIKFSKRDEDGKELAGATM

ELRDSSGKTISTWISDGQVKDFYLYPGKYTFVETAAPDGYEVATAITF

TVNEQGQVTVNGKATKGDAHI

>SEQ ID NO: 41 >Spycatcher-ggs-Survivin
(Homo Sapiens)
GAMVDTLSGLSSEQGQSGDMTIEEDSATHIKFSKRDEDGKELAGATME

LRDSSGKTISTWISDGQVKDFYLYPGKYTFVETAAPDGYEVATAITFT

VNEQGQVTVNGKATKGDAHIggsGAPTLPPAWQPFLKDHRISTFKNWP

FLEGCACTPERMAEAGFIHCPTENEPDLAQCFFCFKELEGWEPDDDPI

EEHKKHSSGCAFLSVKKQFEELTLGEFLKLDRERAKNKIAKETNNKKK

EFEETAKKVRRAIEQLAAMD

>SEQ ID NO: 42 >Survivin(F101A/L102A)-ggs-
Spycatcher (Homo Sapiens)
MGAPTLPPAWQPFLKDHRISTFKNWPFLEGCACTPERMAEAGFIHCPT

ENEPDLAQCFFCFKELEGWEPDDDPIEEHKKHSSGCAFLSVKKQFEEL

TLGEAAKLDRERAKNKIAKETNNKKKEFEETAKKVRRAIEQLAAMDgg sGAMVDTLSGLSSEQGQSGDMTIEEDSATHIKFSKRDEDGKELAGATM

ELRDSSGKTISTWISDGQVKDFYLYPGKYTFVETAAPDGYEVATAITF

TVNEQGQVTVNGKATKGDAHI

>SEQ ID NO: 43 >Spycatcher-ggs-Survivin
(F101A/L102A) (Homo Sapiens)
GAMVDTLSGLSSEQGQSGDMTIEEDSATHIKFSKRDEDGKELAGATME

LRDSSGKTISTWISDGQVKDFYLYPGKYTFVETAAPDGYEVATAITFT

VNEQGQVTVNGKATKGDAHIggsGAPTLPPAWQPFLKDHRISTFKNWP

FLEGCACTPERMAEAGFIHCPTENEPDLAQCFFCFKELEGWEPDDDPI

EEHKKHSSGCAFLSVKKQFEELTLGEAAKLDRERAKNKIAKETNNKKK

EFEETAKKVRRAIEQLAAMD

>SEQ ID NO: 44 >Spycatcher-ggs-Survivin
(F101A/L102A) (Mus Musculus)
GAMVDTLSGLSSEQGQSGDMTIEEDSATHIKFSKRDEDGKELAGATME

LRDSSGKTISTWISDGQVKDFYLYPGKYTFVETAAPDGYEVATAITFT

VNEQGQVTVNGKATKGDAHIGGSGAPALPQIWQLYLKNYRIATFKNWP

FLEDCACTPERMAEAGFIHCPTENEPDLAQCFFCFKELEGWEPDDNPI

EEHRKHSPGCAFLTVKKQMEELTVSEAAKLDRQRAKNKIAKETNNKQK

EFEETAKTTRQSIEQLAASGRF

>SEQ ID NO: 45 >Survivin (F101A/L102A)-ggs-
Spycatcher (Mus Musculus)
GAPALPQIWQLYLKNYRIATFKNWPFLEDCACTPERMAEAGFIHCPTE

NEPDLAQCFFCFKELEGWEPDDNPIEEHRKHSPGCAFLTVKKQMEELT

VSEAAKLDRQRAKNKIAKETNNKQKEFEETAKTTRQSIEQLAAggsGA

MVDTLSGLSSEQGQSGDMTIEEDSATHIKFSKRDEDGKELAGATMELR

DSSGKTISTWISDGQVKDFYLYPGKYTFVETAAPDGYEVATAITFTVN

EQGQVTVNGKATKGDAHI

>SEQ ID NO: 46 >Spycatcher-ggs-Survivin
(Mus Musculus)
GAMVDTLSGLSSEQGQSGDMTIEEDSATHIKFSKRDEDGKELAGATME

LRDSSGKTISTWISDGQVKDFYLYPGKYTFVETAAPDGYEVATAITFT

VNEQGQVTVNGKATKGDAHIGGSGAPALPQIWQLYLKNYRIATFKNWP
```

FLEDCACTPERMAEAGFIHCPTENEPDLAQCFFCFKELEGWEPDDNPI

EEHRKHSPGCAFLTVKKQMEELTVSEFLKLDRQRAKNKIAKETNNKQK

EFEETAKTTRQSIEQLAASGRF

>SEQ ID NO: 47 >Survivin-ggs-Spycatcher
(Mus Musculus)
GAPALPQIWQLYLKNYRIATFKNWPFLEDCACTPERMAEAGFIHCPTE

NEPDLAQCFFCFKELEGWEPDDNPIEEHRKHSPGCAFLTVKKQMEELT

VSEFLKLDRQRAKNKIAKETNNKQKEFEETAKTTRQSIEQLAAGGSGA

MVDTLSGLSSEQGQSGDMTIEEDSATHIKFSKRDEDGKELAGATMELR

DSSGKTISTWISDGQVKDFYLYPGKYTFVETAAPDGYEVATAITFTVN

EQGQVTVNGKATKGDAHI

>SEQ ID NO: 48 >Spycatcher-ggs-Survivin
(F101A/L102A) (Mus Musculus) DNA
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATTGGTGGTAGCGGTGCACCGGCACTGCCGCAGATTTGG

CAGCTGTATCTGAAAAACTATCGTATCGCCACCTTTAAAAACTGGCCG

TTTCTGGAAGATTGTGCATGTACACCGGAACGTATGGCAGAAGCAGGT

TTTATTCATTGTCCGACCGAAAATGAACCGGATCTGGCACAGTGTTTT

TTTTGCTTTAAAGAACTGGAAGGTTGGGAGCCGGATGATAATCCGATT

GAAGAACATCGTAAACATAGTCCGGGTTGTGCATTTCTGACCGTGAAA

AAACAAATGGAAGAACTGACCGTTAGCGAGGCAGCAAAACTGGATCGT

CAGCGTGCCAAAAACAAAATTGCAAAAGAAACCAATAACAAACAGAAA

GAATTCGAAGAAACCGCCAAAACCACCCGTCAGAGCATTGAACAGCTG

GCAGCAagcggccgcttt

>SEQ ID NO: 49 >Survivin (F101A/L102A)-ggs-
Spycatcher (Mus Musculus) DNA
GGTGCACCGGCACTGCCGCAGATTTGGCAGCTGTATCTGAAAAACTAT

CGTATCGCCACCTTTAAAAACTGGCCGTTTCTGGAAGATTGTGCATGT

ACACCGGAACGTATGGCAGAAGCAGGTTTTATTCATTGTCCGACCGAA

AATGAACCGGATCTGGCACAGTGTTTTTTTTGCTTTAAAGAACTGGAA

GGTTGGGAGCCGGATGATAATCCGATTGAAGAACATCGTAAACATAGT

CCGGGTTGTGCATTTCTGACCGTGAAAAAACAAATGGAAGAACTGACC

GTTAGCGAGGCAGCAAAACTGGATCGTCAGCGTGCCAAAAACAAAATT

GCAAAAGAAACCAATAACAAACAGAAAGAATTCGAAGAAACCGCCAAA

ACCACCCGTCAGAGCATTGAACAGCTGGCAGCAGGTGGCAGCGGTGCA

ATGGTTGATACCCTGAGCGGTCTGAGCAGCGAACAGGGTCAGAGCGGT

GATATGACCATTGAAGAAGATAGCGCAACCCACATCAAATTCAGCAAA

CGTGATGAAGATGGTAAAGAACTGGCAGGCGCAACAATGGAACTGCGT

GATAGCAGCGGTAAAACCATTAGCACCTGGATTAGTGATGGTCAGGTG

AAAGATTTTTATCTGTACCCTGGCAAATACACCTTTGTTGAAACCGCA

GCACCGGATGGTTATGAAGTTGCAACCGCAATTACCTTTACCGTTAAT

GAACAGGGCCAGGTTACCGTGAATGGTAAAGCAACCAAAGGTGATGCA

CATATT

>SEQ ID NO: 50 >Spycatcher-ggs-Survivin
(Mus Musculus) DNA
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATTGGTGGTAGCGGTGCACCGGCACTGCCGCAGATTTGG

CAGCTGTATCTGAAAAACTATCGTATCGCCACCTTTAAAAACTGGCCG

TTTCTGGAAGATTGTGCATGTACACCGGAACGTATGGCAGAAGCAGGT

TTTATTCATTGTCCGACCGAAAATGAACCGGATCTGGCACAGTGTTTT

TTTTGCTTTAAAGAACTGGAAGGTTGGGAGCCGGATGATAATCCGATT

GAAGAACATCGTAAACATAGTCCGGGTTGTGCATTTCTGACCGTGAAA

AAACAAATGGAAGAACTGACCGiTAGCGAGTTTCTGAAACTGGATCGT

CAGCGTGCCAAAAACAAAATTGCAAAAGAAACCAATAACAAACAGAAA

GAATTCGAAGAAACCGCCAAAACCACCCGTCAGAGCATTGAACAGCTG

GCAGCAagcggccgcttt

>SEQ ID NO: 51 Survivin-ggs-Spycatcher
(Mus Musculus) DNA
GGTGCACCGGCACTGCCGCAGATTTGGCAGCTGTATCTGAAAAACTAT

CGTATCGCCACCTTTAAAAACTGGCCGTTTCTGGAAGATTGTGCATGT

ACACCGGAACGTATGGCAGAAGCAGGTTTTATTCATTGTCCGACCGAA

AATGAACCGGATCTGGCACAGTGTTTTTTTTGCTTTAAAGAACTGGAA

GGTTGGGAGCCGGATGATAATCCGATTGAAGAACATCGTAAACATAGT

CCGGGTTGTGCATTTCTGACCGTGAAAAAACAAATGGAAGAACTGACC

GTTAGCGAGTTTCTGAAACTGGATCGTCAGCGTGCCAAAAACAAAATT

GCAAAAGAAACCAATAACAAACAGAAAGAATTCGAAGAAACCGCCAAA

ACCACCCGTCAGAGCATTGAACAGCTGGCAGCAGGTGGCAGCGGTGCA

ATGGTTGATACCCTGAGCGGTCTGAGCAGCGAACAGGGTCAGAGCGGT

GATATGACCATTGAAGAAGATAGCGCAACCCACATCAAATTCAGCAAA

CGTGATGAAGATGGTAAAGAACTGGCAGGCGCAACAATGGAACTGCGT

GATAGCAGCGGTAAAACCATTAGCACCTGGATTAGTGATGGTCAGGTG

```
AAAGATTTTTATCTGTACCCTGGCAAATACACCTTTGTTGAAACCGCA

GCACCGGATGGTTATGAAGTTGCAACCGCAATTACCTTTACCGTTAAT

GAACAGGGCCAGGTTACCGTGAATGGTAAAGCAACCAAAGGTGATGCA

CATATT

>SEQ ID NO: 52 >Spycatcher-ggs-CIDR1a-
HIS Protein
GAMVDTLSGLSSEQGQSGDMTIEEDSATHIKFSKRDEDGKELAGATME

LRDSSGKTISTWISDGQVKDFYLYPGKYTFVETAAPDGYEVATAITFT

VNEQGQVTVNGKATKGDAHIGGSKITSFDEFFDFWVRKLLIDTIKWET

ELTYCINNTDVTDCNKCNKNCVCFDKWVKQKEDEWTNIMKLFTNKHDI

PKKYYLNINDLFDSFFFVIYKFNEGEAKWNELKENLKKQIASSKANNG

TKDSEAAIKVLFNHIKEIATICKDNNTN

>SEQ ID NO: 53 >Spycatcher-ggs-CIDR1a-HIS DNA
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATTGGTGGTAGCAAAATAACGTCATTTGATGAATTTTTT

GATTTTTGGGTTAGAAAATTATTAATAGACACTATAAAGTGGGAAACC

GAACTTACGTATTGTATAAATAATACTGATGTCACGGATTGTAATAAA

TGTAACAAAAATTGCGTATGTTTTGACAAATGGGTTAAACAAAAAGAA

GACGAATGGACAAATATAATGAAACTATTCACAAACAAACACGATATA

CCGAAAAAATATTATCTTAATATTAATGATCTTTTTGATAGTTTTTTT

TTCCAAGTTATATATAAGTTTAACGAAGGAGAAGCAAATGGAATGAA

CTTAAAGAAAATTTAAAAAAGCAAATTGCGTCTTCCAAAGCAAATAAC

GGAACCAAAGATTCAGAAGCTGCAATAAAAGTGTTGTTTAATCACATA

AAAGAAATTGCAACAATATGCAAAGATAATAATACAAAC

>SEQ ID NO: 54 >SpyCatcher
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATT

>SEQ ID NO: 55 SpyLigase:
HHHHHHDYDGQSGDGKELAGATMELRDSSGKTISTWISDGQVKDFYLY

PGKYTFVETAAPDGYEVATAITFTVNEQGQVTVNGKATKGGSGGSGGS

GEDSATHI

>SEQ ID NO: 56 isopeptide Spy0128
TDKDMTITFTNKKDAE

>SEQ ID NO: 57 Split-Spy0128
ATTVHGETVVNGAKLTVTKNLDLVNSNALIPNTDFTFKIEPDTTVNED

GNKFKGVALNTPMTKVTYTNSDKGGSNTKTAEFDFSEVTFEKPGVYYY

KVTEEKIDKVPGVSYDTTSYTVQVHVLWNEEQQKPVATYIVGYKEGSK

VPIQFKNSLDSTTLTVKKKVSGTGGDRSKDFNFGLTLKANQYYKASEK

VMIEKTTKGGQAPVQTEASIDQLYHFTLKDGESIKVTNLPVGVDYVVT

EDDYKSEKYTTNVEVSPQDGAVKNIAGNSTEQETSTDKDMTI

>SEQ ID NO: 58 AP205 capsid protein
ANKPMQPITSTANKIVWSDPTRLSTTFSASLLRQRVKVGIAELNNVSG

QYVSVYKRPAPKPEGCADACVIMPNENQSIRTVISGSAENLATLKAEW

ETHKRNVDTLFASGNAGLGFLDPTAAIVSSDTTA

>SEQ ID NO: 59 PhageFr capsid protein
ASNFEEFVLVDNGGTGDVKVAPSNFANGVAEWISSNSRSQAYKVTCSV

RQSSANNRKYTVKVEVPKVATQVQGGVELPVAAWRSYMNMELTIPVFA

TNDDCALIVKALQGTFKTGNPIATAIAANSGIY

>SEQ ID NO: 60 SpyCatcherΔN
DSATHIKFSKRDEDGKELAGATMELRDSSGKTISTWISDGQVKDFYLY

PGKYTFVETAAPDGYEVATAITFTVNEQGQVTVNGKATKGDAHI

>SEQ ID NO: 61 SpyCatcherΔNC
DSATHIKFSKRDEDGKELAGATMELRDSSGKTISTWISDGQVKDFYLY

PGKYTFVETAAPDGYEVATAITFTVNEQGQVTVNGKATKG

>SEQ ID NO: 62 Spy-AP205
MAHIVMVDAYKPTKGSGTAGGGSGSANKPMQPITSTANKIVWSDPTRL

STTFSASLLRQRVKVGIAELNNVSGQYVSVYKRPAPKPEGCADACVIM

PNENQSIRTVISGSAENLATLKAEWETHKRNVDTLFASGNAGLGFLDP

TAAIVSSDTTA

>SEQ ID NO: 63 Spy-AP205
ATGGCACATATTGTTATGGTGGATGCATATAAACCGACCAAAGGTAGC

GGTACAGCCGGTGGTGGTAGTGGTAGCGCAAATAAACCGATGCAGCCG

ATTACCAGCACCGCAAACAAAATTGTTTGGAGCGATCCGACCCGTCTG

AGCACCACCTTTAGCGCAAGCCTGCTGCGTCAGCGTGTTAAAGTTGGT

ATTGCAGAACTGAATAATGTGAGCGGTCAGTATGTTAGCGTGTATAAA

CGTCCGGCACCGAAACCGGAAGGTTGTGCAGATGCATGTGTTATTATG

CCGAATGAAAATCAGAGCATTCGTACCGTTATTAGCGGTAGCGCAGAA

AATCTGGCAACCCTGAAAGCAGAATGGGAAACCCATAAACGTAATGTG

GATACCCTGTTTGCAAGCGGTAATGCAGGTCTGGGTTTTCTGGACCCG

ACCGCAGCAATTGTTAGCAGCGATACCACCGCATAA

>SEQ ID NO: 64 AP205-spy
MANKPMQPITSTANKIVWSDPTRLSTTFSASLLRQRVKVGIAELNNVS

GQYVSVYKRPAPKPEGCADACVIMPNENQSIRTVISGSAENLATLKAE

WETHKRNVDTLFASGNAGLGFLDPTAAIVSSDTTAGTAGGSGAHIVMV

DAYKPTK
```

>SEQ ID NO: 65 AP205-spy
ATGGCAAATAAACCGATGCAGCCGATTACCAGCACCGCAAACAAAATT
GTTTGGAGCGATCCGACCCGTCTGAGCACCACCTTTAGCGCAAGCCTG
CTGCGTCAGCGTGTTAAAGTTGGTATTGCAGAACTGAATAATGTGAGC
GGTCAGTATGTTAGCGTGTATAAACGTCCGGCACCGAAACCGGAAGGT
TGTGCAGATGCATGTGTTATTATGCCGAATGAAAATCAGAGCATTCGT
ACCGTTATTAGCGGTAGCGCAGAAAATCTGGCAACCCTGAAAGCAGAA
TGGGAAACCCATAAACGTAATGTGGATACCCTGTTTGCAAGCGGTAAT
GCAGGTCTGGGTTTTCTGGACCCGACCGCAGCAATTGTTAGCAGCGAT
ACCACCGCAGGTACAGCCGGTGGTAGCGGTGCACATATTGTTATGGTT
GATGCATATAAACCGACCAAATAA >SEQ ID NO: 66 Spy-Phage fr
MAHIVMVDAYKPTKGSGTAGGGSGSASNFEEFVLVDNGGTGDVKVAPS
NFANGVAEWISSNSRSQAYKVTCSVRQSSANNRKYTVKVEVPKVATQV
QGGVELPVAAWRSYMNMELTIPVFATNDDCALIVKALQGTFKTGNPIA
TAIAANSGIY >SEQ ID NO: 67 Spy-Phage fr
ATGGCACATATTGTTATGGTGGATGCATATAAACCGACCAAAGGTAGC
GGTACAGCCGGTGGTGGTAGTGGTAGCGCAAGCAATTTTGAAGAATTT
GTGCTGGTTGATAATGGTGGCACCGGTGATGTTAAAGTTGCACCGAGT
AATTTTGCAAATGGTGTTGCAGAATGGATTAGCAGCAATAGCCGTAGC
CAGGCATATAAAGTTACCTGTAGCGTTCGTCAGAGCAGCGCAAATAAT
CGTAAATATACCGTTAAAGTCGAGGTTCCGAAAGTTGCAACCCAGGTT
CAGGGTGGTGTTGAACTGCCGGTTGCAGCATGGCGTAGCTATATGAAT
ATGGAACTGACCATTCCGGTTTTTGCCACCAATGATGATTGTGCCCTG
ATTGTTAAAGCACTGCAGGGCACCTTTAAAACCGGTAATCCGATTGCA
ACCGCAATTGCAGCAAATAGCGGTATCTATTAA >SEQ ID NO: 68 Ktag-AP205
ATHIKFSKRDGSGTAGGGSGSANKPMQPITSTANKIVWSDPTRLSTTF
SASLLRQRVKVGIAELNNVSGQYVSVYKRPAPKPEGCADACVIMPNEN
QSIRTVISGSAENLATLKAEWETHKRNVDTLFASGNAGLGFLDPTAAI
VSSDTTA >SEQ ID NO: 69 AP205-Ktag
MANKPMQPITSTANKIVWSDPTRLSTTFSASLLRQRVKVGIAELNNVS
GQYVSVYKRPAPKPEGCADACVIMPNENQSIRTVISGSAENLATLKAE
WETHKRNVDTLFASGNAGLGFLDPTAAIVSSDTTAGTAGGSGATHIKF
SKRD >SEQ ID NO: 70 Ktag-Phage fr
ATHIKFSKRDGSGTAGGGSGSASNFEEFVLVDNGGTGDVKVAPSNFAN
GVAEWISSNSRSQAYKVTCSVRQSSANNRKYTVKVEVPKVATQVQGGV
ELPVAAWRSYMNMELTIPVFATNDDCALIVKALQGTFKTGNPIATAIA
ANSGIY >SEQ ID NO: 71 Spy-AP205-Spy
MAHIVMVDAYKPTKGSGTAGGGSGSANKPMQPITSTANKIVWSDPTRL
STTFSASLLRQRVKVGIAELNNVSGQYVSVYKRPAPKPEGCADACVIM
PNENQSIRTVISGSAENLATLKAEWETHKRNVDTLFASGNAGLGFLDP
TAAIVSSDTTAGTAGGSGAHIVMVDAYKPTK >SEQ ID NO: 72 Spy-AP205-Spy
ATGGCACATATTGTTATGGTGGATGCATATAAACCGACCAAAGGTAGC
GGTACAGCCGGTGGTGGTAGTGGTAGCGCAAATAAACCGATGCAGCCG
ATTACCAGCACCGCAAACAAAATTGTTTGGAGCGATCCGACCCGTCTG
AGCACCACCTTTAGCGCAAGCCTGCTGCGTCAGCGTGTTAAAGTTGGT
ATTGCAGAACTGAATAATGTGAGCGGTCAGTATGTTAGCGTGTATAAA
CGTCCGGCACCGAAACCGGAAGGTTGTGCAGATGCATGTGTTATTATG
CCGAATGAAAATCAGAGCATTCGTACCGTTATTAGCGGTAGCGCAGAA
AATCTGGCAACCCTGAAAGCAGAATGGGAAACCCATAAACGTAATGTG
GATACCCTGTTTGCAAGCGGTAATGCAGGTCTGGGTTTTCTGGACCCG
ACCGCAGCAATTGTTAGCAGCGATACCACCGCAGGTACAGCCGGTGGT
AGCGGTGCACATATTGTTATGGTTGATGCATATAAACCGACCAAATAA

>SEQ ID NO: 73 AP205-ggsg-Spycatcher
ATGGCAAATAAACCGATGCAGCCGATTACCAGCACCGCAAACAAAATT
GTTTGGAGCGATCCGACCCGTCTGAGCACCACCTTTAGCGCAAGCCTG
CTGCGTCAGCGTGTTAAAGTTGGTATTGCAGAACTGAATAATGTGAGC
GGTCAGTATGTTAGCGTGTATAAACGTCCGGCACCGAAACCGGAAGGT
TGTGCAGATGCATGTGTTATTATGCCGAATGAAAATCAGAGCATTCGT
ACCGTTATTAGCGGTAGCGCAGAAAATCTGGCAACCCTGAAAGCAGAA
TGGGAAACCCATAAACGTAATGTGGATACCCTGTTTGCAAGCGGTAAT
GCAGGTCTGGGTTTTCTGGACCCGACCGCAGCAATTGTTAGCAGCGAT
ACCACCGCAGGTACAGCCGGTGGTAGCGGTGGTGCAATGGTTGATACC
CTGAGCGGTCTGAGCAGCGAACAGGGTCAGAGCGGTGATATGACCATT
GAAGAAGATAGCGCAACCCACATCAAATTCAGCAAACGTGATGAAGAT
GGTAAAGAACTGGCAGGCGCAACAATGGAACTGCGTGATAGCAGCGGT
AAAACCATTAGCACCTGGATTAGTGATGGTCAGGTGAAAGATTTTTAT
CTGTACCCTGGCAAATACACCTTTGTTGAAACCGCAGCACCGGATGGT
TATGAAGTTGCAACCGCAATTACCTTTACCGTTAATGAACAGGGCCAG
GTTACCGTGAATGGTAAAGCAACCAAAGGTGATGCACATATTtaa >SEQ ID NO: 74 AP205-ggsg-Spycatcher
MANKPMQPITSTANKIVWSDPTRLSTTFSASLLRQRVKVGIAELNNVS
GQYVSVYKRPAPKPEGCADACVIMPNENQSIRTVISGSAENLATLKAE
WETHKRNVDTLFASGNAGLGFLDPTAAIVSSDTTAGTAGGSGGAMVDT
LSGLSSEQGQSGDMTIEEDSATHIKFSKRDEDGKELAGATMELRDSSG
KTISTWISDGQVKDFYLYPGKYTFVETAAPDGYEVATAITFTVNEQGQ
VTVNGKATKGDAHI

```
>SEQ ID NO: 75 SpyCatcher-ggsgs-AP205
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATT***GGTGGTAGCGGTAGCGCA***AATAAACCGATGCAGCCG

ATTACCAGCACCGCAAACAAAATTGTTTGGAGCGATCCGACCCGTCTG

AGCACCACCTTTAGCGCAAGCCTGCTGCGTCAGCGTGTTAAAGTTGGT

ATTGCAGAACTGAATAATGTGAGCGGTCAGTATGTTAGCGTGTATAAA

CGTCCGGCACCGAAACCGGAAGGTTGTGCAGATGCATGTGTTATTATG

CCGAATGAAAATCAGAGCATTCGTACCGTTATTAGCGGTAGCGCAGAA

AATCTGGCAACCCTGAAAGCAGAATGGGAAACCCATAAACGTAATGTG

GATACCCTGTTTGCAAGCGGTAATGCAGGTCTGGGTTTTCTGGACCCG

ACCGCAGCAATTGTTAGCAGCGATACCACCGCATAA

>SEQ ID NO: 76 SpyCatcher-ggsgs-AP205
MVDTLSGLSSEQGQSGDMTIEEDSATHIKFSKRDEDGKELAGATMELR

DSSGKTISTWISDGQVKDFYLYPGKYTFVETAAPDGYEVATAITFTVN

EQGQVTVNGKATKGDAHIGGSGSANKPMQPITSTANKIVWSDPTRLST

TFSASLLRQRVKVGIAELNNVSGQYVSVYKRPAPKPEGCADACVIMPN

ENQSIRTVISGSAENLATLKAEWETHKRNVDTLFASGNAGLGFLDPTA

AIVSSDTTA

>SEQ ID NO: 77 SpyCatcher-ggsgs-Phage fr
GGTGCAATGGTTGATACCCTGAGCGGTCTGAGCAGCGAACAGGGTCAG

AGCGGTGATATGACCATTGAAGAAGATAGCGCAACCCACATCAAATTC

AGCAAACGTGATGAAGATGGTAAAGAACTGGCAGGCGCAACAATGGAA

CTGCGTGATAGCAGCGGTAAAACCATTAGCACCTGGATTAGTGATGGT

CAGGTGAAAGATTTTTATCTGTACCCTGGCAAATACACCTTTGTTGAA

ACCGCAGCACCGGATGGTTATGAAGTTGCAACCGCAATTACCTTTACC

GTTAATGAACAGGGCCAGGTTACCGTGAATGGTAAAGCAACCAAAGGT

GATGCACATATTGGTGGTAGCGGTAGCGCAAGCAATTTGAAGAATTT

GTGCTGGTTGATAATGGTGGCACCGGTGATGTTAAAGTTGCACCGAGT

AATTTTGCAAATGGTGTTGCAGAATGGATTAGCAGCAATAGCCGTAGC

CAGGCATATAAAGTTACCTGTAGCGTTCGTCAGAGCAGCGCAAATAAT

CGTAAATATACCGTTAAAGTCGAGGTTCCGAAAGTTGCAACCCAGGTT

CAGGGTGGTGTTGAACTGCCGGTTGCAGCATGGCGTAGCTATATGAAT

ATGGAACTGACCATTCCGGTTTTTGCCACCAATGATGATTGTGCCCTG

ATTGTTAAAGCACTGCAGGGCACCTTTAAAACCGGTAATCCGATTGCA

ACCGCAATTGCAGCAAATAGCGGTATCTATTAA

>SEQ ID NO: 78 SpyCatcher-ggsgs-Phage fr
MVDTLSGLSSEQGQSGDMTIEEDSATHIKFSKRDEDGKELAGATMELR

DSSGKTISTWISDGQVKDFYLYPGKYTFVETAAPDGYEVATAITFTVN

EQGQVTVNGKATKGDAHIGGSGSASNFEEFVLVDNGGTGDVKVAPSNF

ANGVAEWISSNSRSQAYKVTCSVRQSSANNRKYTVKVEVPKVATQVQG

GVELPVAAWRSYMNMELTIPVFATNDDCALIVKALQGTFKTGNPIATA

IAANSGIY

>SEQ ID NO: 79 >SpyTag-Her2-ECD|23-686-HIS
MAHIVMVDAYKPTKGGSTQVCTGTDMKLRLPASPETHLDMLRHLYQGC

QVVQGNLELTYLPTNASLSFLQDIQEVQGYVLIAHNQVRQVPLQRLRI

VRGTQLFEDNYALAVLDNGDPLNNTTPVTGASPGGLRELQLRSLTEIL

KGGVLIQRNPQLCYQDTILWKDIFHKNNQLALTLIDTNRSRACHPCSP

MCKGSRCWGESSEDCQSLTRTVCAGGCARCKGPLPTDCCHEQCAAGCT

GPKHSDCLACLHFNHSGICELHCPALVTYNTDTFESMPNPEGRYTFGA

SCVTACPYNYLSTDVGSCTLVCPLHNQEVTAEDGTQRCEKCSKPCARV

CYGLGMEHLREVRAVTSANIQEFAGCKKIFGSLAFLPESFDGDPASNT

APLQPEQLQVFETLEEITGYLYISAWPDSLPDLSVFQNLQVIRGRILH

NGAYSLTLQGLGISWLGLRSLRELGSGLALIHHNTHLCFVHTVPWDQL

FRNPHQALLHTANRPEDECVGEGLACHQLCARGHCWGPGPTQCVNCSQ

FLRGQECVEECRVLQGLPREYVNARHCLPCHPECQPQNGSVTCFGPEA

DQCVACAHYKDPPFCVARCPSGVKPDLSYMPIWKFPDEEGACQPCPIN

CTHSCVDLDDKGCPAEQRASPLTSIISAVVGILLVVVLGVVFGILIKR

RQQKIRKYTHHHHHH

>SEQ ID NO: 80 >SpyTag-IL-5(C63T/C105T)
MAHIVMVDAYKPTKGGSIPTEIPTSALVKETLALLSTHRTLLIANETL

RIPVPVHKNHQLTTEEIFQGIGTLESQTVQGGTVERLFKNLSLIKKYI

DGQKKKTGEERRRVNQFLDYLQEFLGVMNTEWIIES*SGRK

>SEQ ID NO: 81 >PCSK9|31-692|:SpyTag
QEDEDGDYEELVLALRSEEDGLAEAPEHGTTATFHRCAKDPWRLPGTY

VVVLKEETHLSQSERTARRLQAQAARRGYLTKILHVFHGLLPGFLVKM

SGDLLELALKLPHVDYIEEDSSVFAQSIPWNLERITPPRYRADEYQPP

DGGSLVEVYLLDTSIQSDHREIEGRVMVTDFENVPEEDGTRFHRQASK

CDSHGTHLAGVVSGRDAGVAKGASMRSLRVLNCQGKGTVSGTLIGLEF

IRKSQLVQPVGPLVVLLPLAGGYSRVLNAACQRLARAGVVLVTAAGNF

RDDACLYSPASAPEVITVGATNAQDQPVTLGTLGTNFGRCVDLFAPGE

DIIGASSDCSTCFVSQSGTSQAAAHVAGIAAMMLSAEPELTLAELRQR

LIHFSAKDVINEAWFPEDQRVLTPNLVAALPPSTHGAGWQLFCRTVWS

AHSGPTRMATAVARCAPDEELLSCSSFSRSGKRRGERMEAQGGKLVCR

AHNAFGGEGVYAIARCCLLPQANCSVHTAPPAEASMGTRVHCHQQGHV

LTGCSSHWEVEDLGTHKPPVLRPRGQPNQCVGHREASIHASCCHAPGL

ECKVKEHGIPAPQEQVTVACEEGWTLTGCSALPGTSHVLGAYAVDNTC

VVRSRDVSTTGSTSEGAVTAVAICCRSRHLAQASQELQGGSAHIVMVD

AYKPTK
```

>SEQ ID NO: 82 SpyTag-ID1|D2a-HIS
AHIVMVDAYKPTKGGSNYIKGDPYFAEYATKLSFILNPSDANNPSGET
ANHNDEACNCNESGISSVGQAQTSGPSSNKTCITHSSIKTNKKKECKD
VKLGVRENDKDLKICVIEDTSLSGVDNCCCQDLLGILQENCSDNKRGS
SSNDSCDNKNQDECQKKLEKVFASLTNGYKCDKCKSGTSRSKKKWIWK
KSSGNEEGLQEEYANTIGLPPRTQSLYLGNLPKLENVCEDVKDINFDT
KEKFLAGCLIVSFHEGKNLKKRYPQNKNSGNKENLCKALEYSFADYGD
LIKGTSIWDNEYTKDLELNLQNNFGKLFGKYIKKNNTAEQDTSYSSLD
ELRESWWNTNKKYIWTAMKHGAEMNITTCNADGSVTGSGSSCDDIPTI
DLIPQYLRFLQEWVENFCEQRQAKVKDVITNCKSCKESGNKCKTECKT
KCKDECEKYKKFIEACGTAGGGIGTAGSPWSKRWDQIYKRYSKHIEDA
KRNRKAGTKNCGTSSTTNAAASTDENKCVQSDIDSFFKHLIDIGLTTP
SSYLSNVLDDNICGADKAPWTTYTTYTTTEKCNKERDKSKSQSSDTLV
VVNVPSPLGNTPYRYKYACQCKIPTNEETCDDRKEYMNQWSCGSARTM
KRGYKNDNYELCKYNGVDVKPTTVRSNSSKLDHHHHHH

>SEQ ID NO: 83 Short flexible linker
GGSGS

>SEQ ID NO: 84 SpyCatcher-Ag85A
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHIGGSFSRPGLPVEYLQVPSPSMGRDIKVQ
FQSGGANSPALYLLDGLRAQDDFSGWDINTPAFEWYDQSGLSVVMPVG
GQSSFYSDWYQPACGKAGCQTYKWETFLTSELPGWLQANRHVKPTGSA
VVGLSMAASSALTLAIYHPQQFVYAGAMSGLLDPSQAMGPTLIGLAMG
DAGGYKASDMWGPKEDPAWQRNDPLLNVGKLIANNTRVWVYCGNGKLS
DLGGNNLPAKFLEGFVRTSNIKFQDAYNAGGGHNGVFDFPDSGTHSWE
YWGAQLNAMKPDLQRALGATPNTGPAPQGA >SEQ ID NO: 85 SpyCatcher-Ag85A DNA
GGTGCAATGGTTGATACCCTGAGCGGTCTGAGCAGCGAACAGGGTCAG
AGCGGTGATATGACCATTGAAGAAGATAGCGCAACCCACATCAAATTC
AGCAAACGTGATGAAGATGGTAAAGAACTGGCAGGCGCAACAATGGAA
CTGCGTGATAGCAGCGGTAAAACCATTAGCACCTGGATTAGTGATGGT
CAGGTGAAAGATTTTTATCTGTACCCTGGCAAATACACCTTTGTTGAA
ACCGCAGCACCGGATGGTTATGAAGTTGCAACCGCAATTACCTTTACC
GTTAATGAACAGGGCCAGGTTACCGTGAATGGTAAAGCAACCAAAGGT
GATGCACATATTGGTGGTAGCTTCTCCCGTCCCGGACTGCCTGTGGAA
TACCTCCAGGTGCCCTCCCCCTCTATGGGTCGTGACATCAAGGTGCAG
TTCCAGTCCGGTGGTGCTAACTCCCCCGCTCTGTACCTGCTGGACGGA
CTGCGTGCTCAGGACGACTTCTCCGGCTGGGACATCAACACTCCCGCT
TTCGAGTGGTACGACCAGTCCGGCCTGTCCGTGGTTATGCCTGTGGGT
GGCCAGTCCTCCTTCTACTCCGACTGGTACCAACCCGCTTGCGGCAAG
GCTGGCTGCCAGACCTACAAGTGGGAGACTTTCCTGACCTCCGAGCTG CCCGGATGGCTGCAGGCTAACCGTCACGTGAAGCCCACCGGTTCCGCT
GTCGTGGGCCTGTCTATGGCTGCTTCCTCCGCTCTGACCCTGGCTATC
TACCACCCCCAGCAGTTCGTGTACGCTGGCGCTATGTCCGGACTGCTG
GACCCCTCTCAGGCTATGGGTCCTACCCTGATCGGCCTGGCTATGGGC
GACGCTGGTGGTTACAAGGCTTCCGACATGTGGGGTCCCAAGGAAGAT
CCCGCTTGGCAGCGTAACGACCCCCTGCTGAACGTGGGCAAGCTGATC
GCTAACAACACCCGTGTGTGGGTGTACTGCGGCAACGGCAAGCTGTCC
GACCTGGGTGGCAACAACCTGCCCGCTAAGTTCCTCGAGGGGTTCGTG
CGCACCTCCAACATCAAGTTCCAGGACGCTTACAACGCTGGCGGTGGT
CACAACGGCGTGTTCGACTTCCCCGACTCCGGAACCCACTCCTGGGAG
TACTGGGGTGCTCAGCTGAACGCTATGAAGCCCGACCTGCAGCGTGCT
CTGGGTGCTACCCCTAACACCGGTCCAGCTCCTCAGGGTGCTTAA >SEQ ID NO: 86: SpyCatcher-ggs-Survivin DNA
GAMVDTLSGLSSEQGQSGDMTIEEDSATHIKFSKRDEDGKELAGATME
LRDSSGKTISTWISDGQVKDFYLYPGKYTFVETAAPDGYEVATAITFT
VNEQGQVTVNGKATKGDAHIGGSGAPALPQIWQLYLKNYRIATFKNWP
FLEDCACTPERMAEAGFIHCPTENEPDLAQCFFCFKELEGWEPDDNPI
EEHRKHSPGCAFLTVKKQMEELTVSEFLKLDRQRAKNKIAKETNNKQK
EFEETAKTTRQSIEQLAA >SEQ ID NO: 87: SpyCatcher-ggs-Survivin DNA
GGTGCAATGGTTGATACCCTGAGCGGTCTGAGCAGCGAACAGGGTCAG
AGCGGTGATATGACCATTGAAGAAGATAGCGCAACCCACATCAAATTC
AGCAAACGTGATGAAGATGGTAAAGAACTGGCAGGCGCAACAATGGAA
CTGCGTGATAGCAGCGGTAAAACCATTAGCACCTGGATTAGTGATGGT
CAGGTGAAAGATTTTTATCTGTACCCTGGCAAATACACCTTTGTTGAA
ACCGCAGCACCGGATGGTTATGAAGTTGCAACCGCAATTACCTTTACC
GTTAATGAACAGGGCCAGGTTACCGTGAATGGTAAAGCAACCAAAGGT
GATGCACATATTGGTGGTAGCGGTGCACCGGCACTGCCGCAGATTTGG
CAGCTGTATCTGAAAAACTATCGTATCGCCACCTTTAAAAACTGGCCG
TTTCTGGAAGATTGTGCATGTACACCGGAACGTATGGCAGAAGCAGGT
TTTATTCATTGTCCGACCGAAAATGAACCGGATCTGGCACAGTGTTTT
TTTTGCTTTAAAGAACTGGAAGGTTGGGAGCCGGATGATAATCCGATT
GAAGAACATCGTAAACATAGTCCGGGTTGTGCATTTCTGACCGTGAAA
AAACAAATGGAAGAACTGACCGTTAGCGAGTTTCTGAAACTGGATCGT
CAGCGTGCCAAAAACAAAATTGCAAAAGAAACCAATAACAAACAGAAA
GAATTCGAAGAAACCGCCAAAACCACCCGTCAGAGCATTGAACAGCTG
GCAGCATAA >SEQ ID NO: 88: Mini-HA-stem-Spytag
MKVKLLVLLCTFTATYADTICIGYHANNSTDTVDTVLEKNVTVTHSVN
LLENGGGGKYVCSAKLRMVTGLRNKPSKQSQGLFGAIAGFTEGGWTGM
VDGWYGYHHQNEQGSGYAADQKSTQNAINGITNKVNSVIEKMNTQYTA
IGCEYNKSERCMKQIEDKIEEIESKIWTYNAELLVLLENERTLDFHDS NVKNLYEKVKSQLKNNAKEIGNGCFEFYHKCNDECMESVKNGTYDYPK
YSEESKLNREKIDGVKLESMGVYQIEGAHIVMVDAYKPTK >SEQ ID NO: 89: Mini-HA-stem-Spytag DNA
ATGAAAGTGAAGCTGCTGGTGCTGCTGTGCACCTTCACCGCCACCTAC
GCCGACACCATCTGCATCGGCTACCACGCCAACAACAGCACCGACACC
GTGGATACCGTGCTGGAAAAGAACGTGACCGTGACCCACAGCGTGAAC
CTGCTGGAAAATGGCGGCGAGGCAAATACGTGTGCAGCGCCAAGCTG
CGGATGGTCACCGGCCTGAGAAACAAGCCCAGCAAGCAGAGCCAGGGC
CTGTTCGGAGCCATTGCCGGCTTTACAGAGGGCGGCTGGACCGGCATG
GTGGATGGGTGGTACGGCTATCACCACCAGAACGAGCAGGGCAGCGGC
TACGCCGCCGATCAGAAGTCTACCCAGAACGCCATCAACGGCATCACC
AACAAAGTGAACAGCGTGATCGAGAAGATGAACACCCAGTACACCGCC
ATCGGCTGCGAGTACAACAAGAGCGAGCGGTGCATGAAGCAGATCGAG
GACAAGATCGAAGAGATCGAGTCTAAGATCTGGACCTACAACGCCGAA
CTGCTGGTGCTGCTGGAAAACGAGCGGACCCTGGACTTCCACGACAGC
AACGTGAAGAACCTGTACGAGAAAGTGAAAAGCCAGCTGAAGAACAAC
GCCAAAGAGATCGGCAACGGCTGCTTCGAGTTCTACCACAAGTGCAAC
GACGAGTGCATGGAAAGCGTGAAGAATGGCACCTACGACTACCCCAAG
TACAGCGAGGAAAGCAAGCTGAACCGCGAGAAGATCGACGGCGTGAAG
CTGGAATCTATGGGCGTGTACCAGATTGAGGGCGCCCACATCGTGATG
GTGGACGCCTACAAGCCTACCAAG >SEQ ID NO: 90: Infectious hematopoietic
necrosis virus (IHNV) G-protein-SpyTag
MDTMITTPLILILITCGANSQTVQPDTASESDQPTWSNPLFTYPEGCT

LDKLSKVNASQLRCPRIFNDENRGLIAYPTSIRSLSVGNDLGNIHTQG

NYIHKVLYRTICSTGFFGGQTIEKALVEMKLSTREAGVYDTTTAAALY

FPAPRCQWYTDNVQNDLIFYYTTQKSVLRDPYTRDFLDSDFIGGKCTK

SPCQTHWSNVVWMGDAGIPACDSSQEIKGHLFVDKISNRVVKATSYGH

HPWGLHHACMIDFCGKPWIRTDLGDLISVEYNSGAKTLSFPKCEDKTV

GMRGNLDDFAYLDDLVKASESREECLEAHAEIISTNSVTPYLLSKFRS

PHPGINDVYAMHKGSIYHGMCMTVAVDEVSKDRTTYRAHRATSFTKWE

RPFGDEWEGFHGLHGNNTTIIPDLEKYVAQYKTSMMEPMSIKSVPHPS

ILAHYNETDVSGISIRKLDSFDLQSLHWSGSGAHIVMVDAYKPTK

>SEQ ID NO: 91: SpyTag-IHNV G-protein
AHIVMVDAYKPTKGGSDTMITTPLILILITCGANSQTVQPDTASESDQ

PTWSNPLFTYPEGCTLDKLSKVNASQLRCPRIFNDENRGLIAYPTSIR

SLSVGNDLGNIHTQGNYIHKVLYRTICSTGFFGGQTIEKALVEMKLST

REAGVYDTTTAAALYFPAPRCQWYTDNVQNDLIFYYTTQKSVLRDPYT

RDFLDSDFIGGKCTKSPCQTHWSNVVWMGDAGIPACDSSQEIKGHLFV

DKISNRVVKATSYGHHPWGLHHACMIDFCGKPWIRTDLGDLISVEYNS

GAKTLSFPKCEDKTVGMRGNLDDFAYLDDLVKASESREECLEAHAEII

-continued

STNSVTPYLLSKFRSPHPGINDVYAMHKGSIYHGMCMTVAVDEVSKDR

TTYRAHRATSFTKWERPFGDEWEGFHGLHGNNTTIIPDLEKYVAQYKT

SMMEPMSIKSVPHPSILAHYNETDVSGISIRKLDSFDLQSLHWS

>SEQ ID NO: 92: LongSpyTag-AP205-LongSpyTag
MAHIVMVDAYKPTKGSGTAGGGSGSANKPMQPITSTANKIVWSDPTRL

STTFSASLLRQRVKVGIAELNNVSGQYVSVYKRPAPKPEGCADACVIM

PNENQSIRTVISGSAENLATLKAEWETHKRNVDTLFASGNAGLGFLDP

TAAIVSSDTTAGTASGGSGGSGAHIVMVDAYKPTK

>SEQ ID NO: 93: LongSpyTag-AP205-LongSpyTag DNA
ATGGCACATATTGTTATGGTGGATGCATATAAACCGACCAAAGGTAGC

GGTACAGCCGGTGGTGGTAGTGGTAGCGCAAATAAACCGATGCAGCCG

ATTACCAGCACCGCAAACAAAATTGTTTGGAGCGATCCGACCCGTCTG

AGCACCACCTTTAGCGCAAGCCTGCTGCGTCAGCGTGTTAAAGTTGGT

ATTGCAGAACTGAATAATGTGAGCGGTCAGTATGTTAGCGTGTATAAA

CGTCCGGCACCGAAACCGGAAGGTTGTGCAGATGCATGTGTTATTATG

CCGAATGAAAATCAGAGCATTCGTACCGTTATTAGCGGTAGCGCAGAA

AATCTGGCAACCCTGAAAGCAGAATGGGAAACCCATAAACGTAATGTG

GATACCCTGTTTGCAAGCGGTAATGCAGGTCTGGGTTTTCTGGACCCG

ACCGCAGCAATTGTTAGCAGCGATACCACCGCAGGTACAGCCAGCGGT

GGTAGCGGTGGTAGCGGTGCACATATTGTTATGGTTGATGCATATAAA

CCGACCAAATAA

>SEQ ID NO: 94: mSA-AP205
MAEAGITGTWYNQHGSTFTVTAGADGNLTGQYENRAQGTGCQNSPYTL

TGRYNGTKLEWRVEWNNSTENCHSRTEWRGQYQGGAEARINTQWNLTY

EGGSGPATEQGQDTFTKVKGGSGSANKPMQPITSTANKIVWSDPTRLS

TTFSASLLRQRVKVGIAELNNVSGQYVSVYKRPAPKPEGCADACVIMP

NENQSIRTVISGSAENLATLKAEWETHKRNVDTLFASGNAGLGFLDPT

AAIVSSDTTA

>SEQ ID NO: 94: mSA-AP205 DNA
ATGGCAGAAGCAGGTATTACCGGCACCTGGTATAATCAGCATGGTAGC

ACCTTTACCGTTACCGCAGGCGCAGATGGTAATCTGACAGGTCAGTAT

GAAAATCGTGCACAGGGCACCGGTTGTCAGAATAGCCCGTATACCCTG

ACCGGTCGTTATAATGGCACCAAACTGGAATGGCGTGTTGAATGGAAT

AATAGCACCGAAAATTGTCATAGCCGTACCGAATGGCGTGGTCAGTAT

CAGGGTGGTGCAGAAGCCCGTATTAATACCCAGTGGAATCTGACCTAT

GAAGGTGGTAGCGGTCCGGCAACCGAACAGGGTCAGGATACCTTTACC

AAAGTTAAAGGTGGCAGCGGTAGCGCAAATAAACCGATGCAGCCGATT

ACCAGCACCGCAAACAAAATTGTTTGGAGCGATCCGACCCGTCTGAGC

ACCACCTTTAGCGCAAGCCTGCTGCGTCAGCGTGTTAAAGTTGGTATT

GCAGAACTGAATAATGTGAGCGGTCAGTATGTTAGCGTGTATAAACGT

CCGGCACCGAAACCGGAAGGTTGTGCAGATGCATGTGTTATTATGCCG

AATGAAAATCAGAGCATTCGTACCGTTATTAGCGGTAGCGCAGAAAAT

CTGGCAACCCTGAAAGCAGAATGGGAAACCCATAAACGTAATGTGGAT

-continued

ACCCTGTTTGCAAGCGGTAATGCAGGTCTGGGTTTTCTGGACCCGACC

GCAGCAATTGTTAGCAGCGATACCACCGCATAA

REFERENCES

Bachmann, M F. and Jennings, Gary T. Vaccine delivery: a matter of size, geometry, kinetics and molecular patterns. Nat Rev Immunol 10(11), 787-796. 2010.

Bachmann M F, Jennings G T. Therapeutic vaccines for chronic diseases: successes and technical challenges. Philosophical Transactions of the Royal Society B: Biological Sciences 2011; 366(1579):2815-2822.

Bachmann M F, Zinkernagel, R M. Neutralizing antiviral B cell responses. Annual review of immunology 15: 235-270. 1997.

Bachmann, M F. et al. The influence of antigen organization on B cell responsiveness. Science. 262(5138), 1448-1451, 1993.

Bachmann, M F, Jennings, G T, 2004a. Virus-like particles: combining innate and adaptive immunity for effective vaccination. In: Kaufmann, P.D.S.H.E. (Ed.), Novel Vaccination Strategies. Wiley-VCH Verlag GmbH & Co, pp. 415-432.

Buck, Christopher B. and Thompson, Cynthia D. Production of Papillomavirus-Based Gene Transfer Vectors. Current Protocols in Cell Biology. 2001.

Chackerian B, Lowy D R, Schiller J T. Induction of autoantibodies to mouse CCR5 with recombinant papiliomavirus particles. *Proceedings of the National Academy of Sciences of the United States of America* 1999; 96(5): 2373-2378.

Chackerian B, Durfee M R, Schiller J T. Virus-Like Display of a Neo-Self Antigen Reverses B Cell Anergy in a B Cell Receptor Transgenic Mouse Model. *Journal of immunology* (Baltimore, Md.: 1950) 2008; 180(9):5816-5825.

Chackerian, B. Virus-like particles: flexible platforms for vaccine development. Expert Review of Vaccines. 6(3), 381-390. 2007.

Fierer J O, Veggiani G, Howarth M. SpyLigase peptide-peptide ligation polymerizes affibodies to enhance magnetic cancer cell capture. *Proceedings of the National Academy of Sciences of the United States of America* 2014; 111(13):E1176-E1181.

Grgacic, Elizabeth V. L. and Anderson, David A. Virus-like particles: Passport to immune recognition. Particle-based Vaccines. Methods 40(1), 60-65. 2006.

Indulis Cielens, Ludmila Jackevica, Amis Strods, Andris Kazaks, Velta Ose, Janis Bogans, Paul Pumpens, Regina Renhofa. Mosaic RNA Phage VLPs Carrying Domain III of the West Nile Virus E Protein. Molecular Biotechnology. 2014

Kouskoff, V. et al. T Cell-Independent Rescue of B Lymphocytes from Peripheral Immune Tolerance, Science 287 (5462), 2501-2503. 2000.

Murray K. Application of recombinant DNA techniques in the development of viral vaccines. Vaccine. 6:164-74.1988.

Peabody D S, Manifold-Wheeler B, Medford A, Jordan S K, Caldeira J do C. Chackerian B. Immunogenic Display of Diverse Peptides on Virus-Like Particles of RNA Phage MS2. *Journal of molecular biology* 2008; 380(1):252-263.

Plotkin, S A. Vaccines: past, present and future. Nat Med. 5-4-2005.

P. Pushko, T. Kozlovskaya, I. Sominskaya, A. Brede, E. Stankevica, V. Ose, P. Pumpens, and E. Grens, Analysis of RNA phage fr coat protein assembly by insertion, deletion and substitution mutagenesis. Protein Eng. 1993.

Pumpens, P. and Grens, E. HBV Core Particles as a Carrier for B Cell/T Cell Epitopes. Intervirology 44(2-3), 98-114. 2001.

Raja, Krishnaswami S. et al. Icosahedral Virus Particles as Polyvalent Carbohydrate Display Platforms. ChemBioChem 4(12), 1348-1351, 2003.

Tissot A C, Renhofa R, Schmitz N, et al, Versatile Virus-Like Particle Carrier for Epitope Based Vaccines. Ho P L, ed, PLoS ONE. 2010

Zakeri, B. et al. J. Am. Chem. Soc, 2010, 132 (13), pp 4526-4527

Zakeri, B. et al. Proceedings of the National Academy of Sciences 109(12), E690-E697. 2012.

The invention claimed is:

1. An immunogenic virus-like particle having a surface, comprising:
   a. an AP205 capsid protein as set forth in SEQ ID NO: 58 or a biologically active variant thereof having at least 95% sequence identity to SEQ ID NO: 58, further comprising a first peptide tag, and
   b. a HER2 antigen as set forth in SEQ ID NO: 18 or a variant thereof having at least 90% sequence identity to SEQ ID NO: 18, further comprising a second peptide tag,
   wherein the HER2 antigen or variant thereof and the AP205 virus capsid protein or variant thereof are linked via an isopeptide bond between the first and second peptide tag, wherein the HER2 antigen is present on the surface of the immunogenic virus-like particle, and
   wherein the first peptide tag and the second peptide tag together represent a peptide tag pair.

2. The immunogenic virus-like particle according to claim 1, wherein the peptide tag pair is selected from the group consisting of i) a SpyTag and SpyCatcher pair, and ii) a split-Spy0128 and Spy isopeptide pair.

3. The immunogenic virus-like particle according to claim 2, wherein the first peptide tag is a SpyTag and the second peptide tag is a SpyCatcher.

4. The immunogenic virus-like particle according to claim 2, wherein the first peptide tag is a SpyCatcher and the second peptide tag is a SpyTag.

5. The immunogenic virus-like particle according to claim 2, wherein the first peptide tag is a split-Spy0128 and the second peptide tag is a Spy isopeptide.

6. The immunogenic virus-like particle according to claim 2, wherein the first peptide tag is a Spy isopeptide and the second peptide tag is a split-Spy0128.

7. The immunogenic virus-like particle according to claim 1, wherein the first peptide tag is fused to the N-terminal end or to the C-terminal end of the capsid protein by a linker.

8. The immunogenic virus-like particle according to claim 1, wherein the first peptide tag is two first peptide tag moieties.

9. The immunogenic virus-like particle according to claim 4, wherein the capsid protein is fused at its C-terminal end to one first peptide tag moiety and at its N-terminal end to another first peptide tag moiety.

10. The immunogenic virus-like particle according, to claim 5, wherein the first peptide tag is fused to the N-terminal end of the capsid protein.

11. The immunogenic virus-like particle according to claim 5, wherein the first peptide tag, is fused to the C-terminal end of the capsid protein.

12. An isolated host cell expressing, the immunogenic virus-like particle of claim 1.

13. The host cell according to claim 12, selected from the group consisting of: bacteria, yeast, fungi, plant, mammalian and insect cells.

14. A method of treatment of a cancer in a subject in need thereof, comprising: providing an immunogenic composition comprising at least one immunogenic virus-like particle according to claim 1, and administering said immunogenic virus-like particle to said subject.

15. The method of according to claim 14, further comprising boosting the immunogenicity of the immunogenic composition by administration in a form or body part different from the previous administration.

16. The method according to claim 14, wherein the immunogenic composition is administered to the area most likely to be the receptacle of a given disease.

17. The method according to claim 14, wherein the immunogenic composition is administered in combination with another immunogenic composition.

18. The method according, to claim 14, wherein the immunogenic composition forms a part of an immunogenic cocktail.

19. The method according to claim 14, wherein the cancer is associated with high HER2 expression.

20. The method according to claim 14, wherein the cancer is selected from the group consisting of a breast cancer, a gastric cancer, an ovarian cancer, a prostate cancer or a uterine serous carcinoma.

* * * * *

SEQUENCE LISTING

```
<160> NUMBER OF SEQ ID NOS: 95

<210> SEQ ID NO 1
<211> LENGTH: 505
<212> TYPE: PRT
<213> ORGANISM: Human papillomavirus

<400> SEQUENCE: 1

Met Lys Arg Ala Ser Ala Thr Gln Leu Tyr Lys Thr Cys Lys Gln Ala
1               5                   10                  15

Gly Thr Cys Pro Pro Asp Ile Ile Pro Lys Val Glu Gly Lys Thr Ile
            20                  25                  30

Ala Asp Gln Ile Leu Gln Tyr Gly Ser Met Gly Val Phe Phe Gly Gly
        35                  40                  45

Leu Gly Ile Gly Thr Gly Ser Gly Thr Gly Gly Arg Thr Gly Tyr Ile
    50                  55                  60

Pro Leu Gly Thr Arg Pro Pro Thr Ala Thr Asp Thr Leu Ala Lys Arg
65                  70                  75                  80
```

```
Ala Ser Val Thr Asp Leu Tyr Lys Thr Cys Lys Gln Ser Gly Thr Cys
                85                  90                  95

Pro Pro Asp Val Val Pro Lys Val Glu Gly Thr Thr Leu Ala Asp Lys
            100                 105                 110

Ile Leu Gln Trp Ser Ser Leu Gly Ile Phe Leu Gly Gly Leu Gly Ile
        115                 120                 125

Gly Thr Gly Ser Gly Thr Gly Gly Arg Thr Gly Tyr Ile Pro Leu Gly
130                 135                 140

Gly Arg Ser Asn Thr Val Val Asp Val Gly Pro Lys Arg Ala Ser Ala
145                 150                 155                 160

Thr Gln Leu Tyr Gln Thr Cys Lys Leu Thr Gly Thr Cys Pro Pro Asp
                165                 170                 175

Val Ile Pro Lys Val Glu His Asn Thr Ile Ala Asp Gln Ile Leu Lys
            180                 185                 190

Trp Gly Ser Leu Gly Val Phe Phe Gly Gly Leu Gly Ile Gly Thr Gly
        195                 200                 205

Ser Gly Thr Gly Gly Arg Thr Gly Tyr Val Pro Leu Gly Thr Ser Ala
210                 215                 220

Lys Pro Ser Ile Thr Ser Gly Pro Lys Arg Ala Ala Pro Lys Asp Ile
225                 230                 235                 240

Tyr Pro Ser Cys Lys Ile Ser Asn Thr Cys Pro Pro Asp Ile Gln Asn
                245                 250                 255

Lys Ile Glu His Thr Thr Ile Ala Asp Lys Ile Leu Gln Tyr Gly Ser
            260                 265                 270

Leu Gly Val Phe Leu Gly Gly Leu Gly Ile Gly Thr Ala Arg Gly Ser
        275                 280                 285

Gly Gly Arg Ile Gly Tyr Thr Pro Leu Gly Glu Gly Gly Gly Val Arg
290                 295                 300

Val Ala Thr Arg Pro Lys Arg Asp Ser Val Thr His Ile Tyr Gln Thr
305                 310                 315                 320

Cys Lys Gln Ala Gly Thr Cys Pro Pro Asp Val Ile Asn Lys Val Glu
                325                 330                 335

Gln Thr Thr Val Ala Asp Asn Ile Leu Lys Tyr Gly Ser Ala Gly Val
            340                 345                 350

Phe Phe Gly Gly Leu Gly Ile Ser Thr Gly Arg Gly Thr Gly Gly Ala
        355                 360                 365

Thr Gly Tyr Val Pro Leu Gly Glu Gly Pro Gly Val Arg Val Gly Gly
370                 375                 380

Thr Pro Gly Gly Ser Gly Ala Met Val Asp Thr Leu Ser Gly Leu Ser
385                 390                 395                 400

Ser Glu Gln Gly Gln Ser Gly Asp Met Thr Ile Glu Glu Asp Ser Ala
                405                 410                 415

Thr His Ile Lys Phe Ser Lys Arg Asp Glu Asp Gly Lys Glu Leu Ala
            420                 425                 430

Gly Ala Thr Met Glu Leu Arg Asp Ser Ser Gly Lys Thr Ile Ser Thr
        435                 440                 445

Trp Ile Ser Asp Gly Gln Val Lys Asp Phe Tyr Leu Tyr Pro Gly Lys
450                 455                 460

Tyr Thr Phe Val Glu Thr Ala Ala Pro Asp Gly Tyr Glu Val Ala Thr
465                 470                 475                 480

Ala Ile Thr Phe Thr Val Asn Glu Gln Gly Gln Val Thr Val Asn Gly
                485                 490                 495

Lys Ala Thr Lys Gly Asp Ala His Ile
```

<210> SEQ ID NO 2
<211> LENGTH: 1518
<212> TYPE: DNA
<213> ORGANISM: Human papillomavirus

<400> SEQUENCE: 2

| | | | | | |
|---|---|---|---|---|---|
| atgaaacgtg | caagcgcaac | ccagctgtat | aaaacctgta | acaggcagg | cacctgtccg | 60 |
| cctgatatca | ttccgaaagt | tgaaggtaaa | accattgccg | atcagattct | gcagtatggt | 120 |
| agcatgggcg | tgttttttgg | tggtctgggt | attggcaccg | tagcggcac | aggtggacgt | 180 |
| accggttaca | ttccgctggg | cacccgtccg | cctaccgcaa | ccgatacct | ggcaaaacgt | 240 |
| gccagcgtta | ccgatctgta | caaaacatgc | aaacagagcg | aacatgtcc | tccggatgtt | 300 |
| gttcctaaag | tggaaggcac | caccctggca | gataaaatcc | tgcagtggtc | aagcctgggt | 360 |
| atttttcctgg | gtggcttagg | cataggtaca | ggtagtggta | caggcggtcg | cacaggctat | 420 |
| atcccgctgg | gtggtcgtag | caataccgtt | gttgatgttg | tccgaaacg | tgcatcagcc | 480 |
| acacagctgt | atcagacctg | caaactgacc | ggtacgtgcc | cacctgatgt | tatcccgaaa | 540 |
| gtggaacata | atacaattgc | agaccagatt | ctgaaatggg | gttcactggg | cgtattcttc | 600 |
| ggaggcctgg | gcatcggaac | cggttcaggt | acgggtggcc | gtaccggcta | tgtgcctctg | 660 |
| ggtacaagcg | caaaaccgag | cattaccagc | ggtcctaaac | gcgcagcacc | gaaagatatt | 720 |
| tatccgagct | gtaaaattag | caataccgtc | cctccggata | tccagaacaa | aattgaacat | 780 |
| accaccattg | ccgacaaaat | cttacagtac | ggttctctgg | gtgtgtttct | gggaggttta | 840 |
| ggtatcggta | cggcacgtgg | tagcggtggt | cgcattggtt | ataccgct | gggtgaaggt | 900 |
| ggtggtgttc | gtgttgcaac | ccgtcctaaa | cgtgatagcg | ttacccatat | ttatcagacg | 960 |
| tgtaaacaag | caggtacttg | tccaccagat | gtgattaaca | aagtggaaca | gacaaccgtt | 1020 |
| gcggataaca | ttctgaaata | tggtagtgcc | ggtgtgtttt | ttggcggact | gggcatttca | 1080 |
| accggtcgtg | gtacgggtgg | tgcaaccggt | tacgtgcctc | tgggcgaagg | tccgggtgtg | 1140 |
| cgtgtgggtg | gtacaccggg | tggtagcggt | gcaatggttg | ataccctgag | cggtctgagc | 1200 |
| agcgaacagg | gtcagagcgg | tgatatgacc | attgaagaag | atagcgcaac | ccacatcaaa | 1260 |
| ttcagcaaac | gtgatgaaga | tggtaaagaa | ctggcaggcg | caacaatgga | actgcgtgat | 1320 |
| agcagcggta | aaaccattag | cacctggatt | agtgatggtc | aggtgaaaga | ttttatctg | 1380 |
| taccctggca | atacacctt | tgttgaaacc | gcagcaccgg | atggttatga | agttgcaacc | 1440 |
| gcaattacct | ttaccgttaa | tgaacagggc | caggttaccg | tgaatggtaa | agcaaccaaa | 1500 |
| ggtgatgcac | atatttaa | | | | | 1518 |

<210> SEQ ID NO 3
<211> LENGTH: 735
<212> TYPE: PRT
<213> ORGANISM: Plasmodium falciparum

<400> SEQUENCE: 3

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

```
Leu Arg Asp Ser Ser Gly Lys Thr Ile Ser Thr Trp Ile Ser Asp Gly
    50                  55                  60
Gln Val Lys Asp Phe Tyr Leu Tyr Pro Gly Lys Tyr Thr Phe Val Glu
65                  70                  75                  80
Thr Ala Ala Pro Asp Gly Tyr Glu Val Ala Thr Ala Ile Thr Phe Thr
                85                  90                  95
Val Asn Glu Gln Gly Gln Val Thr Val Asn Gly Lys Ala Thr Lys Gly
            100                 105                 110
Asp Ala His Ile Gly Gly Ser Arg Ser Thr Ser Glu Asn Arg Asn Lys
            115                 120                 125
Arg Ile Gly Gly Pro Lys Leu Arg Gly Asn Val Thr Ser Asn Ile Lys
    130                 135                 140
Phe Pro Ser Asp Asn Lys Gly Lys Ile Ile Arg Gly Ser Asn Asp Lys
145                 150                 155                 160
Leu Asn Lys Asn Ser Glu Asp Val Leu Glu Gln Ser Glu Lys Ser Leu
                165                 170                 175
Val Ser Glu Asn Val Pro Ser Gly Leu Asp Ile Asp Asp Ile Pro Lys
            180                 185                 190
Glu Ser Ile Phe Ile Gln Glu Asp Gln Glu Gly Gln Thr His Ser Glu
            195                 200                 205
Leu Asn Pro Glu Thr Ser Glu His Ser Lys Asp Leu Asn Asn Asn Gly
    210                 215                 220
Ser Lys Asn Glu Ser Ser Asp Ile Ile Ser Glu Asn Lys Ser Asn
225                 230                 235                 240
Lys Val Gln Asn His Phe Glu Ser Leu Ser Asp Leu Glu Leu Leu Glu
                245                 250                 255
Asn Ser Ser Gln Asp Asn Leu Asp Lys Asp Thr Ile Ser Thr Glu Pro
            260                 265                 270
Phe Pro Asn Gln Lys His Lys Asp Leu Gln Gln Asp Leu Asn Asp Glu
            275                 280                 285
Pro Leu Glu Pro Phe Pro Thr Gln Ile His Lys Asp Tyr Lys Glu Lys
    290                 295                 300
Asn Leu Ile Asn Glu Glu Asp Ser Glu Pro Phe Pro Arg Gln Lys His
305                 310                 315                 320
Lys Lys Val Asp Asn His Asn Glu Glu Lys Asn Val Phe His Glu Asn
                325                 330                 335
Gly Ser Ala Asn Gly Asn Gln Gly Ser Leu Lys Leu Lys Ser Phe Asp
            340                 345                 350
Glu His Leu Lys Asp Glu Lys Ile Glu Asn Glu Pro Leu Val His Glu
            355                 360                 365
Asn Leu Ser Ile Pro Asn Asp Pro Ile Glu Gln Ile Leu Asn Gln Pro
    370                 375                 380
Glu Gln Glu Thr Asn Ile Gln Glu Gln Leu Tyr Asn Glu Lys Gln Asn
385                 390                 395                 400
Val Glu Glu Lys Gln Asn Ser Gln Ile Pro Ser Leu Asp Leu Lys Glu
                405                 410                 415
Pro Thr Asn Glu Asp Ile Leu Pro Asn His Asn Pro Leu Glu Asn Ile
            420                 425                 430
Lys Gln Ser Glu Ser Glu Ile Asn His Val Gln Asp His Ala Leu Pro
            435                 440                 445
Lys Glu Asn Ile Ile Asp Lys Leu Asp Asn Gln Lys Glu His Ile Asp
    450                 455                 460
Gln Ser Gln His Asn Ile Asn Val Leu Gln Glu Asn Asn Ile Asn Asn
```

```
                465                 470                 475                 480
         His Gln Leu Glu Pro Gln Glu Lys Pro Asn Ile Glu Ser Phe Glu Pro
                         485                 490                 495
         Lys Asn Ile Asp Ser Glu Ile Ile Leu Pro Glu Asn Val Glu Thr Glu
                         500                 505                 510
         Glu Ile Ile Asp Asp Val Pro Ser Pro Lys His Ser Asn His Glu Thr
                         515                 520                 525
         Phe Glu Glu Thr Ser Glu Ser Glu His Glu Ala Val Ser Glu
                         530                 535                 540
         Lys Asn Ala His Glu Thr Val Glu His Glu Thr Val Ser Gln Glu
         545                 550                 555                 560
         Ser Asn Pro Glu Lys Ala Asp Asn Asp Gly Asn Val Ser Gln Asn Ser
                         565                 570                 575
         Asn Asn Glu Leu Asn Glu Asn Glu Phe Val Ser Glu Lys Ser Glu
                         580                 585                 590
         His Glu Ala Arg Ser Glu Lys Lys Val Ile His Gly Cys Asn Phe Ser
                         595                 600                 605
         Ser Asn Val Ser Ser Lys His Thr Phe Thr Asp Ser Leu Asp Ile Ser
                         610                 615                 620
         Leu Val Asp Asp Ser Ala His Ile Ser Cys Asn Val His Leu Ser Glu
         625                 630                 635                 640
         Pro Lys Tyr Asn His Leu Val Gly Leu Asn Cys Pro Gly Asp Ile Ile
                         645                 650                 655
         Pro Asp Cys Phe Phe Gln Val Tyr Gln Pro Glu Ser Glu Glu Leu Glu
                         660                 665                 670
         Pro Ser Asn Ile Val Tyr Leu Asp Ser Gln Ile Asn Ile Gly Asp Ile
                         675                 680                 685
         Glu Tyr Tyr Glu Asp Ala Glu Gly Asp Asp Lys Ile Lys Leu Phe Gly
                         690                 695                 700
         Ile Val Gly Ser Ile Pro Lys Thr Thr Ser Phe Thr Cys Ile Cys Lys
         705                 710                 715                 720
         Lys Asp Lys Lys Ser Ala Tyr Met Thr Val Thr Ile Asp Ser Ala
                         725                 730                 735

<210> SEQ ID NO 4
<211> LENGTH: 2205
<212> TYPE: DNA
<213> ORGANISM: Plasmodium falciparum

<400> SEQUENCE: 4
ggtgcaatgg ttgataccct gagcggtctg agcagcgaac agggtcagag cggtgatatg        60
accattgaag aagatagcgc aacccacatc aaattcagca acgtgatga agatggtaaa        120 gaactggcag gcgcaacaat ggaactgcgt gatagcagcg gtaaaaccat agcacctgg        180 attagtgatg gtcaggtgaa agatttttat ctgtaccctg caaatacac ctttgttgaa        240 accgcagcac cggatggtta tgaagttgca accgcaatta cctttaccgt taatgaacag        300
ggccaggtta ccgtgaatgg taaagcaacc aaaggtgatg cacatattgg tggtagcaga        360
tccacaagtg agaatagaaa taacgaatc gggggtccta aattaagggg taatgttaca        420
agtaatataa agttcccatc agataacaaa ggtaaaatta agaggttc gaatgataaa        480 cttaataaaa actctgaaga tgttttagaa caaagcgaaa aatcgcttgt tcagaaaat        540 gttcctagtg gattagatat agatgatatc cctaaagaat ctatttttat tcaagaagat        600
caagaaggtc aaactcattc tgaattaaat cctgaaacat cagaacatag taaagattta        660
```

```
aataataatg gttcaaaaaa tgaatctagt gatattattt cagaaaataa taaatcaaat      720
aaagtacaaa atcattttga atcattatca gatttagaat tacttgaaaa ttcctcacaa      780
gataatttag acaaagatac aatttcaaca gaacctttc ctaatcaaaa acataaagac       840
ttacaacaag atttaaatga tgaacccttta gaacccttc ctacacaaat acataaagat     900
tataaagaaa aaaatttaat aaatgaagaa gattcagaac catttcccag acaaaagcat      960
aaaaaggtag acaatcataa tgaagaaaaa aacgtatttc atgaaaatgg ttctgcaaat     1020
ggtaatcaag gaagtttgaa acttaaatca ttcgatgaac atttaaaaga tgaaaaaata     1080
gaaaatgaac cacttgttca tgaaaattta tccataccaa atgatccaat agaacaaata     1140
ttaaatcaac ctgaacaaga aacaaatatc caggaacaat tgtataatga aaacaaaat     1200 gttgaagaaa aacaaaattc tcaaatacct tcgttagatt taaagaacc aacaaatgaa    1260 gatattttac caaatcataa tccattagaa aatataaaac aaagtgaatc agaaataaat     1320
catgtacaag atcatgcgct accaaaagag aatataaatag acaaacttga taatcaaaaa     1380
gaacacatcg atcaatcaca acataatata aatgtattac aagaaaataa cataaacaat     1440
caccaattag aacctcaaga gaaacctaat attgaatcgt ttgaacctaa aaatatagat     1500
tcagaaatta ttcttcctga aaatgttgaa acagaagaaa taatagatga tgtgccttcc     1560
cctaaacatt ctaaccatga aacatttgaa gaagaaacaa gtgaatctga acatgaagaa     1620
gccgtatctg aaaaaaatgc ccacgaaact gtcgaacatg aagaaactgt gtctcaagaa     1680
agcaatcctg aaaaagctga taatgatgga aatgtatctc aaaacagcaa caacgaatta     1740
aatgaaaatg aattcgttga atcggaaaaa agcgagcatg aagcaagatc cgaaaaaaaa     1800
gtcatacacg gatgtaactt ctcttcaaat gttagttcta aacatacttt tacagatagt     1860
ttagatattt ctttagttga tgatagtgca catatttcat gtaacgtaca tttgtctgaa     1920
ccaaaatata atcatttggt aggtttaaat tgtcctggtg atattatacc agattgcttt     1980
tttcaagtat atcaacctga atcagaagaa cttgaaccat ccaacattgt ttatttagat     2040
tcacaaataa atataggaga tattgaatat tatgaagatg ctgaaggaga tgataaaatt     2100
aaattatttg gtatagttgg aagtatacca aaaacgacat cttttacttg tatatgtaag     2160
aaggataaaa aaagtgctta tatgacagtt actatagatt cagca                    2205
```

<210> SEQ ID NO 5
<211> LENGTH: 261
<212> TYPE: PRT
<213> ORGANISM: Plasmodium falciparum

<400> SEQUENCE: 5

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Arg Ser Glu Lys Lys Val Ile His Gly
        115                 120                 125

Cys Asn Phe Ser Ser Asn Val Ser Ser Lys His Thr Phe Thr Asp Ser
    130                 135                 140

Leu Asp Ile Ser Leu Val Asp Asp Ser Ala His Ile Ser Cys Asn Val
145                 150                 155                 160

His Leu Ser Glu Pro Lys Tyr Asn His Leu Val Gly Leu Asn Cys Pro
                165                 170                 175

Gly Asp Ile Ile Pro Asp Cys Phe Phe Gln Val Tyr Gln Pro Glu Ser
            180                 185                 190

Glu Glu Leu Glu Pro Ser Asn Ile Val Tyr Leu Asp Ser Gln Ile Asn
        195                 200                 205

Ile Gly Asp Ile Glu Tyr Tyr Glu Asp Ala Glu Gly Asp Asp Lys Ile
    210                 215                 220

Lys Leu Phe Gly Ile Val Gly Ser Ile Pro Lys Thr Thr Ser Phe Thr
225                 230                 235                 240

Cys Ile Cys Lys Lys Asp Lys Lys Ser Ala Tyr Met Thr Val Thr Ile
                245                 250                 255

Asp Ser Ala Arg Ser
            260

<210> SEQ ID NO 6
<211> LENGTH: 786
<212> TYPE: DNA
<213> ORGANISM: Plasmodium falcifarum

<400> SEQUENCE: 6
ggtgcaatgg ttgataccct gagcggtctg agcagcgaac agggtcagag cggtgatatg    60
accattgaag aagatagcgc aacccacatc aaattcagca acgtgatga agatggtaaa    120 gaactggcag gcgcaacaat ggaactgcgt gatagcagcg gtaaaaccat tagcacctgg    180
attagtgatg gtcaggtgaa agattttat ctgtaccctg gcaaatacac ctttgttgaa    240
accgcagcac cggatggtta tgaagttgca accgcaatta cctttaccgt taatgaacag    300
ggccaggtta ccgtgaatgg taaagcaacc aaaggtgatg cacatattgg tggtagcaga    360
tccgaaaaaa aagtcataca cggatgtaac ttctcttcaa atgttagttc taaacatact    420
tttacagata gtttagatat ttctttagtt gatgatagtg cacatatttc atgtaacgta    480
catttgtctg aaccaaaata taatcatttg gtaggtttaa attgtcctgg tgatattata    540
ccagattgct tttttcaagt atatcaacct gaatcagaag aacttgaacc atccaacatt    600
gtttatttag attcacaaat aaatatagga gatattgaat attatgaaga tgctgaagga    660
gatgataaaa ttaaattatt tggtatagtt ggaagtatac caaaaacgac atctttact    720 tgtatatgta agaaggataa aaaagtgct tatatgacag ttactataga ttcagcaaga    780
tcttaa                                                               786

<210> SEQ ID NO 7
<211> LENGTH: 1031
<212> TYPE: PRT
<213> ORGANISM: Plasmodium falcifarum

<400> SEQUENCE: 7

Met Ala His Ile Val Met Val Asp Ala Tyr Lys Pro Thr Lys Asn Lys
1               5                   10                  15

```
Ile Glu Glu Tyr Leu Gly Ala Lys Ser Asp Ser Lys Ile Asp Glu
            20                  25                  30

Leu Leu Lys Ala Asp Pro Ser Glu Val Glu Tyr Tyr Arg Ser Gly Gly
        35                  40                  45

Asp Gly Asp Tyr Leu Lys Asn Asn Ile Cys Lys Ile Thr Val Asn His
50                  55                  60

Ser Asp Ser Gly Lys Tyr Asp Pro Cys Glu Lys Lys Leu Pro Pro Tyr
65                  70                  75                  80

Asp Asp Asn Asp Gln Trp Lys Cys Gln Gln Asn Ser Ser Asp Gly Ser
                85                  90                  95

Gly Lys Pro Glu Asn Ile Cys Val Pro Pro Arg Arg Glu Arg Leu Cys
            100                 105                 110

Thr Tyr Asn Leu Glu Asn Leu Lys Phe Asp Lys Ile Arg Asp Asn Asn
        115                 120                 125

Ala Phe Leu Ala Asp Val Leu Leu Thr Ala Arg Asn Glu Gly Glu Lys
    130                 135                 140

Ile Val Gln Asn His Pro Asp Thr Asn Ser Ser Asn Val Cys Asn Ala
145                 150                 155                 160

Leu Glu Arg Ser Phe Ala Asp Leu Ala Asp Ile Ile Arg Gly Thr Asp
                165                 170                 175

Gln Trp Lys Gly Thr Asn Ser Asn Leu Glu Lys Asn Leu Lys Gln Met
            180                 185                 190

Phe Ala Lys Ile Arg Glu Asn Asp Lys Val Leu Gln Asp Lys Tyr Pro
        195                 200                 205

Lys Asp Gln Lys Tyr Thr Lys Leu Arg Glu Ala Trp Trp Asn Ala Asn
    210                 215                 220

Arg Gln Lys Val Trp Glu Val Ile Thr Cys Gly Ala Arg Ser Asn Asp
225                 230                 235                 240

Leu Leu Ile Lys Arg Gly Trp Arg Thr Ser Gly Lys Ser Asp Arg Lys
                245                 250                 255

Lys Asn Phe Glu Leu Cys Arg Lys Cys Gly His Tyr Glu Lys Glu Val
            260                 265                 270

Pro Thr Lys Leu Asp Tyr Val Pro Gln Phe Leu Arg Trp Leu Thr Glu
        275                 280                 285

Trp Ile Glu Asp Phe Tyr Arg Glu Lys Gln Asn Leu Ile Asp Asp Met
    290                 295                 300

Glu Arg His Arg Glu Glu Cys Thr Arg Glu Asp His Lys Ser Lys Glu
305                 310                 315                 320

Gly Thr Ser Tyr Cys Ser Thr Cys Lys Asp Lys Cys Lys Lys Tyr Cys
                325                 330                 335

Glu Cys Val Lys Lys Trp Lys Thr Glu Trp Glu Asn Gln Glu Asn Lys
            340                 345                 350

Tyr Lys Asp Leu Tyr Glu Gln Asn Lys Asn Lys Thr Ser Gln Lys Asn
        355                 360                 365

Thr Ser Arg Tyr Asp Asp Tyr Val Lys Asp Phe Phe Glu Lys Leu Glu
    370                 375                 380

Ala Asn Tyr Ser Ser Leu Glu Asn Tyr Ile Lys Gly Asp Pro Tyr Phe
385                 390                 395                 400

Ala Glu Tyr Ala Thr Lys Leu Ser Phe Ile Leu Asn Pro Ser Asp Ala
                405                 410                 415

Asn Asn Pro Ser Gly Glu Thr Ala Asn His Asn Asp Glu Ala Cys Asn
            420                 425                 430
```

```
Cys Asn Glu Ser Gly Ile Ser Val Gly Gln Ala Gln Thr Ser Gly
            435                 440                 445

Pro Ser Ser Asn Lys Thr Cys Ile Thr His Ser Ser Ile Lys Thr Asn
        450                 455                 460

Lys Lys Lys Glu Cys Lys Asp Val Lys Leu Gly Val Arg Glu Asn Asp
465                 470                 475                 480

Lys Asp Leu Lys Ile Cys Val Ile Glu Asp Thr Ser Leu Ser Gly Val
                485                 490                 495

Asp Asn Cys Cys Cys Gln Asp Leu Leu Gly Ile Leu Gln Glu Asn Cys
            500                 505                 510

Ser Asp Asn Lys Arg Gly Ser Ser Asn Asp Ser Cys Asp Asn Lys
        515                 520                 525

Asn Gln Asp Glu Cys Gln Lys Lys Leu Glu Lys Val Phe Ala Ser Leu
    530                 535                 540

Thr Asn Gly Tyr Lys Cys Asp Lys Cys Lys Ser Gly Thr Ser Arg Ser
545                 550                 555                 560

Lys Lys Lys Trp Ile Trp Lys Lys Ser Ser Gly Asn Glu Glu Gly Leu
                565                 570                 575

Gln Glu Glu Tyr Ala Asn Thr Ile Gly Leu Pro Pro Arg Thr Gln Ser
            580                 585                 590

Leu Tyr Leu Gly Asn Leu Pro Lys Leu Glu Asn Val Cys Glu Asp Val
        595                 600                 605

Lys Asp Ile Asn Phe Asp Thr Lys Glu Lys Phe Leu Ala Gly Cys Leu
610                 615                 620

Ile Val Ser Phe His Glu Gly Lys Asn Leu Lys Lys Arg Tyr Pro Gln
625                 630                 635                 640

Asn Lys Asn Ser Gly Asn Lys Glu Asn Leu Cys Lys Ala Leu Glu Tyr
                645                 650                 655

Ser Phe Ala Asp Tyr Gly Asp Leu Ile Lys Gly Thr Ser Ile Trp Asp
            660                 665                 670

Asn Glu Tyr Thr Lys Asp Leu Glu Leu Asn Leu Gln Asn Asn Phe Gly
        675                 680                 685

Lys Leu Phe Gly Lys Tyr Ile Lys Lys Asn Asn Thr Ala Glu Gln Asp
690                 695                 700

Thr Ser Tyr Ser Ser Leu Asp Glu Leu Arg Glu Ser Trp Trp Asn Thr
705                 710                 715                 720

Asn Lys Lys Tyr Ile Trp Thr Ala Met Lys His Gly Ala Glu Met Asn
                725                 730                 735

Ile Thr Thr Cys Asn Ala Asp Gly Ser Val Thr Gly Ser Gly Ser Ser
            740                 745                 750

Cys Asp Asp Ile Pro Thr Ile Asp Leu Ile Pro Gln Tyr Leu Arg Phe
        755                 760                 765

Leu Gln Glu Trp Val Glu Asn Phe Cys Glu Gln Arg Gln Ala Lys Val
770                 775                 780

Lys Asp Val Ile Thr Asn Cys Lys Ser Cys Lys Glu Ser Gly Asn Lys
785                 790                 795                 800

Cys Lys Thr Glu Cys Lys Thr Lys Cys Lys Asp Glu Cys Glu Lys Tyr
                805                 810                 815

Lys Lys Phe Ile Glu Ala Cys Gly Thr Ala Gly Gly Ile Gly Thr
            820                 825                 830

Ala Gly Ser Pro Trp Ser Lys Arg Trp Asp Gln Ile Tyr Lys Arg Tyr
        835                 840                 845

Ser Lys His Ile Glu Asp Ala Lys Arg Asn Arg Lys Ala Gly Thr Lys
```

```
                    850                 855                 860
Asn Cys Gly Thr Ser Ser Thr Thr Asn Ala Ala Ala Ser Thr Asp Glu
865                 870                 875                 880

Asn Lys Cys Val Gln Ser Asp Ile Asp Ser Phe Phe Lys His Leu Ile
                    885                 890                 895

Asp Ile Gly Leu Thr Thr Pro Ser Ser Tyr Leu Ser Asn Val Leu Asp
                900                 905                 910

Asp Asn Ile Cys Gly Ala Asp Lys Ala Pro Trp Thr Thr Tyr Thr Thr
                915                 920                 925

Tyr Thr Thr Thr Glu Lys Cys Asn Lys Glu Arg Asp Lys Ser Lys Ser
    930                 935                 940

Gln Ser Ser Asp Thr Leu Val Val Val Asn Val Pro Ser Pro Leu Gly
945                 950                 955                 960

Asn Thr Pro Tyr Arg Tyr Lys Tyr Ala Cys Gln Cys Lys Ile Pro Thr
                965                 970                 975

Asn Glu Glu Thr Cys Asp Asp Arg Lys Glu Tyr Met Asn Gln Trp Ser
                980                 985                 990

Cys Gly Ser Ala Arg Thr Met Lys Arg Gly Tyr Lys Asn Asp Asn Tyr
            995                 1000                1005

Glu Leu Cys Lys Tyr Asn Gly Val Asp Val Lys Pro  Thr Thr Val
   1010                1015                1020

Arg Ser Asn Ser Ser Lys Leu Asp
   1025                1030

<210> SEQ ID NO 8
<211> LENGTH: 3093
<212> TYPE: DNA
<213> ORGANISM: Plasmodium falcifarum

<400> SEQUENCE: 8
atggctcaca tcgtgatggt ggacgcttac aagcccacca agaacaagat cgaggaatat     60
ctgggagcta agtccgatga cagcaagatc gacgaactgc tgaaggccga tcctagcgaa    120
gtggagtact acagaagcgg aggcgacggc gactacctga gaacaacat ctgcaagatc     180
accgtgaacc agcgcgatag cggcaagtat gaccccctgc gagaagaagct gccccctac    240
gacgacaacg accagtggaa gtgccagcag aacagcagcg acggcagcgg caagcccgag    300
aacatctgcg tgcccccag acgggagcgg ctgtgcacct acaacctgga aaacctgaag    360
ttcgacaaga tccgggacaa caacgccttc ctggccgacg tgctgctgac cgcccggaac    420
gagggcgaga agatcgtgca gaaccacccc gacaccaaca gcagcaacgt gtgcaacgcc    480
ctggaacggt ccttcgctga cctggctgac atcatccggg gcaccgatca gtggaagggc    540
accaactcca atctggaaaa gaacctgaag cagatgttcg ccaagatcag agaaaacgac    600
aaggtgctgc aggacaagta ccccaaggac cagaagtaca ccaagctgcg ggaggcctgg    660
tggaacgcca accggcagaa agtgtgggaa gtgatcacct gtggcgccag aagcaacgat    720
ctgctgatca gcggggctg gcggaccagc ggcaagagcg accggaagaa aaacttcgag    780
ctgtgccgga gtgcggcca ctacgagaaa gaggtgccca ccaagctgga ctacgtgccc    840
cagttcctgc ggtggctgac cgagtggatc gaggacttct accggagaa gcagaacctg    900
atcgacgcaca tggaacggca ccgggaggaa tgcaccagag aggaccacaa gagcaaagag    960
ggcaccagct actgcagcac atgcaaggac aagtgcaaga aatactgcga gtgcgtgaag   1020
aaatggaaaa ccgagtggga gaaccaggaa aacaagtaca aggacctgta cgagcagaac   1080
```

| | |
|---|---|
| aagaacaaga ccagccagaa gaacaccagc agatacgacg actacgtgaa ggacttcttc | 1140 |
| gagaagctgg aagccaacta cagcagcctg gaaaactaca tcaagggcga cccctatttc | 1200 |
| gctgagtacg ctacaaaact gagcttcatc ctgaacccca gcgacgccaa caaccccagc | 1260 |
| ggcgagacag ccaaccacaa cgacgaggcc tgcaactgca acgagagcgg catcagcagc | 1320 |
| gtgggccagg ctcagacatc cggccctagc agcaacaaga cctgtatcac ccacagctcc | 1380 |
| atcaagacca caagaaaaa agaatgcaag gacgtgaagc tgggcgtgcg ggagaacgac | 1440 |
| aaggatctga agatctgcgt gatcgaggac accagcctga gcggcgtgga caactgctgc | 1500 |
| tgccaggatc tgctgggcat cctgcaggaa aactgcagcg acaacaagcg gggcagcagc | 1560 |
| tccaacgaca gctgcgacaa taagaaccag gacgagtgcc agaaaaagct ggaaaaggtg | 1620 |
| ttcgccagcc tgaccaacgg ctacaagtgc gataagtgca agagcggcac ctcccggtcc | 1680 |
| aagaagaagt ggatctggaa gaagtccagc ggcaacgagg aaggcctgca ggaagagtac | 1740 |
| gccaacacca tcggcctgcc cccaggacc cagagcctgt acctgggcaa tctgcccaaa | 1800 |
| ctggaaaacg tgtgcgagga tgtgaaggac atcaacttcg acaccaaaga gaagtttctg | 1860 |
| gccggctgcc tgatcgtgtc cttccacgag ggcaagaatc tgaagaagcg ctaccccag | 1920 |
| aataagaaca gcgcaacaa agaaaacctg tgcaaggctc tggaatacag cttcgccgac | 1980 |
| tacggcgacc tgatcaaggg cacctccatc tgggacaacg agtacacaaa ggacctggaa | 2040 |
| ctgaatctgc agaacaactt cggcaagctg ttcggcaagt acatcaagaa gaacaatacc | 2100 |
| gccgagcagg acacctccta cagctccctg gacgagctgc gcgagtcttg gtggaatacc | 2160 |
| aataagaagt acatctggac cgccatgaag cacgcgccg agatgaacat caccacctgt | 2220 |
| aacgccgacg gctccgtgac cggcagcggc tccagctgcg acgacatccc caccatcgac | 2280 |
| ctgatccccc agtacctgag atttctgcag gaatgggtcg agaacttctg cgagcagcgg | 2340 |
| caggccaaag tgaaggacgt gatcaccaac tgcaagagct gcaagaatc cggcaacaaa | 2400 |
| tgcaagaccg agtgcaaaac caagtgcaag gatgagtgcg agaagtacaa gaagttcatc | 2460 |
| gaggcctgcg gcacagccgg cggaggcatc ggaacagccg gcagcccctg gtccaagaga | 2520 |
| tgggaccaga tctacaagcg gtacagcaag cacatcgagg acgccaagcg gaaccggaag | 2580 |
| gccggcacca agaactgcgg caccagctcc accaccaacg ccgctgccag caccgacgag | 2640 |
| aataagtgcg tgcagagcga catcgacagc tttttcaagc acctgatcga tatcggcctg | 2700 |
| accaccccca gcagctacct gagcaacgtg ctggacgaca catctgtgg cgccgacaag | 2760 |
| gccccctgga caacctatac aacatacact acaaccgaga agtgcaacaa agagcgggac | 2820 |
| aagagcaaga gccagagcag cgacacctg gtggtggtga acgtgcccag cccctgggc | 2880 |
| aacacaccct accggtacaa gtacgcctgc cagtgcaaga tccccaccaa cgaggaaaca | 2940 |
| tgcgacgacc ggaaagaata catgaaccag tggtcctgcg ggagcgctcg gaccatgaag | 3000 |
| agagggtata agaacgataa ctacgaactg tgcaagtaca acggcgtgga tgtgaagccc | 3060 |
| accaccgtgc ggagcaactc cagcaagctg gac | 3093 |

<210> SEQ ID NO 9
<211> LENGTH: 237
<212> TYPE: PRT
<213> ORGANISM: Mus musculus

<400> SEQUENCE: 9

Phe Thr Ile Thr Ala Pro Lys Asp Leu Tyr Val Val Glu Tyr Gly Ser
1               5                   10                  15

Asn Val Thr Met Glu Cys Arg Phe Pro Val Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His Gly Gly Ser
210                 215                 220

Ala His Ile Val Met Val Asp Ala Tyr Lys Pro Thr Lys
225                 230                 235

<210> SEQ ID NO 10
<211> LENGTH: 714
<212> TYPE: DNA
<213> ORGANISM: Mus musculus

<400> SEQUENCE: 10
ttcaccatca ccgctcccaa ggacctgtac gtggtcgagt acggttccaa cgtgacaatg     60
gaatgccgtt tccccgtcga gcgcgagctg acctgttgg cttgtggtgg tactgggag    120 aaggaagatg agcaagtcat ccagttcgtg gctggcgaag aggacctgaa gccccagcac    180
tccaacttcc gtggtcgtgc ttccctgcct aaggaccagc tgctgaaggg caacgctgct    240
ctgcagatca ccgacgtgaa gctgcaggac gctggtgtct actgctgcat catctcctac    300
ggtggtgctg actacaagcg tatcaccctc aaagtgaacg ctccctaccg caagatcaac    360
cagcgcatct ccgtggaccc cgctacctct gagcacgagc tgatctgcca ggctgagggt    420
taccccgagg ctgaagtgat ctggaccaac tccgaccacc agcccgtgtc cggaaagcgt    480
tccgtgacca cctctcgtac cgagggcatg ctgctgaacg tgacctcctc cctgcgtgtg    540
aacgctaccg ctaacgacgt gttctactgc accttctggc gttcccagcc cggccagaac    600
cacaccgctg agctgatcat ccccgagctg cctgctaccc accccctca aaaccgtacc    660 cacggtggtt ccgctcacat cgtgatggtg gacgcttaca gcccactaa ataa    714

<210> SEQ ID NO 11
<211> LENGTH: 142
<212> TYPE: PRT
<213> ORGANISM: Mus musculus

<400> SEQUENCE: 11

Glu Ala Ile Gln Val Thr Gln Pro Ser Val Val Leu Ala Ser Ser His
1               5                   10                  15

Gly Val Ala Ser Phe Pro Cys Glu Tyr Ser Pro Ser His Asn Thr Asp
            20                  25                  30

Glu Val Arg Val Thr Val Leu Arg Gln Thr Asn Asp Gln Met Thr Glu
        35                  40                  45

Val Cys Ala Thr Thr Phe Thr Glu Lys Asn Thr Val Gly Phe Leu Asp
    50                  55                  60

Tyr Pro Phe Cys Ser Gly Thr Phe Asn Glu Ser Arg Val Asn Leu Thr
65                  70                  75                  80

Ile Gln Gly Leu Arg Ala Val Asp Thr Gly Leu Tyr Leu Cys Lys Val
                85                  90                  95

Glu Leu Met Tyr Pro Pro Pro Tyr Phe Val Gly Met Gly Asn Gly Thr
            100                 105                 110

Gln Ile Tyr Val Ile Asp Pro Glu Pro Ser Pro Asp Ser Asp Gly Gly
        115                 120                 125

Ser Ala His Ile Val Met Val Asp Ala Tyr Lys Pro Thr Lys
    130                 135                 140

<210> SEQ ID NO 12
<211> LENGTH: 429
<212> TYPE: DNA
<213> ORGANISM: Mus musculus

<400> SEQUENCE: 12
gaggctatcc aagtgaccca gccctccgtg gtgctggctt cctctcacgg tgttgccagc      60
ttcccttgcg agtactcccc ctcccacaac accgacgaag tgcgtgtgac cgtgctgcgt     120
cagaccaacg accagatgac cgaagtgtgc gctaccacct tcaccgagaa gaacaccgtc     180
ggtttcttgg actacccctt ctgctccggc accttcaacg agtcccgtgt gaacctgacc     240
atccagggcc tgcgtgctgt ggacaccgga ctgtacctgt gcaaggtcga gctgatgtac     300 cctccccccct acttcgtggg catgggcaac ggcacccaga tctacgtgat cgaccccgag     360
ccttcccccg actctgacgg tggttctgct cacatcgtga tggtggacgc ttacaagccc     420
actaaataa                                                             429

<210> SEQ ID NO 13
<211> LENGTH: 539
<212> TYPE: PRT
<213> ORGANISM: Plasmodium falciparum

<400> SEQUENCE: 13

Gln Asn Tyr Trp Glu His Pro Tyr Gln Asn Ser Asp Val Tyr Arg Pro
1               5                   10                  15

Ile Asn Glu His Arg Glu His Pro Lys Glu Tyr Glu Tyr Pro Leu His
            20                  25                  30

Gln Glu His Thr Tyr Gln Gln Glu Asp Ser Gly Glu Asp Glu Asn Thr
        35                  40                  45

Leu Gln His Ala Tyr Pro Ile Asp His Glu Gly Ala Glu Pro Ala Pro
    50                  55                  60

Gln Glu Gln Asn Leu Phe Ser Ser Ile Glu Ile Val Glu Arg Ser Asn
65                  70                  75                  80

Tyr Met Gly Asn Pro Trp Thr Glu Tyr Met Ala Lys Tyr Asp Ile Glu
                85                  90                  95

```
Glu Val His Gly Ser Gly Ile Arg Val Asp Leu Gly Glu Asp Ala Glu
            100                 105                 110

Val Ala Gly Thr Gln Tyr Arg Leu Pro Ser Gly Lys Cys Pro Val Phe
        115                 120                 125

Gly Lys Gly Ile Ile Ile Glu Asn Ser Asn Thr Thr Phe Leu Thr Pro
    130                 135                 140

Val Ala Thr Gly Asn Gln Tyr Leu Lys Asp Gly Gly Phe Ala Phe Pro
145                 150                 155                 160

Pro Thr Glu Pro Leu Met Ser Pro Met Thr Leu Asp Glu Met Arg His
                165                 170                 175

Phe Tyr Lys Asp Asn Lys Tyr Val Lys Asn Leu Asp Glu Leu Thr Leu
            180                 185                 190

Cys Ser Arg His Ala Gly Asn Met Ile Pro Asp Asn Asp Lys Asn Ser
        195                 200                 205

Asn Tyr Lys Tyr Pro Ala Val Tyr Asp Asp Lys Asp Lys Lys Cys His
    210                 215                 220

Ile Leu Tyr Ile Ala Ala Gln Glu Asn Asn Gly Pro Arg Tyr Cys Asn
225                 230                 235                 240

Lys Asp Glu Ser Lys Arg Asn Ser Met Phe Cys Phe Arg Pro Ala Lys
                245                 250                 255

Asp Ile Ser Phe Gln Asn Tyr Thr Tyr Leu Ser Lys Asn Val Val Asp
            260                 265                 270

Asn Trp Glu Lys Val Cys Pro Arg Lys Asn Leu Gln Asn Ala Lys Phe
        275                 280                 285

Gly Leu Trp Val Asp Gly Asn Cys Glu Asp Ile Pro His Val Asn Glu
    290                 295                 300

Phe Pro Ala Ile Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
                325                 330                 335

Glu Lys Ile Lys Glu Gly Phe Lys Asn Lys Asn Ala Ser Met Ile Lys
            340                 345                 350

Ser Ala Phe Leu Pro Thr Gly Ala Phe Lys Ala Asp Arg Tyr Lys Ser
        355                 360                 365

His Gly Lys Gly Tyr Asn Trp Gly Asn Tyr Asn Thr Glu Thr Gln Lys
    370                 375                 380

Cys Glu Ile Phe Asn Val Lys Pro Thr Cys Leu Ile Asn Asn Ser Ser
385                 390                 395                 400

Tyr Ile Ala Thr Thr Ala Leu Ser His Pro Ile Glu Val Glu Asn Asn
                405                 410                 415

Phe Pro Cys Ser Leu Tyr Lys Asp Glu Ile Met Lys Glu Ile Glu Arg
            420                 425                 430

Glu Ser Lys Arg Ile Lys Leu Asn Asp Asn Asp Glu Gly Asn Lys
        435                 440                 445

Lys Ile Ile Ala Pro Arg Ile Phe Ile Ser Asp Asp Lys Asp Ser Leu
    450                 455                 460

Lys Cys Pro Cys Asp Pro Glu Met Val Ser Asn Ser Thr Cys Arg Phe
465                 470                 475                 480

Phe Val Cys Lys Cys Val Glu Arg Arg Ala Glu Val Thr Ser Asn Asn
                485                 490                 495

Glu Val Val Lys Glu Glu Tyr Lys Asp Glu Tyr Ala Asp Ile Pro
            500                 505                 510
```

```
Glu His Lys Pro Thr Tyr Asp Lys Met Lys Gly Gly Ser Gly Ala His
        515                 520                 525

Ile Val Met Val Asp Ala Tyr Lys Pro Thr Lys
    530                 535

<210> SEQ ID NO 14
<211> LENGTH: 147
<212> TYPE: PRT
<213> ORGANISM: Dermatophagoides pteronyssinus

<400> SEQUENCE: 14

Ala His Ile Val Met Val Asp Ala Tyr Lys Pro Thr Lys Gly Gly Ser
1               5                  10                  15

Asp Gln Val Asp Val Lys Asp Cys Ala Asn His Glu Ile Lys Lys Val
            20                  25                  30

Leu Val Pro Gly Cys His Gly Ser Glu Pro Cys Ile Ile His Arg Gly
        35                  40                  45

Lys Pro Phe Gln Leu Glu Ala Val Phe Glu Ala Asn Gln Asn Ser Lys
    50                  55                  60

Thr Ala Lys Ile Glu Ile Lys Ala Ser Ile Asp Gly Leu Glu Val Asp
65                  70                  75                  80

Val Pro Gly Ile Asp Pro Asn Ala Cys His Tyr Met Lys Cys Pro Leu
                85                  90                  95

Val Lys Gly Gln Gln Tyr Asp Ile Lys Tyr Thr Trp Asn Val Pro Lys
            100                 105                 110

Ile Ala Pro Lys Ser Glu Asn Val Val Val Thr Val Lys Val Met Gly
        115                 120                 125

Asp Asp Gly Val Leu Ala Cys Ala Ile Ala Thr His Ala Lys Ile Arg
    130                 135                 140

Asp Ala Ser
145

<210> SEQ ID NO 15
<211> LENGTH: 441
<212> TYPE: DNA
<213> ORGANISM: Dermatophagoides pteronyssinus

<400> SEQUENCE: 15
gctcacatcg tgatggtgga cgcttacaag cccaccaagg gtggatccga tcaagtcgat    60
gtcaaagatt gtgccaatca tgaaatcaaa aaagttttgg taccaggatg ccatggttca   120
gaaccatgta tcattcatcg tggtaaacca ttccaattgg aagccgtttt cgaagccaac   180
caaaactcaa aaccgctaaa aattgaaatc aaagcttcaa tcgatggttt agaagttgat   240
gttcccggta tcgatccaaa tgcatgccat tatatgaaat gtccattggt taaaggacaa   300
caatatgata ttaaatatac atggaatgtt ccgaaaattg caccaaaatc tgaaaatgtt   360
gtcgtcactg tcaaagttat gggtgatgat ggtgttttgg cctgtgctat tgctactcat   420
gctaaaatcc gcgatgctag c                                             441

<210> SEQ ID NO 16
<211> LENGTH: 289
<212> TYPE: PRT
<213> ORGANISM: influenza virus

<400> SEQUENCE: 16

Met Lys Val Lys Leu Leu Val Leu Leu Cys Thr Phe Thr Ala Thr Tyr
1               5                  10                  15
```

```
Ala Asp Thr Ile Cys Ile Gly Tyr His Ala Asn Asn Ser Thr Asp Thr
             20                  25                  30

Val Asp Thr Val Leu Glu Lys Asn Val Thr Val Thr His Ser Val Asn
         35                  40                  45

Leu Leu Glu Asn Gly Gly Gly Lys Tyr Val Cys Ser Ala Lys Leu
 50                  55                  60

Arg Met Val Thr Gly Leu Arg Asn Lys Pro Ser Lys Gln Ser Gln Gly
 65                  70                  75                  80

Leu Phe Gly Ala Ile Ala Gly Phe Thr Glu Gly Gly Trp Thr Gly Met
                 85                  90                  95

Val Asp Gly Trp Tyr Gly Tyr His His Gln Asn Glu Gln Gly Ser Gly
                100                 105                 110

Tyr Ala Ala Asp Gln Lys Ser Thr Gln Asn Ala Ile Asn Gly Ile Thr
            115                 120                 125

Asn Lys Val Asn Ser Val Ile Glu Lys Met Asn Thr Gln Tyr Thr Ala
    130                 135                 140

Ile Gly Cys Glu Tyr Asn Lys Ser Glu Arg Cys Met Lys Gln Ile Glu
145                 150                 155                 160

Asp Lys Ile Glu Glu Ile Glu Ser Lys Ile Trp Thr Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly His His His His
            260                 265                 270

His His Gly Gly Ala His Ile Val Met Val Asp Ala Tyr Lys Pro Thr
        275                 280                 285

Lys

<210> SEQ ID NO 17
<211> LENGTH: 870
<212> TYPE: DNA
<213> ORGANISM: influenza virus

<400> SEQUENCE: 17
atgaaagtga agctgctggt gctgctgtgc accttcaccg ccacctacgc cgacaccatc      60
tgcatcggct accacgccaa caacagcacc gacaccgtgg ataccgtgct ggaaaagaac     120
gtgaccgtga cccacagcgt gaacctgctg gaaaatggcg gcggaggcaa atacgtgtgc     180
agcgccaagc tgcggatggt caccggcctg agaaacaagc ccagcaagca gagccagggc     240
ctgttcggag ccattgccgg ctttacagag ggcggctgga ccggcatggt ggatgggtgg     300
tacggctatc accaccagaa cgagcagggc agcggctacg ccgccgatca gaagtctacc     360
cagaacgcca tcaacggcat caccaacaaa gtgaacagcg tgatcgagaa gatgaacacc     420
cagtacaccg ccatcggctg cgagtacaac aagagcgagc ggtgcatgaa gcagatcgag     480
gacaagatcg aagagatcga gtctaagatc tggacctaca acgccgaact gctggtgctg     540
```

-continued

```
ctggaaaacg agcggaccct ggacttccac gacagcaacg tgaagaacct gtacgagaaa    600
gtgaaaagcc agctgaagaa caacgccaaa gagatcggca acggctgctt cgagttctac    660
cacaagtgca cgacgagtg catggaaagc gtgaagaatg cacctacga ctaccccaag    720 tacagcgagg aaagcaagct gaaccgcgag aagatcgacg gcgtgaagct ggaatctatg    780
ggcgtgtacc agattgaggg ccaccaccat caccatcatc acggcggagc ccacatcgtg    840
atggtggacg cctacaagcc caccaaataa    870
```

<210> SEQ ID NO 18
<211> LENGTH: 789
<212> TYPE: PRT
<213> ORGANISM: Homo sapiens

<400> SEQUENCE: 18

```
Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Thr Gln Val Cys Thr Gly Thr Asp Met
        115                 120                 125

Lys Leu Arg Leu Pro Ala Ser Pro Glu Thr His Leu Asp Met Leu Arg
    130                 135                 140

His Leu Tyr Gln Gly Cys Gln Val Val Gln Gly Asn Leu Glu Leu Thr
145                 150                 155                 160

Tyr Leu Pro Thr Asn Ala Ser Leu Ser Phe Leu Gln Asp Ile Gln Glu
                165                 170                 175

Val Gln Gly Tyr Val Leu Ile Ala His Asn Gln Val Arg Gln Val Pro
            180                 185                 190

Leu Gln Arg Leu Arg Ile Val Arg Gly Thr Gln Leu Phe Glu Asp Asn
        195                 200                 205

Tyr Ala Leu Ala Val Leu Asp Asn Gly Asp Pro Leu Asn Asn Thr Thr
    210                 215                 220

Pro Val Thr Gly Ala Ser Pro Gly Gly Leu Arg Glu Leu Gln Leu Arg
225                 230                 235                 240

Ser Leu Thr Glu Ile Leu Lys Gly Gly Val Leu Ile Gln Arg Asn Pro
                245                 250                 255

Gln Leu Cys Tyr Gln Asp Thr Ile Leu Trp Lys Asp Ile Phe His Lys
            260                 265                 270

Asn Asn Gln Leu Ala Leu Thr Leu Ile Asp Thr Asn Arg Ser Arg Ala
        275                 280                 285

Cys His Pro Cys Ser Pro Met Cys Lys Gly Ser Arg Cys Trp Gly Glu
    290                 295                 300

Ser Ser Glu Asp Cys Gln Ser Leu Thr Arg Thr Val Cys Ala Gly Gly
305                 310                 315                 320
```

Cys Ala Arg Cys Lys Gly Pro Leu Pro Thr Asp Cys Cys His Glu Gln
              325                 330                 335

Cys Ala Ala Gly Cys Thr Gly Pro Lys His Ser Asp Cys Leu Ala Cys
              340                 345                 350

Leu His Phe Asn His Ser Gly Ile Cys Glu Leu His Cys Pro Ala Leu
              355                 360                 365

Val Thr Tyr Asn Thr Asp Thr Phe Glu Ser Met Pro Asn Pro Glu Gly
370                 375                 380

Arg Tyr Thr Phe Gly Ala Ser Cys Val Thr Ala Cys Pro Tyr Asn Tyr
385                 390                 395                 400

Leu Ser Thr Asp Val Gly Ser Cys Thr Leu Val Cys Pro Leu His Asn
              405                 410                 415

Gln Glu Val Thr Ala Glu Asp Gly Thr Gln Arg Cys Glu Lys Cys Ser
              420                 425                 430

Lys Pro Cys Ala Arg Val Cys Tyr Gly Leu Gly Met Glu His Leu Arg
              435                 440                 445

Glu Val Arg Ala Val Thr Ser Ala Asn Ile Gln Glu Phe Ala Gly Cys
              450                 455                 460

Lys Lys Ile Phe Gly Ser Leu Ala Phe Leu Pro Glu Ser Phe Asp Gly
465                 470                 475                 480

Asp Pro Ala Ser Asn Thr Ala Pro Leu Gln Pro Glu Gln Leu Gln Val
              485                 490                 495

Phe Glu Thr Leu Glu Glu Ile Thr Gly Tyr Leu Tyr Ile Ser Ala Trp
              500                 505                 510

Pro Asp Ser Leu Pro Asp Leu Ser Val Phe Gln Asn Leu Gln Val Ile
              515                 520                 525

Arg Gly Arg Ile Leu His Asn Gly Ala Tyr Ser Leu Thr Leu Gln Gly
              530                 535                 540

Leu Gly Ile Ser Trp Leu Gly Leu Arg Ser Leu Arg Glu Leu Gly Ser
545                 550                 555                 560

Gly Leu Ala Leu Ile His His Asn Thr His Leu Cys Phe Val His Thr
              565                 570                 575

Val Pro Trp Asp Gln Leu Phe Arg Asn Pro His Gln Ala Leu Leu His
              580                 585                 590

Thr Ala Asn Arg Pro Glu Asp Glu Cys Val Gly Glu Gly Leu Ala Cys
              595                 600                 605

His Gln Leu Cys Ala Arg Gly His Cys Trp Gly Pro Gly Pro Thr Gln
              610                 615                 620

Cys Val Asn Cys Ser Gln Phe Leu Arg Gly Gln Glu Cys Val Glu Glu
625                 630                 635                 640

Cys Arg Val Leu Gln Gly Leu Pro Arg Glu Tyr Val Asn Ala Arg His
              645                 650                 655

Cys Leu Pro Cys His Pro Glu Cys Gln Pro Gln Asn Gly Ser Val Thr
              660                 665                 670

Cys Phe Gly Pro Glu Ala Asp Gln Cys Val Ala Cys Ala His Tyr Lys
              675                 680                 685

Asp Pro Pro Phe Cys Val Ala Arg Cys Pro Ser Gly Val Lys Pro Asp
              690                 695                 700

Leu Ser Tyr Met Pro Ile Trp Lys Phe Pro Asp Glu Glu Gly Ala Cys
705                 710                 715                 720

Gln Pro Cys Pro Ile Asn Cys Thr His Ser Cys Val Asp Leu Asp Asp
              725                 730                 735

```
Lys Gly Cys Pro Ala Glu Gln Arg Ala Ser Pro Leu Thr Ser Ile Ile
            740                 745                 750

Ser Ala Val Val Gly Ile Leu Leu Val Val Leu Gly Val Val Phe
        755                 760                 765

Gly Ile Leu Ile Lys Arg Arg Gln Gln Lys Ile Arg Lys Tyr Thr His
770                 775                 780

His His His His His
785

<210> SEQ ID NO 19
<211> LENGTH: 238
<212> TYPE: PRT
<213> ORGANISM: Homo sapiens

<400> SEQUENCE: 19

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Ile Pro Thr Glu Ile Pro Thr Ser Ala
        115                 120                 125

Leu Val Lys Glu Thr Leu Ala Leu Leu Ser Thr His Arg Thr Leu Leu
130                 135                 140

Ile Ala Asn Glu Thr Leu Arg Ile Pro Val Pro Val His Lys Asn His
145                 150                 155                 160

Gln Leu Thr Thr Glu Glu Ile Phe Gln Gly Ile Gly Thr Leu Glu Ser
                165                 170                 175

Gln Thr Val Gln Gly Gly Thr Val Glu Arg Leu Phe Lys Asn Leu Ser
            180                 185                 190

Leu Ile Lys Lys Tyr Ile Asp Gly Gln Lys Lys Thr Gly Glu Glu
        195                 200                 205

Arg Arg Arg Val Asn Gln Phe Leu Asp Tyr Leu Gln Glu Phe Leu Gly
210                 215                 220

Val Met Asn Thr Glu Trp Ile Ile Glu Ser Ser Gly Arg Lys
225                 230                 235

<210> SEQ ID NO 20
<211> LENGTH: 787
<212> TYPE: PRT
<213> ORGANISM: Homo sapiens

<400> SEQUENCE: 20

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30
```

```
Thr Phe His Arg Cys Ala Lys Asp Pro Trp Arg Leu Pro Gly Thr Tyr
            35                  40                  45

Val Val Val Leu Lys Glu Glu Thr His Leu Ser Gln Ser Glu Arg Thr
 50                  55                  60

Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
                    85                  90                  95

Ser Gly Asp Leu Leu Glu Leu Ala Leu Lys Leu Pro His Val Asp Tyr
                100                 105                 110

Ile Glu Glu Asp Ser Ser Val Phe Ala Gln Ser Ile Pro Trp Asn Leu
                115                 120                 125

Glu Arg Ile Thr Pro Pro Arg Tyr Arg Ala Asp Glu Tyr Gln Pro Pro
                130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
                180                 185                 190

Cys Asp Ser His Gly Thr His Leu Ala Gly Val Val Ser Gly Arg Asp
                195                 200                 205

Ala Gly Val Ala Lys Gly Ala Ser Met Arg Ser Leu Arg Val Leu Asn
                210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
                260                 265                 270

Arg Leu Ala Arg Ala Gly Val Val Leu Val Thr Ala Ala Gly Asn Phe
                275                 280                 285

Arg Asp Asp Ala Cys Leu Tyr Ser Pro Ala Ser Ala Pro Glu Val Ile
                290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
                355                 360                 365

Met Leu Ser Ala Glu Pro Glu Leu Thr Leu Ala Glu Leu Arg Gln Arg
                370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Val Ala Arg Cys Ala
                435                 440                 445

Pro Asp Glu Glu Leu Leu Ser Cys Ser Ser Phe Ser Arg Ser Gly Lys
```

```
            450                 455                 460
Arg Arg Gly Glu Arg Met Glu Ala Gln Gly Gly Lys Leu Val Cys Arg
465                 470                 475                 480

Ala His Asn Ala Phe Gly Gly Glu Val Tyr Ala Ile Ala Arg Cys
                    485                 490                 495

Cys Leu Leu Pro Gln Ala Asn Cys Ser Val His Thr Ala Pro Pro Ala
                500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
        530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                    565                 570                 575

Glu Cys Lys Val Lys Glu His Gly Ile Pro Ala Pro Gln Glu Gln Val
                580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
        610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
                    645                 650                 655

Ala Ser Gln Glu Leu Gln Gly Gly Ser Gly Ala Met Val Asp Thr Leu
                660                 665                 670

Ser Gly Leu Ser Ser Glu Gln Gly Gln Ser Gly Asp Met Thr Ile Glu
            675                 680                 685

Glu Asp Ser Ala Thr His Ile Lys Phe Ser Lys Arg Asp Glu Asp Gly
        690                 695                 700

Lys Glu Leu Ala Gly Ala Thr Met Glu Leu Arg Asp Ser Ser Gly Lys
705                 710                 715                 720

Thr Ile Ser Thr Trp Ile Ser Asp Gly Gln Val Lys Asp Phe Tyr Leu
                    725                 730                 735

Tyr Pro Gly Lys Tyr Thr Phe Val Glu Thr Ala Ala Pro Asp Gly Tyr
                740                 745                 750

Glu Val Ala Thr Ala Ile Thr Phe Thr Val Asn Glu Gln Gly Gln Val
            755                 760                 765

Thr Val Asn Gly Lys Ala Thr Lys Gly Asp Ala His Ile His His His
        770                 775                 780

His His His
785

<210> SEQ ID NO 21
<211> LENGTH: 765
<212> TYPE: PRT
<213> ORGANISM: Plasmodium falciparum

<400> SEQUENCE: 21

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30
```

-continued

Ser Lys Arg Asp Glu Asp Gly Lys Glu Leu Ala Gly Ala Thr Met Glu
             35                  40                  45

Leu Arg Asp Ser Ser Gly Lys Thr Ile Ser Thr Trp Ile Ser Asp Gly
 50                  55                  60

Gln Val Lys Asp Phe Tyr Leu Tyr Pro Gly Lys Tyr Thr Phe Val Glu
 65                  70                  75                  80

Thr Ala Ala Pro Asp Gly Tyr Glu Val Ala Thr Ala Ile Thr Phe Thr
                 85                  90                  95

Val Asn Glu Gln Gly Gln Val Thr Val Asn Gly Lys Ala Thr Lys Gly
                100                 105                 110

Asp Ala His Ile Gly Gly Ser Asn Tyr Ile Lys Gly Asp Pro Tyr Phe
             115                 120                 125

Ala Glu Tyr Ala Thr Lys Leu Ser Phe Ile Leu Asn Pro Ser Asp Ala
         130                 135                 140

Asn Asn Pro Ser Gly Glu Thr Ala Asn His Asn Asp Glu Ala Cys Asn
145                 150                 155                 160

Cys Asn Glu Ser Gly Ile Ser Ser Val Gly Gln Ala Gln Thr Ser Gly
                165                 170                 175

Pro Ser Ser Asn Lys Thr Cys Ile Thr His Ser Ser Ile Lys Thr Asn
             180                 185                 190

Lys Lys Lys Glu Cys Lys Asp Val Lys Leu Gly Val Arg Glu Asn Asp
         195                 200                 205

Lys Asp Leu Lys Ile Cys Val Ile Glu Asp Thr Ser Leu Ser Gly Val
         210                 215                 220

Asp Asn Cys Cys Cys Gln Asp Leu Leu Gly Ile Leu Gln Glu Asn Cys
225                 230                 235                 240

Ser Asp Asn Lys Arg Gly Ser Ser Ser Asn Asp Ser Cys Asp Asn Lys
                245                 250                 255

Asn Gln Asp Glu Cys Gln Lys Lys Leu Glu Lys Val Phe Ala Ser Leu
             260                 265                 270

Thr Asn Gly Tyr Lys Cys Asp Lys Cys Lys Ser Gly Thr Ser Arg Ser
         275                 280                 285

Lys Lys Lys Trp Ile Trp Lys Lys Ser Ser Gly Asn Glu Glu Gly Leu
         290                 295                 300

Gln Glu Glu Tyr Ala Asn Thr Ile Gly Leu Pro Pro Arg Thr Gln Ser
305                 310                 315                 320

Leu Tyr Leu Gly Asn Leu Pro Lys Leu Glu Asn Val Cys Glu Asp Val
                325                 330                 335

Lys Asp Ile Asn Phe Asp Thr Lys Glu Lys Phe Leu Ala Gly Cys Leu
             340                 345                 350

Ile Val Ser Phe His Glu Gly Lys Asn Leu Lys Lys Arg Tyr Pro Gln
         355                 360                 365

Asn Lys Asn Ser Gly Asn Lys Glu Asn Leu Cys Lys Ala Leu Glu Tyr
         370                 375                 380

Ser Phe Ala Asp Tyr Gly Asp Leu Ile Lys Gly Thr Ser Ile Trp Asp
385                 390                 395                 400

Asn Glu Tyr Thr Lys Asp Leu Glu Leu Asn Leu Gln Asn Asn Phe Gly
                405                 410                 415

Lys Leu Phe Gly Lys Tyr Ile Lys Lys Asn Asn Thr Ala Glu Gln Asp
             420                 425                 430

Thr Ser Tyr Ser Ser Leu Asp Glu Leu Arg Glu Ser Trp Trp Asn Thr
         435                 440                 445

Asn Lys Lys Tyr Ile Trp Thr Ala Met Lys His Gly Ala Glu Met Asn

```
                450                 455                 460
Ile Thr Thr Cys Asn Ala Asp Gly Ser Val Thr Gly Ser Gly Ser Ser
465                 470                 475                 480

Cys Asp Asp Ile Pro Thr Ile Asp Leu Ile Pro Gln Tyr Leu Arg Phe
                485                 490                 495

Leu Gln Glu Trp Val Glu Asn Phe Cys Glu Gln Arg Gln Ala Lys Val
                500                 505                 510

Lys Asp Val Ile Thr Asn Cys Lys Ser Cys Lys Glu Ser Gly Asn Lys
            515                 520                 525

Cys Lys Thr Glu Cys Lys Thr Lys Cys Lys Asp Glu Cys Lys Tyr
            530                 535                 540

Lys Lys Phe Ile Glu Ala Cys Gly Thr Ala Gly Gly Ile Gly Thr
545                 550                 555                 560

Ala Gly Ser Pro Trp Ser Lys Arg Trp Asp Gln Ile Tyr Lys Arg Tyr
                565                 570                 575

Ser Lys His Ile Glu Asp Ala Lys Arg Asn Arg Lys Ala Gly Thr Lys
            580                 585                 590

Asn Cys Gly Thr Ser Thr Thr Asn Ala Ala Ala Ser Thr Asp Glu
            595                 600                 605

Asn Lys Cys Val Gln Ser Asp Ile Asp Ser Phe Phe Lys His Leu Ile
            610                 615                 620

Asp Ile Gly Leu Thr Thr Pro Ser Ser Tyr Leu Ser Asn Val Leu Asp
625                 630                 635                 640

Asp Asn Ile Cys Gly Ala Asp Lys Ala Pro Trp Thr Thr Tyr Thr Thr
                645                 650                 655

Tyr Thr Thr Thr Glu Lys Cys Asn Lys Glu Arg Asp Lys Ser Lys Ser
                660                 665                 670

Gln Ser Ser Asp Thr Leu Val Val Asn Val Pro Ser Pro Leu Gly
            675                 680                 685

Asn Thr Pro Tyr Arg Tyr Lys Tyr Ala Cys Gln Cys Lys Ile Pro Thr
                690                 695                 700

Asn Glu Glu Thr Cys Asp Asp Arg Lys Glu Tyr Met Asn Gln Trp Ser
705                 710                 715                 720

Cys Gly Ser Ala Arg Thr Met Lys Arg Gly Tyr Lys Asn Asp Asn Tyr
                725                 730                 735

Glu Leu Cys Lys Tyr Asn Gly Val Asp Val Lys Pro Thr Thr Val Arg
                740                 745                 750

Ser Asn Ser Ser Lys Leu Asp His His His His His
            755                 760                 765

<210> SEQ ID NO 22
<211> LENGTH: 775
<212> TYPE: PRT
<213> ORGANISM: Plasmodium falciparum

<400> SEQUENCE: 22

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
                20                  25                  30

Ser Lys Arg Asp Glu Asp Gly Lys Glu Leu Ala Gly Ala Thr Met Glu
            35                  40                  45

Leu Arg Asp Ser Ser Gly Lys Thr Ile Ser Thr Trp Ile Ser Asp Gly
50                  55                  60
```

```
Gln Val Lys Asp Phe Tyr Leu Tyr Pro Gly Lys Tyr Thr Phe Val Glu
 65                  70                  75                  80

Thr Ala Ala Pro Asp Gly Tyr Glu Val Ala Thr Ala Ile Thr Phe Thr
             85                  90                  95

Val Asn Glu Gln Gly Gln Val Thr Val Asn Gly Lys Ala Thr Lys Gly
         100                 105                 110

Asp Ala His Ile Gly Gly Ser Thr Ser Glu Asn Arg Asn Lys Arg Ile
             115                 120                 125

Gly Gly Pro Lys Leu Arg Gly Asn Val Thr Ser Asn Ile Lys Phe Pro
     130                 135                 140

Ser Asp Asn Lys Gly Lys Ile Ile Arg Gly Ser Asn Asp Lys Leu Asn
145                 150                 155                 160

Lys Asn Ser Glu Asp Val Leu Glu Gln Ser Glu Lys Ser Leu Val Ser
                 165                 170                 175

Glu Asn Val Pro Ser Gly Leu Asp Ile Asp Ile Pro Lys Glu Ser
             180                 185                 190

Ile Phe Ile Gln Glu Asp Gln Glu Gly Gln Thr His Ser Glu Leu Asn
     195                 200                 205

Pro Glu Thr Ser Glu His Ser Lys Asp Leu Asn Asn Asn Gly Ser Lys
     210                 215                 220

Asn Glu Ser Ser Asp Ile Ile Ser Glu Asn Asn Lys Ser Asn Lys Val
225                 230                 235                 240

Gln Asn His Phe Glu Ser Leu Ser Asp Leu Glu Leu Leu Glu Asn Ser
                 245                 250                 255

Ser Gln Asp Asn Leu Asp Lys Asp Thr Ile Ser Thr Glu Pro Phe Pro
             260                 265                 270

Asn Gln Lys His Lys Asp Leu Gln Gln Asp Leu Asn Asp Glu Pro Leu
     275                 280                 285

Glu Pro Phe Pro Thr Gln Ile His Lys Asp Tyr Lys Glu Lys Asn Leu
     290                 295                 300

Ile Asn Glu Glu Asp Ser Glu Pro Phe Pro Arg Gln Lys His Lys Lys
305                 310                 315                 320

Val Asp Asn His Asn Glu Glu Lys Asn Val Phe His Glu Asn Gly Ser
                 325                 330                 335

Ala Asn Gly Asn Gln Gly Ser Leu Lys Leu Lys Ser Phe Asp Glu His
             340                 345                 350

Leu Lys Asp Glu Lys Ile Glu Asn Glu Pro Leu Val His Glu Asn Leu
         355                 360                 365

Ser Ile Pro Asn Asp Pro Ile Glu Gln Ile Leu Asn Gln Pro Glu Gln
     370                 375                 380

Glu Thr Asn Ile Gln Glu Gln Leu Tyr Asn Glu Lys Gln Asn Val Glu
385                 390                 395                 400

Glu Lys Gln Asn Ser Gln Ile Pro Ser Leu Asp Leu Lys Glu Pro Thr
                 405                 410                 415

Asn Glu Asp Ile Leu Pro Asn His Asn Pro Leu Glu Asn Ile Lys Gln
             420                 425                 430

Ser Glu Ser Glu Ile Asn His Val Gln Asp His Ala Leu Pro Lys Glu
         435                 440                 445

Asn Ile Ile Asp Lys Leu Asp Asn Gln Lys Glu His Ile Asp Gln Ser
             450                 455                 460

Gln His Asn Ile Asn Val Leu Gln Glu Asn Asn Ile Asn Asn His Gln
465                 470                 475                 480

Leu Glu Pro Gln Glu Lys Pro Asn Ile Glu Ser Phe Glu Pro Lys Asn
```

```
                485                 490                 495
Ile Asp Ser Glu Ile Ile Leu Pro Glu Asn Val Glu Thr Glu Glu Ile
            500                 505                 510
Ile Asp Asp Val Pro Ser Pro Lys His Ser Asn His Glu Thr Phe Glu
            515                 520                 525
Glu Glu Thr Ser Glu Ser Glu His Glu Glu Ala Val Ser Glu Lys Asn
            530                 535                 540
Ala His Glu Thr Val Glu His Glu Glu Thr Val Ser Gln Glu Ser Asn
545                 550                 555                 560
Pro Glu Lys Ala Asp Asn Asp Gly Asn Val Ser Gln Asn Ser Asn Asn
                565                 570                 575
Glu Leu Asn Glu Asn Glu Phe Val Glu Ser Glu Lys Ser Glu His Glu
            580                 585                 590
Ala Arg Ser Lys Ala Lys Glu Ala Ser Ser Tyr Asp Tyr Ile Leu Gly
            595                 600                 605
Trp Glu Phe Gly Gly Gly Val Pro His Lys Lys Glu Glu Asn Met
            610                 615                 620
Leu Ser His Leu Tyr Val Ser Ser Lys Asp Lys Glu Asn Ile Ser Lys
625                 630                 635                 640
Glu Asn Asp Asp Val Leu Asp Glu Lys Glu Glu Ala Glu Glu Thr
                645                 650                 655
Glu Glu Glu Glu Leu Glu Glu Lys Asn Glu Glu Thr Glu Ser Glu
            660                 665                 670
Ile Ser Glu Asp Glu Glu Glu Glu Glu Glu Glu Lys Glu Glu
            675                 680                 685
Glu Asn Asp Lys Lys Lys Glu Gln Lys Glu Gln Ser Asn Glu Asn
690                 695                 700
Asn Asp Gln Lys Lys Asp Met Glu Ala Gln Asn Leu Ile Ser Lys Asn
705                 710                 715                 720
Gln Asn Asn Asn Glu Lys Asn Val Lys Glu Ala Ala Glu Ser Ile Met
                725                 730                 735
Lys Thr Leu Ala Gly Leu Ile Lys Gly Asn Asn Gln Ile Asp Ser Thr
            740                 745                 750
Leu Lys Asp Leu Val Glu Glu Leu Ser Lys Tyr Phe Lys Asn His Arg
            755                 760                 765
Ser His His His His His His
            770                 775

<210> SEQ ID NO 23
<211> LENGTH: 595
<212> TYPE: PRT
<213> ORGANISM: Plasmodium falciparum

<400> SEQUENCE: 23

Gly Ser Thr Ser Glu Asn Arg Asn Lys Arg Ile Gly Gly Pro Lys Leu
1               5                   10                  15
Arg Gly Asn Val Thr Ser Asn Ile Lys Phe Pro Ser Asp Asn Lys Gly
                20                  25                  30
Lys Ile Ile Arg Gly Ser Asn Asp Lys Leu Asn Lys Asn Ser Glu Asp
            35                  40                  45
Val Leu Glu Gln Ser Glu Lys Ser Leu Val Ser Glu Asn Val Pro Ser
        50                  55                  60
Gly Leu Asp Ile Asp Asp Ile Pro Lys Glu Ser Ile Phe Ile Gln Glu
65                  70                  75                  80
```

```
Asp Gln Glu Gly Gln Thr His Ser Glu Leu Asn Pro Glu Thr Ser Glu
                85                  90                  95
His Ser Lys Asp Leu Asn Asn Asn Gly Ser Lys Asn Glu Ser Ser Asp
            100                 105                 110
Ile Ile Ser Glu Asn Asn Lys Ser Asn Lys Val Gln Asn His Phe Glu
            115                 120                 125
Ser Leu Ser Asp Leu Glu Leu Leu Glu Asn Ser Ser Gln Asp Asn Leu
    130                 135                 140
Asp Lys Asp Thr Ile Ser Thr Glu Pro Phe Pro Asn Gln Lys His Lys
145                 150                 155                 160
Asp Leu Gln Gln Asp Leu Asn Asp Glu Pro Leu Glu Pro Phe Pro Thr
                165                 170                 175
Gln Ile His Lys Asp Tyr Lys Glu Lys Asn Leu Ile Asn Glu Glu Asp
                180                 185                 190
Ser Glu Pro Phe Pro Arg Gln Lys His Lys Lys Val Asp Asn His Asn
                195                 200                 205
Glu Glu Lys Asn Val Phe His Glu Asn Gly Ser Ala Asn Gly Asn Gln
    210                 215                 220
Gly Ser Leu Lys Leu Lys Ser Phe Asp Glu His Leu Lys Asp Glu Lys
225                 230                 235                 240
Ile Glu Asn Glu Pro Leu Val His Glu Asn Leu Ser Ile Pro Asn Asp
                245                 250                 255
Pro Ile Glu Gln Ile Leu Asn Gln Pro Glu Gln Thr Asn Ile Gln
                260                 265                 270
Glu Gln Leu Tyr Asn Glu Lys Gln Asn Val Glu Glu Lys Gln Asn Ser
                275                 280                 285
Gln Ile Pro Ser Leu Asp Leu Lys Glu Pro Thr Asn Glu Asp Ile Leu
    290                 295                 300
Pro Asn His Asn Pro Leu Glu Asn Ile Lys Gln Ser Glu Ser Glu Ile
305                 310                 315                 320
Asn His Val Gln Asp His Ala Leu Pro Lys Glu Asn Ile Ile Asp Lys
                325                 330                 335
Leu Asp Asn Gln Lys Glu His Ile Asp Gln Ser Gln His Asn Ile Asn
                340                 345                 350
Val Leu Gln Glu Asn Asn Ile Asn Asn His Gln Leu Glu Pro Gln Glu
    355                 360                 365
Lys Pro Asn Ile Glu Ser Phe Glu Pro Lys Asn Ile Asp Ser Glu Ile
    370                 375                 380
Ile Leu Pro Glu Asn Val Glu Thr Glu Glu Ile Ile Asp Asp Val Pro
385                 390                 395                 400
Ser Pro Lys His Ser Asn His Glu Thr Phe Glu Glu Glu Thr Ser Glu
                405                 410                 415
Ser Glu His Glu Glu Ala Val Ser Glu Lys Asn Ala His Glu Thr Val
            420                 425                 430
Glu His Glu Glu Thr Val Ser Gln Glu Ser Asn Pro Glu Lys Ala Asp
    435                 440                 445
Asn Asp Gly Asn Val Ser Gln Asn Ser Asn Asn Glu Leu Asn Glu Asn
    450                 455                 460
Glu Phe Val Glu Ser Glu Lys Ser Glu His Glu Ala Gly Gly Ser Gly
465                 470                 475                 480
Ala Met Val Asp Thr Leu Ser Gly Leu Ser Ser Glu Gln Gly Gln Ser
                485                 490                 495
Gly Asp Met Thr Ile Glu Glu Asp Ser Ala Thr His Ile Lys Phe Ser
```

```
            500                 505                 510
Lys Arg Asp Glu Asp Gly Lys Glu Leu Ala Gly Ala Thr Met Glu Leu
            515                 520                 525

Arg Asp Ser Ser Gly Lys Thr Ile Ser Thr Trp Ile Ser Asp Gly Gln
        530                 535                 540

Val Lys Asp Phe Tyr Leu Tyr Pro Gly Lys Tyr Thr Phe Val Glu Thr
545                 550                 555                 560

Ala Ala Pro Asp Gly Tyr Glu Val Ala Thr Ala Ile Thr Phe Thr Val
                565                 570                 575

Asn Glu Gln Gly Gln Val Thr Val Asn Gly Lys Ala Thr Lys Gly Asp
            580                 585                 590

Ala His Ile
        595

<210> SEQ ID NO 24
<211> LENGTH: 769
<212> TYPE: PRT
<213> ORGANISM: Plasmodium falciparum

<400> SEQUENCE: 24

Gly Ser Thr Ser Glu Asn Arg Asn Lys Arg Ile Gly Gly Pro Lys Leu
1               5                   10                  15

Arg Gly Asn Val Thr Ser Asn Ile Lys Phe Pro Ser Asp Asn Lys Gly
            20                  25                  30

Lys Ile Ile Arg Gly Ser Asn Asp Lys Leu Asn Lys Asn Ser Glu Asp
        35                  40                  45

Val Leu Glu Gln Ser Glu Lys Ser Leu Val Ser Glu Asn Val Pro Ser
50                  55                  60

Gly Leu Asp Ile Asp Asp Ile Pro Lys Glu Ser Ile Phe Ile Gln Glu
65                  70                  75                  80

Asp Gln Glu Gly Gln Thr His Ser Glu Leu Asn Pro Glu Thr Ser Glu
                85                  90                  95

His Ser Lys Asp Leu Asn Asn Asn Gly Ser Lys Asn Glu Ser Ser Asp
            100                 105                 110

Ile Ile Ser Glu Asn Asn Lys Ser Asn Lys Val Gln Asn His Phe Glu
        115                 120                 125

Ser Leu Ser Asp Leu Glu Leu Leu Glu Asn Ser Ser Gln Asp Asn Leu
130                 135                 140

Asp Lys Asp Thr Ile Ser Thr Glu Pro Phe Pro Asn Gln Lys His Lys
145                 150                 155                 160

Asp Leu Gln Gln Asp Leu Asn Asp Glu Pro Leu Glu Pro Phe Pro Thr
                165                 170                 175

Gln Ile His Lys Asp Tyr Lys Glu Lys Asn Leu Ile Asn Glu Glu Asp
            180                 185                 190

Ser Glu Pro Phe Pro Arg Gln Lys His Lys Lys Val Asp Asn His Asn
        195                 200                 205

Glu Glu Lys Asn Val Phe His Glu Asn Gly Ser Ala Asn Gly Asn Gln
210                 215                 220

Gly Ser Leu Lys Leu Lys Ser Phe Asp Glu His Leu Lys Asp Glu Lys
225                 230                 235                 240

Ile Glu Asn Glu Pro Leu Val His Glu Asn Leu Ser Ile Pro Asn Asp
                245                 250                 255

Pro Ile Glu Gln Ile Leu Asn Gln Pro Glu Gln Glu Thr Asn Ile Gln
            260                 265                 270
```

```
Glu Gln Leu Tyr Asn Glu Lys Gln Asn Val Glu Lys Gln Asn Ser
            275                 280                 285
Gln Ile Pro Ser Leu Asp Leu Lys Glu Pro Thr Asn Glu Asp Ile Leu
    290                 295                 300
Pro Asn His Asn Pro Leu Glu Asn Ile Lys Gln Ser Glu Ser Glu Ile
305                 310                 315                 320
Asn His Val Gln Asp His Ala Leu Pro Lys Glu Asn Ile Ile Asp Lys
                325                 330                 335
Leu Asp Asn Gln Lys Glu His Ile Asp Gln Ser Gln His Asn Ile Asn
            340                 345                 350
Val Leu Gln Glu Asn Asn Ile Asn Asn His Gln Leu Glu Pro Gln Glu
        355                 360                 365
Lys Pro Asn Ile Glu Ser Phe Glu Pro Lys Asn Ile Asp Ser Glu Ile
    370                 375                 380
Ile Leu Pro Glu Asn Val Glu Thr Glu Glu Ile Ile Asp Asp Val Pro
385                 390                 395                 400
Ser Pro Lys His Ser Asn His Glu Thr Phe Glu Glu Thr Ser Glu
                405                 410                 415
Ser Glu His Glu Glu Ala Val Ser Glu Lys Asn Ala His Glu Thr Val
                420                 425                 430
Glu His Glu Glu Thr Val Ser Gln Glu Ser Asn Pro Glu Lys Ala Asp
            435                 440                 445
Asn Asp Gly Asn Val Ser Gln Asn Ser Asn Asn Glu Leu Asn Glu Asn
            450                 455                 460
Glu Phe Val Glu Ser Glu Lys Ser Glu His Glu Ala Arg Ser Lys Ala
465                 470                 475                 480
Lys Glu Ala Ser Ser Tyr Asp Tyr Ile Leu Gly Trp Glu Phe Gly Gly
                485                 490                 495
Gly Val Pro Glu His Lys Lys Glu Glu Asn Met Leu Ser His Leu Tyr
            500                 505                 510
Val Ser Ser Lys Asp Lys Glu Asn Ile Ser Lys Glu Asn Asp Asp Val
            515                 520                 525
Leu Asp Glu Lys Glu Glu Ala Glu Thr Glu Glu Glu Glu Leu
530                 535                 540
Glu Glu Lys Asn Glu Glu Glu Thr Glu Ser Glu Ile Ser Glu Asp Glu
545                 550                 555                 560
Glu Glu Glu Glu Glu Glu Glu Lys Glu Glu Asn Asp Lys Lys
                565                 570                 575
Lys Glu Gln Glu Lys Glu Gln Ser Asn Glu Asn Asn Gln Lys Lys
            580                 585                 590
Asp Met Glu Ala Gln Asn Leu Ile Ser Lys Asn Gln Asn Asn Glu
            595                 600                 605
Lys Asn Val Lys Glu Ala Ala Glu Ser Ile Met Lys Thr Leu Ala Gly
            610                 615                 620
Leu Ile Lys Gly Asn Asn Gln Ile Asp Ser Thr Leu Lys Asp Leu Val
625                 630                 635                 640
Glu Glu Leu Ser Lys Tyr Phe Lys Asn His Gly Gly Ser Gly Ala Met
                645                 650                 655
Val Asp Thr Leu Ser Gly Leu Ser Glu Gln Gly Gln Ser Gly Asp
            660                 665                 670
Met Thr Ile Glu Glu Asp Ser Ala Thr His Ile Lys Phe Ser Lys Arg
            675                 680                 685
Asp Glu Asp Gly Lys Glu Leu Ala Gly Ala Thr Met Glu Leu Arg Asp
```

|     |     |     |     | 690 |     |     |     | 695 |     |     |     | 700 |     |     |     |

| Ser | Ser | Gly | Lys | Thr | Ile | Ser | Thr | Trp | Ile | Ser | Asp | Gly | Gln | Val | Lys |
| 705 |     |     |     | 710 |     |     |     | 715 |     |     |     | 720 |     |     |     |

| Asp | Phe | Tyr | Leu | Tyr | Pro | Gly | Lys | Tyr | Thr | Phe | Val | Glu | Thr | Ala | Ala |
|     |     |     |     | 725 |     |     |     | 730 |     |     |     | 735 |     |     |     |

| Pro | Asp | Gly | Tyr | Glu | Val | Ala | Thr | Ala | Ile | Thr | Phe | Thr | Val | Asn | Glu |
|     |     |     |     | 740 |     |     |     | 745 |     |     |     | 750 |     |     |     |

| Gln | Gly | Gln | Val | Thr | Val | Asn | Gly | Lys | Ala | Thr | Lys | Gly | Asp | Ala | His |
|     |     |     |     | 755 |     |     |     | 760 |     |     |     | 765 |     |     |     |

Ile

<210> SEQ ID NO 25
<211> LENGTH: 692
<212> TYPE: PRT
<213> ORGANISM: Plasmodium falciparum

<400> SEQUENCE: 25

| Gly | Ser | Thr | Ser | Glu | Asn | Arg | Asn | Lys | Arg | Ile | Gly | Gly | Pro | Lys | Leu |
| 1   |     |     |     | 5   |     |     |     | 10  |     |     |     | 15  |     |     |     |

| Arg | Gly | Asn | Val | Thr | Ser | Asn | Ile | Lys | Phe | Pro | Ser | Asp | Asn | Lys | Gly |
|     |     |     |     | 20  |     |     |     | 25  |     |     |     | 30  |     |     |     |

| Lys | Ile | Ile | Arg | Gly | Ser | Asn | Asp | Lys | Leu | Asn | Lys | Asn | Ser | Glu | Asp |
|     |     |     |     | 35  |     |     |     | 40  |     |     |     | 45  |     |     |     |

| Val | Leu | Glu | Gln | Ser | Glu | Lys | Ser | Leu | Val | Ser | Glu | Asn | Val | Pro | Ser |
|     |     |     |     | 50  |     |     |     | 55  |     |     |     | 60  |     |     |     |

| Gly | Leu | Asp | Ile | Asp | Ile | Pro | Lys | Glu | Ser | Ile | Phe | Ile | Gln | Glu |
| 65  |     |     |     | 70  |     |     |     | 75  |     |     |     |     |     | 80  |

| Asp | Gln | Glu | Gly | Gln | Thr | His | Ser | Glu | Leu | Asn | Pro | Glu | Thr | Ser | Glu |
|     |     |     |     | 85  |     |     |     | 90  |     |     |     | 95  |     |     |     |

| His | Ser | Lys | Asp | Leu | Asn | Asn | Asn | Gly | Ser | Lys | Asn | Glu | Ser | Ser | Asp |
|     |     |     |     | 100 |     |     |     | 105 |     |     |     | 110 |     |     |     |

| Ile | Ile | Ser | Glu | Asn | Asn | Lys | Ser | Asn | Lys | Val | Gln | Asn | His | Phe | Glu |
|     |     |     |     | 115 |     |     |     | 120 |     |     |     | 125 |     |     |     |

| Ser | Leu | Ser | Asp | Leu | Glu | Leu | Leu | Glu | Asn | Ser | Ser | Gln | Asp | Asn | Leu |
|     |     |     |     | 130 |     |     |     | 135 |     |     |     | 140 |     |     |     |

| Asp | Lys | Asp | Thr | Ile | Ser | Thr | Glu | Pro | Phe | Pro | Asn | Gln | Lys | His | Lys |
| 145 |     |     |     | 150 |     |     |     | 155 |     |     |     | 160 |     |     |     |

| Asp | Leu | Gln | Gln | Asp | Leu | Asn | Asp | Glu | Pro | Leu | Glu | Pro | Phe | Pro | Thr |
|     |     |     |     | 165 |     |     |     | 170 |     |     |     | 175 |     |     |     |

| Gln | Ile | His | Lys | Asp | Tyr | Lys | Glu | Lys | Asn | Leu | Ile | Asn | Glu | Glu | Asp |
|     |     |     |     | 180 |     |     |     | 185 |     |     |     | 190 |     |     |     |

| Ser | Glu | Pro | Phe | Pro | Arg | Gln | Lys | His | Lys | Lys | Val | Asp | Asn | His | Asn |
|     |     |     |     | 195 |     |     |     | 200 |     |     |     | 205 |     |     |     |

| Glu | Glu | Lys | Asn | Val | Phe | His | Glu | Asn | Gly | Ser | Ala | Asn | Gly | Asn | Gln |
|     |     |     |     | 210 |     |     |     | 215 |     |     |     | 220 |     |     |     |

| Gly | Ser | Leu | Lys | Leu | Lys | Ser | Phe | Asp | Glu | His | Leu | Lys | Asp | Glu | Lys |
| 225 |     |     |     | 230 |     |     |     | 235 |     |     |     | 240 |     |     |     |

| Ile | Glu | Asn | Glu | Pro | Leu | Val | His | Glu | Asn | Leu | Ser | Ile | Pro | Asn | Asp |
|     |     |     |     | 245 |     |     |     | 250 |     |     |     | 255 |     |     |     |

| Pro | Ile | Glu | Gln | Ile | Leu | Asn | Gln | Pro | Glu | Glu | Thr | Asn | Ile | Gln |
|     |     |     |     | 260 |     |     |     | 265 |     |     |     | 270 |     |     |

| Glu | Gln | Leu | Tyr | Asn | Glu | Lys | Gln | Asn | Val | Glu | Glu | Lys | Gln | Asn | Ser |
|     |     |     |     | 275 |     |     |     | 280 |     |     |     | 285 |     |     |     |

| Gln | Ile | Pro | Ser | Leu | Asp | Leu | Lys | Glu | Pro | Thr | Asn | Glu | Asp | Ile | Leu |

```
                    290                 295                 300
Pro Asn His Asn Pro Leu Glu Asn Ile Lys Gln Ser Glu Ser Glu Ile
305                 310                 315                 320

Asn His Val Gln Asp His Ala Leu Pro Lys Glu Asn Ile Ile Asp Lys
                325                 330                 335

Leu Asp Asn Gln Lys Glu His Ile Asp Gln Ser Gln His Asn Ile Asn
                340                 345                 350

Val Leu Gln Glu Asn Asn Ile Asn Asn His Gln Leu Glu Pro Gln Glu
                355                 360                 365

Lys Pro Asn Ile Glu Ser Phe Glu Pro Lys Asn Ile Asp Ser Glu Ile
370                 375                 380

Ile Leu Pro Glu Asn Val Glu Thr Glu Glu Ile Ile Asp Asp Val Pro
385                 390                 395                 400

Ser Pro Lys His Ser Asn His Glu Thr Phe Glu Glu Glu Thr Ser Glu
                405                 410                 415

Ser Glu His Glu Glu Ala Val Ser Glu Lys Asn Ala His Glu Thr Val
                420                 425                 430

Glu His Glu Glu Thr Val Ser Gln Glu Ser Asn Pro Glu Lys Ala Asp
                435                 440                 445

Asn Asp Gly Asn Val Ser Gln Asn Ser Asn Asn Glu Leu Asn Glu Asn
450                 455                 460

Glu Phe Val Glu Ser Glu Lys Ser Glu His Glu Ala Arg Ser Lys Thr
465                 470                 475                 480

Lys Glu Tyr Ala Glu Lys Ala Lys Asn Ala Tyr Glu Lys Ala Lys Asn
                485                 490                 495

Ala Tyr Gln Lys Ala Asn Gln Ala Val Leu Lys Ala Lys Glu Ala Ser
                500                 505                 510

Ser Tyr Asp Tyr Ile Leu Gly Trp Glu Phe Gly Gly Val Pro Glu
                515                 520                 525

His Lys Lys Glu Glu Asn Met Leu Ser His Leu Tyr Val Ser Ser Lys
                530                 535                 540

Asp Lys Glu Asn Ile Ser Lys Glu Asn Asp Asp Val Leu Asp Glu Lys
545                 550                 555                 560

Glu Glu Glu Ala Glu Glu Thr Glu Glu Glu Glu Leu Glu Gly Gly Ser
                565                 570                 575

Gly Ala Met Val Asp Thr Leu Ser Gly Leu Ser Ser Gln Gly Gln
                580                 585                 590

Ser Gly Asp Met Thr Ile Glu Glu Asp Ser Ala Thr His Ile Lys Phe
                595                 600                 605

Ser Lys Arg Asp Glu Asp Gly Lys Glu Leu Ala Gly Ala Thr Met Glu
610                 615                 620

Leu Arg Asp Ser Ser Gly Lys Thr Ile Ser Thr Trp Ile Ser Asp Gly
625                 630                 635                 640

Gln Val Lys Asp Phe Tyr Leu Tyr Pro Gly Lys Tyr Thr Phe Val Glu
                645                 650                 655

Thr Ala Ala Pro Asp Gly Tyr Glu Val Ala Thr Ala Ile Thr Phe Thr
                660                 665                 670

Val Asn Glu Gln Gly Gln Val Thr Val Asn Gly Lys Ala Thr Lys Gly
                675                 680                 685

Asp Ala His Ile
690

<210> SEQ ID NO 26
```

-continued

```
<211> LENGTH: 629
<212> TYPE: PRT
<213> ORGANISM: Plasmodium falciparum

<400> SEQUENCE: 26
```

| | | | | | | | | | | | | | | |
|---|---|---|---|---|---|---|---|---|---|---|---|---|---|---|
| Gly | Ala | Met | Val | Asp | Thr | Leu | Ser | Gly | Leu | Ser | Ser | Glu | Gln | Gly | Gln |
| 1 | | | | 5 | | | | | 10 | | | | | 15 | |
| Ser | Gly | Asp | Met | Thr | Ile | Glu | Glu | Asp | Ser | Ala | Thr | His | Ile | Lys | Phe |
| | | | 20 | | | | | 25 | | | | | 30 | | |
| Ser | Lys | Arg | Asp | Glu | Asp | Gly | Lys | Glu | Leu | Ala | Gly | Ala | Thr | Met | Glu |
| | | 35 | | | | | 40 | | | | | 45 | | | |
| Leu | Arg | Asp | Ser | Ser | Gly | Lys | Thr | Ile | Ser | Thr | Trp | Ile | Ser | Asp | Gly |
| | 50 | | | | | 55 | | | | | 60 | | | | |
| Gln | Val | Lys | Asp | Phe | Tyr | Leu | Tyr | Pro | Gly | Lys | Tyr | Thr | Phe | Val | Glu |
| 65 | | | | | 70 | | | | | 75 | | | | | 80 |
| Thr | Ala | Ala | Pro | Asp | Gly | Tyr | Glu | Val | Ala | Thr | Ala | Ile | Thr | Phe | Thr |
| | | | | 85 | | | | | 90 | | | | | 95 | |
| Val | Asn | Glu | Gln | Gly | Gln | Val | Thr | Val | Asn | Gly | Lys | Ala | Thr | Lys | Gly |
| | | | | 100 | | | | | 105 | | | | | 110 | |
| Asp | Ala | His | Ile | Gly | Gly | Ser | Leu | Ser | Phe | Glu | Asn | Ala | Ile | Lys | Lys |
| | | | 115 | | | | | 120 | | | | | 125 | | |
| Thr | Lys | Asn | Gln | Glu | Asn | Asn | Leu | Thr | Leu | Leu | Pro | Ile | Lys | Ser | Thr |
| | 130 | | | | | 135 | | | | | 140 | | | | |
| Glu | Glu | Glu | Lys | Asp | Asp | Ile | Lys | Asn | Gly | Lys | Asp | Ile | Lys | Lys | Glu |
| 145 | | | | | 150 | | | | | 155 | | | | | 160 |
| Ile | Asp | Asn | Asp | Lys | Glu | Asn | Ile | Lys | Thr | Asn | Asn | Ala | Lys | Asp | His |
| | | | | 165 | | | | | 170 | | | | | 175 | |
| Ser | Thr | Tyr | Ile | Lys | Ser | Tyr | Leu | Asn | Thr | Asn | Val | Asn | Asp | Gly | Leu |
| | | | 180 | | | | | 185 | | | | | 190 | | |
| Lys | Tyr | Leu | Phe | Ile | Pro | Ser | His | Asn | Ser | Phe | Ile | Lys | Lys | Tyr | Ser |
| | | 195 | | | | | 200 | | | | | 205 | | | |
| Val | Phe | Asn | Gln | Ile | Asn | Asp | Gly | Met | Leu | Leu | Asn | Glu | Lys | Asn | Asp |
| | 210 | | | | | 215 | | | | | 220 | | | | |
| Val | Lys | Asn | Asn | Glu | Asp | Tyr | Lys | Asn | Val | Asp | Tyr | Lys | Asn | Val | Asn |
| 225 | | | | | 230 | | | | | 235 | | | | | 240 |
| Phe | Leu | Gln | Tyr | His | Phe | Lys | Glu | Leu | Ser | Asn | Tyr | Asn | Ile | Ala | Asn |
| | | | | 245 | | | | | 250 | | | | | 255 | |
| Ser | Ile | Asp | Ile | Leu | Gln | Glu | Lys | Glu | Gly | His | Leu | Asp | Phe | Val | Ile |
| | | | 260 | | | | | 265 | | | | | 270 | | |
| Ile | Pro | His | Tyr | Thr | Phe | Leu | Asp | Tyr | Tyr | Lys | His | Leu | Ser | Tyr | Asn |
| | | 275 | | | | | 280 | | | | | 285 | | | |
| Ser | Ile | Tyr | His | Lys | Tyr | Ser | Thr | Tyr | Gly | Lys | Tyr | Ile | Ala | Val | Asp |
| | 290 | | | | | 295 | | | | | 300 | | | | |
| Ala | Phe | Ile | Lys | Lys | Ile | Asn | Glu | Thr | Tyr | Asp | Lys | Val | Lys | Ser | Lys |
| 305 | | | | | 310 | | | | | 315 | | | | | 320 |
| Cys | Asn | Asp | Ile | Lys | Asn | Asp | Leu | Ile | Ala | Thr | Ile | Lys | Lys | Leu | Glu |
| | | | | 325 | | | | | 330 | | | | | 335 | |
| His | Pro | Tyr | Asp | Ile | Asn | Asn | Lys | Asn | Asp | Asp | Ser | Tyr | Arg | Tyr | Asp |
| | | | 340 | | | | | 345 | | | | | 350 | | |
| Ile | Ser | Glu | Glu | Ile | Asp | Asp | Lys | Ser | Glu | Glu | Thr | Asp | Asp | Glu | Thr |
| | | 355 | | | | | 360 | | | | | 365 | | | |
| Glu | Glu | Val | Glu | Asp | Ser | Ile | Gln | Asp | Thr | Asp | Ser | Asn | His | Thr | Pro |
| | 370 | | | | | 375 | | | | | 380 | | | | |
| Ser | Asn | Lys | Lys | Lys | Asn | Asp | Leu | Met | Asn | Arg | Thr | Phe | Lys | Lys | Met |

```
385                 390                 395                 400
Met Asp Glu Tyr Asn Thr Lys Lys Lys Leu Ile Lys Cys Ile Lys
                405                 410                 415

Asn His Glu Asn Asp Phe Asn Lys Ile Cys Met Asp Met Lys Asn Tyr
            420                 425                 430

Gly Thr Asn Leu Phe Glu Gln Leu Ser Cys Tyr Asn Asn Phe Cys
            435                 440                 445

Asn Thr Asn Gly Ile Arg Phe His Tyr Asp Glu Tyr Ile His Lys Leu
    450                 455                 460

Ile Leu Ser Val Lys Ser Lys Asn Leu Asn Lys Asp Leu Ser Asp Met
465                 470                 475                 480

Thr Asn Ile Leu Gln Gln Ser Glu Leu Leu Leu Thr Asn Leu Asn Lys
                485                 490                 495

Lys Met Gly Ser Tyr Ile Tyr Ile Asp Thr Ile Lys Phe Ile His Lys
                500                 505                 510

Glu Met Lys His Ile Phe Asn Arg Ile Glu Tyr His Thr Lys Ile Ile
            515                 520                 525

Asn Asp Lys Thr Lys Ile Ile Gln Asp Lys Ile Lys Leu Asn Ile Trp
    530                 535                 540

Arg Thr Phe Gln Lys Asp Glu Leu Leu Lys Arg Ile Leu Asp Met Ser
545                 550                 555                 560

Asn Glu Tyr Ser Leu Phe Ile Thr Ser Asp His Leu Arg Gln Met Leu
                565                 570                 575

Tyr Asn Thr Phe Tyr Ser Lys Glu Lys His Leu Asn Asn Ile Phe His
                580                 585                 590

His Leu Ile Tyr Val Leu Gln Met Lys Phe Asn Asp Val Pro Ile Lys
            595                 600                 605

Met Glu Tyr Phe Gln Thr Tyr Lys Lys Asn Lys Pro Leu Thr Gln His
    610                 615                 620

His His His His His
625

<210> SEQ ID NO 27
<211> LENGTH: 335
<212> TYPE: PRT
<213> ORGANISM: Plasmodium falciparum

<400> SEQUENCE: 27

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Asn Lys Leu Tyr Ser Leu Phe Leu Phe
        115                 120                 125
```

```
Leu Phe Ile Gln Leu Ser Ile Lys Tyr Asn Asn Ala Lys Val Thr Val
            130                 135                 140

Asp Thr Val Cys Lys Arg Gly Phe Leu Ile Gln Met Ser Gly His Leu
145                 150                 155                 160

Glu Cys Lys Cys Glu Asn Asp Leu Val Leu Val Asn Glu Glu Thr Cys
                165                 170                 175

Glu Glu Lys Val Leu Lys Cys Asp Glu Lys Thr Val Asn Lys Pro Cys
            180                 185                 190

Gly Asp Phe Ser Lys Cys Ile Lys Ile Asp Gly Asn Pro Val Ser Tyr
        195                 200                 205

Ala Cys Lys Cys Asn Leu Gly Tyr Asp Met Val Asn Asn Val Cys Ile
    210                 215                 220

Pro Asn Glu Cys Lys Asn Val Thr Cys Gly Asn Gly Lys Cys Ile Leu
225                 230                 235                 240

Asp Thr Ser Asn Pro Val Lys Thr Gly Val Cys Ser Cys Asn Ile Gly
                245                 250                 255

Lys Val Pro Asn Val Gln Asp Gln Asn Lys Cys Ser Lys Asp Gly Glu
            260                 265                 270

Thr Lys Cys Ser Leu Lys Cys Leu Lys Glu Asn Glu Thr Cys Lys Ala
        275                 280                 285

Val Asp Gly Ile Tyr Lys Cys Asp Cys Lys Asp Gly Phe Ile Ile Asp
    290                 295                 300

Asn Glu Ser Ser Ile Cys Thr Ala Phe Ser Ala Tyr Asn Ile Leu Asn
305                 310                 315                 320

Leu Ser Ile Met Phe Ile Leu Phe Ser Val Cys Phe Phe Ile Met
                325                 330                 335

<210> SEQ ID NO 28
<211> LENGTH: 424
<212> TYPE: PRT
<213> ORGANISM: Plasmodium falciparum

<400> SEQUENCE: 28

Lys Leu Lys Gln Pro Ala Asp Gly Asn Pro Asp Pro Asn Ala Asn Pro
1               5                   10                  15

Asn Val Asp Pro Asn Ala Asn Pro Val Asp Pro Asn Ala Asn Pro
            20                  25                  30

Asn Val Asp Pro Asn Ala Asn Pro Asn Ala Asn Pro Asn Ala Asn Pro
        35                  40                  45

Asn Ala Asn Pro Asn Ala Asn Pro Asn Ala Asn Pro Asn Ala Asn Pro
    50                  55                  60

Asn Ala Asn Pro Asn Ala Asn Pro Asn Ala Asn Pro Asn Ala Asn Pro
65                  70                  75                  80

Asn Ala Asn Pro Asn Ala Asn Pro Asn Ala Asn Pro Asn Ala Asn Pro
                85                  90                  95

Asn Ala Asn Pro Asn Ala Asn Pro Asn Val Asp Pro Asn Ala Asn Pro
            100                 105                 110

Asn Ala Asn Pro Asn Ala Asn Pro Asn Ala Asn Pro Asn Ala Asn Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175
```

```
Asn Ala Asn Pro Asn Lys Asn Asn Gln Gly Asn Gly Gln Gly His Asn
                180                 185                 190

Met Pro Asn Asp Pro Asn Arg Asn Val Asp Glu Asn Ala Asn Ala Asn
            195                 200                 205

Ser Ala Val Lys Asn Asn Asn Glu Glu Pro Ser Asp Lys His Ile
210                 215                 220

Lys Glu Tyr Leu Asn Lys Ile Gln Asn Ser Leu Ser Thr Glu Trp Ser
225                 230                 235                 240

Pro Cys Ser Val Thr Cys Gly Asn Gly Ile Gln Val Arg Ile Lys Pro
                245                 250                 255

Gly Ser Ala Asn Lys Pro Lys Asp Glu Leu Asp Tyr Ala Asn Asp Ile
                260                 265                 270

Glu Lys Lys Ile Cys Lys Met Glu Lys Cys Ser Ser Val Phe Asn Val
                275                 280                 285

Val Asn Ser Ser Ile Gly Leu Ile Met Val Leu Ser Phe Leu Phe Leu
290                 295                 300

Asn Gly Gly Ser Gly Ala Met Val Asp Thr Leu Ser Gly Leu Ser Ser
305                 310                 315                 320

Glu Gln Gly Gln Ser Gly Asp Met Thr Ile Glu Glu Asp Ser Ala Thr
                325                 330                 335

His Ile Lys Phe Ser Lys Arg Asp Glu Asp Gly Lys Glu Leu Ala Gly
                340                 345                 350

Ala Thr Met Glu Leu Arg Asp Ser Ser Gly Lys Thr Ile Ser Thr Trp
                355                 360                 365

Ile Ser Asp Gly Gln Val Lys Asp Phe Tyr Leu Tyr Pro Gly Lys Tyr
                370                 375                 380

Thr Phe Val Glu Thr Ala Ala Pro Asp Gly Tyr Glu Val Ala Thr Ala
385                 390                 395                 400

Ile Thr Phe Thr Val Asn Glu Gln Gly Gln Val Thr Val Asn Gly Lys
                405                 410                 415

Ala Thr Lys Gly Asp Ala His Ile
                420

<210> SEQ ID NO 29
<211> LENGTH: 2979
<212> TYPE: DNA
<213> ORGANISM: Homo sapiens

<400> SEQUENCE: 29
tttcatatgc caagtacgcc ccctattgac gtcaatgacg gtaaatggcc cgcctggcat      60
tatgcccagt acatgacctt atgggacttt cctacttggc agtacatcta cgtattagtc     120
atcgctatta ccatggtgat gcggttttgg cagtacatca atgggcgtgg atagcggttt     180
gactcacggg gatttccaag tctccacccc attgacgtca atgggagttt gttttggcac     240
caaaatcaac gggactttcc aaaatgtcgt aacaactccg ccccattgac gcaaatgggc     300
ggtaggcgtg tacggtggga ggtctatata agcagagctc tctggctaac tagagaaccc     360
actgcttact ggcttatcga aattaatacg actcactata gggagaccca agctggctag     420
cgtttaaact taagcttagc gcagaggctt ggggcagccg agcggcagcc aggcccggc      480 ccgggcctcg gttccagaag ggagaggagc cgccaaggc gcgcaagaga gcgggctgcc     540
tcgcagtccg agccggagag ggagcgcgag ccgcgccggc cccggacggc ctccgaaacc     600
atgcaggaag atgaggacgg cgactacgag gaactggtgc tggccctgcg gagcgaagag     660
```

```
gatggactgg ccgaggcccc tgagcacggc accaccgcca ccttccacag atgcgccaag    720
gacccttggc ggctgcccgg cacatacgtg gtggtgctga agaggaaac  ccacctgagc    780
cagagcgagc ggaccgccag aaggctgcag gcccaggccg ccagaagagg ctacctgacc    840
aagatcctgc acgtgttcca cggcctgctg cccggcttcc tggtgaaaat gagcggcgac    900
ctgctggaac tggccctgaa gctgccccac gtggactaca tcgaagagga cagcagcgtg    960
ttcgcccaga gcatcccctg gaacctggaa cggatcaccc ccccagata  ccgggccgac   1020
gagtaccagc ctcctgacgg cggcagcctg gtggaagtgt acctgctgga caccagcatc   1080
cagagcgacc accgcgagat cgagggcaga gtgatggtga cagacttcga gaacgtgccc   1140
gaagaggacg gcacccggtt ccacagacag gccagcaagt gcgacagcca cggcacacat   1200
ctggccggcg tggtgtctgg cagagatgcc ggcgtggcca agggcgccag catgagaagc   1260
ctgcgggtgc tgaactgcca gggcaagggc accgtgtccg gcaccctgat cggcctggaa   1320
ttcatccgga gtcccagct  ggtgcagccc gtgggccctc tggtggtgct gctgcctctg   1380
gctggcggct acagcagagt gctgaacgcc gcctgccaga gactggccag agctggcgtg   1440
gtgctggtga cagccgccgg aaacttccgg gacgacgcct gcctgtacag ccccgcctct   1500
gcccccgaag tgatcaccgt gggcgccacc aacgcccagg accagcctgt gacactgggc   1560
accctgggca caaacttcgg cagatgcgtg gacctgttcg cccctggcga ggacatcatc   1620
ggcgccagca gcgactgcag cacctgtttc gtgtcccaga gcggcaccag ccaggccgct   1680
gcccatgtgg ccggaatcgc cgccatgatg ctgagcgccg agcctgagct gaccctggcc   1740
gagctgcggc agcggctgat ccacttctcc gccaaggacg tgatcaacga ggcctggttc   1800
cccgaggacc agagagtgct gacccccaac ctggtggccg ccctgcctcc ttctacacac   1860
ggcgctggct ggcagctgtt ctgcaggaca gtgtggtccg cccacagcgg ccccaccaga   1920
atggccacag ccgtggccag atgcgcccct gatgaggaac tgctgagctg cagcagcttc   1980
tccagaagcg gcaagcggag aggcgagcgg atggaagccc agggcggcaa gctcgtgtgc   2040
agagcccaca atgccttcgg cggcgagggc gtgtacgcca ttgccagatg ctgcctgctg   2100
cctcaggcca actgcagcgt gcacacagcc cctccagccg aggccagcat gggcaccaga   2160
gtgcactgcc accagcaggg ccacgtgctg accggctgta gcagccactg ggaggtggaa   2220
gatctgggca cccacaagcc cccgtgctg  aggcccagag ccagcctaa  tcagtgcgtg   2280
ggccacagag aggcctccat ccacgccagc tgttgccacg cccctggcct ggaatgcaaa   2340
gtgaaagagc acggcatccc tgcccccag  gaacaggtca cagtggcctg cgaggaaggc   2400
tggaccctga caggctgttc cgccctgcca ggcacctctc acgtgctggg cgcctacgcc   2460
gtggacaata cctgcgtcgt gcgcagccgg gacgtgtcca caaccggctc tacaagcgag   2520
ggcgccgtga ccgccgtggc catctgctgc agaagcagac cctggcccca ggcctcccag   2580
gaactgcagg gcggatctgg tgcaatggtt gataccctga gcggtctgag cagcgaacag   2640
ggtcagagcg gtgatatgac cattgaagaa gatagcgcaa cccacatcaa attcagcaaa   2700
cgtgatgaag atggtaaaga actggcaggc gcaacaatgg aactgcgtga tagcagcggt   2760
aaaaccatta gcacctggat tagtgatggt caggtgaaag atttttatct gtaccctggc   2820
aaatacacct tgttgaaac  cgcagcaccg gatggttatg aagttgcaac cgcaattacc   2880
tttaccgtta tgaacagggg ccaggttacc gtgaatggta agcaaccaa  aggtgatgca   2940
catattcacc accaccatca ccactaagcg gccgcttt                           2979
```

<210> SEQ ID NO 30
<211> LENGTH: 2358
<212> TYPE: DNA
<213> ORGANISM: Homo sapiens

<400> SEQUENCE: 30

| | | | | | |
|---|---|---|---|---|---|
| ggtgcaatgg | ttgatacccct | gagcggtctg | agcagcgaac | agggtcagag | cggtgatatg | 60 |
| accattgaag | aagatagcgc | aacccacatc | aaattcagca | aacgtgatga | agatggtaaa | 120 |
| gaactggcag | gcgcaacaat | ggaactgcgt | gatagcagcg | gtaaaaccat | tagcacctgg | 180 |
| attagtgatg | gtcaggtgaa | agatttttat | ctgtaccctg | gcaaatacac | ctttgttgaa | 240 |
| accgcagcac | cggatggtta | tgaagttgca | accgcaatta | cctttaccgt | taatgaacag | 300 |
| ggccaggtta | ccgtgaatgg | taaagcaacc | aaaggtgatg | cacatattgg | tggtagcggt | 360 |
| ccggcaaccg | aacagggtca | ggatacccttt | accaaagtta | aggtggcag | caactatatc | 420 |
| aaaggcgatc | cgtattttgc | agagtatgca | accaaactga | gctttattct | gaatccgagt | 480 |
| gatgcaaata | atccgagcgg | tgaaaccgca | aatcacaatg | atgaagcctg | taattgtaac | 540 |
| gaaagcggta | ttagcagcgt | tggtcaggca | cagaccagcg | gtccgagcag | caataaaacc | 600 |
| tgtattaccc | atagcagcat | taaaaccaat | aaaaagaaag | aatgcaaaga | tgtgaaactg | 660 |
| ggcgtgcgcg | aaaatgataa | agatctgaaa | atttgcgtga | tcgaggatac | cagcctgagc | 720 |
| ggtgttgata | ttgttgttg | tcaggatctg | ctgggtattc | tgcaagaaaa | ttgcagcgat | 780 |
| aataaacgtg | gtagcagcag | caatgatagc | tgcgataaca | aaaatcagga | tgaatgccag | 840 |
| aaaaaactgg | aaaagttttt | tgccagcctg | acgaatggtt | acaaatgcga | taaatgtaaa | 900 |
| agcggcacca | gccgcagcaa | aaagaaatgg | atttggaaaa | aaagcagcgg | caatgaagaa | 960 |
| ggtctgcaag | aggaatatgc | aaataccatt | ggtctgcctc | cgcgtaccca | gagcctgtat | 1020 |
| ctgggtaatc | tgccgaaact | ggaaaatgtg | tgtgaagatg | tgaaagatat | caatttttgat | 1080 |
| accaaagaaa | aatttctggc | aggctgcctg | attgtgagct | tcatgaagg | taaaaacctg | 1140 |
| aaaaaacgct | atccgcagaa | taaaaacagc | ggtaacaaag | aaaatctgtg | caaagcactg | 1200 |
| gaatacagct | ttgcagatta | tggcgatctg | attaaaggca | ccagcatttg | ggataacgag | 1260 |
| tataccaaag | atctggaact | gaatctgcag | aacaatttcg | gtaaactgtt | cggcaaatat | 1320 |
| atcaaaaaaa | acaataccgc | agagcaggat | accagctata | gcagcctgga | tgaactgcgt | 1380 |
| gaaagttggt | ggaataccaa | caaaaaatac | atttggaccg | ccatgaaaca | tggtgccgaa | 1440 |
| atgaatatta | ccacctgtaa | tgcagatggt | agcgttaccg | gtagcggtag | cagctgtgat | 1500 |
| gatattccga | ccattgatct | gattccgcag | tatctgcgtt | ttctgcaaga | atgggttgaa | 1560 |
| aactttgtg | aacagcgtca | ggcgaaagtg | aaagatgtta | ttaccaattg | caaaagctgc | 1620 |
| aaagaaagcg | gcaataaatg | caaaaccgag | tgcaaaacca | aatgcaaaga | cgagtgcgag | 1680 |
| aaatacaaaa | aattcattga | agcatgtggt | acagccggtg | gtggtattgg | caccgcaggt | 1740 |
| agcccgtggt | caaacgttg | ggatcagatc | tataaacgct | acagcaaaca | catcgaagat | 1800 |
| gccaaacgta | atcgtaaagc | aggcaccaaa | aattgtggca | ccagcagcac | caccaatgca | 1860 |
| gcagcaagca | ccgatgaaaa | caatgtgtt | cagagcgata | tcgatagctt | cttcaaacat | 1920 |
| ctgattgata | ttggtctgac | caccccgagc | agctatctga | gcaatgttct | ggatgataac | 1980 |
| atttgcggtg | cagataaagc | accgtggacc | acctatacca | catataccac | cacagaaaaa | 2040 |
| tgcaacaaag | agcgcgataa | aagcaaaagc | cagagcagcg | ataccctggt | tgttgttaat | 2100 |
| gttccgagtc | cgctgggtaa | taccccgtat | cgttataagt | atgcctgcca | gtgtaaaatc | 2160 |

```
ccgaccaatg aagaaacctg tgatgatcgc aaagaataca tgaatcagtg gtcatgtggt    2220
agcgcacgta ccatgaaacg tggctataaa aacgataatt atgaactgtg caaatataac    2280
ggcgtggatg ttaaaccgac caccgttcgt agcaatagca gcaaactgga tcatcatcat    2340
caccatcatt aaggatcc                                                  2358
```

<210> SEQ ID NO 31
<211> LENGTH: 2337
<212> TYPE: DNA
<213> ORGANISM: Plasmodium falcifarum

<400> SEQUENCE: 31

```
ggtgcaatgg ttgatacccct gagcggtctg agcagcgaac agggtcagag cggtgatatg     60
accattgaag aagatagcgc aacccacatc aaattcagca acgtgatga agatggtaaa    120 gaactggcag gcgcaacaat ggaactgcgt gatagcagcg gtaaaaccat tagcacctgg    180
attagtgatg gtcaggtgaa agatttttat ctgtaccctg gcaaatacac ctttgttgaa    240
accgcagcac cggatggtta tgaagttgca accgcaatta cctttaccgt taatgaacag    300
ggccaggtta ccgtgaatgg taaagcaacc aaaggtgatg cacatattgg tggtagcaca    360
agtgagaata gaaataaacg aatcgggggt cctaaattaa ggggtaatgt tacaagtaat    420
ataaagttcc catcagataa caaaggtaaa attataagag gttcgaatga taaacttaat    480
aaaaactctg aagatgtttt agaacaaagc gaaaaatcgc ttgtttcaga aaatgttcct    540
agtggattag atatagatga tatccctaaa gaatctattt ttattcaaga agatcaagaa    600
ggtcaaactc attctgaatt aaatcctgaa acatcagaac atagtaaaga tttaaataat    660
aatggttcaa aaaatgaatc tagtgatatt atttcagaaa ataataaatc aaataaagta    720
caaaatcatt ttgaatcatt atcagattta gaattacttg aaaattcctc acaagataat    780
ttagacaaag atacaatttc aacagaacct tttcctaatc aaaaacataa agacttacaa    840
caagatttaa atgatgaacc tttagaaccc tttcctacac aaatacataa agattataaa    900
gaaaaaaatt taataaatga agaagattca gaaccatttc ccagacaaaa gcataaaaag    960
gtagacaatc ataatgaaga aaaaaacgta tttcatgaaa atggttctgc aaatggtaat   1020
caaggaagtt tgaaacttaa atcattcgat gaacatttaa aagatgaaaa aatagaaaat   1080
gaaccacttg ttcatgaaaa tttatccata ccaaatgatc caatagaaca atattaaat   1140 caacctgaac aagaaacaaa tatccaggaa caattgtata tgaaaaaaca aaatgttgaa   1200
gaaaaacaaa attctcaaat accttcgtta gatttaaaag aaccaacaaa tgaagatatt   1260
ttaccaaatc ataatccatt agaaaatata aaacaaagtg aatcagaaat aaatcatgta   1320
caagatcatg cgctaccaaa agagaatata atagacaaac ttgataatca aaaagaacac   1380
atcgatcaat cacaacataa tataaatgta ttacaagaaa ataacataaa caatcaccaa   1440
ttagaacctc aagagaaacc taatattgaa tcgtttgaac ctaaaaatat agattcagaa   1500
attattcttc ctgaaaatgt tgaaacagaa gaaataatag atgatgtgcc ttcccctaaa   1560
cattctaacc atgaaacatt tgaagaagaa acaagtgaat ctgaacatga gaagccgta   1620 tctgaaaaaa atgcccacga aactgtcgaa catgaagaaa ctgtgtctca agaaagcaat   1680
cctgaaaaag ctgataatga tggaaatgta tctcaaaaca gcaacaacga attaaatgaa   1740
aatgaattcg ttgaatcgga aaaaagcgag catgaagcaa gatccaaagc aaaagaagct   1800
tctagttatg attatatttt aggttgggaa tttggaggag cgttccaga acacaaaaaa   1860 gaagaaaata tgttatcaca tttatatgtt tcttcaaagg ataaggaaaa tatatctaag   1920
```

```
gaaaatgatg atgtattaga tgagaaggaa gaagaggcag aagaaacaga agaagaagaa     1980
cttgaagaaa aaaatgaaga agaaacagaa tcagaaataa gtgaagatga agaagaagaa     2040
gaagaagaag aagaaaagga agaagaaaat gacaaaaaaa aagaacaaga aaaagaacaa     2100
agtaatgaaa ataatgatca aaaaaaagat atggaagcac agaatttaat ttctaaaaac     2160
cagaataata atgagaaaaa cgtaaaagaa gctgctgaaa gcatcatgaa aactttagct     2220
ggtttaatca agggaaataa tcaaatagat tctaccttaa aagatttagt agaagaatta     2280
tccaaatatt ttaaaaatca tagatctcat caccatcatc accattaggg atcctt       2337
```

<210> SEQ ID NO 32
<211> LENGTH: 1785
<212> TYPE: DNA
<213> ORGANISM: Plasmodium falciparum

<400> SEQUENCE: 32

```
ggatccacaa gtgagaatag aaataaacga atcgggggtc ctaaattaag gggtaatgtt       60
acaagtaata taaagttccc atcagataac aaaggtaaaa ttataagagg ttcgaatgat      120
aaacttaata aaaactctga agatgtttta gaacaaagcg aaaaatcgct tgtttcagaa      180
aatgttccta gtggattaga tatagatgat atccctaaag aatctatttt tattcaagaa      240
gatcaagaag gtcaaactca ttctgaatta aatcctgaaa catcagaaca tagtaaagat      300
ttaaataata atggttcaaa aaatgaatct agtgatatta tttcagaaaa taataaatca      360
aataaagtac aaaatcattt tgaatcatta tcagatttag aattacttga aaattcctca      420
caagataatt tagacaaaga tacaatttca acagaaacctt ttcctaatca aaaacataaa      480
gacttacaac aagatttaaa tgatgaacct ttagaaccct ttcctacaca aatacataaa      540
gattataaag aaaaaaattt aataaatgaa gaagattcag aaccatttcc cagacaaaag      600
cataaaaagg tagacaatca taatgaagaa aaaaacgtat ttcatgaaaa tggttctgca      660
aatggtaatc aaggaagttt gaaacttaaa tcattcgatg aacatttaaa agatgaaaaa      720
atagaaaatg aaccacttgt tcatgaaaat ttatccatac caaatgatcc aatagaacaa      780
atattaaatc aacctgaaca agaaacaaat atccaggaac aattgtataa tgaaaaacaa      840
aatgttgaag aaaaacaaaa ttctcaaata ccttcgttag atttaaaaga accaacaaat      900
gaagatattt taccaaatca taatccatta gaaaatataa acaaagtga atcagaaata      960 aatcatgtac aagatcatgc gctaccaaaa gagaatataa tagacaaact tgataatcaa     1020
aaagaacaca tcgatcaatc acaacataat ataaatgtat acaagaaaaa taacataaac     1080
aatcaccaat tagaacctca agagaaacct aatattgaat cgtttgaacc taaaaatata     1140
gattcagaaa ttattcttcc tgaaaatgtt gaaacagaag aaataataga tgatgtgcct     1200
tcccctaaac attctaacca tgaaacattt gaagaagaaa caagtgaatc tgaacatgaa     1260
gaagccgtat ctgaaaaaaa tgcccacgaa actgtcgaac atgaagaaac tgtgtctcaa     1320
gaaagcaatc ctgaaaaagc tgataatgat ggaaatgtat ctcaaaacag caacaacgaa     1380
ttaaatgaaa atgaattcgt tgaatcggaa aaaagcgagc atgaagcagg tggtagcggt     1440
gcaatggttg ataccctgag cggtctgagc agcgaacagg tcagagcgg tgatatgacc     1500 attgaagaag atagcgcaac ccacatcaaa ttcagcaaac gtgatgaaga tggtaaagaa     1560
ctggcaggcg caacaatgga actgcgtgat agcagcggta aaaccattag cacctggatt     1620
agtgatggtc aggtgaaaga ttttatctg taccctggca atacacctt tgttgaaacc     1680
```

```
gcagcaccgg atggttatga agttgcaacc gcaattacct ttaccgttaa tgaacagggc    1740
caggttaccg tgaatggtaa agcaaccaaa ggtgatgcac atatt                    1785

<210> SEQ ID NO 33
<211> LENGTH: 2307
<212> TYPE: DNA
<213> ORGANISM: Plasmodium falcifarum

<400> SEQUENCE: 33
ggatccacaa gtgagaatag aaataaacga atcgggggtc ctaaattaag gggtaatgtt      60
acaagtaata taaagttccc atcagataac aaaggtaaaa ttataagagg ttcgaatgat     120
aaacttaata aaaactctga agatgtttta gaacaaagcg aaaaatcgct tgtttcagaa     180
aatgttccta gtggattaga tatagatgat atccctaaag aatctatttt tattcaagaa     240
gatcaagaag gtcaaactca ttctgaatta aatcctgaaa catcagaaca tagtaaagat     300
ttaaataata atggttcaaa aaatgaatct agtgatatta tttcagaaaa taataaatca     360
aataaagtac aaaatcattt tgaatcatta tcagatttag aattacttga aaattcctca     420
caagataatt tagacaaaga tacaatttca acagaacctt ttcctaatca aaaacataaa     480
gacttacaac aagatttaaa tgatgaacct ttagaaccct ttcctacaca aatacataaa     540
gattataaag aaaaaaattt aataaatgaa gaagattcag aaccatttcc cagacaaaag     600
cataaaaagg tagacaatca taatgaagaa aaaaacgtat ttcatgaaaa tggttctgca     660
aatggtaatc aaggaagttt gaaacttaaa tcattcgatg aacatttaaa agatgaaaaa     720
atagaaaatg aaccacttgt tcatgaaaat ttatccatac caaatgatcc aatagaacaa     780
atattaaatc aacctgaaca agaaacaaat atccaggaac aattgtataa tgaaaaacaa     840
aatgttgaag aaaaacaaaa ttctcaaata ccttcgttag atttaaaaga accaacaaat     900
gaagatattt taccaaatca taatccatta gaaaatataa acaaagtga atcagaaata     960 aatcatgtac aagatcatgc gctaccaaaa gagaatataa tagacaaact tgataatcaa    1020
aaagaacaca tcgatcaatc acaacataat ataaatgtat tacaagaaaa taacataaac    1080
aatcaccaat tagaacctca agagaaacct aatattgaat cgtttgaacc taaaaatata    1140
gattcagaaa ttattcttcc tgaaaatgtt gaaacagaag aaataataga tgatgtgcct    1200 tccctaaac attctaacca tgaaacattt gaagaagaaa caagtgaatc tgaacatgaa    1260
gaagccgtat ctgaaaaaaa tgcccacgaa actgtcgaac atgaagaaac tgtgtctcaa    1320
gaaagcaatc ctgaaaaagc tgataatgat ggaaatgtat ctcaaaacag caacaacgaa    1380
ttaaatgaaa atgaattcgt tgaatcggaa aaaagcgagc atgaagcaag atccaaagca    1440
aaagaagctt ctagttatga ttatatttta ggttgggaat ttggaggagg cgttccagaa    1500
cacaaaaaag aagaaaatat gttatcacat ttatatgttt cttcaaagga taaggaaaat    1560
atatctaagg aaaatgatga tgtattagat gagaaggaag aagaggcaga agaaacagaa    1620
gaagaagaac ttgaagaaaa aaatgaagaa gaaacagaat cagaaataag tgaagatgaa    1680
gaagaagaag aagaagaaga agaaaaggaa gaagaaaatg acaaaaaaaa agaacaagaa    1740
aaagaacaaa gtaatgaaaa taatgatcaa aaaaaagata tggaagcaca gaatttaatt    1800
tctaaaaacc agaataataa tgagaaaaac gtaaagaag ctgctgaaag catcatgaaa    1860
actttagctg gtttaatcaa gggaaataat caaatagatt ctaccttaaa agatttagta    1920
gaagaattat ccaaatattt taaaaatcat ggtggtagcg gtgcaatggt tgatacccctg    1980 agcggtctga gcagcgaaca gggtcagagc ggtgatatga ccattgaaga agatagcgca    2040
```

| | |
|---|---:|
| acccacatca aattcagcaa acgtgatgaa gatggtaaag aactggcagg cgcaacaatg | 2100 |
| gaactgcgtg atagcagcgg taaaaccatt agcacctgga ttagtgatgg tcaggtgaaa | 2160 |
| gatttttatc tgtaccctgg caaatacacc tttgttgaaa ccgcagcacc ggatggttat | 2220 |
| gaagttgcaa ccgcaattac ctttaccgtt aatgaacagg ccaggttac cgtgaatggt | 2280 |
| aaagcaacca aaggtgatgc acatatt | 2307 |

<210> SEQ ID NO 34
<211> LENGTH: 2076
<212> TYPE: DNA
<213> ORGANISM: Plasmodium falciparum

<400> SEQUENCE: 34

| | |
|---|---:|
| ggatccacaa gtgagaatag aaataaacga atcgggggtc ctaaattaag gggtaatgtt | 60 |
| acaagtaata taaagttccc atcagataac aaaggtaaaa ttataagagg ttcgaatgat | 120 |
| aaacttaata aaaactctga agatgtttta gaacaaagcg aaaaatcgct tgtttcagaa | 180 |
| aatgttccta gtggattaga tatagatgat atccctaaag aatctatttt tattcaagaa | 240 |
| gatcaagaag gtcaaactca ttctgaatta aatcctgaaa catcagaaca tagtaaagat | 300 |
| ttaaataata atggttcaaa aaatgaatct agtgatatta tttcagaaaa taataaatca | 360 |
| aataaagtac aaaatcattt tgaatcatta tcagatttag aattacttga aaattcctca | 420 |
| caagataatt tagacaaaga tacaatttca acagaaccct ttcctaatca aaaacataaa | 480 |
| gacttacaac aagatttaaa tgatgaacct ttagaaccct ttcctacaca aatacataaa | 540 |
| gattataaag aaaaaaattt aataaatgaa gaagattcag aaccatttcc cagacaaaag | 600 |
| cataaaaagg tagacaatca taatgaagaa aaaaacgtat ttcatgaaaa tggttctgca | 660 |
| aatggtaatc aaggaagttt gaaacttaaa tcattcgatg aacatttaaa agatgaaaaa | 720 |
| atagaaaatg aaccacttgt tcatgaaaat ttatccatac caaatgatcc aatagaacaa | 780 |
| atattaaatc aacctgaaca agaaacaaat atccaggaac aattgtataa tgaaaaacaa | 840 |
| aatgttgaag aaaaacaaaa ttctcaaata ccttcgttag atttaaaaga accaacaaat | 900 |
| gaagatattt taccaaatca taatccatta gaaaatataa acaaagtga atcagaaata | 960 |
| aatcatgtac aagatcatgc gctaccaaaa gagaatataa tagacaaact tgataatcaa | 1020 |
| aaagaacaca tcgatcaatc acaacataat ataaatgtat tacaagaaaa taacataaac | 1080 |
| aatcaccaat tagaacctca agagaaacct aatattgaat cgtttgaacc taaaaatata | 1140 |
| gattcagaaa ttattcttcc tgaaaatgtt gaaacagaaa aataataga tgatgtgcct | 1200 |
| tcccctaaac attctaacca tgaaacattt gaagaagaaa caagtgaatc tgaacatgaa | 1260 |
| gaagccgtat ctgaaaaaaa tgcccacgaa actgtcgaac atgaagaaac tgtgtctcaa | 1320 |
| gaaagcaatc ctgaaaaagc tgataatgat ggaaatgtat ctcaaaacag caacaacgaa | 1380 |
| ttaaatgaaa atgaattcgt tgaatcggaa aaaagcgagc atgaagcaag atccaaaaca | 1440 |
| aaagaatatg ctgaaaaagc aaaaaatgct tatgaaaagg caaaaaatgc ttatcaaaaa | 1500 |
| gcaaaccaag ctgtttttaaa agcaaaagaa gcttctagtt atgattatat tttaggttgg | 1560 |
| gaatttggag gaggcgttcc agaacacaaa aaagaagaaa atatgttatc acatttatat | 1620 |
| gtttcttcaa aggataagga aaatatatct aaggaaaatg atgatgtatt agatgagaag | 1680 |
| gaagaagagg cagaagaaac agaagaagaa gaacttgaag gtggtagcgg tgcaatggtt | 1740 |
| gataccctga gcggtctgag cagcgaacag ggtcagagcg gtgatatgac cattgaagaa | 1800 |

| | |
|---|---|
| gatagcgcaa cccacatcaa attcagcaaa cgtgatgaag atggtaaaga actggcaggc | 1860 |
| gcaacaatgg aactgcgtga tagcagcggt aaaaccatta gcacctggat tagtgatggt | 1920 |
| caggtgaaag atttttatct gtaccctggc aaatacacct ttgttgaaac cgcagcaccg | 1980 |
| gatggttatg aagttgcaac cgcaattacc tttaccgtta atgaacaggg ccaggttacc | 2040 |
| gtgaatggta agcaaccaa aggtgatgca catatt | 2076 |

<210> SEQ ID NO 35
<211> LENGTH: 1887
<212> TYPE: DNA
<213> ORGANISM: Plasmodium falciparum

<400> SEQUENCE: 35

| | |
|---|---|
| ggtgcaatgg ttgataccct gagcggtctg agcagcgaac agggtcagag cggtgatatg | 60 |
| accattgaag aagatagcgc aacccacatc aaattcagca acgtgatga agatggtaaa | 120 |
| gaactggcag gcgcaacaat ggaactgcgt gatagcagcg gtaaaaccat tagcacctgg | 180 |
| attagtgatg gtcaggtgaa agatttttat ctgtaccctg gcaaatacac ctttgttgaa | 240 |
| accgcagcac cggatggtta tgaagttgca accgcaatta cctttaccgt taatgaacag | 300 |
| ggccaggtta ccgtgaatgg taaagcaacc aaaggtgatg cacatattgg tggtagcctg | 360 |
| tccttcgaga cgccatcaa gaagaccaag aaccaggaaa caacctgac cctgctgccc | 420 |
| atcaagtcca ccgaggaaga aaggacgac atcaagaacg gcaaggatat caagaaggaa | 480 |
| atcgacaacg acaaggaaaa catcaagacc aacaacgcca aggaccactc cacctacatc | 540 |
| aagtcttacc tgaacaccaa cgtgaacgac ggcctgaagt acctgttcat cccatcccac | 600 |
| aacagcttca tcaagaagta ctccgttttc aaccagatca cgacggcat gctgctgaac | 660 |
| gagaagaacg acgtgaagaa caacgaggac tacaagaacg tcgactacaa gaacgtgaac | 720 |
| ttcctgcagt accacttcaa ggaactgtcc aactacaaca tcgccaactc catcgacatc | 780 |
| ctgcaagaaa aggaaggcca cctggacttc gtgatcatcc cccactacac tttcttggac | 840 |
| tactacaagc acctgtccta aacagcatc taccacaagt acagcaccta cggcaagtac | 900 |
| atcgctgtgg acgctttcat caagaagatc aacgagactt acgacaaagt gaagtccaag | 960 |
| tgtaacgata tcaagaacga cctgatcgcc accatcaaga agctcgagca cccctacgac | 1020 |
| atcaacaaca gaacgacga cagctaccgc tacgacatct ccgaagagat cgacgacaag | 1080 |
| tccgaggaaa ccgacgacga gactgaggaa gtcgaggact ccatccagga caccgactcc | 1140 |
| aaccacaccc cctccaacaa gaagaagaac gatctgatga accgcacctt caagaagatg | 1200 |
| atggacgagt acaacactaa gaagaagaag ctgatcaagt gcatcaagaa ccacgagaac | 1260 |
| gacttcaaca gatctgcat ggacatgaag aactacggca ccaacctgtt cgagcagctg | 1320 |
| tcctgctaca caacaacttt ctgcaacact aacggcatcc gcttccacta cgatgagtac | 1380 |
| atccacaagc tgatcctgtc cgtcaagagc aagaacctga caaggacct gagcgacatg | 1440 |
| accaacatcc tccagcagtc cgagctgctg ctgaccaact tgaacaagaa gatgggctcc | 1500 |
| tacatctaca tcgacactat caagttcatc cacaaggaaa tgaagcacat cttcaaccgc | 1560 |
| atcgagtacc acaccaagat catcaacgat aagactaaga tcatccaaga caagatcaag | 1620 |
| ctgaacatct ggcgcacttt ccaaaaggac gaactgctga gcgtatcct ggacatgtct | 1680 |
| aacgagtact ccctcttcat cacctccgac cacctgaggc agatgctgta caacaccttc | 1740 |
| tactccaagg aaaagcaccct caacaacatc ttccaccacc tgatctacgt gctgcagatg | 1800 |
| aagttcaacg acgtccccat caagatggaa tacttccaga cctacaagaa gaacaagccc | 1860 | ctgacccagc atcatcacca ccaccac                                                              1887

<210> SEQ ID NO 36
<211> LENGTH: 13
<212> TYPE: PRT
<213> ORGANISM: Streptococcus pyogenes

<400> SEQUENCE: 36

Ala His Ile Val Met Val Asp Ala Tyr Lys Pro Thr Lys
1               5                   10

<210> SEQ ID NO 37
<211> LENGTH: 116
<212> TYPE: PRT
<213> ORGANISM: Streptococcus pyogenes

<400> SEQUENCE: 37

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile
        115

<210> SEQ ID NO 38
<211> LENGTH: 10
<212> TYPE: PRT
<213> ORGANISM: Streptococcus pyogenes

<400> SEQUENCE: 38

Ala Thr His Ile Lys Phe Ser Lys Arg Asp
1               5                   10

<210> SEQ ID NO 39
<211> LENGTH: 39
<212> TYPE: DNA
<213> ORGANISM: Streptococcus pyogenes

<400> SEQUENCE: 39
gctcacatcg tgatggtgga cgcttacaag cccaccaag                                                   39

<210> SEQ ID NO 40
<211> LENGTH: 261
<212> TYPE: PRT
<213> ORGANISM: Homo Sapiens

<400> SEQUENCE: 40

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala

```
                20                  25                  30
Cys Thr Pro Glu Arg Met Ala Glu Ala Gly Phe Ile His Cys Pro Thr
         35                  40                  45
Glu Asn Glu Pro Asp Leu Ala Gln Cys Phe Phe Cys Phe Lys Glu Leu
 50                  55                  60
Glu Gly Trp Glu Pro Asp Asp Pro Ile Glu His Lys Lys His
 65                  70                  75                  80
Ser Ser Gly Cys Ala Phe Leu Ser Val Lys Lys Gln Phe Glu Glu Leu
                 85                  90                  95
Thr Leu Gly Glu Phe Leu Lys Leu Asp Arg Glu Arg Ala Lys Asn Lys
             100                 105                 110
Ile Ala Lys Glu Thr Asn Asn Lys Lys Glu Phe Glu Glu Thr Ala
         115                 120                 125
Lys Lys Val Arg Arg Ala Ile Glu Gln Leu Ala Ala Met Asp Gly Gly
         130                 135                 140
Ser Gly Ala Met Val Asp Thr Leu Ser Gly Leu Ser Ser Glu Gln Gly
145                 150                 155                 160
Gln Ser Gly Asp Met Thr Ile Glu Glu Asp Ser Ala Thr His Ile Lys
                 165                 170                 175
Phe Ser Lys Arg Asp Glu Asp Gly Lys Glu Leu Ala Gly Ala Thr Met
             180                 185                 190
Glu Leu Arg Asp Ser Ser Gly Lys Thr Ile Ser Thr Trp Ile Ser Asp
         195                 200                 205
Gly Gln Val Lys Asp Phe Tyr Leu Tyr Pro Gly Lys Tyr Thr Phe Val
         210                 215                 220
Glu Thr Ala Ala Pro Asp Gly Tyr Glu Val Ala Thr Ala Ile Thr Phe
225                 230                 235                 240
Thr Val Asn Glu Gln Gly Gln Val Thr Val Asn Gly Lys Ala Thr Lys
                 245                 250                 255
Gly Asp Ala His Ile
             260

<210> SEQ ID NO 41
<211> LENGTH: 260
<212> TYPE: PRT
<213> ORGANISM: Homo Sapiens

<400> SEQUENCE: 41

Gly Ala Met Val Asp Thr Leu Ser Gly Leu Ser Ser Glu Gln Gly Gln
 1               5                  10                  15
Ser Gly Asp Met Thr Ile Glu Glu Asp Ser Ala Thr His Ile Lys Phe
                 20                  25                  30
Ser Lys Arg Asp Glu Asp Gly Lys Glu Leu Ala Gly Ala Thr Met Glu
             35                  40                  45
Leu Arg Asp Ser Ser Gly Lys Thr Ile Ser Thr Trp Ile Ser Asp Gly
 50                  55                  60
Gln Val Lys Asp Phe Tyr Leu Tyr Pro Gly Lys Tyr Thr Phe Val Glu
 65                  70                  75                  80
Thr Ala Ala Pro Asp Gly Tyr Glu Val Ala Thr Ala Ile Thr Phe Thr
                 85                  90                  95
Val Asn Glu Gln Gly Gln Val Thr Val Asn Gly Lys Ala Thr Lys Gly
             100                 105                 110
Asp Ala His Ile Gly Gly Ser Gly Ala Pro Thr Leu Pro Pro Ala Trp
         115                 120                 125
```

```
Gln Pro Phe Leu Lys Asp His Arg Ile Ser Thr Phe Lys Asn Trp Pro
            130                 135                 140

Phe Leu Glu Gly Cys Ala Cys Thr Pro Glu Arg Met Ala Glu Ala Gly
145                 150                 155                 160

Phe Ile His Cys Pro Thr Glu Asn Glu Pro Asp Leu Ala Gln Cys Phe
                165                 170                 175

Phe Cys Phe Lys Glu Leu Glu Gly Trp Glu Pro Asp Asp Pro Ile
            180                 185                 190

Glu Glu His Lys Lys His Ser Ser Gly Cys Ala Phe Leu Ser Val Lys
                195                 200                 205

Lys Gln Phe Glu Glu Leu Thr Leu Gly Glu Phe Leu Lys Leu Asp Arg
210                 215                 220

Glu Arg Ala Lys Asn Lys Ile Ala Lys Glu Thr Asn Asn Lys Lys Lys
225                 230                 235                 240

Glu Phe Glu Glu Thr Ala Lys Lys Val Arg Arg Ala Ile Glu Gln Leu
                245                 250                 255

Ala Ala Met Asp
            260

<210> SEQ ID NO 42
<211> LENGTH: 261
<212> TYPE: PRT
<213> ORGANISM: Homo Sapiens

<400> SEQUENCE: 42

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Ala Ala Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp Gly Gly
130                 135                 140

Ser Gly Ala Met Val Asp Thr Leu Ser Gly Leu Ser Ser Glu Gln Gly
145                 150                 155                 160

Gln Ser Gly Asp Met Thr Ile Glu Glu Asp Ser Ala Thr His Ile Lys
                165                 170                 175

Phe Ser Lys Arg Asp Glu Asp Gly Lys Glu Leu Ala Gly Ala Thr Met
            180                 185                 190

Glu Leu Arg Asp Ser Ser Gly Lys Thr Ile Ser Thr Trp Ile Ser Asp
        195                 200                 205

Gly Gln Val Lys Asp Phe Tyr Leu Tyr Pro Gly Lys Tyr Thr Phe Val
    210                 215                 220

Glu Thr Ala Ala Pro Asp Gly Tyr Glu Val Ala Thr Ala Ile Thr Phe
225                 230                 235                 240
```

Thr Val Asn Glu Gln Gly Gln Val Thr Val Asn Gly Lys Ala Thr Lys
                245                 250                 255

Gly Asp Ala His Ile
            260

<210> SEQ ID NO 43
<211> LENGTH: 260
<212> TYPE: PRT
<213> ORGANISM: Homo Sapiens

<400> SEQUENCE: 43

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Gly Ala Pro Thr Leu Pro Pro Ala Trp
        115                 120                 125

Gln Pro Phe Leu Lys Asp His Arg Ile Ser Thr Phe Lys Asn Trp Pro
    130                 135                 140

Phe Leu Glu Gly Cys Ala Cys Thr Pro Glu Arg Met Ala Glu Ala Gly
145                 150                 155                 160

Phe Ile His Cys Pro Thr Glu Asn Glu Pro Asp Leu Ala Gln Cys Phe
                165                 170                 175

Phe Cys Phe Lys Glu Leu Glu Gly Trp Glu Pro Asp Asp Asp Pro Ile
            180                 185                 190

Glu Glu His Lys Lys His Ser Ser Gly Cys Ala Phe Leu Ser Val Lys
        195                 200                 205

Lys Gln Phe Glu Glu Leu Thr Leu Gly Glu Ala Ala Lys Leu Asp Arg
    210                 215                 220

Glu Arg Ala Lys Asn Lys Ile Ala Lys Glu Thr Asn Asn Lys Lys Lys
225                 230                 235                 240

Glu Phe Glu Glu Thr Ala Lys Lys Val Arg Arg Ala Ile Glu Gln Leu
                245                 250                 255

Ala Ala Met Asp
            260

<210> SEQ ID NO 44
<211> LENGTH: 262
<212> TYPE: PRT
<213> ORGANISM: Mus Musculus

<400> SEQUENCE: 44

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

-continued

Ser Lys Arg Asp Glu Asp Gly Lys Glu Leu Ala Gly Ala Thr Met Glu
    35                  40                  45

Leu Arg Asp Ser Ser Gly Lys Thr Ile Ser Thr Trp Ile Ser Asp Gly
 50                  55                  60

Gln Val Lys Asp Phe Tyr Leu Tyr Pro Gly Lys Tyr Thr Phe Val Glu
 65                  70                  75                  80

Thr Ala Ala Pro Asp Gly Tyr Glu Val Ala Thr Ala Ile Thr Phe Thr
                 85                  90                  95

Val Asn Glu Gln Gly Gln Val Thr Val Asn Gly Lys Ala Thr Lys Gly
                100                 105                 110

Asp Ala His Ile Gly Gly Ser Gly Ala Pro Ala Leu Pro Gln Ile Trp
                115                 120                 125

Gln Leu Tyr Leu Lys Asn Tyr Arg Ile Ala Thr Phe Lys Asn Trp Pro
    130                 135                 140

Phe Leu Glu Asp Cys Ala Cys Thr Pro Glu Arg Met Ala Glu Ala Gly
145                 150                 155                 160

Phe Ile His Cys Pro Thr Glu Asn Glu Pro Asp Leu Ala Gln Cys Phe
                165                 170                 175

Phe Cys Phe Lys Glu Leu Glu Gly Trp Glu Pro Asp Asp Asn Pro Ile
                180                 185                 190

Glu Glu His Arg Lys His Ser Pro Gly Cys Ala Phe Leu Thr Val Lys
                195                 200                 205

Lys Gln Met Glu Glu Leu Thr Val Ser Glu Ala Lys Leu Asp Arg
    210                 215                 220

Gln Arg Ala Lys Asn Lys Ile Ala Lys Glu Thr Asn Asn Lys Gln Lys
225                 230                 235                 240

Glu Phe Glu Glu Thr Ala Lys Thr Thr Arg Gln Ser Ile Glu Gln Leu
                245                 250                 255

Ala Ala Ser Gly Arg Phe
                260

<210> SEQ ID NO 45
<211> LENGTH: 258
<212> TYPE: PRT
<213> ORGANISM: Mus Musculus

<400> SEQUENCE: 45

Gly Ala Pro Ala Leu Pro Gln Ile Trp Gln Leu Tyr Leu Lys Asn Tyr
1               5                   10                  15

Arg Ile Ala Thr Phe Lys Asn Trp Pro Phe Leu Glu Asp Cys Ala Cys
            20                  25                  30

Thr Pro Glu Arg Met Ala Glu Ala Gly Phe Ile His Cys Pro Thr Glu
        35                  40                  45

Asn Glu Pro Asp Leu Ala Gln Cys Phe Phe Cys Phe Lys Glu Leu Glu
    50                  55                  60

Gly Trp Glu Pro Asp Asp Asn Pro Ile Glu Glu His Arg Lys His Ser
65                  70                  75                  80

Pro Gly Cys Ala Phe Leu Thr Val Lys Lys Gln Met Glu Glu Leu Thr
                85                  90                  95

Val Ser Glu Ala Ala Lys Leu Asp Arg Gln Arg Ala Lys Asn Lys Ile
                100                 105                 110

Ala Lys Glu Thr Asn Asn Lys Gln Lys Glu Phe Glu Glu Thr Ala Lys
            115                 120                 125

Thr Thr Arg Gln Ser Ile Glu Gln Leu Ala Ala Gly Gly Ser Gly Ala

```
              130                 135                 140
Met Val Asp Thr Leu Ser Gly Leu Ser Ser Glu Gln Gly Gln Ser Gly
145                 150                 155                 160

Asp Met Thr Ile Glu Glu Asp Ser Ala Thr His Ile Lys Phe Ser Lys
                165                 170                 175

Arg Asp Glu Asp Gly Lys Glu Leu Ala Gly Ala Thr Met Glu Leu Arg
            180                 185                 190

Asp Ser Ser Gly Lys Thr Ile Ser Thr Trp Ile Ser Asp Gly Gln Val
                195                 200                 205

Lys Asp Phe Tyr Leu Tyr Pro Gly Lys Tyr Thr Phe Val Glu Thr Ala
    210                 215                 220

Ala Pro Asp Gly Tyr Glu Val Ala Thr Ala Ile Thr Phe Thr Val Asn
225                 230                 235                 240

Glu Gln Gly Gln Val Thr Val Asn Gly Lys Ala Thr Lys Gly Asp Ala
                245                 250                 255

His Ile

<210> SEQ ID NO 46
<211> LENGTH: 262
<212> TYPE: PRT
<213> ORGANISM: Mus Musculus

<400> SEQUENCE: 46

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
                20                  25                  30

Ser Lys Arg Asp Glu Asp Gly Lys Glu Leu Ala Gly Ala Thr Met Glu
            35                  40                  45

Leu Arg Asp Ser Ser Gly Lys Thr Ile Ser Thr Trp Ile Ser Asp Gly
        50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Gly Ala Pro Ala Leu Pro Gln Ile Trp
        115                 120                 125

Gln Leu Tyr Leu Lys Asn Tyr Arg Ile Ala Thr Phe Lys Asn Trp Pro
130                 135                 140

Phe Leu Glu Asp Cys Ala Cys Thr Pro Glu Arg Met Ala Glu Ala Gly
145                 150                 155                 160

Phe Ile His Cys Pro Thr Glu Asn Glu Pro Asp Leu Ala Gln Cys Phe
                165                 170                 175

Phe Cys Phe Lys Glu Leu Glu Gly Trp Glu Pro Asp Asp Asn Pro Ile
            180                 185                 190

Glu Glu His Arg Lys His Ser Pro Gly Cys Ala Phe Leu Thr Val Lys
        195                 200                 205

Lys Gln Met Glu Glu Leu Thr Val Ser Glu Phe Leu Lys Leu Asp Arg
    210                 215                 220

Gln Arg Ala Lys Asn Lys Ile Ala Lys Glu Thr Asn Asn Lys Gln Lys
225                 230                 235                 240

Glu Phe Glu Glu Thr Ala Lys Thr Thr Arg Gln Ser Ile Glu Gln Leu
```

Ala Ala Ser Gly Arg Phe
        260

<210> SEQ ID NO 47
<211> LENGTH: 258
<212> TYPE: PRT
<213> ORGANISM: Mus Musculus

<400> SEQUENCE: 47

Gly Ala Pro Ala Leu Pro Gln Ile Trp Gln Leu Tyr Leu Lys Asn Tyr
1               5                   10                  15

Arg Ile Ala Thr Phe Lys Asn Trp Pro Phe Leu Glu Asp Cys Ala Cys
            20                  25                  30

Thr Pro Glu Arg Met Ala Glu Ala Gly Phe Ile His Cys Pro Thr Glu
        35                  40                  45

Asn Glu Pro Asp Leu Ala Gln Cys Phe Phe Cys Phe Lys Glu Leu Glu
    50                  55                  60

Gly Trp Glu Pro Asp Asp Asn Pro Ile Glu Glu His Arg Lys His Ser
65                  70                  75                  80

Pro Gly Cys Ala Phe Leu Thr Val Lys Lys Gln Met Glu Glu Leu Thr
                85                  90                  95

Val Ser Glu Phe Leu Lys Leu Asp Arg Gln Arg Ala Lys Asn Lys Ile
            100                 105                 110

Ala Lys Glu Thr Asn Asn Lys Gln Lys Glu Phe Glu Glu Thr Ala Lys
        115                 120                 125

Thr Thr Arg Gln Ser Ile Glu Gln Leu Ala Ala Gly Gly Ser Gly Ala
    130                 135                 140

Met Val Asp Thr Leu Ser Gly Leu Ser Ser Glu Gln Gly Gln Ser Gly
145                 150                 155                 160

Asp Met Thr Ile Glu Glu Asp Ser Ala Thr His Ile Lys Phe Ser Lys
                165                 170                 175

Arg Asp Glu Asp Gly Lys Glu Leu Ala Gly Ala Thr Met Glu Leu Arg
            180                 185                 190

Asp Ser Ser Gly Lys Thr Ile Ser Thr Trp Ile Ser Asp Gly Gln Val
        195                 200                 205

Lys Asp Phe Tyr Leu Tyr Pro Gly Lys Tyr Thr Phe Val Glu Thr Ala
    210                 215                 220

Ala Pro Asp Gly Tyr Glu Val Ala Thr Ala Ile Thr Phe Thr Val Asn
225                 230                 235                 240

Glu Gln Gly Gln Val Thr Val Asn Gly Lys Ala Thr Lys Gly Asp Ala
                245                 250                 255

His Ile

<210> SEQ ID NO 48
<211> LENGTH: 786
<212> TYPE: DNA
<213> ORGANISM: Mus Musculus

<400> SEQUENCE: 48
ggtgcaatgg ttgataccct gagcggtctg agcagcgaac agggtcagag cggtgatatg      60
accattgaag aagatagcgc aacccacatc aaattcagca acgtgatga agatggtaaa      120 gaactggcag cgcaacaat ggaactgcgt gatagcagcg gtaaaaccat tagcacctgg      180
attagtgatg gtcaggtgaa agatttttat ctgtaccctg gcaaatacac ctttgttgaa      240

```
accgcagcac cggatggtta tgaagttgca accgcaatta cctttaccgt taatgaacag    300
ggccaggtta ccgtgaatgg taaagcaacc aaaggtgatg cacatattgg tggtagcggt    360
gcaccggcac tgccgcagat tggcagctg tatctgaaaa actatcgtat cgccaccttt     420
aaaaactggc cgtttctgga agattgtgca tgtacaccgg aacgtatggc agaagcaggt    480
tttattcatt gtccgaccga aaatgaaccg gatctggcac agtgtttttt ttgctttaaa    540
gaactggaag gttgggagcc ggatgataat ccgattgaag aacatcgtaa acatagtccg    600
ggttgtgcat ttctgaccgt gaaaaaacaa atggaagaac tgaccgttag cgaggcagca    660
aaactggatc gtcagcgtgc caaaaacaaa attgcaaaag aaaccaataa caaacagaaa    720
gaattcgaag aaaccgccaa aaccacccgt cagagcattg aacagctggc agcaagcggc    780
cgcttt                                                               786

<210> SEQ ID NO 49
<211> LENGTH: 774
<212> TYPE: DNA
<213> ORGANISM: Mus Musculus

<400> SEQUENCE: 49
ggtgcaccgg cactgccgca gatttggcag ctgtatctga aaaactatcg tatcgccacc     60
tttaaaaact ggccgtttct ggaagattgt gcatgtacac cggaacgtat ggcagaagca    120
ggttttattc attgtccgac cgaaaatgaa ccggatctgg cacagtgttt ttttgctttt    180
aaagaactgg aaggttggga gccggatgat aatccgattg aagaacatcg taaacatagt    240
ccgggttgtg catttctgac cgtgaaaaaa caaatggaag aactgaccgt tagcgaggca    300
gcaaaactgg atcgtcagcg tgccaaaaac aaaattgcaa agaaaccaa taacaaacag    360
aaagaattcg aagaaaccgc caaaaccacc cgtcagagca ttgaacagct ggcagcaggt    420
ggcagcggtg caatggttga taccctgagc ggtctgagca gcgaacaggg tcagagcggt    480
gatatgacca ttgaagaaga tagcgcaacc cacatcaaat tcagcaaacg tgatgaagat    540
ggtaaagaac tggcaggcgc aacaatggaa ctgcgtgata gcagcggtaa aaccattagc    600
acctggatta gtgatggtca ggtgaaagat ttttatctgt accctggcaa atacaccttt    660
gttgaaaccg cagcaccgga tggttatgaa gttgcaaccg caattacctt taccgttaat    720
gaacagggcc aggttaccgt gaatggtaaa gcaaccaaag gtgatgcaca tatt          774

<210> SEQ ID NO 50
<211> LENGTH: 786
<212> TYPE: DNA
<213> ORGANISM: Mus Musculus

<400> SEQUENCE: 50
ggtgcaatgg ttgataccct gagcggtctg agcagcgaac agggtcagag cggtgatatg     60
accattgaag aagatagcgc aacccacatc aaattcagca acgtgatga agatggtaaa    120
gaactggcag gcgcaacaat ggaactgcgt gatagcagcg gtaaaaccat tagcacctgg    180
attagtgatg gtcaggtgaa agatttttat ctgtaccctg gcaaatacac ctttgttgaa    240
accgcagcac cggatggtta tgaagttgca accgcaatta cctttaccgt taatgaacag    300
ggccaggtta ccgtgaatgg taaagcaacc aaaggtgatg cacatattgg tggtagcggt    360
gcaccggcac tgccgcagat tggcagctg tatctgaaaa actatcgtat cgccaccttt     420
aaaaactggc cgtttctgga agattgtgca tgtacaccgg aacgtatggc agaagcaggt    480
tttattcatt gtccgaccga aaatgaaccg gatctggcac agtgtttttt ttgctttaaa    540
```

-continued

```
gaactggaag gttgggagcc ggatgataat ccgattgaag aacatcgtaa acatagtccg    600
ggttgtgcat ttctgaccgt gaaaaaacaa atggaagaac tgaccgttag cgagtttctg    660
aaactggatc gtcagcgtgc caaaaacaaa attgcaaaag aaccaataa caaacagaaa    720 gaattcgaag aaaccgccaa aaccacccgt cagagcattg aacagctggc agcaagcggc    780
cgcttt                                                                786
```

<210> SEQ ID NO 51
<211> LENGTH: 774
<212> TYPE: DNA
<213> ORGANISM: Mus Musculus

<400> SEQUENCE: 51

```
ggtgcaccgg cactgccgca gatttggcag ctgtatctga aaaactatcg tatcgccacc     60
tttaaaaact ggccgtttct ggaagattgt gcatgtacac cggaacgtat ggcagaagca    120
ggttttattc attgtccgac cgaaaatgaa ccggatctgg cacagtgttt tttttgcttt    180
aaagaactgg aaggttggga gccggatgat aatccgattg aagaacatcg taaacatagt    240
ccgggttgtg catttctgac cgtgaaaaaa caaatggaag aactgaccgt tagcgagttt    300
ctgaaactgg atcgtcagcg tgccaaaaac aaaattgcaa agaaaccaa taacaaacag    360 aaagaattcg aagaaaccgc caaaaccacc cgtcagagca ttgaacagct ggcagcaggt    420
ggcagcggtg caatggttga ccctgagc ggtctgagca gcgaacaggg tcagagcggt    480
gatatgacca ttgaagaaga tagcgcaacc cacatcaaat tcagcaaacg tgatgaagat    540
ggtaaagaac tggcaggcgc aacaatggaa ctgcgtgata gcagcggtaa aaccattagc    600
acctggatta gtgatggtca ggtgaaagat ttttatctgt accctggcaa atacaccttt    660
gttgaaaccg cagcaccgga tggttatgaa gttgcaaccg caattacctt taccgttaat    720
gaacagggcc aggttaccgt gaatggtaaa gcaaccaaag gtgatgcaca tatt          774
```

<210> SEQ ID NO 52
<211> LENGTH: 269
<212> TYPE: PRT
<213> ORGANISM: Plasmodium falciparum

<400> SEQUENCE: 52

```
Gly Ala Met Val Asp Thr Leu Ser Gly Leu Ser Ser Glu Gln Gly Gln
 1               5                  10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Lys Ile Thr Ser Phe Asp Glu Phe Phe
        115                 120                 125

Asp Phe Trp Val Arg Lys Leu Leu Ile Asp Thr Ile Lys Trp Glu Thr
    130                 135                 140
```

```
Glu Leu Thr Tyr Cys Ile Asn Asn Thr Asp Val Thr Asp Cys Asn Lys
145                 150                 155                 160

Cys Asn Lys Asn Cys Val Cys Phe Asp Lys Trp Val Lys Gln Lys Glu
            165                 170                 175

Asp Glu Trp Thr Asn Ile Met Lys Leu Phe Thr Asn Lys His Asp Ile
        180                 185                 190

Pro Lys Lys Tyr Tyr Leu Asn Ile Asn Asp Leu Phe Asp Ser Phe Phe
            195                 200                 205

Phe Gln Val Ile Tyr Lys Phe Asn Glu Gly Glu Ala Lys Trp Asn Glu
        210                 215                 220

Leu Lys Glu Asn Leu Lys Lys Gln Ile Ala Ser Ser Lys Ala Asn Asn
225                 230                 235                 240

Gly Thr Lys Asp Ser Glu Ala Ala Ile Lys Val Leu Phe Asn His Ile
            245                 250                 255

Lys Glu Ile Ala Thr Ile Cys Lys Asp Asn Asn Thr Asn
        260                 265
```

<210> SEQ ID NO 53
<211> LENGTH: 807
<212> TYPE: DNA
<213> ORGANISM: Plasmodium falcifarum

<400> SEQUENCE: 53

```
ggtgcaatgg ttgataccct gagcggtctg agcagcgaac agggtcagag cggtgatatg      60
accattgaag aagatagcgc aacccacatc aaattcagca acgtgatga agatggtaaa     120
gaactggcag gcgcaacaat ggaactgcgt gatagcagcg gtaaaaccat tagcacctgg     180
attagtgatg gtcaggtgaa agattttat ctgtaccctg gcaaatacac ctttgttgaa     240
accgcagcac cggatggtta tgaagttgca accgcaatta cctttaccgt taatgaacag     300
ggccaggtta ccgtgaatgg taaagcaacc aaaggtgatg cacatattgg tggtagcaaa     360
ataacgtcat ttgatgaatt ttttgatttt tgggttagaa aattattaat agacactata     420
aagtgggaaa ccgaacttac gtattgtata ataatactg atgtcacgga ttgtaataaa     480
tgtaacaaaa attgcgtatg ttttgacaaa tgggttaaac aaaaagaaga cgaatggaca     540
aatataatga actattcac aaacaaacac gatataccga aaaatatta tcttaatatt     600
aatgatcttt ttgatagttt tttttttccaa gttatatata agtttaacga aggagaagca     660
aaatggaatg aacttaaaga aaatttaaaa aagcaaattg cgtcttccaa agcaaataac     720
ggaaccaaag attcagaagc tgcaataaaa gtgttgttta tcacataaa agaaattgca     780
acaatatgca agataataa tacaaac                                         807
```

<210> SEQ ID NO 54
<211> LENGTH: 348
<212> TYPE: DNA
<213> ORGANISM: Streptococcus pyogenes

<400> SEQUENCE: 54

```
ggtgcaatgg ttgataccct gagcggtctg agcagcgaac agggtcagag cggtgatatg      60
accattgaag aagatagcgc aacccacatc aaattcagca acgtgatga agatggtaaa     120
gaactggcag gcgcaacaat ggaactgcgt gatagcagcg gtaaaaccat tagcacctgg     180
attagtgatg gtcaggtgaa agattttat ctgtaccctg gcaaatacac ctttgttgaa     240
accgcagcac cggatggtta tgaagttgca accgcaatta cctttaccgt taatgaacag     300
```

```
ggccaggtta ccgtgaatgg taaagcaacc aaaggtgatg cacatatt                    348
```

<210> SEQ ID NO 55
<211> LENGTH: 104
<212> TYPE: PRT
<213> ORGANISM: Streptococcus pyogenes

<400> SEQUENCE: 55

His His His His His His Asp Tyr Asp Gly Gln Ser Gly Asp Gly Lys
1               5                   10                  15

Glu Leu Ala Gly Ala Thr Met Glu Leu Arg Asp Ser Ser Gly Lys Thr
            20                  25                  30

Ile Ser Thr Trp Ile Ser Asp Gly Gln Val Lys Asp Phe Tyr Leu Tyr
        35                  40                  45

Pro Gly Lys Tyr Thr Phe Val Glu Thr Ala Ala Pro Asp Gly Tyr Glu
    50                  55                  60

Val Ala Thr Ala Ile Thr Phe Thr Val Asn Glu Gln Gly Gln Val Thr
65                  70                  75                  80

Val Asn Gly Lys Ala Thr Lys Gly Gly Ser Gly Gly Ser Gly Gly Ser
                85                  90                  95

Gly Glu Asp Ser Ala Thr His Ile
            100

<210> SEQ ID NO 56
<211> LENGTH: 16
<212> TYPE: PRT
<213> ORGANISM: Streptococcus pyogenes

<400> SEQUENCE: 56

Thr Asp Lys Asp Met Thr Ile Thr Phe Thr Asn Lys Lys Asp Ala Glu
1               5                   10                  15

<210> SEQ ID NO 57
<211> LENGTH: 282
<212> TYPE: PRT
<213> ORGANISM: Streptococcus pyogenes

<400> SEQUENCE: 57

Ala Thr Thr Val His Gly Glu Thr Val Val Asn Gly Ala Lys Leu Thr
1               5                   10                  15

Val Thr Lys Asn Leu Asp Leu Val Asn Ser Asn Ala Leu Ile Pro Asn
            20                  25                  30

Thr Asp Phe Thr Phe Lys Ile Glu Pro Asp Thr Thr Val Asn Glu Asp
        35                  40                  45

Gly Asn Lys Phe Lys Gly Val Ala Leu Asn Thr Pro Met Thr Lys Val
    50                  55                  60

Thr Tyr Thr Asn Ser Asp Lys Gly Gly Ser Asn Thr Lys Thr Ala Glu
65                  70                  75                  80

Phe Asp Phe Ser Glu Val Thr Phe Glu Lys Pro Gly Val Tyr Tyr Tyr
                85                  90                  95

Lys Val Thr Glu Glu Lys Ile Asp Lys Val Pro Gly Val Ser Tyr Asp
            100                 105                 110

Thr Thr Ser Tyr Thr Val Gln Val His Val Leu Trp Asn Glu Glu Gln
        115                 120                 125

Gln Lys Pro Val Ala Thr Tyr Ile Val Gly Tyr Lys Glu Gly Ser Lys
    130                 135                 140

Val Pro Ile Gln Phe Lys Asn Ser Leu Asp Ser Thr Thr Leu Thr Val
145                 150                 155                 160

```
Lys Lys Lys Val Ser Gly Thr Gly Gly Asp Arg Ser Lys Asp Phe Asn
                165                 170                 175

Phe Gly Leu Thr Leu Lys Ala Asn Gln Tyr Tyr Lys Ala Ser Glu Lys
            180                 185                 190

Val Met Ile Glu Lys Thr Thr Lys Gly Gly Gln Ala Pro Val Gln Thr
        195                 200                 205

Glu Ala Ser Ile Asp Gln Leu Tyr His Phe Thr Leu Lys Asp Gly Glu
    210                 215                 220

Ser Ile Lys Val Thr Asn Leu Pro Val Gly Val Asp Tyr Val Val Thr
225                 230                 235                 240

Glu Asp Asp Tyr Lys Ser Glu Lys Tyr Thr Thr Asn Val Glu Val Ser
                245                 250                 255

Pro Gln Asp Gly Ala Val Lys Asn Ile Ala Gly Asn Ser Thr Glu Gln
            260                 265                 270

Glu Thr Ser Thr Asp Lys Asp Met Thr Ile
        275                 280

<210> SEQ ID NO 58
<211> LENGTH: 130
<212> TYPE: PRT
<213> ORGANISM: acinetobacter phage AP205

<400> SEQUENCE: 58

Ala Asn Lys Pro Met Gln Pro Ile Thr Ser Thr Ala Asn Lys Ile Val
1               5                   10                  15

Trp Ser Asp Pro Thr Arg Leu Ser Thr Thr Phe Ser Ala Ser Leu Leu
            20                  25                  30

Arg Gln Arg Val Lys Val Gly Ile Ala Glu Leu Asn Asn Val Ser Gly
        35                  40                  45

Gln Tyr Val Ser Val Tyr Lys Arg Pro Ala Pro Lys Pro Glu Gly Cys
    50                  55                  60

Ala Asp Ala Cys Val Ile Met Pro Asn Glu Asn Gln Ser Ile Arg Thr
65                  70                  75                  80

Val Ile Ser Gly Ser Ala Glu Asn Leu Ala Thr Leu Lys Ala Glu Trp
                85                  90                  95

Glu Thr His Lys Arg Asn Val Asp Thr Leu Phe Ala Ser Gly Asn Ala
            100                 105                 110

Gly Leu Gly Phe Leu Asp Pro Thr Ala Ala Ile Val Ser Ser Asp Thr
        115                 120                 125

Thr Ala
    130

<210> SEQ ID NO 59
<211> LENGTH: 129
<212> TYPE: PRT
<213> ORGANISM: bacteriophage fr

<400> SEQUENCE: 59

Ala Ser Asn Phe Glu Glu Phe Val Leu Val Asp Asn Gly Gly Thr Gly
1               5                   10                  15

Asp Val Lys Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Asn Asn Arg Lys Tyr Thr Val Lys Val Glu Val
    50                  55                  60
```

```
Pro Lys Val Ala Thr Gln Val Gln Gly Gly Val Glu Leu Pro Val Ala
65                  70                  75                  80

Ala Trp Arg Ser Tyr Met Asn Met Glu Leu Thr Ile Pro Val Phe Ala
                85                  90                  95

Thr Asn Asp Asp Cys Ala Leu Ile Val Lys Ala Leu Gln Gly Thr Phe
            100                 105                 110

Lys Thr Gly Asn Pro Ile Ala Thr Ala Ile Ala Asn Ser Gly Ile
        115                 120                 125

Tyr

<210> SEQ ID NO 60
<211> LENGTH: 92
<212> TYPE: PRT
<213> ORGANISM: artificial sequence
<220> FEATURE:
<223> OTHER INFORMATION: N-terminal truncation mutant of SpyCatcher
<220> FEATURE:
<221> NAME/KEY: MISC_FEATURE
<222> LOCATION: (1)..(92)
<223> OTHER INFORMATION: Truncation of the 25 N-terminal amino acids of
      SpyCatcher

<400> SEQUENCE: 60

Asp Ser Ala Thr His Ile Lys Phe Ser Lys Arg Asp Glu Asp Gly Lys
1               5                   10                  15

Glu Leu Ala Gly Ala Thr Met Glu Leu Arg Asp Ser Ser Gly Lys Thr
            20                  25                  30

Ile Ser Thr Trp Ile Ser Asp Gly Gln Val Lys Asp Phe Tyr Leu Tyr
        35                  40                  45

Pro Gly Lys Tyr Thr Phe Val Glu Thr Ala Ala Pro Asp Gly Tyr Glu
    50                  55                  60

Val Ala Thr Ala Ile Thr Phe Thr Val Asn Glu Gln Gly Gln Val Thr
65                  70                  75                  80

Val Asn Gly Lys Ala Thr Lys Gly Asp Ala His Ile
            85                  90

<210> SEQ ID NO 61
<211> LENGTH: 88
<212> TYPE: PRT
<213> ORGANISM: artificial sequence
<220> FEATURE:
<223> OTHER INFORMATION: Truncation of 25 N-terminal amino acids and 4
      C-terminal amino acids of SpyCatcher
<220> FEATURE:
<221> NAME/KEY: MISC_FEATURE
<222> LOCATION: (1)..(88)
<223> OTHER INFORMATION: Truncation of 25 N-terminal amino acids and 4
      C-terminal amino acids of SpyCatcher

<400> SEQUENCE: 61

Asp Ser Ala Thr His Ile Lys Phe Ser Lys Arg Asp Glu Asp Gly Lys
1               5                   10                  15

Glu Leu Ala Gly Ala Thr Met Glu Leu Arg Asp Ser Ser Gly Lys Thr
            20                  25                  30

Ile Ser Thr Trp Ile Ser Asp Gly Gln Val Lys Asp Phe Tyr Leu Tyr
        35                  40                  45

Pro Gly Lys Tyr Thr Phe Val Glu Thr Ala Ala Pro Asp Gly Tyr Glu
    50                  55                  60

Val Ala Thr Ala Ile Thr Phe Thr Val Asn Glu Gln Gly Gln Val Thr
65                  70                  75                  80
```

Val Asn Gly Lys Ala Thr Lys Gly
            85

<210> SEQ ID NO 62
<211> LENGTH: 155
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(155)
<223> OTHER INFORMATION: SpyTag-AP205

<400> SEQUENCE: 62

Met Ala His Ile Val Met Val Asp Ala Tyr Lys Pro Thr Lys Gly Ser
1               5                   10                  15

Gly Thr Ala Gly Gly Gly Ser Gly Ser Ala Asn Lys Pro Met Gln Pro
            20                  25                  30

Ile Thr Ser Thr Ala Asn Lys Ile Val Trp Ser Asp Pro Thr Arg Leu
        35                  40                  45

Ser Thr Thr Phe Ser Ala Ser Leu Leu Arg Gln Arg Val Lys Val Gly
    50                  55                  60

Ile Ala Glu Leu Asn Asn Val Ser Gly Gln Tyr Val Ser Val Tyr Lys
65                  70                  75                  80

Arg Pro Ala Pro Lys Pro Glu Gly Cys Ala Asp Ala Cys Val Ile Met
                85                  90                  95

Pro Asn Glu Asn Gln Ser Ile Arg Thr Val Ile Ser Gly Ser Ala Glu
            100                 105                 110

Asn Leu Ala Thr Leu Lys Ala Glu Trp Glu Thr His Lys Arg Asn Val
        115                 120                 125

Asp Thr Leu Phe Ala Ser Gly Asn Ala Gly Leu Gly Phe Leu Asp Pro
    130                 135                 140

Thr Ala Ala Ile Val Ser Ser Asp Thr Thr Ala
145                 150                 155

<210> SEQ ID NO 63
<211> LENGTH: 468
<212> TYPE: PRT
<213> ORGANISM: artificial sequence
<220> FEATURE:
<223> OTHER INFORMATION: DNA sequence encoding fusion protein
<220> FEATURE:
<221> NAME/KEY: MISC_FEATURE
<222> LOCATION: (1)..(468)
<223> OTHER INFORMATION: SyTag-AP205 DNA sequence

<400> SEQUENCE: 63

Ala Thr Gly Gly Cys Ala Cys Ala Thr Ala Thr Gly Thr Thr Ala
1               5                   10                  15

Thr Gly Gly Thr Gly Gly Ala Thr Gly Cys Ala Thr Ala Thr Ala Ala
            20                  25                  30

Ala Cys Cys Gly Ala Cys Cys Ala Ala Gly Gly Thr Ala Gly Cys
            35                  40                  45

Gly Gly Thr Ala Cys Ala Gly Cys Gly Gly Thr Gly Gly Thr Gly
    50                  55                  60

Gly Thr Ala Gly Thr Gly Gly Thr Ala Gly Cys Gly Cys Ala Ala
65                  70                  75                  80

Thr Ala Ala Ala Cys Cys Gly Ala Thr Gly Cys Ala Gly Cys Cys Gly
                85                  90                  95

```
Ala Thr Thr Ala Cys Cys Ala Gly Cys Ala Cys Cys Gly Cys Ala Ala
            100                 105                 110

Ala Cys Ala Ala Ala Ala Thr Thr Gly Thr Thr Thr Gly Gly Ala Gly
        115                 120                 125

Cys Gly Ala Thr Cys Cys Gly Ala Cys Cys Cys Gly Thr Cys Thr Gly
    130                 135                 140

Ala Gly Cys Ala Cys Cys Ala Cys Cys Thr Thr Thr Ala Gly Cys Gly
145                 150                 155                 160

Cys Ala Ala Gly Cys Cys Thr Gly Cys Thr Gly Cys Gly Thr Cys Ala
                165                 170                 175

Gly Cys Gly Thr Gly Thr Thr Ala Ala Ala Gly Thr Thr Gly Gly Thr
            180                 185                 190

Ala Thr Thr Gly Cys Ala Gly Ala Ala Cys Thr Gly Ala Ala Thr Ala
        195                 200                 205

Ala Thr Gly Thr Gly Ala Gly Cys Gly Gly Thr Cys Ala Gly Thr Ala
    210                 215                 220

Thr Gly Thr Thr Ala Gly Cys Gly Thr Gly Thr Ala Thr Ala Ala Ala
225                 230                 235                 240

Cys Gly Thr Cys Cys Gly Gly Cys Ala Cys Cys Gly Ala Ala Ala Cys
                245                 250                 255

Cys Gly Gly Ala Ala Gly Gly Thr Thr Gly Thr Gly Cys Ala Gly Ala
            260                 265                 270

Thr Gly Cys Ala Thr Gly Thr Gly Thr Thr Ala Thr Thr Ala Thr Gly
        275                 280                 285

Cys Cys Gly Ala Ala Thr Gly Ala Ala Ala Ala Thr Cys Ala Gly Ala
    290                 295                 300

Gly Cys Ala Thr Thr Cys Gly Thr Ala Cys Cys Gly Thr Thr Ala Thr
305                 310                 315                 320

Thr Ala Gly Cys Gly Gly Thr Ala Gly Cys Gly Cys Ala Gly Ala Ala
                325                 330                 335

Ala Ala Thr Cys Thr Gly Gly Cys Ala Ala Cys Cys Cys Thr Gly Ala
            340                 345                 350

Ala Ala Gly Cys Ala Gly Ala Ala Thr Gly Gly Gly Ala Ala Ala Cys
        355                 360                 365

Cys Cys Ala Thr Ala Ala Ala Cys Gly Thr Ala Ala Thr Gly Thr Gly
    370                 375                 380

Gly Ala Thr Ala Cys Cys Cys Thr Gly Thr Thr Thr Gly Cys Ala Ala
385                 390                 395                 400

Gly Cys Gly Gly Thr Ala Ala Thr Gly Cys Ala Gly Gly Thr Cys Thr
                405                 410                 415

Gly Gly Gly Thr Thr Thr Thr Cys Thr Gly Gly Ala Cys Cys Cys Gly
            420                 425                 430

Ala Cys Cys Gly Cys Ala Gly Cys Ala Ala Thr Thr Gly Thr Thr Ala
        435                 440                 445

Gly Cys Ala Gly Cys Gly Ala Thr Ala Cys Cys Ala Cys Cys Gly Cys
    450                 455                 460

Ala Thr Ala Ala
465
```

```
<210> SEQ ID NO 64
<211> LENGTH: 151
<212> TYPE: PRT
<213> ORGANISM: artificial sequence
<220> FEATURE:
<223> OTHER INFORMATION: Fusion protein
```

<220> FEATURE:
<221> NAME/KEY: MISC_FEATURE
<222> LOCATION: (1)..(151)
<223> OTHER INFORMATION: AP205-SpyTag fusion

<400> SEQUENCE: 64

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala Gly Thr Ala Gly Gly Ser Gly Ala His Ile Val Met Val
    130                 135                 140

Asp Ala Tyr Lys Pro Thr Lys
145                 150

<210> SEQ ID NO 65
<211> LENGTH: 456
<212> TYPE: DNA
<213> ORGANISM: artificial sequence
<220> FEATURE:
<223> OTHER INFORMATION: DNA sequence encoding fusion protein
<220> FEATURE:
<221> NAME/KEY: misc_feature
<222> LOCATION: (1)..(456)
<223> OTHER INFORMATION: AP205-SpyTag fusion

<400> SEQUENCE: 65
atggcaaata aaccgatgca gccgattacc agcaccgcaa acaaaattgt ttggagcgat      60
ccgacccgtc tgagcaccac ctttagcgca agcctgctgc gtcagcgtgt taaagttggt     120
attgcagaac tgaataatgt gagcggtcag tatgttagcg tgtataaacg tccggcaccg     180
aaaccggaag ttgtgcaga tgcatgtgtt attatgccga tgaaaatca gagcattcgt       240 accgttatta gcggtagcgc agaaaatctg gcaaccctga agcagaatg ggaaacccat      300 aaacgtaatg tggataccct gtttgcaagc ggtaatgcag gtctgggttt tctggacccg     360
accgcagcaa ttgttagcag cgataccacc gcaggtacag ccggtggtag cggtgcacat     420
attgttatgg ttgatgcata taaaccgacc aaataa                               456

<210> SEQ ID NO 66
<211> LENGTH: 154
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(154)
<223> OTHER INFORMATION: SpyTag-fr capsid protein fusion

<400> SEQUENCE: 66

Met Ala His Ile Val Met Val Asp Ala Tyr Lys Pro Thr Lys Gly Ser
1               5                   10                  15

Gly Thr Ala Gly Gly Gly Ser Gly Ser Ala Ser Asn Phe Glu Glu Phe
            20                  25                  30

Val Leu Val Asp Asn Gly Gly Thr Gly Asp Val Lys Val Ala Pro Ser
            35                  40                  45

Asn Phe Ala Asn Gly Val Ala Glu Trp Ile Ser Ser Asn Ser Arg Ser
        50                  55                  60

Gln Ala Tyr Lys Val Thr Cys Ser Val Arg Gln Ser Ser Ala Asn Asn
65                  70                  75                  80

Arg Lys Tyr Thr Val Lys Val Glu Val Pro Lys Val Ala Thr Gln Val
                85                  90                  95

Gln Gly Gly Val Glu Leu Pro Val Ala Ala Trp Arg Ser Tyr Met Asn
            100                 105                 110

Met Glu Leu Thr Ile Pro Val Phe Ala Thr Asn Asp Asp Cys Ala Leu
            115                 120                 125

Ile Val Lys Ala Leu Gln Gly Thr Phe Lys Thr Gly Asn Pro Ile Ala
    130                 135                 140

Thr Ala Ile Ala Ala Asn Ser Gly Ile Tyr
145                 150

<210> SEQ ID NO 67
<211> LENGTH: 465
<212> TYPE: DNA
<213> ORGANISM: Artificial sequence
<220> FEATURE:
<223> OTHER INFORMATION: DNA sequence encoding fusion protein
<220> FEATURE:
<221> NAME/KEY: misc_feature
<222> LOCATION: (1)..(465)
<223> OTHER INFORMATION: SpyTag-fr capsid protein fusion

<400> SEQUENCE: 67
atggcacata ttgttatggt ggatgcatat aaaccgacca aaggtagcgg tacagccggt      60
ggtggtagtg gtagcgcaag caattttgaa gaatttgtgc tggttgataa tggtggcacc     120
ggtgatgtta agttgcacc gagtaatttt gcaaatggtg ttgcagaatg gattagcagc      180
aatagccgta gccaggcata taaagttacc tgtagcgttc gtcagagcag cgcaaataat     240
cgtaaatata ccgttaaagt cgaggttccg aaagttgcaa cccaggttca gggtggtgtt     300
gaactgccgg ttgcagcatg gcgtagctat atgaatatgg aactgaccat tccggttttt     360
gccaccaatg atgattgtgc cctgattgtt aaagcactgc agggcacctt taaaaccggt     420
aatccgattg caaccgcaat tgcagcaaat agcggtatct attaa                     465

<210> SEQ ID NO 68
<211> LENGTH: 151
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(151)
<223> OTHER INFORMATION: KTag-AP205 fusion

<400> SEQUENCE: 68

Ala Thr His Ile Lys Phe Ser Lys Arg Asp Gly Ser Gly Thr Ala Gly
1               5                   10                  15

```
Gly Gly Ser Gly Ser Ala Asn Lys Pro Met Gln Pro Ile Thr Ser Thr
            20                  25                  30

Ala Asn Lys Ile Val Trp Ser Asp Pro Thr Arg Leu Ser Thr Thr Phe
         35                  40                  45

Ser Ala Ser Leu Leu Arg Gln Arg Val Lys Val Gly Ile Ala Glu Leu
     50                  55                  60

Asn Asn Val Ser Gly Gln Tyr Val Ser Val Tyr Lys Arg Pro Ala Pro
 65                  70                  75                  80

Lys Pro Glu Gly Cys Ala Asp Ala Cys Val Ile Met Pro Asn Glu Asn
             85                  90                  95

Gln Ser Ile Arg Thr Val Ile Ser Gly Ser Ala Glu Asn Leu Ala Thr
            100                 105                 110

Leu Lys Ala Glu Trp Glu Thr His Lys Arg Asn Val Asp Thr Leu Phe
        115                 120                 125

Ala Ser Gly Asn Ala Gly Leu Gly Phe Leu Asp Pro Thr Ala Ala Ile
        130                 135                 140

Val Ser Ser Asp Thr Thr Ala
145                 150

<210> SEQ ID NO 69
<211> LENGTH: 148
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(148)
<223> OTHER INFORMATION: AP205-KTag fusion

<400> SEQUENCE: 69

Met Ala Asn Lys Pro Met Gln Pro Ile Thr Ser Thr Ala Asn Lys Ile
 1               5                  10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
         35                  40                  45

Gly Gln Tyr Val Ser Val Tyr Lys Arg Pro Ala Pro Lys Pro Glu Gly
     50                  55                  60

Cys Ala Asp Ala Cys Val Ile Met Pro Asn Glu Asn Gln Ser Ile Arg
 65                  70                  75                  80

Thr Val Ile Ser Gly Ser Ala Glu Asn Leu Ala Thr Leu Lys Ala Glu
             85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala Gly Thr Ala Gly Gly Ser Gly Ala Thr His Ile Lys Phe
        130                 135                 140

Ser Lys Arg Asp
145

<210> SEQ ID NO 70
<211> LENGTH: 150
<212> TYPE: PRT
<213> ORGANISM: artificial sequence
<220> FEATURE:
<223> OTHER INFORMATION: Fusion protein
<220> FEATURE:
```

<221> NAME/KEY: MISC_FEATURE
<222> LOCATION: (1)..(150)
<223> OTHER INFORMATION: Ktag-fr capsid protein fusion

<400> SEQUENCE: 70

Ala Thr His Ile Lys Phe Ser Lys Arg Asp Gly Ser Gly Thr Ala Gly
1               5                   10                  15

Gly Gly Ser Gly Ser Ala Ser Asn Phe Glu Glu Phe Val Leu Val Asp
                20                  25                  30

Asn Gly Gly Thr Gly Asp Val Lys Val Ala Pro Ser Asn Phe Ala Asn
            35                  40                  45

Gly Val Ala Glu Trp Ile Ser Ser Asn Ser Arg Ser Gln Ala Tyr Lys
50                  55                  60

Val Thr Cys Ser Val Arg Gln Ser Ser Ala Asn Asn Arg Lys Tyr Thr
65                  70                  75                  80

Val Lys Val Glu Val Pro Lys Val Ala Thr Gln Val Gln Gly Gly Val
                85                  90                  95

Glu Leu Pro Val Ala Ala Trp Arg Ser Tyr Met Asn Met Glu Leu Thr
            100                 105                 110

Ile Pro Val Phe Ala Thr Asn Asp Asp Cys Ala Leu Ile Val Lys Ala
        115                 120                 125

Leu Gln Gly Thr Phe Lys Thr Gly Asn Pro Ile Ala Thr Ala Ile Ala
130                 135                 140

Ala Asn Ser Gly Ile Tyr
145                 150

<210> SEQ ID NO 71
<211> LENGTH: 175
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(175)
<223> OTHER INFORMATION: SpyTag-AP205-SpyTag fusion

<400> SEQUENCE: 71

Met Ala His Ile Val Met Val Asp Ala Tyr Lys Pro Thr Lys Gly Ser
1               5                   10                  15

Gly Thr Ala Gly Gly Ser Ser Ala Asn Lys Pro Met Gln Pro
                20                  25                  30

Ile Thr Ser Thr Ala Asn Lys Ile Val Trp Ser Asp Pro Thr Arg Leu
            35                  40                  45

Ser Thr Thr Phe Ser Ala Ser Leu Leu Arg Gln Arg Val Lys Val Gly
50                  55                  60

Ile Ala Glu Leu Asn Asn Val Ser Gly Gln Tyr Val Ser Val Tyr Lys
65                  70                  75                  80

Arg Pro Ala Pro Lys Pro Glu Gly Cys Ala Asp Ala Cys Val Ile Met
                85                  90                  95

Pro Asn Glu Asn Gln Ser Ile Arg Thr Val Ile Ser Gly Ser Ala Glu
            100                 105                 110

Asn Leu Ala Thr Leu Lys Ala Glu Trp Glu Thr His Lys Arg Asn Val
        115                 120                 125

Asp Thr Leu Phe Ala Ser Gly Asn Ala Gly Leu Gly Phe Leu Asp Pro
130                 135                 140

Thr Ala Ala Ile Val Ser Ser Asp Thr Thr Ala Gly Thr Ala Gly Gly
145                 150                 155                 160

Ser Gly Ala His Ile Val Met Val Asp Ala Tyr Lys Pro Thr Lys
            165                 170                 175

<210> SEQ ID NO 72
<211> LENGTH: 528
<212> TYPE: DNA
<213> ORGANISM: artificial sequence
<220> FEATURE:
<223> OTHER INFORMATION: DNA sequence encoding fusion protein
<220> FEATURE:
<221> NAME/KEY: misc_feature
<222> LOCATION: (1)..(528)
<223> OTHER INFORMATION: SpyTag-AP205-SpyTag

<400> SEQUENCE: 72
atggcacata ttgttatggt ggatgcatat aaaccgacca aaggtagcgg tacagccggt       60
ggtggtagtg gtagcgcaaa taaaccgatg cagccgatta ccagcaccgc aaacaaaatt      120
gtttggagcg atccgacccg tctgagcacc acctttagcg caagcctgct gcgtcagcgt      180
gttaaagttg gtattgcaga actgaataat gtgagcggtc agtatgttag cgtgtataaa      240
cgtccggcac cgaaaccgga aggttgtgca gatgcatgtg ttattatgcc gaatgaaaat      300
cagagcattc gtaccgttat agcggtagcg cagaaaatc tggcaaccct gaaagcagaa       360
tgggaaaccc ataaacgtaa tgtggatacc ctgtttgcaa gcggtaatgc aggtctgggt      420
tttctggacc cgaccgcagc aattgttagc agcgatacca ccgcaggtac agccggtggt      480
agcggtgcac atattgttat ggttgatgca tataaaccga ccaaataa                  528

<210> SEQ ID NO 73
<211> LENGTH: 765
<212> TYPE: DNA
<213> ORGANISM: artificial sequence
<220> FEATURE:
<223> OTHER INFORMATION: DNA sequence encoding fusion protein

<400> SEQUENCE: 73
atggcaaata aaccgatgca gccgattacc agcaccgcaa acaaaattgt ttggagcgat       60
ccgacccgtc tgagcaccac ctttagcgca agcctgctgc gtcagcgtgt aaagttggt      120 attgcagaac tgaataatgt gagcggtcag tatgttagcg tgtataaacg tccggcaccg      180
aaaccggaag ttgtgcaga tgcatgtgtt attatgccga tgaaaatca gagcattcgt        240 accgttatta gcggtagcgc agaaaatctg gcaaccctga aagcagaatg gaaacccat       300 aaacgtaatg tggatacct gtttgcaagc ggtaatgcag gtctgggttt tctggacccg       360
accgcagcaa ttgttagcag cgataccacc gcaggtacag ccggtggtag cggtggtgca      420
atggttgata ccctgagcgg tctgagcagc gaacagggtc agagcggtga tatgaccatt      480
gaagaagata gcgcaaccca catcaaattc agcaaacgtg atgaagatgg taagaactg       540 gcaggcgcaa caatggaact gcgtgatagc agcggtaaaa ccattagcac ctggattagt      600
gatggtcagg tgaaagattt ttatctgtac cctggcaaat acacctttgt tgaaaccgca      660
gcaccggatg gttatgaagt tgcaaccgca attacctta ccgttaatga acagggccag       720
gttaccgtga atggtaaagc aaccaaaggt gatgcacata tttaa                      765

<210> SEQ ID NO 74
<211> LENGTH: 254
<212> TYPE: PRT
<213> ORGANISM: artificial sequence
<220> FEATURE:
<223> OTHER INFORMATION: Fusion protein

<400> SEQUENCE: 74

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala Gly Thr Ala Gly Gly Ser Gly Gly Ala Met Val Asp Thr
130                 135                 140

Leu Ser Gly Leu Ser Ser Glu Gln Gly Gln Ser Gly Asp Met Thr Ile
145                 150                 155                 160

Glu Glu Asp Ser Ala Thr His Ile Lys Phe Ser Lys Arg Asp Glu Asp
                165                 170                 175

Gly Lys Glu Leu Ala Gly Ala Thr Met Glu Leu Arg Asp Ser Ser Gly
            180                 185                 190

Lys Thr Ile Ser Thr Trp Ile Ser Asp Gly Gln Val Lys Asp Phe Tyr
        195                 200                 205

Leu Tyr Pro Gly Lys Tyr Thr Phe Val Glu Thr Ala Ala Pro Asp Gly
    210                 215                 220

Tyr Glu Val Ala Thr Ala Ile Thr Phe Thr Val Asn Glu Gln Gly Gln
225                 230                 235                 240

Val Thr Val Asn Gly Lys Ala Thr Lys Gly Asp Ala His Ile
                245                 250

<210> SEQ ID NO 75
<211> LENGTH: 756
<212> TYPE: DNA
<213> ORGANISM: artificial sequence
<220> FEATURE:
<223> OTHER INFORMATION: DNA sequence encoding fusion protein
<220> FEATURE:
<221> NAME/KEY: misc_feature
<222> LOCATION: (1)..(756)
<223> OTHER INFORMATION: SpyCatcher-GGSGS-AP205

<400> SEQUENCE: 75
ggtgcaatgg ttgataccct gagcggtctg agcagcgaac agggtcagag cggtgatatg      60
accattgaag aagatagcgc aacccacatc aaattcagca acgtgatga agatggtaaa      120 gaactggcag cgcaacaat ggaactgcgt gatagcagcg gtaaaaccat tagcacctgg      180
attagtgatg gtcaggtgaa agatttttat ctgtaccctg gcaaatacac ctttgttgaa      240
accgcagcac cggatggtta tgaagttgca accgcaatta cctttaccgt taatgaacag      300
ggccaggtta ccgtgaatgg taaagcaacc aaaggtgatg cacatattgg tggtagcggt      360
agcgcaaata aaccgatgca gccgattacc agcaccgcaa acaaaattgt ttggagcgat      420

```
ccgacccgtc tgagcaccac ctttagcgca agcctgctgc gtcagcgtgt taaagttggt    480
attgcagaac tgaataatgt gagcggtcag tatgttagcg tgtataaacg tccggcaccg    540
aaaccggaag gttgtgcaga tgcatgtgtt attatgccga atgaaaatca gagcattcgt    600
accgttatta gcggtagcgc agaaaatctg gcaaccctga aagcagaatg gaaaccccat    660
aaacgtaatg tggatacact gtttgcaagc ggtaatgcag gtctgggttt tctggacccg    720
accgcagcaa ttgttagcag cgataccacc gcataa                              756
```

```
<210> SEQ ID NO 76
<211> LENGTH: 249
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(249)
<223> OTHER INFORMATION: SpyCatcher-ggsgs-AP205

<400> SEQUENCE: 76
```

Met Val Asp Thr Leu Ser Gly Leu Ser Ser Glu Gln Gly Gln Ser Gly
1               5                   10                  15

Asp Met Thr Ile Glu Glu Asp Ser Ala Thr His Ile Lys Phe Ser Lys
            20                  25                  30

Arg Asp Glu Asp Gly Lys Glu Leu Ala Gly Ala Thr Met Glu Leu Arg
        35                  40                  45

Asp Ser Ser Gly Lys Thr Ile Ser Thr Trp Ile Ser Asp Gly Gln Val
    50                  55                  60

Lys Asp Phe Tyr Leu Tyr Pro Gly Lys Tyr Thr Phe Val Glu Thr Ala
65                  70                  75                  80

Ala Pro Asp Gly Tyr Glu Val Ala Thr Ala Ile Thr Phe Thr Val Asn
                85                  90                  95

Glu Gln Gly Gln Val Thr Val Asn Gly Lys Ala Thr Lys Gly Asp Ala
            100                 105                 110

His Ile Gly Gly Ser Gly Ser Ala Asn Lys Pro Met Gln Pro Ile Thr
        115                 120                 125

Ser Thr Ala Asn Lys Ile Val Trp Ser Asp Pro Thr Arg Leu Ser Thr
    130                 135                 140

Thr Phe Ser Ala Ser Leu Leu Arg Gln Arg Val Lys Val Gly Ile Ala
145                 150                 155                 160

Glu Leu Asn Asn Val Ser Gly Gln Tyr Val Ser Val Tyr Lys Arg Pro
                165                 170                 175

Ala Pro Lys Pro Glu Gly Cys Ala Asp Ala Cys Val Ile Met Pro Asn
            180                 185                 190

Glu Asn Gln Ser Ile Arg Thr Val Ile Ser Gly Ser Ala Glu Asn Leu
        195                 200                 205

Ala Thr Leu Lys Ala Glu Trp Glu Thr His Lys Arg Asn Val Asp Thr
    210                 215                 220

Leu Phe Ala Ser Gly Asn Ala Gly Leu Gly Phe Leu Asp Pro Thr Ala
225                 230                 235                 240

Ala Ile Val Ser Ser Asp Thr Thr Ala
                245

```
<210> SEQ ID NO 77
<211> LENGTH: 753
<212> TYPE: DNA
<213> ORGANISM: artificial sequence
```

<220> FEATURE:
<223> OTHER INFORMATION: DNA sequence encoding fusion protein
<220> FEATURE:
<221> NAME/KEY: misc_feature
<222> LOCATION: (1)..(753)
<223> OTHER INFORMATION: SpyCatcher-ggsgs-Phage fr DNA

<400> SEQUENCE: 77

```
ggtgcaatgg ttgataccct gagcggtctg agcagcgaac agggtcagag cggtgatatg      60
accattgaag aagatagcgc aacccacatc aaattcagca acgtgatga agatggtaaa     120
gaactggcag gcgcaacaat ggaactgcgt gatagcagcg gtaaaaccat tagcacctgg     180
attagtgatg gtcaggtgaa agatttttat ctgtaccctg gcaaatacac ctttgttgaa     240
accgcagcac cggatggtta tgaagttgca accgcaatta cctttaccgt taatgaacag     300
ggccaggtta ccgtgaatgg taaagcaacc aaaggtgatg cacatattgg tggtagcggt     360
agcgcaagca ttttgaaga atttgtgctg gttgataatg gtggcaccgg tgatgttaaa     420
gttgcaccga gtaattttgc aaatggtgtt gcagaatgga ttagcagcaa tagccgtagc     480
caggcatata aagttacctg tagcgttcgt cagagcagcg caaataatcg taaatatacc     540
gttaaagtcg aggttccgaa agttgcaacc caggttcagg gtggtgttga actgccggtt     600
gcagcatggc gtagctatat gaatatggaa ctgaccattc cggttttgc caccaatgat     660
gattgtgccc tgattgttaa agcactgcag ggcacctta aaaccggtaa tccgattgca     720
accgcaattg cagcaaatag cggtatctat taa                                 753
```

<210> SEQ ID NO 78
<211> LENGTH: 248
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(248)
<223> OTHER INFORMATION: SpyCatcher-ggsgs-Phage fr

<400> SEQUENCE: 78

```
Met Val Asp Thr Leu Ser Gly Leu Ser Ser Glu Gln Gly Gln Ser Gly
1               5                   10                  15

Asp Met Thr Ile Glu Glu Asp Ser Ala Thr His Ile Lys Phe Ser Lys
            20                  25                  30

Arg Asp Glu Asp Gly Lys Glu Leu Ala Gly Ala Thr Met Glu Leu Arg
        35                  40                  45

Asp Ser Ser Gly Lys Thr Ile Ser Thr Trp Ile Ser Asp Gly Gln Val
    50                  55                  60

Lys Asp Phe Tyr Leu Tyr Pro Gly Lys Tyr Thr Phe Val Glu Thr Ala
65                  70                  75                  80

Ala Pro Asp Gly Tyr Glu Val Ala Thr Ala Ile Thr Phe Thr Val Asn
                85                  90                  95

Glu Gln Gly Gln Val Thr Val Asn Gly Lys Ala Thr Lys Gly Asp Ala
            100                 105                 110

His Ile Gly Gly Ser Gly Ser Ala Ser Asn Phe Glu Glu Phe Val Leu
        115                 120                 125

Val Asp Asn Gly Gly Thr Gly Asp Val Lys Val Ala Pro Ser Asn Phe
    130                 135                 140

Ala Asn Gly Val Ala Glu Trp Ile Ser Ser Asn Ser Arg Ser Gln Ala
145                 150                 155                 160
```

```
Tyr Lys Val Thr Cys Ser Val Arg Gln Ser Ala Asn Asn Arg Lys
            165                 170                 175

Tyr Thr Val Lys Val Glu Val Pro Lys Val Ala Thr Gln Val Gln Gly
            180                 185                 190

Gly Val Glu Leu Pro Val Ala Ala Trp Arg Ser Tyr Met Asn Met Glu
            195                 200                 205

Leu Thr Ile Pro Val Phe Ala Thr Asn Asp Asp Cys Ala Leu Ile Val
            210                 215                 220

Lys Ala Leu Gln Gly Thr Phe Lys Thr Gly Asn Pro Ile Ala Thr Ala
225                 230                 235                 240

Ile Ala Ala Asn Ser Gly Ile Tyr
            245

<210> SEQ ID NO 79
<211> LENGTH: 687
<212> TYPE: PRT
<213> ORGANISM: Homo sapiens

<400> SEQUENCE: 79

Met Ala His Ile Val Met Val Asp Ala Tyr Lys Pro Thr Lys Gly Gly
1               5                   10                  15

Ser Thr Gln Val Cys Thr Gly Thr Asp Met Lys Leu Arg Leu Pro Ala
            20                  25                  30

Ser Pro Glu Thr His Leu Asp Met Leu Arg His Leu Tyr Gln Gly Cys
        35                  40                  45

Gln Val Val Gln Gly Asn Leu Glu Leu Thr Tyr Leu Pro Thr Asn Ala
    50                  55                  60

Ser Leu Ser Phe Leu Gln Asp Ile Gln Glu Val Gln Gly Tyr Val Leu
65                  70                  75                  80

Ile Ala His Asn Gln Val Arg Gln Val Pro Leu Gln Arg Leu Arg Ile
                85                  90                  95

Val Arg Gly Thr Gln Leu Phe Glu Asp Asn Tyr Ala Leu Ala Val Leu
            100                 105                 110

Asp Asn Gly Asp Pro Leu Asn Asn Thr Thr Pro Val Thr Gly Ala Ser
        115                 120                 125

Pro Gly Gly Leu Arg Glu Leu Gln Leu Arg Ser Leu Thr Glu Ile Leu
    130                 135                 140

Lys Gly Gly Val Leu Ile Gln Arg Asn Pro Gln Leu Cys Tyr Gln Asp
145                 150                 155                 160

Thr Ile Leu Trp Lys Asp Ile Phe His Lys Asn Asn Gln Leu Ala Leu
                165                 170                 175

Thr Leu Ile Asp Thr Asn Arg Ser Arg Ala Cys His Pro Cys Ser Pro
            180                 185                 190

Met Cys Lys Gly Ser Arg Cys Trp Gly Glu Ser Ser Glu Asp Cys Gln
        195                 200                 205

Ser Leu Thr Arg Thr Val Cys Ala Gly Gly Cys Ala Arg Cys Lys Gly
    210                 215                 220

Pro Leu Pro Thr Asp Cys Cys His Glu Gln Cys Ala Ala Gly Cys Thr
225                 230                 235                 240

Gly Pro Lys His Ser Asp Cys Leu Ala Cys Leu His Phe Asn His Ser
                245                 250                 255

Gly Ile Cys Glu Leu His Cys Pro Ala Leu Val Thr Tyr Asn Thr Asp
            260                 265                 270

Thr Phe Glu Ser Met Pro Asn Pro Glu Gly Arg Tyr Thr Phe Gly Ala
        275                 280                 285
```

```
Ser Cys Val Thr Ala Cys Pro Tyr Asn Tyr Leu Ser Thr Asp Val Gly
    290                 295                 300

Ser Cys Thr Leu Val Cys Pro Leu His Asn Gln Glu Val Thr Ala Glu
305                 310                 315                 320

Asp Gly Thr Gln Arg Cys Glu Lys Cys Ser Lys Pro Cys Ala Arg Val
                325                 330                 335

Cys Tyr Gly Leu Gly Met Glu His Leu Arg Glu Val Arg Ala Val Thr
                340                 345                 350

Ser Ala Asn Ile Gln Glu Phe Ala Gly Cys Lys Lys Ile Phe Gly Ser
            355                 360                 365

Leu Ala Phe Leu Pro Glu Ser Phe Asp Gly Asp Pro Ala Ser Asn Thr
        370                 375                 380

Ala Pro Leu Gln Pro Glu Gln Leu Gln Val Phe Glu Thr Leu Glu Glu
385                 390                 395                 400

Ile Thr Gly Tyr Leu Tyr Ile Ser Ala Trp Pro Asp Ser Leu Pro Asp
                405                 410                 415

Leu Ser Val Phe Gln Asn Leu Gln Val Ile Arg Gly Arg Ile Leu His
                420                 425                 430

Asn Gly Ala Tyr Ser Leu Thr Leu Gln Gly Leu Gly Ile Ser Trp Leu
            435                 440                 445

Gly Leu Arg Ser Leu Arg Glu Leu Gly Ser Gly Leu Ala Leu Ile His
        450                 455                 460

His Asn Thr His Leu Cys Phe Val His Thr Val Pro Trp Asp Gln Leu
465                 470                 475                 480

Phe Arg Asn Pro His Gln Ala Leu Leu His Thr Ala Asn Arg Pro Glu
                485                 490                 495

Asp Glu Cys Val Gly Glu Gly Leu Ala Cys His Gln Leu Cys Ala Arg
                500                 505                 510

Gly His Cys Trp Gly Pro Gly Pro Thr Gln Cys Val Asn Cys Ser Gln
            515                 520                 525

Phe Leu Arg Gly Gln Glu Cys Val Glu Glu Cys Arg Val Leu Gln Gly
        530                 535                 540

Leu Pro Arg Glu Tyr Val Asn Ala Arg His Cys Leu Pro Cys His Pro
545                 550                 555                 560

Glu Cys Gln Pro Gln Asn Gly Ser Val Thr Cys Phe Gly Pro Glu Ala
                565                 570                 575

Asp Gln Cys Val Ala Cys Ala His Tyr Lys Asp Pro Pro Phe Cys Val
                580                 585                 590

Ala Arg Cys Pro Ser Gly Val Lys Pro Asp Leu Ser Tyr Met Pro Ile
            595                 600                 605

Trp Lys Phe Pro Asp Glu Glu Gly Ala Cys Gln Pro Cys Pro Ile Asn
        610                 615                 620

Cys Thr His Ser Cys Val Asp Leu Asp Asp Lys Gly Cys Pro Ala Glu
625                 630                 635                 640

Gln Arg Ala Ser Pro Leu Thr Ser Ile Ile Ser Ala Val Val Gly Ile
                645                 650                 655

Leu Leu Val Val Val Leu Gly Val Val Phe Gly Ile Leu Ile Lys Arg
                660                 665                 670

Arg Gln Gln Lys Ile Arg Lys Tyr Thr His His His His His His
        675                 680                 685

<210> SEQ ID NO 80
<211> LENGTH: 136
```

-continued

```
<212> TYPE: PRT
<213> ORGANISM: Homo sapiens

<400> SEQUENCE: 80

Met Ala His Ile Val Met Val Asp Ala Tyr Lys Pro Thr Lys Gly Gly
1               5                   10                  15

Ser Ile Pro Thr Glu Ile Pro Thr Ser Ala Leu Val Lys Glu Thr Leu
            20                  25                  30

Ala Leu Leu Ser Thr His Arg Thr Leu Leu Ile Ala Asn Glu Thr Leu
        35                  40                  45

Arg Ile Pro Val Pro Val His Lys Asn His Gln Leu Thr Thr Glu Glu
    50                  55                  60

Ile Phe Gln Gly Ile Gly Thr Leu Glu Ser Gln Thr Val Gln Gly Gly
65                  70                  75                  80

Thr Val Glu Arg Leu Phe Lys Asn Leu Ser Leu Ile Lys Lys Tyr Ile
                85                  90                  95

Asp Gly Gln Lys Lys Lys Thr Gly Glu Glu Arg Arg Arg Val Asn Gln
            100                 105                 110

Phe Leu Asp Tyr Leu Gln Glu Phe Leu Gly Val Met Asn Thr Glu Trp
        115                 120                 125

Ile Ile Glu Ser Ser Gly Arg Lys
    130                 135

<210> SEQ ID NO 81
<211> LENGTH: 678
<212> TYPE: PRT
<213> ORGANISM: Homo sapiens

<400> SEQUENCE: 81

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205
```

```
Ala Gly Val Ala Lys Gly Ala Ser Met Arg Ser Leu Arg Val Leu Asn
210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                245                 250                 255
Leu Pro Leu Ala Gly Gly Tyr Ser Arg Val Leu Asn Ala Ala Cys Gln
            260                 265                 270
Arg Leu Ala Arg Ala Gly Val Leu Val Thr Ala Ala Gly Asn Phe
        275                 280                 285
Arg Asp Asp Ala Cys Leu Tyr Ser Pro Ala Ser Ala Pro Glu Val Ile
290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
            340                 345                 350
Ser Gly Thr Ser Gln Ala Ala His Val Ala Gly Ile Ala Ala Met
        355                 360                 365
Met Leu Ser Ala Glu Pro Glu Leu Thr Leu Ala Glu Leu Arg Gln Arg
370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
                405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Val Ala Arg Cys Ala
        435                 440                 445
Pro Asp Glu Glu Leu Leu Ser Cys Ser Ser Phe Ser Arg Ser Gly Lys
450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
            500                 505                 510
Glu Ala Ser Met Gly Thr Arg Val His Cys His Gln Gln Gly His Val
        515                 520                 525
Leu Thr Gly Cys Ser Ser His Trp Glu Val Glu Asp Leu Gly Thr His
530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys His Ala Pro Gly Leu
                565                 570                 575
Glu Cys Lys Val Lys Glu His Gly Ile Pro Ala Pro Gln Glu Gln Val
            580                 585                 590
Thr Val Ala Cys Glu Glu Gly Trp Thr Leu Thr Gly Cys Ser Ala Leu
        595                 600                 605
Pro Gly Thr Ser His Val Leu Gly Ala Tyr Ala Val Asp Asn Thr Cys
610                 615                 620
Val Val Arg Ser Arg Asp Val Ser Thr Thr Gly Ser Thr Ser Glu Gly
```

```
                625                 630                 635                 640
        Ala Val Thr Ala Val Ala Ile Cys Cys Arg Ser Arg His Leu Ala Gln
                            645                 650                 655
        Ala Ser Gln Glu Leu Gln Gly Gly Ser Ala His Ile Val Met Val Asp
                            660                 665                 670
        Ala Tyr Lys Pro Thr Lys
                    675

<210> SEQ ID NO 82
<211> LENGTH: 662
<212> TYPE: PRT
<213> ORGANISM: Plasmodium falciparum

<400> SEQUENCE: 82

Ala His Ile Val Met Val Asp Ala Tyr Lys Pro Thr Lys Gly Gly Ser
 1               5                  10                  15

Asn Tyr Ile Lys Gly Asp Pro Tyr Phe Ala Glu Tyr Ala Thr Lys Leu
             20                  25                  30

Ser Phe Ile Leu Asn Pro Ser Asp Ala Asn Asn Pro Ser Gly Glu Thr
         35                  40                  45

Ala Asn His Asn Asp Glu Ala Cys Asn Cys Asn Glu Ser Gly Ile Ser
     50                  55                  60

Ser Val Gly Gln Ala Gln Thr Ser Gly Pro Ser Ser Asn Lys Thr Cys
65                  70                  75                  80

Ile Thr His Ser Ser Ile Lys Thr Asn Lys Lys Glu Cys Lys Asp
                 85                  90                  95

Val Lys Leu Gly Val Arg Glu Asn Asp Lys Asp Leu Lys Ile Cys Val
            100                 105                 110

Ile Glu Asp Thr Ser Leu Ser Gly Val Asp Asn Cys Cys Cys Gln Asp
        115                 120                 125

Leu Leu Gly Ile Leu Gln Glu Asn Cys Ser Asp Asn Lys Arg Gly Ser
    130                 135                 140

Ser Ser Asn Asp Ser Cys Asp Asn Lys Asn Gln Asp Glu Cys Gln Lys
145                 150                 155                 160

Lys Leu Glu Lys Val Phe Ala Ser Leu Thr Asn Gly Tyr Lys Cys Asp
                165                 170                 175

Lys Cys Lys Ser Gly Thr Ser Arg Ser Lys Lys Lys Trp Ile Trp Lys
            180                 185                 190

Lys Ser Ser Gly Asn Glu Glu Gly Leu Gln Glu Glu Tyr Ala Asn Thr
        195                 200                 205

Ile Gly Leu Pro Pro Arg Thr Gln Ser Leu Tyr Leu Gly Asn Leu Pro
    210                 215                 220

Lys Leu Glu Asn Val Cys Glu Asp Val Lys Asp Ile Asn Phe Asp Thr
225                 230                 235                 240

Lys Glu Lys Phe Leu Ala Gly Cys Leu Ile Val Ser Phe His Glu Gly
                245                 250                 255

Lys Asn Leu Lys Lys Arg Tyr Pro Gln Asn Lys Asn Ser Gly Asn Lys
            260                 265                 270

Glu Asn Leu Cys Lys Ala Leu Glu Tyr Ser Phe Ala Asp Tyr Gly Asp
        275                 280                 285

Leu Ile Lys Gly Thr Ser Ile Trp Asp Asn Glu Tyr Thr Lys Asp Leu
    290                 295                 300

Glu Leu Asn Leu Gln Asn Asn Phe Gly Lys Leu Phe Gly Lys Tyr Ile
305                 310                 315                 320
```

```
Lys Lys Asn Asn Thr Ala Glu Gln Asp Thr Ser Tyr Ser Ser Leu Asp
            325                 330                 335

Glu Leu Arg Glu Ser Trp Trp Asn Thr Asn Lys Lys Tyr Ile Trp Thr
        340                 345                 350

Ala Met Lys His Gly Ala Glu Met Asn Ile Thr Thr Cys Asn Ala Asp
    355                 360                 365

Gly Ser Val Thr Gly Ser Gly Ser Ser Cys Asp Ile Pro Thr Ile
370                 375                 380

Asp Leu Ile Pro Gln Tyr Leu Arg Phe Leu Gln Glu Trp Val Glu Asn
385                 390                 395                 400

Phe Cys Glu Gln Arg Gln Ala Lys Val Lys Asp Val Ile Thr Asn Cys
            405                 410                 415

Lys Ser Cys Lys Glu Ser Gly Asn Lys Cys Lys Thr Glu Cys Lys Thr
            420                 425                 430

Lys Cys Lys Asp Glu Cys Glu Lys Tyr Lys Lys Phe Ile Glu Ala Cys
            435                 440                 445

Gly Thr Ala Gly Gly Ile Gly Thr Ala Gly Ser Pro Trp Ser Lys
    450                 455                 460

Arg Trp Asp Gln Ile Tyr Lys Arg Tyr Ser Lys His Ile Glu Asp Ala
465                 470                 475                 480

Lys Arg Asn Arg Lys Ala Gly Thr Lys Asn Cys Gly Thr Ser Ser Thr
            485                 490                 495

Thr Asn Ala Ala Ala Ser Thr Asp Glu Asn Lys Cys Val Gln Ser Asp
            500                 505                 510

Ile Asp Ser Phe Phe Lys His Leu Ile Asp Ile Gly Leu Thr Thr Pro
            515                 520                 525

Ser Ser Tyr Leu Ser Asn Val Leu Asp Asp Asn Ile Cys Gly Ala Asp
            530                 535                 540

Lys Ala Pro Trp Thr Thr Tyr Thr Thr Tyr Thr Thr Thr Glu Lys Cys
545                 550                 555                 560

Asn Lys Glu Arg Asp Lys Ser Lys Ser Gln Ser Ser Asp Thr Leu Val
            565                 570                 575

Val Val Asn Val Pro Ser Pro Leu Gly Asn Thr Pro Tyr Arg Tyr Lys
            580                 585                 590

Tyr Ala Cys Gln Cys Lys Ile Pro Thr Asn Glu Glu Thr Cys Asp Asp
            595                 600                 605

Arg Lys Glu Tyr Met Asn Gln Trp Ser Cys Gly Ser Ala Arg Thr Met
            610                 615                 620

Lys Arg Gly Tyr Lys Asn Asp Asn Tyr Glu Leu Cys Lys Tyr Asn Gly
625                 630                 635                 640

Val Asp Val Lys Pro Thr Thr Val Arg Ser Asn Ser Ser Lys Leu Asp
            645                 650                 655

His His His His His His
            660

<210> SEQ ID NO 83
<211> LENGTH: 5
<212> TYPE: PRT
<213> ORGANISM: artificial sequence
<220> FEATURE:
<223> OTHER INFORMATION: Examplary linker sequence
<220> FEATURE:
<221> NAME/KEY: MISC_FEATURE
<222> LOCATION: (1)..(5)
<223> OTHER INFORMATION: Example of a linker

<400> SEQUENCE: 83
```

Gly Gly Ser Gly Ser
1               5

<210> SEQ ID NO 84
<211> LENGTH: 414
<212> TYPE: PRT
<213> ORGANISM: Mycobacterium tuberculosis

<400> SEQUENCE: 84

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
                20                  25                  30

Ser Lys Arg Asp Glu Asp Gly Lys Glu Leu Ala Gly Ala Thr Met Glu
            35                  40                  45

Leu Arg Asp Ser Ser Gly Lys Thr Ile Ser Thr Trp Ile Ser Asp Gly
        50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile Gly Gly Ser Phe Ser Arg Pro Gly Leu Pro Val Glu
        115                 120                 125

Tyr Leu Gln Val Pro Ser Pro Ser Met Gly Arg Asp Ile Lys Val Gln
130                 135                 140

Phe Gln Ser Gly Gly Ala Asn Ser Pro Ala Leu Tyr Leu Leu Asp Gly
145                 150                 155                 160

Leu Arg Ala Gln Asp Asp Phe Ser Gly Trp Asp Ile Asn Thr Pro Ala
                165                 170                 175

Phe Glu Trp Tyr Asp Gln Ser Gly Leu Ser Val Val Met Pro Val Gly
            180                 185                 190

Gly Gln Ser Ser Phe Tyr Ser Asp Trp Tyr Gln Pro Ala Cys Gly Lys
        195                 200                 205

Ala Gly Cys Gln Thr Tyr Lys Trp Glu Thr Phe Leu Thr Ser Glu Leu
    210                 215                 220

Pro Gly Trp Leu Gln Ala Asn Arg His Val Lys Pro Thr Gly Ser Ala
225                 230                 235                 240

Val Val Gly Leu Ser Met Ala Ala Ser Ser Ala Leu Thr Leu Ala Ile
                245                 250                 255

Tyr His Pro Gln Gln Phe Val Tyr Ala Gly Ala Met Ser Gly Leu Leu
            260                 265                 270

Asp Pro Ser Gln Ala Met Gly Pro Thr Leu Ile Gly Leu Ala Met Gly
        275                 280                 285

Asp Ala Gly Gly Tyr Lys Ala Ser Asp Met Trp Gly Pro Lys Glu Asp
    290                 295                 300

Pro Ala Trp Gln Arg Asn Asp Pro Leu Leu Asn Val Gly Lys Leu Ile
305                 310                 315                 320

Ala Asn Asn Thr Arg Val Trp Val Tyr Cys Gly Asn Gly Lys Leu Ser
                325                 330                 335

Asp Leu Gly Gly Asn Asn Leu Pro Ala Lys Phe Leu Glu Gly Phe Val
            340                 345                 350

Arg Thr Ser Asn Ile Lys Phe Gln Asp Ala Tyr Asn Ala Gly Gly Gly

```
            355                 360                 365
His Asn Gly Val Phe Asp Phe Pro Asp Ser Gly Thr His Ser Trp Glu
    370                 375                 380

Tyr Trp Gly Ala Gln Leu Asn Ala Met Lys Pro Asp Leu Gln Arg Ala
385                 390                 395                 400

Leu Gly Ala Thr Pro Asn Thr Gly Pro Ala Pro Gln Gly Ala
                405                 410
```

<210> SEQ ID NO 85
<211> LENGTH: 1245
<212> TYPE: DNA
<213> ORGANISM: Mycobacterium tuberculosis

<400> SEQUENCE: 85

```
ggtgcaatgg ttgataccct gagcggtctg agcagcgaac agggtcagag cggtgatatg     60
accattgaag aagatagcgc aacccacatc aaattcagca acgtgatga agatggtaaa     120
gaactggcag cgcaacaat ggaactgcgt gatagcagcg gtaaaaccat tagcacctgg     180
attagtgatg gtcaggtgaa agatttttat ctgtaccctg gcaaatacac ctttgttgaa    240
accgcagcac cggatggtta tgaagttgca accgcaatta cctttaccgt taatgaacag    300
ggccaggtta ccgtgaatgg taaagcaacc aaaggtgatg cacatattgg tggtagcttc    360
tcccgtcccg gactgcctgt ggaataccte caggtgccct ccccctctat gggtcgtgac    420
atcaaggtgc agttccagtc cggtggtgct aactccccg ctctgtacct gctggacgga    480
ctgcgtgctc aggacgactt ctccggctgg gacatcaaca ctcccgcttt cgagtggtac    540
gaccagtccg gcctgtccgt ggttatgcct gtgggtggcc agtcctcctt ctactccgac    600
tggtaccaac ccgcttgcgg caaggctggc tgccagacct acaagtggga gacttcctg    660
acctccgagc tgcccggatg gctgcaggct aaccgtcacg tgaagcccac cggttccgct    720
gtcgtgggcc tgtctatggc tgcttcctcc gctctgaccc tggctatcta ccacccccag    780
cagttcgtgt acgctggcgc tatgtccgga ctgctggacc cctctcaggc tatgggtcct    840
accctgatcg gcctggctat gggcgacgct ggtggttaca aggcttccga catgtggggt    900
cccaaggaag atcccgcttg cagcgtaac gaccccctgc tgaacgtggg caagctgatc    960
gctaacaaca cccgtgtgtg ggtgtactgc ggcaacggca agctgtccga cctgggtggc   1020
aacaacctgc cgctaagtt cctcgagggt ttcgtgcgca cctccaacat caagttccag   1080
gacgcttaca acgctggcgg tggtcacaac ggcgtgttcg acttccccga ctccggaacc   1140
cactcctggg agtactgggg tgctcagctg aacgctatga gcccgaccct gcagcgtgct   1200
ctgggtgcta cccctaacac cggtccagct cctcagggtg cttaa                   1245
```

<210> SEQ ID NO 86
<211> LENGTH: 258
<212> TYPE: PRT
<213> ORGANISM: Homo sapiens

<400> SEQUENCE: 86

```
Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
                20                  25                  30

Ser Lys Arg Asp Glu Asp Gly Lys Glu Leu Ala Gly Ala Thr Met Glu
            35                  40                  45

Leu Arg Asp Ser Ser Gly Lys Thr Ile Ser Thr Trp Ile Ser Asp Gly
```

```
                50                  55                  60
Gln Val Lys Asp Phe Tyr Leu Tyr Pro Gly Lys Tyr Thr Phe Val Glu
 65                  70                  75                  80

Thr Ala Ala Pro Asp Gly Tyr Glu Val Ala Thr Ala Ile Thr Phe Thr
                 85                  90                  95

Val Asn Glu Gln Gly Gln Val Thr Val Asn Gly Lys Ala Thr Lys Gly
                100                 105                 110

Asp Ala His Ile Gly Gly Ser Gly Ala Pro Ala Leu Pro Gln Ile Trp
            115                 120                 125

Gln Leu Tyr Leu Lys Asn Tyr Arg Ile Ala Thr Phe Lys Asn Trp Pro
        130                 135                 140

Phe Leu Glu Asp Cys Ala Cys Thr Pro Glu Arg Met Ala Glu Ala Gly
145                 150                 155                 160

Phe Ile His Cys Pro Thr Glu Asn Glu Pro Asp Leu Ala Gln Cys Phe
                165                 170                 175

Phe Cys Phe Lys Glu Leu Glu Gly Trp Glu Pro Asp Asp Asn Pro Ile
            180                 185                 190

Glu Glu His Arg Lys His Ser Pro Gly Cys Ala Phe Leu Thr Val Lys
        195                 200                 205

Lys Gln Met Glu Glu Leu Thr Val Ser Glu Phe Leu Lys Leu Asp Arg
    210                 215                 220

Gln Arg Ala Lys Asn Lys Ile Ala Lys Glu Thr Asn Asn Lys Gln Lys
225                 230                 235                 240

Glu Phe Glu Glu Thr Ala Lys Thr Thr Arg Gln Ser Ile Glu Gln Leu
                245                 250                 255

Ala Ala

<210> SEQ ID NO 87
<211> LENGTH: 777
<212> TYPE: DNA
<213> ORGANISM: Homo sapiens

<400> SEQUENCE: 87
ggtgcaatgg ttgatacccc gagcggtctg agcagcgaac agggtcagag cggtgatatg    60
accattgaag aagatagcgc aacccacatc aaattcagca acgtgatga agatggtaaa   120 gaactggcag cgcaacaat ggaactgcgt gatagcagcg gtaaaaccat agcaccctgg   180
attagtgatg gtcaggtgaa agatttttat ctgtaccctg gcaaatacac ctttgttgaa   240
accgcagcac cggatggtta tgaagttgca accgcaatta cctttaccgt taatgaacag   300
ggccaggtta ccgtgaatgg taaagcaacc aaaggtgatg cacatattgg tggtagcggt   360
gcaccggcac tgccgcagat ttggcagctg tatctgaaaa actatcgtat cgccaccttt   420
aaaaactggc cgtttctgga agattgtgca tgtacaccgg aacgtatggc agaagcaggt   480
tttattcatt gtccgaccga aaatgaaccg gatctggcac agtgttttt ttgctttaaa   540 gaactggaag ttgggagcc ggatgataat ccgattgaag aacatcgtaa acatagtccg   600
ggttgtgcat ttctgaccgt gaaaaaacaa atggaagaac tgaccgttag cgagtttctg   660
aaactggatc gtcagcgtgc caaaaacaaa attgcaaaag aaaccaataa caaacagaaa   720
gaattcgaag aaaccgccaa aaccacccgt cagagcattg aacagctggc agcataa      777

<210> SEQ ID NO 88
<211> LENGTH: 280
<212> TYPE: PRT
<213> ORGANISM: influenza virus
```

<400> SEQUENCE: 88

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
130                 135                 140

Ile Gly Cys Glu Tyr Asn Lys Ser Glu Arg Cys Met Lys Gln Ile Glu
145                 150                 155                 160

Asp Lys Ile Glu Glu Ile Glu Ser Lys Ile Trp Thr Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly Ala His Ile Val Met
            260                 265                 270

Val Asp Ala Tyr Lys Pro Thr Lys
        275                 280

<210> SEQ ID NO 89
<211> LENGTH: 840
<212> TYPE: DNA
<213> ORGANISM: influenza virus

<400> SEQUENCE: 89
atgaaagtga agctgctggt gctgctgtgc accttcaccg ccacctacgc cgacaccatc      60
tgcatcggct accacgccaa caacagcacc gacaccgtgg ataccgtgct ggaaaagaac     120
gtgaccgtga cccacagcgt gaacctgctg gaaaatggcg gcggaggcaa atacgtgtgc     180
agcgccaagc tgcggatggt caccggcctg agaaacaagc ccagcaagca gagccagggc     240
ctgttcggag ccattgccgg ctttacagag ggcggctgga ccggcatggt ggatgggtgg     300
tacggctatc accaccagaa cgagcagggc agcggctacg ccgccgatca gaagtctacc     360
cagaacgcca tcaacggcat caccaacaaa gtgaacagcg tgatcgagaa gatgaacacc     420

```
cagtacaccg ccatcggctg cgagtacaac aagagcgagc ggtgcatgaa gcagatcgag     480
gacaagatcg aagagatcga gtctaagatc tggacctaca acgccgaact gctggtgctg     540
ctggaaaacg agcggaccct ggacttccac gacagcaacg tgaagaacct gtacgagaaa     600
gtgaaaagcc agctgaagaa caacgccaaa gagatcggca acggctgctt cgagttctac     660
cacaagtgca cgacgagtg catggaaagc gtgaagaatg cacctacga ctaccccaag       720 tacagcgagg aaagcaagct gaaccgcgag aagatcgacg gcgtgaagct ggaatctatg     780
ggcgtgtacc agattgaggg cgcccacatc gtgatggtgg acgcctacaa gcctaccaag     840
```

<210> SEQ ID NO 90
<211> LENGTH: 477
<212> TYPE: PRT
<213> ORGANISM: Infectious hematopoietic necrosis virus

<400> SEQUENCE: 90

```
Met Asp Thr Met Ile Thr Thr Pro Leu Ile Leu Ile Thr Cys
 1               5                  10                  15

Gly Ala Asn Ser Gln Thr Val Gln Pro Asp Thr Ala Ser Glu Ser Asp
             20                  25                  30

Gln Pro Thr Trp Ser Asn Pro Leu Phe Thr Tyr Pro Glu Gly Cys Thr
         35                  40                  45

Leu Asp Lys Leu Ser Lys Val Asn Ala Ser Gln Leu Arg Cys Pro Arg
     50                  55                  60

Ile Phe Asn Asp Glu Asn Arg Gly Leu Ile Ala Tyr Pro Thr Ser Ile
 65                  70                  75                  80

Arg Ser Leu Ser Val Gly Asn Asp Leu Gly Asn Ile His Thr Gln Gly
                 85                  90                  95

Asn Tyr Ile His Lys Val Leu Tyr Arg Thr Ile Cys Ser Thr Gly Phe
            100                 105                 110

Phe Gly Gly Gln Thr Ile Glu Lys Ala Leu Val Glu Met Lys Leu Ser
        115                 120                 125

Thr Arg Glu Ala Gly Val Tyr Asp Thr Thr Thr Ala Ala Ala Leu Tyr
    130                 135                 140

Phe Pro Ala Pro Arg Cys Gln Trp Tyr Thr Asp Asn Val Gln Asn Asp
145                 150                 155                 160

Leu Ile Phe Tyr Tyr Thr Thr Gln Lys Ser Val Leu Arg Asp Pro Tyr
                165                 170                 175

Thr Arg Asp Phe Leu Asp Ser Asp Phe Ile Gly Gly Lys Cys Thr Lys
            180                 185                 190

Ser Pro Cys Gln Thr His Trp Ser Asn Val Val Trp Met Gly Asp Ala
        195                 200                 205

Gly Ile Pro Ala Cys Asp Ser Ser Gln Glu Ile Lys Gly His Leu Phe
    210                 215                 220

Val Asp Lys Ile Ser Asn Arg Val Val Lys Ala Thr Ser Tyr Gly His
225                 230                 235                 240

His Pro Trp Gly Leu His Ala Cys Met Ile Asp Phe Cys Gly Lys
                245                 250                 255

Pro Trp Ile Arg Thr Asp Leu Gly Asp Leu Ile Ser Val Glu Tyr Asn
            260                 265                 270

Ser Gly Ala Lys Thr Leu Ser Phe Pro Lys Cys Glu Asp Lys Thr Val
        275                 280                 285

Gly Met Arg Gly Asn Leu Asp Asp Phe Ala Tyr Leu Asp Asp Leu Val
    290                 295                 300
```

```
Lys Ala Ser Glu Ser Arg Glu Glu Cys Leu Glu Ala His Ala Glu Ile
305                 310                 315                 320

Ile Ser Thr Asn Ser Val Thr Pro Tyr Leu Leu Ser Lys Phe Arg Ser
                325                 330                 335

Pro His Pro Gly Ile Asn Asp Val Tyr Ala Met His Lys Gly Ser Ile
            340                 345                 350

Tyr His Gly Met Cys Met Thr Val Ala Val Asp Glu Val Ser Lys Asp
        355                 360                 365

Arg Thr Thr Tyr Arg Ala His Arg Ala Thr Ser Phe Thr Lys Trp Glu
    370                 375                 380

Arg Pro Phe Gly Asp Glu Trp Glu Gly Phe His Gly Leu His Gly Asn
385                 390                 395                 400

Asn Thr Thr Ile Ile Pro Asp Leu Glu Lys Tyr Val Ala Gln Tyr Lys
                405                 410                 415

Thr Ser Met Met Glu Pro Met Ser Ile Lys Ser Val Pro His Pro Ser
            420                 425                 430

Ile Leu Ala His Tyr Asn Glu Thr Asp Val Ser Gly Ile Ser Ile Arg
        435                 440                 445

Lys Leu Asp Ser Phe Asp Leu Gln Ser Leu His Trp Ser Gly Ser Gly
450                 455                 460

Ala His Ile Val Met Val Asp Ala Tyr Lys Pro Thr Lys
465                 470                 475

<210> SEQ ID NO 91
<211> LENGTH: 476
<212> TYPE: PRT
<213> ORGANISM: Infectious hematopoietic necrosis virus

<400> SEQUENCE: 91

Ala His Ile Val Met Val Asp Ala Tyr Lys Pro Thr Lys Gly Gly Ser
1               5                   10                  15

Asp Thr Met Ile Thr Thr Pro Leu Ile Leu Ile Leu Thr Cys Gly
                20                  25                  30

Ala Asn Ser Gln Thr Val Gln Pro Asp Thr Ala Ser Glu Ser Asp Gln
            35                  40                  45

Pro Thr Trp Ser Asn Pro Leu Phe Thr Tyr Pro Glu Gly Cys Thr Leu
    50                  55                  60

Asp Lys Leu Ser Lys Val Asn Ala Ser Gln Leu Arg Cys Pro Arg Ile
65                  70                  75                  80

Phe Asn Asp Glu Asn Arg Gly Leu Ile Ala Tyr Pro Thr Ser Ile Arg
                85                  90                  95

Ser Leu Ser Val Gly Asn Asp Leu Gly Asn Ile His Thr Gln Gly Asn
            100                 105                 110

Tyr Ile His Lys Val Leu Tyr Arg Thr Ile Cys Ser Thr Gly Phe Phe
        115                 120                 125

Gly Gly Gln Thr Ile Glu Lys Ala Leu Val Glu Met Lys Leu Ser Thr
    130                 135                 140

Arg Glu Ala Gly Val Tyr Asp Thr Thr Thr Ala Ala Ala Leu Tyr Phe
145                 150                 155                 160

Pro Ala Pro Arg Cys Gln Trp Tyr Thr Asp Asn Val Gln Asn Asp Leu
                165                 170                 175

Ile Phe Tyr Tyr Thr Thr Gln Lys Ser Val Leu Arg Asp Pro Tyr Thr
            180                 185                 190

Arg Asp Phe Leu Asp Ser Asp Phe Ile Gly Gly Lys Cys Thr Lys Ser
        195                 200                 205
```

Pro Cys Gln Thr His Trp Ser Asn Val Val Trp Met Gly Asp Ala Gly
    210                 215                 220

Ile Pro Ala Cys Asp Ser Ser Gln Glu Ile Lys Gly His Leu Phe Val
225                 230                 235                 240

Asp Lys Ile Ser Asn Arg Val Val Lys Ala Thr Ser Tyr Gly His His
                245                 250                 255

Pro Trp Gly Leu His His Ala Cys Met Ile Asp Phe Cys Gly Lys Pro
            260                 265                 270

Trp Ile Arg Thr Asp Leu Gly Asp Leu Ile Ser Val Glu Tyr Asn Ser
        275                 280                 285

Gly Ala Lys Thr Leu Ser Phe Pro Lys Cys Asp Lys Thr Val Gly
290                 295                 300

Met Arg Gly Asn Leu Asp Asp Phe Ala Tyr Leu Asp Leu Val Lys
305                 310                 315                 320

Ala Ser Glu Ser Arg Glu Glu Cys Leu Glu Ala His Ala Glu Ile Ile
                325                 330                 335

Ser Thr Asn Ser Val Thr Pro Tyr Leu Leu Ser Lys Phe Arg Ser Pro
                340                 345                 350

His Pro Gly Ile Asn Asp Val Tyr Ala Met His Lys Gly Ser Ile Tyr
            355                 360                 365

His Gly Met Cys Met Thr Val Ala Val Asp Glu Val Ser Lys Asp Arg
    370                 375                 380

Thr Thr Tyr Arg Ala His Arg Ala Thr Ser Phe Thr Lys Trp Glu Arg
385                 390                 395                 400

Pro Phe Gly Asp Glu Trp Glu Gly Phe His Gly Leu His Gly Asn Asn
                405                 410                 415

Thr Thr Ile Ile Pro Asp Leu Glu Lys Tyr Val Ala Gln Tyr Lys Thr
            420                 425                 430

Ser Met Met Glu Pro Met Ser Ile Lys Ser Val Pro His Pro Ser Ile
        435                 440                 445

Leu Ala His Tyr Asn Glu Thr Asp Val Ser Gly Ile Ser Ile Arg Lys
    450                 455                 460

Leu Asp Ser Phe Asp Leu Gln Ser Leu His Trp Ser
465                 470                 475

<210> SEQ ID NO 92
<211> LENGTH: 179
<212> TYPE: PRT
<213> ORGANISM: artificial sequence
<220> FEATURE:
<223> OTHER INFORMATION: Fusion protein
<220> FEATURE:
<221> NAME/KEY: MISC_FEATURE
<222> LOCATION: (1)..(179)
<223> OTHER INFORMATION: LongSpyTag-AP205-LongSpyTag

<400> SEQUENCE: 92

Met Ala His Ile Val Met Val Asp Ala Tyr Lys Pro Thr Lys Gly Ser
1               5                   10                  15

Gly Thr Ala Gly Gly Gly Ser Gly Ser Ala Asn Lys Pro Met Gln Pro
            20                  25                  30

Ile Thr Ser Thr Ala Asn Lys Ile Val Trp Ser Asp Pro Thr Arg Leu
        35                  40                  45

Ser Thr Thr Phe Ser Ala Ser Leu Leu Arg Gln Arg Val Lys Val Gly
    50                  55                  60

Ile Ala Glu Leu Asn Asn Val Ser Gly Gln Tyr Val Ser Val Tyr Lys

```
                65                  70                  75                  80
Arg Pro Ala Pro Lys Pro Glu Gly Cys Ala Asp Ala Cys Val Ile Met
                        85                  90                  95

Pro Asn Glu Asn Gln Ser Ile Arg Thr Val Ile Ser Gly Ser Ala Glu
                100                 105                 110

Asn Leu Ala Thr Leu Lys Ala Glu Trp Glu Thr His Lys Arg Asn Val
            115                 120                 125

Asp Thr Leu Phe Ala Ser Gly Asn Ala Gly Leu Gly Phe Leu Asp Pro
        130                 135                 140

Thr Ala Ala Ile Val Ser Ser Asp Thr Ala Gly Thr Ala Ser Gly
145                 150                 155                 160

Gly Ser Gly Gly Ser Gly Ala His Ile Val Met Val Asp Ala Tyr Lys
                165                 170                 175

Pro Thr Lys
```

<210> SEQ ID NO 93
<211> LENGTH: 540
<212> TYPE: DNA
<213> ORGANISM: artificial sequence
<220> FEATURE:
<223> OTHER INFORMATION: DNA sequence encoding fusion protein
<220> FEATURE:
<221> NAME/KEY: misc_feature
<222> LOCATION: (1)..(540)
<223> OTHER INFORMATION: LongSpyTag-AP205-LongSpyTag

<400> SEQUENCE: 93

```
atggcacata ttgttatggt ggatgcatat aaaccgacca aaggtagcgg tacagccggt      60
ggtggtagtg gtagcgcaaa taaaccgatg cagccgatta ccagcaccgc aaacaaaatt     120
gtttggagcg atccgacccg tctgagcacc acctttagcg caagcctgct gcgtcagcgt     180
gttaaagttg gtattgcaga actgaataat gtgagcggtc agtatgttag cgtgtataaa     240
cgtccggcac cgaaaccgga aggttgtgca gatgcatgtg ttattatgcc gaatgaaaat     300
cagagcattc gtaccgttat tagcggtagc gcagaaaatc tggcaaccct gaaagcagaa     360
tgggaaaccc ataaacgtaa tgtggatacc ctgtttgcaa gcggtaatgc aggtctgggt     420
tttctggacc cgaccgcagc aattgttagc agcgatacca ccgcaggtac agccagcggt     480
ggtagcggtg gtagcggtgc acatattgtt atggttgatg catataaacc gaccaaataa     540
```

<210> SEQ ID NO 94
<211> LENGTH: 250
<212> TYPE: PRT
<213> ORGANISM: Artificial sequence
<220> FEATURE:
<223> OTHER INFORMATION: Chain A, Structure Based Engineering Of
      Streptavidin Monomer With A Reduced Biotin Dissociation Rate;
      Demonte et al., 2013

<400> SEQUENCE: 94

```
Met Ala Glu Ala Gly Ile Thr Gly Thr Trp Tyr Asn Gln His Gly Ser
1               5                   10                  15

Thr Phe Thr Val Thr Ala Gly Ala Asp Gly Asn Leu Thr Gly Gln Tyr
            20                  25                  30

Glu Asn Arg Ala Gln Gly Thr Gly Cys Gln Asn Ser Pro Tyr Thr Leu
        35                  40                  45

Thr Gly Arg Tyr Asn Gly Thr Lys Leu Glu Trp Arg Val Glu Trp Asn
    50                  55                  60

Asn Ser Thr Glu Asn Cys His Ser Arg Thr Glu Trp Arg Gly Gln Tyr
```

```
                65                  70                  75                  80
Gln Gly Gly Ala Glu Ala Arg Ile Asn Thr Gln Trp Asn Leu Thr Tyr
                    85                  90                  95
Glu Gly Gly Ser Gly Pro Ala Thr Glu Gln Gly Gln Asp Thr Phe Thr
                100                 105                 110
Lys Val Lys Gly Gly Ser Gly Ser Ala Asn Lys Pro Met Gln Pro Ile
            115                 120                 125
Thr Ser Thr Ala Asn Lys Ile Val Trp Ser Asp Pro Thr Arg Leu Ser
        130                 135                 140
Thr Thr Phe Ser Ala Ser Leu Leu Arg Gln Arg Val Lys Val Gly Ile
145                 150                 155                 160
Ala Glu Leu Asn Asn Val Ser Gly Gln Tyr Val Ser Val Tyr Lys Arg
                165                 170                 175
Pro Ala Pro Lys Pro Glu Gly Cys Ala Asp Ala Cys Val Ile Met Pro
            180                 185                 190
Asn Glu Asn Gln Ser Ile Arg Thr Val Ile Ser Gly Ser Ala Glu Asn
        195                 200                 205
Leu Ala Thr Leu Lys Ala Glu Trp Glu Thr His Lys Arg Asn Val Asp
    210                 215                 220
Thr Leu Phe Ala Ser Gly Asn Ala Gly Leu Gly Phe Leu Asp Pro Thr
225                 230                 235                 240
Ala Ala Ile Val Ser Ser Asp Thr Thr Ala
                245                 250

<210> SEQ ID NO 95
<211> LENGTH: 753
<212> TYPE: DNA
<213> ORGANISM: Artificial sequence
<220> FEATURE:
<223> OTHER INFORMATION: Chain A, Structure Based Engineering Of
      Streptavidin Monomer With A Reduced Biotin Dissociation Rate;
      Demonte et al., 2013

<400> SEQUENCE: 95
atggcagaag caggtattac cggcacctgg tataatcagc atggtagcac ctttaccgtt    60
accgcaggcg cagatggtaa tctgacaggt cagtatgaaa tcgtgcaca gggcaccggt    120 tgtcagaata gcccgtatac cctgaccggt cgttataatg caccaaaact ggaatggcgt    180
gttgaatgga ataatagcac cgaaaattgt catagccgta ccgaatggcg tggtcagtat    240
cagggtggtg cagaagcccg tattaatacc cagtggaatc tgacctatga aggtggtagc    300
ggtccggcaa ccgaacaggg tcaggatacc tttaccaaag ttaaaggtgg cagcggtagc    360
gcaaataaac cgatgcagcc gattaccagc accgcaaaca aaattgtttg gagcgatccg    420
acccgtctga gcaccacctt tagcgcaagc ctgctgcgtc agcgtgttaa agttggtatt    480
gcagaactga ataatgtgag cggtcagtat gttagcgtgt ataaacgtcc ggcaccgaaa    540
ccggaaggtt gtgcagatgc atgtgttatt atgccgaatg aaaatcagag cattcgtacc    600
gttattagcg gtagcgcaga aaatctggca accctgaaag cagaatggga aacccataaa    660
cgtaatgtgg ataccctgtt tgcaagcggt aatgcaggtc tgggttttct ggacccgacc    720
gcagcaattg ttagcagcga taccaccgca taa                                 753
```